(12) United States Patent
Dlugos, Jr. et al.

(10) Patent No.: US 8,152,710 B2
(45) Date of Patent: Apr. 10, 2012

(54) PHYSIOLOGICAL PARAMETER ANALYSIS FOR AN IMPLANTABLE RESTRICTION DEVICE AND A DATA LOGGER

(75) Inventors: Daniel F. Dlugos, Jr., Middletown, OH (US); Peter Brockmeier, Cincinnati, OH (US); Matthew A Berger, Cincinnati, OH (US); Randal T. Byrum, South Lebanon, OH (US); Kevin R. Doll, Mason, OH (US); Gaspar M. Gayoso, Cincinnati, OH (US); Dustin R. Jensen, Loveland, OH (US); David T. Krumanaker, Cincinnati, OH (US); Amy L. Marcotte, Mason, OH (US); Mark S. Ortiz, Milford, OH (US); David N. Plescia, Cincinnati, OH (US); David C. Yates, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 987 days.

(21) Appl. No.: 12/039,014

(22) Filed: Feb. 28, 2008

(65) Prior Publication Data
US 2009/0222065 A1    Sep. 3, 2009

Related U.S. Application Data

(63) Continuation-in-part of application No. 11/398,940, filed on Apr. 6, 2006, now Pat. No. 8,016,745.

(51) Int. Cl.
*A61B 5/00* (2006.01)
(52) U.S. Cl. .............................. 600/37; 600/29; 702/19
(58) Field of Classification Search .................. 128/898, 128/903; 600/29–31, 37, 484, 32, 558, 483; 604/27, 28; 606/139–141, 157, 201–203, 606/213, 151; 607/41, 9, 30, 40, 60; 623/23.64–67; 702/19, 57

See application file for complete search history.

(56) References Cited

U.S. PATENT DOCUMENTS

RE3,036 E    7/1868 Shunk
(Continued)

FOREIGN PATENT DOCUMENTS

AU    729467    2/2001
(Continued)

OTHER PUBLICATIONS

"Application Specific Integrated Circuits (ASICs)", Honeywell product information from website http://www.honeywell.com/sites/portal?smap=aerospace&page=Radiation-Hardened-Electronics3&theme=T18&catID=CE06BEF88-65F8-6A1E-4ED1-6A1EC1B7AE7A&id=HA0E380D3-C27B-9EBF-AAC8-9FAF8851256D&sel=1&sel4=1; 1 page.

(Continued)

*Primary Examiner* — John P Lacyk
*Assistant Examiner* — Joshua D Lannu
(74) *Attorney, Agent, or Firm* — Nutter McClennen & Fish LLP

(57) ABSTRACT

An implantable restriction device can be configured to provide a restriction in a patient, for example as a function of the pressure of fluid. The implantable restriction device can include one or more sensors configured to sense a variety of parameters, such as pressure of the fluid within the implantable restriction device, pulse width, pulse amplitude, pulse count, pulse duration, or frequency, electrical characteristics, or other parameters. Data obtained by the one or more sensors (for example, the data representing pressure, pulse characteristics, and so on) may be communicated to a device located external to the patient, such as a data logger, using telemetry coils or other communicators. The data logger may store the data, and may communicate the data to a remote location via a network such as the Internet. A docking station may be provided to couple the data logger to a network and/or to recharge a cell in the data logger. The logged data may be analyzed and/or displayed using a variety of techniques to assess and/or track the condition of the restriction device or of the patient, to monitor patient physiology, or for other purposes.

28 Claims, 61 Drawing Sheets

U.S. PATENT DOCUMENTS

| | | |
|---|---|---|
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 225,145 A | 8/1880 | Kleinberger |
| 236,373 A | 1/1881 | Spilman |
| 322,388 A | 7/1885 | Lord |
| 400,401 A | 3/1889 | Gutzkow |
| D23,637 S | 9/1894 | Casad et al. |
| D24,900 S | 11/1895 | Clemecet |
| D25,318 S | 3/1896 | Perky |
| D27,151 S | 6/1897 | Moulten |
| D29,715 S | 11/1898 | Wheeler |
| D29,745 S | 11/1898 | Bunker |
| D29,885 S | 12/1898 | Gillespie et al. |
| D30,690 S | 5/1899 | Schwedtmann |
| D30,966 S | 6/1899 | Howe |
| D31,230 S | 7/1899 | Hogan |
| 689,758 A | 12/1901 | Shaw |
| 724,913 A | 4/1903 | Montgomery |
| 899,477 A | 9/1908 | Williams |
| 926,197 A | 6/1909 | Kim |
| 943,915 A | 12/1909 | Comer |
| 953,875 A | 4/1910 | Waring |
| 991,192 A | 5/1911 | Batttenfeld |
| 1,087,988 A | 2/1914 | Sheldon |
| 1,210,701 A | 1/1917 | Ryden |
| 1,219,296 A | 3/1917 | Hahn |
| 1,224,355 A | 5/1917 | Brown |
| 1,263,914 A | 4/1918 | Martin |
| 1,310,290 A | 7/1919 | Piechowicz |
| 1,384,873 A | 7/1921 | Strickland |
| 1,421,507 A | 7/1922 | Lindberg |
| 1,551,525 A | 8/1925 | Hamer |
| 1,560,973 A | 11/1925 | Cheron |
| 1,620,633 A | 3/1927 | Colvin |
| 1,623,403 A | 4/1927 | Friel |
| 1,689,085 A | 10/1928 | Russel et al. |
| 1,794,071 A | 6/1930 | Foulke |
| 1,782,704 A | 11/1930 | Woodruff |
| 1,807,107 A | 5/1931 | Sternberch |
| 1,865,446 A | 7/1932 | Sears |
| 1,882,338 A | 10/1932 | Reed at al. |
| 1,924,781 A | 8/1933 | Gaiser |
| 2,024,203 A | 12/1935 | Berger |
| 2,027,875 A | 1/1936 | Odend'hal |
| 2,063,430 A | 12/1936 | Graser |
| 2,099,160 A | 11/1937 | Charch |
| 2,105,127 A | 1/1938 | Petrone |
| 2,106,192 A | 1/1938 | Saville |
| 2,143,429 A | 1/1939 | Auble |
| 2,166,603 A | 7/1939 | Menzer |
| 2,168,427 A | 8/1939 | McConkey |
| 2,174,525 A | 10/1939 | Padernal |
| 2,177,564 A | 10/1939 | Havill |
| 2,178,463 A | 10/1939 | Bahnson |
| 2,180,599 A | 11/1939 | Menasco |
| 2,203,460 A | 6/1940 | Fieber |
| 2,206,038 A | 7/1940 | Lang Ford |
| 2,216,374 A | 10/1940 | Martin |
| 2,223,699 A | 12/1940 | Norgren |
| 2,225,145 A | 12/1940 | Baumbach |
| 2,225,880 A | 12/1940 | Montelius |
| 2,261,060 A | 10/1941 | Giesler |
| 2,261,355 A | 11/1941 | Flynn |
| 2,295,539 A | 9/1942 | Beach |
| 2,303,108 A | 11/1942 | Blackburn |
| 2,303,502 A | 12/1942 | Rous |
| 2,318,819 A | 5/1943 | Verson |
| 2,327,407 A | 8/1943 | Edyvean |
| 2,327,615 A | 8/1943 | Ankarlo |
| 2,354,571 A | 7/1944 | Blain |
| 2,396,351 A | 3/1946 | Thompson |
| 2,426,392 A | 8/1947 | Fennema |
| 2,426,817 A | 9/1947 | Charlton et al. |
| 2,440,260 A | 4/1948 | Gall |
| 2,442,573 A | 6/1948 | Stafford |
| 2,453,217 A | 11/1948 | Gregg et al. |
| 2,455,859 A | 12/1948 | Foley |
| 2,477,922 A | 8/1949 | Emery et al. |
| 2,478,876 A | 8/1949 | Nelson |
| 2,482,392 A | 9/1949 | Whitaker |
| 2,494,881 A | 1/1950 | Kost |
| 2,509,210 A | 5/1950 | Clark |
| 2,509,673 A | 5/1950 | Church |
| 2,511,765 A | 6/1950 | Bradbury |
| 2,520,056 A | 8/1950 | Pozun |
| 2,521,976 A | 9/1950 | Hays |
| 2,533,924 A | 12/1950 | Foley |
| 2,538,259 A | 1/1951 | Merriman |
| 2,581,479 A | 1/1952 | Grashman |
| 2,600,324 A | 6/1952 | Rappaport |
| 2,606,003 A | 8/1952 | McNeill |
| 2,615,940 A | 10/1952 | Williams |
| 2,632,447 A | 3/1953 | Dobes |
| 2,639,342 A | 5/1953 | Cope |
| 2,640,119 A | 5/1953 | Bradford, Jr. |
| 2,641,742 A | 6/1953 | Wolfe |
| 2,651,304 A | 9/1953 | Browner |
| 2,665,577 A | 1/1954 | Sanowskis |
| 2,673,999 A | 4/1954 | Shey |
| 2,676,609 A | 4/1954 | Pfarrer |
| 2,684,118 A | 7/1954 | Osmun |
| 2,689,611 A | 9/1954 | Martinson |
| 2,697,435 A | 12/1954 | Ray |
| 2,723,323 A | 11/1955 | Niemi |
| 2,734,992 A | 2/1956 | Elliot et al. |
| 2,740,007 A | 3/1956 | Amelang |
| 2,740,853 A | 4/1956 | Hatman, Jr. |
| 2,742,323 A | 4/1956 | Shey |
| 2,747,332 A | 5/1956 | Morehouse |
| 2,753,876 A | 7/1956 | Kurt |
| 2,756,883 A | 7/1956 | Schreck |
| 2,756,983 A | 7/1956 | Furcini |
| 2,761,603 A | 9/1956 | Fairchild |
| 2,773,312 A | 12/1956 | Peck |
| 2,783,728 A | 3/1957 | Hoffmann |
| 2,787,875 A | 4/1957 | Johnson |
| 2,793,379 A | 5/1957 | Moore |
| 2,795,460 A | 6/1957 | Bletcher |
| 2,804,514 A | 8/1957 | Peters |
| 2,822,113 A | 2/1958 | Joiner, Jr. |
| 2,831,478 A | 4/1958 | Uddenberg et al. |
| 2,864,393 A | 12/1958 | Drake |
| 2,865,541 A | 12/1958 | Hicks |
| 2,870,024 A | 1/1959 | Martin |
| 2,883,995 A | 4/1959 | Bialous et al. |
| 2,886,355 A | 5/1959 | Wurzel |
| 2,895,215 A | 7/1959 | Neher et al. |
| 2,899,493 A | 8/1959 | Levine |
| 2,902,861 A | 9/1959 | Frost et al. |
| 2,923,531 A | 2/1960 | Bauer et al. |
| 2,924,263 A | 2/1960 | Landis |
| 2,924,432 A | 2/1960 | Arps et al. |
| 2,930,170 A | 3/1960 | Holsman et al. |
| 2,938,592 A | 5/1960 | Charske et al. |
| 2,941,338 A | 6/1960 | Santschi |
| 2,943,682 A | 7/1960 | Ingram, Jr. et al. |
| 2,958,781 A | 11/1960 | Marchal et al. |
| 2,961,479 A | 11/1960 | Bertling |
| 2,976,355 A | 3/1961 | Levine |
| 2,976,686 A | 3/1961 | Stelzer |
| 2,977,876 A | 4/1961 | Meyers |
| 2,986,715 A | 5/1961 | Church et al. |
| 2,989,019 A | 6/1961 | Van Sciver, II |
| 3,010,692 A | 11/1961 | Jentoft |
| 3,013,234 A | 12/1961 | Bourns |
| 3,018,791 A | 1/1962 | Knox |
| 3,034,356 A | 5/1962 | Bieganski |
| 3,040,800 A | 6/1962 | Hartley |
| 3,054,618 A | 9/1962 | Abrams et al. |
| 3,060,262 A | 10/1962 | Hoer |
| 3,070,373 A | 12/1962 | Mathews et al. |
| 3,082,414 A | 3/1963 | Papaminas |
| 3,085,577 A | 4/1963 | Berman et al. |
| 3,096,410 A | 7/1963 | Anderson |
| 3,099,262 A | 7/1963 | Bigliano |

| | | | | | |
|---|---|---|---|---|---|
| 3,125,028 A | 3/1964 | Rohde | 3,445,335 A | 5/1969 | Gluntz |
| 3,126,029 A | 3/1964 | Englesson | 3,447,281 A | 6/1969 | Bufford et al. |
| 3,129,072 A | 4/1964 | Cook et al. | 3,450,153 A | 6/1969 | Hildebrandt et al. |
| 3,135,914 A | 6/1964 | Callan et al. | 3,453,546 A | 7/1969 | Fryer |
| 3,144,017 A | 8/1964 | Muth | 3,453,848 A | 7/1969 | Williamson |
| 3,151,258 A | 9/1964 | Sonderegger et al. | 3,456,134 A | 7/1969 | Ko |
| 3,153,460 A | 10/1964 | Raskin | 3,457,909 A | 7/1969 | Laird |
| 3,161,051 A | 12/1964 | Perry, Jr. | 3,460,557 A | 8/1969 | Gallant |
| 3,167,044 A | 1/1965 | Henrickson | 3,463,338 A | 8/1969 | Schneider |
| 3,171,549 A | 3/1965 | Orloff | 3,469,818 A | 9/1969 | Cowan |
| 3,172,700 A | 3/1965 | Haas | 3,470,725 A | 10/1969 | Brown et al. |
| 3,173,269 A | 3/1965 | Imbertson | 3,472,230 A | 10/1969 | Fogarty |
| 3,182,494 A | 5/1965 | Beatty et al. | 3,478,344 A | 11/1969 | Schwitzgebel et al. |
| 3,187,181 A | 6/1965 | Keller | 3,482,449 A | 12/1969 | Werner |
| 3,187,745 A | 6/1965 | Baum et al. | 3,482,816 A | 12/1969 | Arnold |
| 3,190,388 A | 6/1965 | Moser et al. | 3,487,959 A | 1/1970 | Pearne et al. |
| 3,205,547 A | 9/1965 | Riekse | 3,491,842 A | 1/1970 | Delacour et al. |
| 3,208,255 A | 9/1965 | Burk | 3,492,638 A | 1/1970 | Lane |
| 3,209,570 A | 10/1965 | Hills | 3,502,829 A | 3/1970 | Reynolds |
| 3,221,468 A | 12/1965 | Casey | 3,503,116 A | 3/1970 | Strack |
| 3,228,703 A | 1/1966 | Wilson | 3,504,664 A | 4/1970 | Haddad |
| 3,229,684 A | 1/1966 | Nagumo et al. | 3,505,808 A | 4/1970 | Eschle |
| 3,236,088 A | 2/1966 | Moller | 3,509,754 A | 5/1970 | Massingill et al. |
| 3,238,624 A | 3/1966 | McCabe | 3,512,517 A | 5/1970 | Kadish et al. |
| 3,240,510 A | 3/1966 | Spouge | 3,514,919 A | 6/1970 | Ashton et al. |
| 3,245,642 A | 4/1966 | Dicke | 3,516,220 A | 6/1970 | Buford et al. |
| 3,255,568 A | 6/1966 | Martin et al. | 3,517,553 A | 6/1970 | Williams et al. |
| 3,260,091 A | 7/1966 | Shaw, Jr. | 3,527,226 A | 9/1970 | Hakin et al. |
| 3,265,822 A | 8/1966 | Moulten | 3,529,908 A | 9/1970 | Smith |
| 3,266,487 A | 8/1966 | Watkins et al. | 3,530,449 A | 9/1970 | Anderson |
| 3,273,447 A | 9/1966 | Frank | 3,533,403 A | 10/1970 | Woodson |
| 3,283,352 A | 11/1966 | Hu | 3,534,728 A | 10/1970 | Barrows |
| 3,290,919 A | 12/1966 | Malinak et al. | 3,534,872 A | 10/1970 | Roth et al. |
| 3,292,493 A | 12/1966 | Franklin | 3,535,914 A | 10/1970 | Veith et al. |
| 3,292,888 A | 12/1966 | Fischer | 3,535,917 A | 10/1970 | Blair et al. |
| 3,294,988 A | 12/1966 | Packard | 3,539,009 A | 11/1970 | Kudlaty |
| 3,299,603 A | 1/1967 | Shaw | 3,543,744 A | 12/1970 | LePar |
| 3,299,882 A | 1/1967 | Masino | 3,545,275 A | 12/1970 | Harrison et al. |
| 3,301,514 A | 1/1967 | Sugaya | 3,550,583 A | 12/1970 | Chiku |
| 3,302,457 A | 2/1967 | Mayes | 3,550,847 A | 12/1970 | Scott |
| 3,306,384 A | 2/1967 | Ross | 3,563,094 A | 2/1971 | Rieschel |
| 3,313,314 A | 4/1967 | Burke et al. | 3,563,245 A | 2/1971 | McLean et al. |
| 3,316,935 A | 5/1967 | Kaiser et al. | 3,566,083 A | 2/1971 | McMillin |
| 3,320,750 A | 5/1967 | Haise et al. | 3,566,875 A | 3/1971 | Stoehr |
| 3,321,035 A | 5/1967 | Tarpley | 3,568,367 A | 3/1971 | Myers |
| 3,332,788 A | 7/1967 | Barnby | 3,568,636 A | 3/1971 | Lockwood |
| 3,334,510 A | 8/1967 | Hallesy | 3,570,495 A | 3/1971 | Wright |
| 3,339,401 A | 9/1967 | Peters | 3,576,554 A | 4/1971 | Temps, Jr. et al. |
| 3,340,868 A | 9/1967 | Darling | 3,580,082 A | 5/1971 | Strack |
| 3,347,162 A | 10/1967 | Braznell | 3,581,402 A | 6/1971 | London et al. |
| 3,350,944 A | 11/1967 | De Michele | 3,583,387 A | 6/1971 | Garner et al. |
| 3,353,364 A | 11/1967 | Blanding et al. | 3,587,204 A | 6/1971 | George |
| 3,353,481 A | 11/1967 | Antonucci | 3,590,809 A | 7/1971 | London |
| 3,356,334 A | 12/1967 | Scaramucci | 3,590,818 A | 7/1971 | Lemole |
| 3,356,510 A | 12/1967 | Barnby | 3,590,992 A | 7/1971 | Soderstrom et al. |
| 3,357,218 A | 12/1967 | Mitchell | 3,592,183 A | 7/1971 | Watkins et al. |
| 3,357,461 A | 12/1967 | Friendship | 3,594,519 A | 7/1971 | Schmidlin |
| 3,359,741 A | 12/1967 | Nelson | 3,602,885 A | 8/1971 | Grajeda |
| 3,361,300 A | 1/1968 | Kaplan | 3,610,016 A | 10/1971 | Bultman |
| 3,364,929 A | 1/1968 | Ide et al. | 3,610,851 A | 10/1971 | Krupski |
| 3,365,684 A | 1/1968 | Stemke | 3,611,811 A | 10/1971 | Lissau |
| 3,378,456 A | 4/1968 | Roberts | 3,614,926 A | 10/1971 | Brechtel |
| 3,380,445 A | 4/1968 | Frasier | 3,614,955 A | 10/1971 | Mirowski et al. |
| 3,380,649 A | 4/1968 | Roberts | 3,619,742 A | 11/1971 | Rud, Jr. |
| 3,385,022 A | 5/1968 | Anderson | 3,623,371 A | 11/1971 | Jullien-Davin |
| 3,389,355 A | 6/1968 | Schroeder, Jr. | 3,624,854 A | 12/1971 | Strong |
| 3,393,612 A | 7/1968 | Gorgens et al. | 3,630,242 A | 12/1971 | Schieser et al. |
| 3,396,561 A | 8/1968 | Day | 3,631,847 A | 1/1972 | Hobbs, II |
| 3,399,667 A | 9/1968 | Nishimoto et al. | 3,633,881 A | 1/1972 | Yurdin |
| 3,400,734 A | 9/1968 | Rosenberg | 3,635,061 A | 1/1972 | Rydell et al. |
| 3,403,237 A | 9/1968 | Wysong | 3,635,074 A | 1/1972 | Moos et al. |
| 3,409,924 A | 11/1968 | Slama | 3,638,496 A | 2/1972 | King |
| 3,411,347 A | 11/1968 | Wirth et al. | 3,644,883 A | 2/1972 | Borman et al. |
| 3,417,476 A | 12/1968 | Martens | 3,648,687 A | 3/1972 | Ramsey, III |
| 3,420,325 A | 1/1969 | McAlister et al. | 3,651,289 A | 3/1972 | Nagashima et al. |
| 3,422,324 A | 1/1969 | Webb | 3,651,405 A | 3/1972 | Whitney et al. |
| 3,426,165 A | 2/1969 | Beaman | 3,653,671 A | 4/1972 | Shipes |
| 3,438,391 A | 4/1969 | Yocum | 3,659,615 A | 5/1972 | Enger |
| 3,443,608 A | 5/1969 | Copping et al. | 3,677,685 A | 7/1972 | Aoki et al. |

| | | | |
|---|---|---|---|
| 3,686,958 A | 8/1972 | Porter et al. | |
| 3,688,568 A | 9/1972 | Karper et al. | |
| 3,701,392 A | 10/1972 | Wirth et al. | |
| 3,702,677 A | 11/1972 | Heffington | |
| 3,703,099 A | 11/1972 | Rouse et al. | |
| 3,712,138 A | 1/1973 | Alinari et al. | |
| 3,713,124 A | 1/1973 | Durland et al. | |
| 3,719,524 A | 3/1973 | Ripley et al. | |
| 3,721,412 A | 3/1973 | Kindorf | |
| 3,723,247 A | 3/1973 | Leine et al. | |
| 3,724,000 A | 4/1973 | Eakman | |
| 3,727,463 A | 4/1973 | Intraub | |
| 3,727,616 A | 4/1973 | Lenzkes | |
| 3,730,174 A | 5/1973 | Madison | |
| 3,730,560 A | 5/1973 | Abildgaard et al. | |
| 3,731,679 A | 5/1973 | Wilhelmson et al. | |
| 3,731,681 A | 5/1973 | Blackshear et al. | |
| 3,732,731 A | 5/1973 | Fussell, Jr. | |
| 3,735,040 A | 5/1973 | Punt et al. | |
| 3,736,930 A | 6/1973 | Georgi | |
| 3,738,356 A | 6/1973 | Workman | |
| 3,740,921 A | 6/1973 | Meyer et al. | |
| 3,746,111 A | 7/1973 | Berthiaume et al. | |
| 3,748,678 A | 7/1973 | Ballou | |
| 3,749,098 A | 7/1973 | De Bennetot et al. | |
| 3,749,422 A | 7/1973 | Abildgaard et al. | |
| 3,749,423 A | 7/1973 | Abildgaard et al. | |
| 3,750,194 A | 8/1973 | Summers | |
| 3,757,770 A | 9/1973 | Brayshaw et al. | |
| 3,759,095 A | 9/1973 | Short, Jr. et al. | |
| 3,759,248 A * | 9/1973 | Valiquette | 600/516 |
| 3,760,638 A | 9/1973 | Lawson et al. | |
| 3,763,960 A | 10/1973 | John et al. | |
| 3,765,142 A | 10/1973 | Lindquist et al. | |
| 3,765,494 A | 10/1973 | Kielman, Jr. | |
| 3,769,156 A | 10/1973 | Brecy et al. | |
| 3,769,830 A | 11/1973 | Porter et al. | |
| 3,774,243 A | 11/1973 | Ng et al. | |
| 3,776,333 A | 12/1973 | Mathauser | |
| 3,778,051 A | 12/1973 | Allen et al. | |
| 3,780,578 A | 12/1973 | Sellman et al. | |
| 3,781,902 A | 12/1973 | Shim et al. | |
| 3,783,585 A | 1/1974 | Hoyland et al. | |
| 3,789,667 A | 2/1974 | Porter et al. | |
| 3,796,095 A | 3/1974 | Fussell, Jr. | |
| 3,807,219 A | 4/1974 | Wallskog | |
| 3,811,429 A | 5/1974 | Fletcher et al. | |
| 3,815,722 A | 6/1974 | Sessoms | |
| 3,818,765 A | 6/1974 | Eriksen et al. | |
| 3,820,400 A | 6/1974 | Russo | |
| 3,820,795 A | 6/1974 | Taylor | |
| 3,823,610 A | 7/1974 | Fussell, Jr. | |
| 3,825,065 A | 7/1974 | Lloyd et al. | |
| 3,825,963 A | 7/1974 | Abildgaard et al. | |
| 3,825,964 A | 7/1974 | Groswith, III et al. | |
| 3,828,672 A | 8/1974 | Gazzola et al. | |
| 3,828,766 A | 8/1974 | Krasnow | |
| 3,831,588 A | 8/1974 | Rindner | |
| 3,831,942 A | 8/1974 | Del Mar | |
| 3,833,238 A | 9/1974 | Liard et al. | |
| 3,834,167 A | 9/1974 | Tabor | |
| 3,834,739 A | 9/1974 | Abildgaard et al. | |
| 3,835,523 A | 9/1974 | Stansfield et al. | |
| 3,839,708 A | 10/1974 | Bredesen et al. | |
| 3,840,018 A | 10/1974 | Heifetz | |
| 3,842,483 A | 10/1974 | Cramer | |
| 3,842,668 A | 10/1974 | Lippke et al. | |
| 3,845,664 A | 11/1974 | Perry, Jr. | |
| 3,845,751 A | 11/1974 | Runstetler | |
| 3,845,757 A | 11/1974 | Weyer | |
| 3,847,434 A | 11/1974 | Weman et al. | |
| 3,850,208 A | 11/1974 | Hamilton | |
| 3,853,117 A | 12/1974 | Murr | |
| 3,854,469 A | 12/1974 | Giori et al. | |
| 3,855,902 A | 12/1974 | Kirst et al. | |
| 3,857,399 A | 12/1974 | Zacouto et al. | |
| 3,857,452 A | 12/1974 | Hartman | |
| 3,857,745 A | 12/1974 | Grausch et al. | |
| 3,858,581 A | 1/1975 | Kamen | |
| 3,863,622 A | 2/1975 | Buuck | |
| 3,863,933 A | 2/1975 | Tredway | |
| 3,867,950 A | 2/1975 | Fischell | |
| 3,868,008 A | 2/1975 | Brumbaugh | |
| 3,868,679 A | 2/1975 | Arneson | |
| 3,871,599 A | 3/1975 | Takada et al. | |
| 3,872,285 A | 3/1975 | Shum et al. | |
| 3,874,388 A | 4/1975 | King et al. | |
| 3,876,980 A | 4/1975 | Haemmig et al. | |
| 3,878,908 A | 4/1975 | Andersson et al. | |
| 3,881,528 A | 5/1975 | Mackenzie | |
| 3,886,948 A | 6/1975 | Hakim | |
| 3,893,111 A | 7/1975 | Cotter | |
| 3,893,451 A | 7/1975 | Durand et al. | |
| 3,895,681 A | 7/1975 | Griffin et al. | |
| 3,899,862 A | 8/1975 | Muys et al. | |
| 3,904,234 A | 9/1975 | Hill et al. | |
| 3,908,334 A | 9/1975 | Rychiger et al. | |
| 3,908,461 A | 9/1975 | Turpen | |
| 3,908,721 A | 9/1975 | McGahey et al. | |
| 3,910,087 A | 10/1975 | Jones | |
| 3,912,168 A | 10/1975 | Mullins et al. | |
| 3,912,304 A | 10/1975 | Abildgaard et al. | |
| 3,918,286 A | 11/1975 | Whitehead | |
| 3,918,291 A | 11/1975 | Pauly et al. | |
| 3,920,965 A | 11/1975 | Sohrwardy et al. | |
| 3,921,682 A | 11/1975 | McGahey et al. | |
| 3,922,951 A | 12/1975 | Linsinger et al. | |
| 3,923,060 A | 12/1975 | Ellinwood, Jr. | |
| 3,924,635 A | 12/1975 | Hakim et al. | |
| 3,926,177 A * | 12/1975 | Hardway et al. | 600/535 |
| 3,928,980 A | 12/1975 | Ganzinotti et al. | |
| 3,929,175 A | 12/1975 | Coone | |
| 3,930,682 A | 1/1976 | Booth | |
| 3,930,852 A | 1/1976 | Tanaka et al. | |
| 3,936,028 A | 2/1976 | Norton et al. | |
| 3,939,823 A | 2/1976 | Kaye et al. | |
| 3,940,122 A | 2/1976 | Janzen et al. | |
| 3,940,630 A | 2/1976 | Bergonz | |
| 3,942,299 A | 3/1976 | Bory et al. | |
| 3,942,382 A | 3/1976 | Hok et al. | |
| 3,942,516 A | 3/1976 | Glynn et al. | |
| 3,942,536 A | 3/1976 | Mirowski et al. | |
| 3,943,915 A | 3/1976 | Severson | |
| 3,945,704 A | 3/1976 | Kraus et al. | |
| 3,946,613 A | 3/1976 | Silver | |
| 3,946,615 A | 3/1976 | Hluchan | |
| 3,946,724 A | 3/1976 | La Balme et al. | |
| 3,948,141 A | 4/1976 | Shinjo et al. | |
| 3,949,388 A | 4/1976 | Fuller | |
| 3,953,289 A | 4/1976 | Costes et al. | |
| 3,954,271 A | 5/1976 | Tredway, Sr. | |
| 3,958,558 A | 5/1976 | Dunphy et al. | |
| 3,960,142 A | 6/1976 | Elliott et al. | |
| 3,961,425 A | 6/1976 | Swanson et al. | |
| 3,961,646 A | 6/1976 | Schon et al. | |
| 3,962,895 A | 6/1976 | Rydell et al. | |
| 3,962,921 A | 6/1976 | Lips | |
| 3,963,019 A | 6/1976 | Quandt | |
| 3,963,028 A | 6/1976 | Cooley et al. | |
| 3,964,485 A | 6/1976 | Neumeier | |
| 3,964,770 A | 6/1976 | Abildgaard et al. | |
| 3,967,737 A | 7/1976 | Peralta et al. | |
| 3,968,473 A | 7/1976 | Patton et al. | |
| 3,968,694 A | 7/1976 | Clark | |
| 3,972,320 A | 8/1976 | Kalman | |
| 3,973,753 A | 8/1976 | Wheeler | |
| 3,973,858 A | 8/1976 | Poisson et al. | |
| 3,974,655 A | 8/1976 | Halpern et al. | |
| 3,974,865 A | 8/1976 | Fenton et al. | |
| 3,976,278 A | 8/1976 | Dye et al. | |
| 3,977,391 A | 8/1976 | Fleischmann | |
| 3,980,871 A | 9/1976 | Lindstrom et al. | |
| 3,982,571 A | 9/1976 | Fenton et al. | |
| 3,983,948 A | 10/1976 | Jeter | |
| 3,985,133 A | 10/1976 | Jenkins et al. | |
| 3,987,860 A | 10/1976 | Jabsen | |
| 3,989,005 A | 11/1976 | Bowler, Jr. et al. | |
| 3,991,749 A | 11/1976 | Zent | |

| | | | | | | |
|---|---|---|---|---|---|---|
| 3,992,948 A | 11/1976 | D'Antonio et al. | | 4,120,097 A | 10/1978 | Jeter |
| 3,993,149 A | 11/1976 | Harvey | | 4,120,134 A | 10/1978 | Scholle |
| 3,996,927 A | 12/1976 | Frank | | 4,121,635 A | 10/1978 | Hansel |
| 3,996,962 A | 12/1976 | Sutherland | | 4,123,310 A | 10/1978 | Varon et al. |
| 4,003,141 A | 1/1977 | Le Roy | | 4,124,023 A | 11/1978 | Fleischmann et al. |
| 4,005,282 A | 1/1977 | Jennings | | 4,127,110 A | 11/1978 | Bullara |
| 4,005,593 A | 2/1977 | Goldberg | | 4,130,169 A | 12/1978 | Denison |
| 4,006,735 A | 2/1977 | Hittman et al. | | 4,131,596 A | 12/1978 | Allen |
| 4,009,375 A | 2/1977 | White et al. | | 4,133,355 A | 1/1979 | Mayer |
| 4,009,591 A | 3/1977 | Hester | | 4,133,367 A | 1/1979 | Abell |
| 4,010,449 A | 3/1977 | Faggin et al. | | 4,135,509 A | 1/1979 | Shannon |
| 4,014,319 A | 3/1977 | Favre et al. | | 4,140,131 A | 2/1979 | Dutcher et al. |
| 4,014,321 A | 3/1977 | March | | 4,141,348 A | 2/1979 | Hittman |
| 4,016,764 A | 4/1977 | Rice | | 4,141,349 A | 2/1979 | Ory et al. |
| 4,017,329 A | 4/1977 | Larson | | 4,143,661 A | 3/1979 | LaForge et al. |
| 4,018,134 A | 4/1977 | Linsinger et al. | | 4,146,029 A | 3/1979 | Ellinwood, Jr. |
| 4,022,190 A | 5/1977 | Meyer | | 4,147,161 A | 4/1979 | Ikebe et al. |
| 4,024,864 A | 5/1977 | Davies et al. | | 4,148,096 A | 4/1979 | Haas et al. |
| 4,025,912 A | 5/1977 | Rice | | 4,149,423 A | 4/1979 | Frosch et al. |
| 4,026,276 A | 5/1977 | Chubbuck | | 4,151,823 A | 5/1979 | Grosse et al. |
| 4,027,661 A | 6/1977 | Lyon et al. | | 4,153,085 A | 5/1979 | Adams |
| 4,031,899 A | 6/1977 | Renirie et al. | | 4,156,422 A | 5/1979 | Hildebrandt et al. |
| 4,036,775 A | 7/1977 | Trautvetter et al. | | 4,160,448 A | 7/1979 | Jackson |
| 4,039,069 A | 8/1977 | Kwan et al. | | 4,160,971 A | 7/1979 | Jones et al. |
| 4,041,954 A | 8/1977 | Ohara et al. | | 4,166,469 A | 9/1979 | Littleford |
| 4,042,504 A | 8/1977 | Drori et al. | | 4,167,304 A | 9/1979 | Gelbke |
| 4,045,345 A | 8/1977 | Drori et al. | | 4,167,952 A | 9/1979 | Reinicke |
| 4,047,296 A | 9/1977 | Ishida et al. | | 4,168,567 A | 9/1979 | Leguy et al. |
| 4,047,851 A | 9/1977 | Bender | | 4,170,280 A | 10/1979 | Schwarz |
| 4,048,494 A | 9/1977 | Liesting et al. | | 4,171,218 A | 10/1979 | Hoshino et al. |
| 4,048,879 A | 9/1977 | Cox | | 4,173,228 A | 11/1979 | Van Steenwyk et al. |
| 4,049,004 A | 9/1977 | Walters | | 4,183,124 A | 1/1980 | Hoffman |
| 4,051,338 A | 9/1977 | Harris, III | | 4,183,247 A | 1/1980 | Allen et al. |
| 4,052,991 A | 10/1977 | Zacouto et al. | | 4,185,641 A | 1/1980 | Minior et al. |
| 4,055,074 A | 10/1977 | Thimons et al. | | 4,186,287 A | 1/1980 | Scott |
| 4,055,175 A | 10/1977 | Clemens et al. | | 4,186,749 A | 2/1980 | Fryer |
| 4,056,854 A | 11/1977 | Boretos et al. | | 4,186,751 A | 2/1980 | Fleischmann |
| 4,058,007 A | 11/1977 | Exner et al. | | 4,190,057 A | 2/1980 | Hill et al. |
| 4,062,351 A | 12/1977 | Hastwell et al. | | 4,191,004 A | 3/1980 | Gmuer et al. |
| 4,062,354 A | 12/1977 | Taylor et al. | | 4,191,187 A | 3/1980 | Wright et al. |
| 4,062,360 A | 12/1977 | Bentley | | 4,192,192 A | 3/1980 | Schnell |
| 4,063,439 A | 12/1977 | Besson et al. | | 4,193,397 A | 3/1980 | Tucker et al. |
| 4,064,879 A | 12/1977 | Leibinsohn | | 4,201,218 A | 5/1980 | Feldman et al. |
| 4,064,882 A | 12/1977 | Johnson et al. | | 4,204,547 A | 5/1980 | Allocca |
| 4,070,239 A | 1/1978 | Bevilacqua | | 4,206,755 A | 6/1980 | Klein et al. |
| 4,072,047 A | 2/1978 | Reismuller et al. | | 4,206,761 A | 6/1980 | Cosman |
| 4,073,292 A | 2/1978 | Edelman | | 4,206,762 A | 6/1980 | Cosman |
| 4,075,099 A | 2/1978 | Pelton et al. | | 4,207,903 A | 6/1980 | O'Neill |
| 4,075,602 A | 2/1978 | Clothier | | 4,212,074 A | 7/1980 | Kuno et al. |
| 4,077,072 A | 3/1978 | Dezura et al. | | 4,217,221 A | 8/1980 | Masso |
| 4,077,394 A | 3/1978 | McCurdy | | 4,217,588 A | 8/1980 | Freeny, Jr. |
| 4,077,405 A | 3/1978 | Haerten et al. | | 4,220,189 A | 9/1980 | Marquez |
| 4,077,882 A | 3/1978 | Gangemi | | 4,221,219 A | 9/1980 | Tucker |
| 4,078,620 A | 3/1978 | Westlake et al. | | 4,221,523 A | 9/1980 | Eberle |
| 4,080,653 A | 3/1978 | Barnes, Jr. et al. | | 4,222,377 A | 9/1980 | Burton |
| 4,084,752 A | 4/1978 | Hagiwara et al. | | 4,223,837 A | 9/1980 | Gubbiotti et al. |
| 4,086,488 A | 4/1978 | Hill | | 4,226,124 A | 10/1980 | Kersten et al. |
| 4,087,568 A | 5/1978 | Fay et al. | | 4,226,229 A | 10/1980 | Eckhart et al. |
| 4,088,417 A | 5/1978 | Kosmowski | | 4,227,533 A | 10/1980 | Godfrey |
| 4,089,329 A | 5/1978 | Couvillon, Jr. et al. | | 4,231,376 A | 11/1980 | Lyon et al. |
| 4,090,802 A | 5/1978 | Bilz et al. | | 4,232,682 A | 11/1980 | Veth |
| 4,092,719 A | 5/1978 | Salmon et al. | | 4,237,900 A | 12/1980 | Schulman et al. |
| 4,092,925 A | 6/1978 | Fromson | | 4,241,247 A | 12/1980 | Byrne et al. |
| 4,096,866 A | 6/1978 | Fischell | | 4,241,870 A | 12/1980 | Marcus |
| 4,098,293 A | 7/1978 | Kramer et al. | | 4,245,593 A | 1/1981 | Stein |
| 4,103,496 A | 8/1978 | Colamussi et al. | | 4,246,877 A | 1/1981 | Kennedy |
| 4,106,370 A | 8/1978 | Kraus et al. | | 4,247,850 A | 1/1981 | Marcus |
| 4,107,689 A | 8/1978 | Jellinek | | 4,248,238 A | 2/1981 | Joseph et al. |
| 4,107,995 A | 8/1978 | Ligman et al. | | 4,248,241 A | 2/1981 | Tacchi |
| 4,108,148 A | 8/1978 | Cannon, III | | 4,256,094 A | 3/1981 | Kapp et al. |
| 4,108,575 A | 8/1978 | Schal et al. | | 4,256,118 A | 3/1981 | Nagel et al. |
| 4,109,148 A | 8/1978 | Jaulmes et al. | | 4,262,343 A | 4/1981 | Claycomb |
| 4,109,518 A | 8/1978 | Dooley et al. | | 4,262,632 A | 4/1981 | Hanton et al. |
| 4,109,644 A | 8/1978 | Kojima | | 4,265,241 A | 5/1981 | Portner et al. |
| 4,111,056 A | 9/1978 | Mastromatteo | | 4,265,252 A | 5/1981 | Chubbuck et al. |
| 4,111,629 A | 9/1978 | Nussbaumer et al. | | 4,271,018 A | 6/1981 | Drori et al. |
| 4,114,424 A | 9/1978 | Johnson | | 4,273,070 A | 6/1981 | Hoefelmayr et al. |
| 4,114,603 A | 9/1978 | Wilkinson | | 4,274,444 A | 6/1981 | Ruyak |
| 4,114,606 A | 9/1978 | Seylar | | 4,275,600 A | 6/1981 | Turner et al. |

| | | | | | |
|---|---|---|---|---|---|
| 4,275,913 A | 6/1981 | Marcus | 4,431,365 A | 2/1984 | Sturtz, Jr. |
| 4,278,540 A | 7/1981 | Drori et al. | 4,432,363 A | 2/1984 | Kakegawa et al. |
| 4,280,036 A | 7/1981 | Fukatsu et al. | 4,435,173 A | 3/1984 | Siposs et al. |
| 4,280,775 A | 7/1981 | Wood | 4,439,186 A | 3/1984 | Kuhl et al. |
| 4,281,666 A | 8/1981 | Cosman | 4,441,491 A | 4/1984 | Evans, Sr. |
| 4,281,667 A | 8/1981 | Cosman | 4,441,501 A | 4/1984 | Parent |
| 4,284,073 A | 8/1981 | Krause et al. | 4,444,194 A | 4/1984 | Burcham |
| 4,285,770 A | 8/1981 | Chi et al. | 4,444,498 A | 4/1984 | Heinemann |
| 4,291,699 A | 9/1981 | Geddes et al. | 4,445,385 A | 5/1984 | Endo |
| 4,295,963 A | 10/1981 | Drori et al. | 4,446,290 A | 5/1984 | Ikematu et al. |
| 4,297,927 A | 11/1981 | Kuroda et al. | 4,446,711 A | 5/1984 | Valente |
| 4,303,075 A | 12/1981 | Heilman et al. | 4,447,224 A | 5/1984 | DeCant, Jr. et al. |
| 4,305,402 A | 12/1981 | Katims | 4,449,493 A | 5/1984 | Kopec et al. |
| 4,312,374 A | 1/1982 | Drori et al. | 4,450,811 A | 5/1984 | Ichikawa et al. |
| 4,314,480 A | 2/1982 | Becker | 4,450,946 A | 5/1984 | Olding et al. |
| 4,316,693 A | 2/1982 | Baxter et al. | 4,451,033 A | 5/1984 | Nestegard |
| 4,325,387 A | 4/1982 | Helfer | 4,453,537 A | 6/1984 | Spitzer |
| 4,327,804 A | 5/1982 | Reed | 4,453,578 A | 6/1984 | Wilder |
| 4,328,654 A | 5/1982 | Van Ginkel et al. | 4,460,835 A | 7/1984 | Masuoka et al. |
| 4,332,254 A | 6/1982 | Lundquist | 4,464,170 A | 8/1984 | Clemens et al. |
| 4,332,255 A | 6/1982 | Hakim et al. | 4,465,015 A | 8/1984 | Osta et al. |
| 4,339,831 A | 7/1982 | Johnson | 4,465,474 A | 8/1984 | Mardorf et al. |
| 4,342,218 A | 8/1982 | Fox | 4,466,290 A | 8/1984 | Frick |
| 4,342,308 A | 8/1982 | Trick | 4,468,172 A | 8/1984 | Dixon et al. |
| 4,346,604 A | 8/1982 | Snook et al. | 4,468,762 A | 8/1984 | Jurgens et al. |
| 4,347,851 A | 9/1982 | Jundanian | 4,469,365 A | 9/1984 | Marcus et al. |
| 4,350,647 A | 9/1982 | de la Cruz | 4,471,182 A | 9/1984 | Wielgos et al. |
| 4,350,970 A | 9/1982 | von Tomkewitsch et al. | 4,471,635 A | 9/1984 | Winter et al. |
| 4,351,037 A | 9/1982 | Scherbatskoy | 4,471,786 A | 9/1984 | Inagaki et al. |
| 4,351,116 A | 9/1982 | Scott, Jr. | 4,473,067 A | 9/1984 | Schiff |
| 4,356,486 A | 10/1982 | Mount | 4,473,078 A | 9/1984 | Angel |
| 4,360,010 A | 11/1982 | Finney | 4,476,721 A | 10/1984 | Hochreuther et al. |
| 4,360,277 A | 11/1982 | Daniel et al. | 4,478,213 A | 10/1984 | Redding |
| 4,361,153 A | 11/1982 | Slocum et al. | 4,478,538 A | 10/1984 | Kakino et al. |
| 4,363,236 A | 12/1982 | Meyers | 4,483,196 A | 11/1984 | Kurtz et al. |
| 4,364,276 A | 12/1982 | Shimazoe et al. | 4,484,135 A | 11/1984 | Ishihara et al. |
| 4,365,425 A | 12/1982 | Gotchel | 4,485,813 A | 12/1984 | Anderson et al. |
| 4,368,937 A | 1/1983 | Palombo et al. | 4,489,916 A | 12/1984 | Stevens |
| 4,369,013 A | 1/1983 | Abildgaard et al. | 4,490,750 A | 12/1984 | Yoshinaka |
| 4,373,527 A | 2/1983 | Fischell | 4,492,632 A | 1/1985 | Mattson |
| 4,376,523 A | 3/1983 | Goyen et al. | 4,494,411 A | 1/1985 | Koschke et al. |
| 4,378,809 A | 4/1983 | Cosman | 4,494,950 A | 1/1985 | Fischell |
| 4,380,427 A | 4/1983 | Hehl et al. | 4,497,176 A | 2/1985 | Rubin et al. |
| 4,385,636 A | 5/1983 | Cosman | 4,497,201 A | 2/1985 | Allen et al. |
| 4,386,422 A | 5/1983 | Mumby et al. | 4,499,394 A | 2/1985 | Koal |
| 4,387,715 A | 6/1983 | Hakim et al. | 4,499,691 A | 2/1985 | Karazim et al. |
| 4,387,907 A | 6/1983 | Hiestand et al. | 4,499,750 A | 2/1985 | Gerber et al. |
| 4,392,368 A | 7/1983 | Folkesson et al. | 4,503,678 A | 3/1985 | Wimbush et al. |
| 4,393,899 A | 7/1983 | Tsuji et al. | 4,511,974 A | 4/1985 | Nakane et al. |
| 4,393,951 A | 7/1983 | Horst-Rudolf et al. | 4,513,295 A | 4/1985 | Jones et al. |
| 4,395,232 A | 7/1983 | Koch | 4,515,004 A | 5/1985 | Jaenson |
| 4,395,258 A | 7/1983 | Wang et al. | 4,515,750 A | 5/1985 | Pardini et al. |
| 4,395,916 A | 8/1983 | Martin | 4,516,866 A | 5/1985 | Yamauchi et al. |
| 4,398,983 A | 8/1983 | Suzuki et al. | 4,518,637 A | 5/1985 | Takeda et al. |
| 4,399,705 A | 8/1983 | Weiger et al. | 4,519,401 A | 5/1985 | Ko et al. |
| 4,399,707 A | 8/1983 | Wamstad | 4,520,443 A | 5/1985 | Yuki et al. |
| 4,399,809 A | 8/1983 | Baro et al. | 4,522,213 A | 6/1985 | Wallroth et al. |
| 4,399,821 A | 8/1983 | Bowers | 4,527,568 A | 7/1985 | Rickards et al. |
| 4,403,984 A | 9/1983 | Ash et al. | 4,529,401 A | 7/1985 | Leslie et al. |
| 4,404,968 A | 9/1983 | Evans, Sr. | 4,531,526 A | 7/1985 | Genest |
| 4,404,974 A | 9/1983 | Titus | 4,531,936 A | 7/1985 | Gordon |
| 4,405,318 A | 9/1983 | Whitney et al. | 4,534,361 A * | 8/1985 | Berger et al. .................. 600/493 |
| 4,407,125 A | 10/1983 | Parsons et al. | 4,536,000 A | 8/1985 | Rohm et al. |
| 4,407,271 A | 10/1983 | Schiff | 4,537,005 A | 8/1985 | Hoyland et al. |
| 4,407,296 A | 10/1983 | Anderson | 4,537,129 A | 8/1985 | Heinemann et al. |
| 4,407,326 A | 10/1983 | Wilhelm | 4,538,616 A | 9/1985 | Rogoff |
| 4,408,597 A | 10/1983 | Tenney, Jr. | 4,540,404 A | 9/1985 | Wolvek |
| 4,408,615 A | 10/1983 | Grossman | 4,542,461 A | 9/1985 | Eldridge et al. |
| 4,415,071 A | 11/1983 | Butler et al. | 4,544,339 A | 10/1985 | Itoh |
| 4,416,282 A | 11/1983 | Saulson et al. | 4,544,369 A | 10/1985 | Skakoon et al. |
| 4,418,899 A | 12/1983 | Zimmermann et al. | 4,545,185 A | 10/1985 | Chikatani et al. |
| 4,419,393 A | 12/1983 | Hanson et al. | 4,546,524 A | 10/1985 | Kreft |
| 4,421,124 A | 12/1983 | Marshall | 4,548,209 A | 10/1985 | Wielders et al. |
| 4,421,505 A | 12/1983 | Schwartz | 4,551,128 A | 11/1985 | Hakim et al. |
| 4,424,720 A | 1/1984 | Bucchianeri | 4,552,150 A | 11/1985 | Zacouto et al. |
| 4,428,228 A | 1/1984 | Banzhaf et al. | 4,553,226 A | 11/1985 | Scherbatskoy |
| 4,428,365 A | 1/1984 | Hakky et al. | 4,556,063 A | 12/1985 | Thompson et al. |
| 4,430,899 A | 2/1984 | Wessel et al. | 4,556,086 A | 12/1985 | Raines |
| 4,431,009 A | 2/1984 | Marino, Jr. et al. | 4,557,269 A | 12/1985 | Reynolds et al. |

| | | |
|---|---|---|
| 4,557,332 A | 12/1985 | Denison et al. |
| 4,559,815 A | 12/1985 | Needham et al. |
| 4,560,979 A | 12/1985 | Rosskopf et al. |
| 4,561,442 A | 12/1985 | Vollmann et al. |
| 4,562,751 A | 1/1986 | Nason et al. |
| 4,563,175 A | 1/1986 | LaFond |
| 4,565,116 A | 1/1986 | Hehl et al. |
| 4,566,456 A | 1/1986 | Koning et al. |
| 4,569,623 A | 2/1986 | Goldmann |
| 4,570,351 A | 2/1986 | Szanto et al. |
| 4,571,161 A | 2/1986 | Leblanc et al. |
| 4,571,749 A | 2/1986 | Fischell |
| 4,571,995 A | 2/1986 | Timme |
| 4,573,835 A | 3/1986 | Eckardt et al. |
| 4,574,792 A | 3/1986 | Trick |
| 4,576,181 A | 3/1986 | Wallace et al. |
| 4,576,183 A | 3/1986 | Plicchi et al. |
| 4,577,512 A | 3/1986 | Lowenheck et al. |
| 4,581,018 A | 4/1986 | Jassawalla et al. |
| 4,581,915 A | 4/1986 | Haulsee et al. |
| 4,587,840 A | 5/1986 | Dobler et al. |
| 4,589,805 A | 5/1986 | Duffner et al. |
| 4,592,339 A | 6/1986 | Kuzmak et al. |
| 4,592,340 A | 6/1986 | Boyles |
| 4,593,703 A | 6/1986 | Cosman |
| 4,595,228 A | 6/1986 | Chu |
| 4,595,390 A | 6/1986 | Hakim et al. |
| 4,596,563 A | 6/1986 | Pande |
| 4,599,943 A | 7/1986 | Kobler et al. |
| 4,600,855 A | 7/1986 | Strachan et al. |
| 4,602,541 A | 7/1986 | Benzinger et al. |
| 4,604,089 A | 8/1986 | Santangelo et al. |
| 4,605,354 A | 8/1986 | Daly |
| 4,606,419 A | 8/1986 | Perini |
| 4,606,478 A | 8/1986 | Hack et al. |
| 4,610,256 A | 9/1986 | Wallace |
| 4,614,137 A | 9/1986 | Jones |
| 4,615,691 A | 10/1986 | Hakim et al. |
| 4,617,016 A | 10/1986 | Blomberg et al. |
| 4,618,861 A | 10/1986 | Gettens et al. |
| 4,619,653 A | 10/1986 | Fischell |
| 4,620,807 A | 11/1986 | Polit |
| 4,621,331 A | 11/1986 | Iwata et al. |
| 4,622,871 A | 11/1986 | Van Sickle et al. |
| 4,626,462 A | 12/1986 | Kober et al. |
| 4,633,304 A | 12/1986 | Nagasaki et al. |
| 4,633,878 A | 1/1987 | Bombardieri et al. |
| 4,634,443 A | 1/1987 | Haber |
| 4,635,182 A | 1/1987 | Hintz |
| 4,636,553 A | 1/1987 | Katto et al. |
| 4,637,736 A | 1/1987 | Andeen et al. |
| 4,638,665 A | 1/1987 | Benson et al. |
| 4,644,246 A | 2/1987 | Knapen et al. |
| 4,646,553 A | 3/1987 | Tufte et al. |
| 4,648,363 A | 3/1987 | Kronich |
| 4,648,406 A | 3/1987 | Miller |
| 4,658,358 A | 4/1987 | Leach et al. |
| 4,658,760 A | 4/1987 | Zebuhr |
| 4,660,568 A | 4/1987 | Cosman |
| 4,665,511 A | 5/1987 | Rodney et al. |
| 4,665,896 A | 5/1987 | LaForge et al. |
| 4,669,484 A | 6/1987 | Masters |
| 4,672,974 A | 6/1987 | Lee |
| 4,674,457 A | 6/1987 | Berger et al. |
| 4,674,546 A | 6/1987 | Fournier et al. |
| 4,678,408 A | 7/1987 | Nason et al. |
| 4,681,559 A | 7/1987 | Hooven |
| 4,683,850 A | 8/1987 | Bauder et al. |
| 4,685,463 A | 8/1987 | Williams |
| 4,685,469 A | 8/1987 | Keller et al. |
| 4,685,903 A | 8/1987 | Cable et al. |
| 4,686,979 A | 8/1987 | Gruen et al. |
| 4,686,987 A | 8/1987 | Salo et al. |
| 4,687,530 A | 8/1987 | Berscheid et al. |
| 4,689,979 A | 9/1987 | Otsuka et al. |
| 4,691,694 A | 9/1987 | Boyd et al. |
| 4,691,710 A | 9/1987 | Dickens et al. |
| 4,693,253 A | 9/1987 | Adams |
| 4,695,237 A | 9/1987 | Inaba et al. |
| 4,696,189 A | 9/1987 | Hochreuther et al. |
| 4,697,574 A | 10/1987 | Karcher et al. |
| 4,698,038 A | 10/1987 | Key et al. |
| 4,700,497 A | 10/1987 | Sato et al. |
| 4,700,610 A | 10/1987 | Bauer et al. |
| 4,701,143 A | 10/1987 | Key et al. |
| 4,702,235 A | 10/1987 | Hong |
| 4,703,756 A | 11/1987 | Gough et al. |
| 4,705,507 A | 11/1987 | Boyles |
| 4,706,948 A | 11/1987 | Kroecher et al. |
| 4,711,249 A | 12/1987 | Brooks |
| 4,712,562 A | 12/1987 | Ohayon et al. |
| 4,718,425 A | 1/1988 | Tanaka et al. |
| 4,722,348 A | 2/1988 | Ligtenberg et al. |
| 4,724,806 A | 2/1988 | Hartwig et al. |
| 4,724,830 A | 2/1988 | Fischell |
| 4,725,826 A | 2/1988 | Hunter |
| 4,727,887 A | 3/1988 | Haber |
| 4,728,479 A | 3/1988 | Merkovsky |
| 4,729,517 A | 3/1988 | Krokor et al. |
| 4,730,188 A | 3/1988 | Milheiser |
| 4,730,420 A | 3/1988 | Stratmann et al. |
| 4,730,619 A | 3/1988 | Koning et al. |
| 4,731,058 A | 3/1988 | Doan |
| 4,735,205 A | 4/1988 | Chachques et al. |
| 4,738,267 A | 4/1988 | Lazorthes et al. |
| 4,738,268 A | 4/1988 | Kipnis |
| 4,741,345 A | 5/1988 | Matthews et al. |
| 4,741,732 A | 5/1988 | Crankshaw et al. |
| 4,743,129 A | 5/1988 | Keryhuel et al. |
| 4,745,541 A | 5/1988 | Vaniglia et al. |
| 4,745,830 A | 5/1988 | Gulino |
| 4,746,830 A | 5/1988 | Holland |
| 4,750,495 A | 6/1988 | Moore et al. |
| 4,752,115 A | 6/1988 | Murray, Jr. et al. |
| 4,752,658 A | 6/1988 | Mack |
| 4,757,463 A | 7/1988 | Ballou et al. |
| 4,759,386 A | 7/1988 | Grouw, III |
| 4,763,649 A | 8/1988 | Merrick |
| 4,765,001 A | 8/1988 | Smith |
| 4,767,406 A | 8/1988 | Wadham et al. |
| 4,769,001 A | 9/1988 | Prince |
| 4,772,257 A | 9/1988 | Hakim et al. |
| 4,772,896 A | 9/1988 | Nakatsu et al. |
| 4,773,401 A | 9/1988 | Citak et al. |
| 4,774,950 A | 10/1988 | Cohen |
| 4,774,955 A | 10/1988 | Jones |
| 4,777,953 A | 10/1988 | Ash et al. |
| 4,779,626 A | 10/1988 | Peel et al. |
| 4,781,192 A | 11/1988 | Demer |
| 4,782,826 A | 11/1988 | Fogarty |
| 4,783,106 A | 11/1988 | Nutter |
| 4,785,822 A | 11/1988 | Wallace |
| 4,788,847 A | 12/1988 | Sterghos |
| 4,791,318 A | 12/1988 | Lewis et al. |
| 4,794,803 A | 1/1989 | Osterhout et al. |
| 4,796,641 A | 1/1989 | Mills et al. |
| 4,798,211 A | 1/1989 | Goor et al. |
| 4,798,227 A | 1/1989 | Goodwin |
| 4,799,491 A | 1/1989 | Eckerle |
| 4,799,625 A | 1/1989 | Weaver, Jr. et al. |
| 4,802,488 A | 2/1989 | Eckerle |
| 4,803,987 A | 2/1989 | Calfee et al. |
| 4,804,368 A | 2/1989 | Skakoon et al. |
| 4,807,321 A | 2/1989 | Grasselli et al. |
| 4,808,167 A | 2/1989 | Mann et al. |
| 4,812,823 A | 3/1989 | Dickerson |
| 4,819,656 A | 4/1989 | Spector |
| 4,820,265 A | 4/1989 | DeSatnick et al. |
| 4,820,953 A | 4/1989 | Saubolle et al. |
| 4,821,167 A | 4/1989 | Wiebe |
| 4,821,723 A | 4/1989 | Baker, Jr. et al. |
| 4,823,779 A | 4/1989 | Daly et al. |
| 4,830,006 A | 5/1989 | Haluska et al. |
| 4,832,034 A | 5/1989 | Pizziconi et al. |
| 4,833,384 A | 5/1989 | Munro et al. |
| 4,834,731 A | 5/1989 | Nowak et al. |
| 4,838,857 A | 6/1989 | Strowe et al. |
| 4,840,068 A | 6/1989 | Mayhew, Jr. |

| Patent No. | Date | Inventor |
|---|---|---|
| 4,840,350 A | 6/1989 | Cook |
| 4,844,002 A | 7/1989 | Yasui et al. |
| 4,846,153 A | 7/1989 | Berci |
| 4,846,191 A | 7/1989 | Brockway et al. |
| 4,846,664 A | 7/1989 | Hehl et al. |
| 4,854,328 A | 8/1989 | Pollack |
| 4,863,470 A | 9/1989 | Carter |
| 4,865,587 A | 9/1989 | Walling |
| 4,867,160 A | 9/1989 | Schaldach et al. |
| 4,867,498 A | 9/1989 | Delphia et al. |
| 4,867,618 A | 9/1989 | Brohammer |
| 4,869,252 A | 9/1989 | Gilli |
| 4,870,258 A | 9/1989 | Mochizuki et al. |
| 4,871,351 A | 10/1989 | Feingold et al. |
| 4,872,483 A | 10/1989 | Shah |
| 4,872,869 A | 10/1989 | Johns |
| 4,873,677 A | 10/1989 | Sakamoto et al. |
| 4,875,483 A | 10/1989 | Vollmann et al. |
| 4,880,004 A | 11/1989 | Baker, Jr. et al. |
| 4,882,678 A | 11/1989 | Hollis et al. |
| 4,886,392 A | 12/1989 | Iio et al. |
| 4,893,630 A | 1/1990 | Bray, Jr. |
| 4,895,151 A | 1/1990 | Grevis et al. |
| 4,896,594 A | 1/1990 | Baur et al. |
| 4,898,158 A | 2/1990 | Daly et al. |
| 4,898,578 A | 2/1990 | Rubalcaba, Jr. |
| 4,898,585 A | 2/1990 | Borsanyi et al. |
| 4,899,751 A | 2/1990 | Cohen |
| 4,899,752 A | 2/1990 | Cohen |
| 4,902,277 A | 2/1990 | Mathies et al. |
| 4,903,701 A | 2/1990 | Moore et al. |
| 4,905,698 A | 3/1990 | Strohl, Jr. et al. |
| 4,909,678 A | 3/1990 | Kakimoto et al. |
| 4,913,147 A | 4/1990 | Fahlstrom et al. |
| 4,919,143 A | 4/1990 | Ayers |
| 4,924,872 A | 5/1990 | Frank |
| 4,926,903 A | 5/1990 | Kawai et al. |
| 4,932,406 A | 6/1990 | Berkovits |
| 4,934,369 A | 6/1990 | Maxwell |
| 4,936,304 A | 6/1990 | Kresh et al. |
| 4,940,037 A | 7/1990 | Eckert et al. |
| 4,941,718 A | 7/1990 | Alexander, III et al. |
| 4,942,004 A | 7/1990 | Catanzaro |
| 4,944,050 A | 7/1990 | Shames et al. |
| 4,944,298 A | 7/1990 | Sholder |
| 4,944,307 A | 7/1990 | Hon et al. |
| 4,945,761 A | 8/1990 | Lessi et al. |
| 4,949,724 A | 8/1990 | Mahutte et al. |
| 4,952,205 A | 8/1990 | Mauerer et al. |
| 4,952,928 A | 8/1990 | Carroll et al. |
| 4,953,563 A | 9/1990 | Kaiser et al. |
| 4,954,677 A | 9/1990 | Alberter et al. |
| 4,958,630 A | 9/1990 | Rosenbluth et al. |
| 4,958,645 A | 9/1990 | Cadell et al. |
| 4,960,424 A | 10/1990 | Grooters |
| 4,960,966 A | 10/1990 | Evans et al. |
| 4,967,585 A | 11/1990 | Grimaldo |
| 4,967,761 A | 11/1990 | Nathanielsz |
| 4,970,823 A | 11/1990 | Chen et al. |
| 4,971,251 A | 11/1990 | Dobrick et al. |
| 4,977,896 A | 12/1990 | Robinson et al. |
| 4,978,335 A | 12/1990 | Arthur, III |
| 4,978,338 A | 12/1990 | Melsky et al. |
| 4,979,730 A | 12/1990 | Holbrook et al. |
| 4,980,671 A | 12/1990 | McCurdy |
| 4,981,141 A | 1/1991 | Segalowitz |
| 4,981,173 A | 1/1991 | Perkins et al. |
| 4,981,426 A | 1/1991 | Aoki et al. |
| 4,987,897 A | 1/1991 | Funke et al. |
| 4,988,337 A | 1/1991 | Ito et al. |
| 4,992,794 A | 2/1991 | Brouwers et al. |
| 4,997,556 A | 3/1991 | Yano et al. |
| 5,001,528 A | 3/1991 | Bahraman |
| 5,003,807 A | 4/1991 | Terrell et al. |
| 5,003,975 A | 4/1991 | Hafelfinger et al. |
| 5,003,976 A | 4/1991 | Alt et al. |
| 5,004,472 A | 4/1991 | Wallace |
| 5,004,873 A | 4/1991 | Schnut |
| 5,005,574 A | 4/1991 | Fearnot et al. |
| 5,005,586 A | 4/1991 | Lahr |
| 5,006,844 A | 4/1991 | Ohta et al. |
| 5,006,884 A | 4/1991 | Kazuhito et al. |
| 5,006,997 A | 4/1991 | Reich |
| 5,007,401 A | 4/1991 | Grohn et al. |
| 5,007,430 A | 4/1991 | Dardik |
| 5,007,919 A | 4/1991 | Silva et al. |
| 5,009,662 A | 4/1991 | Wallace et al. |
| 5,010,893 A | 4/1991 | Sholder |
| 5,012,286 A | 4/1991 | Kawano et al. |
| 5,012,810 A | 5/1991 | Strand et al. |
| 5,013,292 A | 5/1991 | Lemay et al. |
| 5,014,040 A | 5/1991 | Weaver et al. |
| 5,019,032 A | 5/1991 | Robertson |
| 5,019,041 A | 5/1991 | Robinson et al. |
| 5,020,845 A | 6/1991 | Falcoff et al. |
| 5,021,046 A | 6/1991 | Wallace |
| 5,022,395 A | 6/1991 | Russie |
| 5,024,965 A | 6/1991 | Chang et al. |
| 5,026,180 A | 6/1991 | Tajima et al. |
| 5,026,360 A | 6/1991 | Johnsen et al. |
| 5,028,918 A | 7/1991 | Giles et al. |
| 5,032,822 A | 7/1991 | Sweet |
| 5,036,869 A | 8/1991 | Inahara et al. |
| 5,038,800 A | 8/1991 | Oba et al. |
| 5,041,086 A | 8/1991 | Koenig et al. |
| 5,041,826 A | 8/1991 | Milheiser |
| 5,042,503 A | 8/1991 | Torok et al. |
| 5,044,770 A | 9/1991 | Haghkar |
| 5,046,661 A | 9/1991 | Kimura et al. |
| 5,048,060 A | 9/1991 | Arai et al. |
| 5,050,922 A | 9/1991 | Falcoff |
| 5,052,910 A | 10/1991 | Hehl et al. |
| 5,053,008 A | 10/1991 | Bajaj |
| 5,057,078 A | 10/1991 | Foote et al. |
| 5,058,583 A | 10/1991 | Geddes et al. |
| 5,061,239 A | 10/1991 | Shiels |
| 5,062,052 A | 10/1991 | Sparer et al. |
| 5,062,053 A | 10/1991 | Shirai et al. |
| 5,062,559 A | 11/1991 | Falcoff |
| 5,064,974 A | 11/1991 | Vigneau et al. |
| 5,067,960 A | 11/1991 | Grandjean et al. |
| 5,068,779 A | 11/1991 | Sullivan et al. |
| 5,069,680 A | 12/1991 | Grandjean et al. |
| 5,077,102 A | 12/1991 | Chong |
| 5,077,667 A * | 12/1991 | Brown et al. .................. 607/5 |
| 5,077,870 A | 1/1992 | Melbye et al. |
| 5,078,139 A | 1/1992 | Strand et al. |
| 5,082,006 A | 1/1992 | Jonasson et al. |
| 5,083,563 A | 1/1992 | Collins et al. |
| 5,084,699 A | 1/1992 | DeMichele |
| 5,085,224 A | 2/1992 | Galen et al. |
| 5,085,258 A | 2/1992 | Fink, Jr. et al. |
| 5,089,673 A | 2/1992 | Strzodka et al. |
| 5,089,979 A | 2/1992 | McEachern et al. |
| 5,095,309 A | 3/1992 | Troyk et al. |
| 5,096,271 A | 3/1992 | Portman |
| 5,097,831 A | 3/1992 | Lekholm |
| 5,098,384 A | 3/1992 | Abrams |
| 5,099,845 A | 3/1992 | Besz et al. |
| 5,103,832 A | 4/1992 | Jackson |
| 5,105,810 A | 4/1992 | Collins et al. |
| 5,107,850 A | 4/1992 | Olive |
| 5,112,344 A | 5/1992 | Petros et al. |
| 5,113,859 A | 5/1992 | Funke et al. |
| 5,113,869 A | 5/1992 | Nappholz et al. |
| 5,115,676 A | 5/1992 | Lee |
| 5,117,825 A | 6/1992 | Grevious |
| 5,120,313 A | 6/1992 | Elftman |
| 5,121,777 A | 6/1992 | Leininger et al. |
| 5,127,451 A | 7/1992 | Fink, Jr. et al. |
| 5,129,394 A | 7/1992 | Mehra |
| 5,129,806 A | 7/1992 | Hehl et al. |
| 5,131,145 A | 7/1992 | Badoureaux et al. |
| 5,131,388 A | 7/1992 | Pless et al. |
| 5,133,358 A | 7/1992 | Gustafson et al. |
| 5,135,488 A | 8/1992 | Foote et al. |
| 5,139,484 A | 8/1992 | Hazon et al. |
| 5,144,949 A | 9/1992 | Olson |

| Patent | Date | Inventor |
|---|---|---|
| 5,148,580 A | 9/1992 | Dyckow et al. |
| 5,148,695 A | 9/1992 | Ellis |
| 5,152,770 A | 10/1992 | Bengmark et al. |
| 5,152,776 A | 10/1992 | Pinchuk |
| 5,154,170 A | 10/1992 | Bennett et al. |
| 5,154,171 A | 10/1992 | Chirife et al. |
| 5,154,693 A | 10/1992 | East et al. |
| 5,156,972 A | 10/1992 | Issachar et al. |
| 5,158,078 A | 10/1992 | Bennett et al. |
| 5,163,429 A | 11/1992 | Cohen |
| 5,163,904 A | 11/1992 | Lampropoulos et al. |
| 5,167,615 A | 12/1992 | East et al. |
| 5,168,757 A | 12/1992 | Rabenau et al. |
| 5,168,982 A | 12/1992 | Hakanen et al. |
| 5,171,299 A | 12/1992 | Heitzmann et al. |
| 5,173,873 A | 12/1992 | Wu et al. |
| 5,174,286 A | 12/1992 | Chirife et al. |
| 5,174,291 A | 12/1992 | Schoonen et al. |
| 5,176,502 A | 1/1993 | Sanderson et al. |
| 5,178,197 A | 1/1993 | Healy |
| 5,181,423 A | 1/1993 | Philipps et al. |
| 5,181,517 A | 1/1993 | Hickey |
| 5,184,132 A | 2/1993 | Baird |
| 5,184,614 A | 2/1993 | Collins et al. |
| 5,184,619 A | 2/1993 | Austin |
| 5,185,535 A | 2/1993 | Farb et al. |
| 5,186,224 A | 2/1993 | Schirmacher et al. |
| 5,188,106 A | 2/1993 | Nappholz et al. |
| 5,188,604 A | 2/1993 | Orth |
| 5,192,314 A | 3/1993 | Daskalakis |
| 5,195,362 A | 3/1993 | Eason |
| 5,197,322 A | 3/1993 | Indravudh |
| 5,199,427 A | 4/1993 | Strickland |
| 5,199,428 A | 4/1993 | Obel et al. |
| 5,201,753 A | 4/1993 | Lampropoulos et al. |
| 5,204,670 A | 4/1993 | Stinton |
| 5,207,429 A | 5/1993 | Walmsley et al. |
| 5,209,223 A | 5/1993 | McGorry et al. |
| 5,209,731 A | 5/1993 | Sterman et al. |
| 5,209,732 A | 5/1993 | Lampropoulos et al. |
| 5,211,129 A | 5/1993 | Taylor et al. |
| 5,211,161 A | 5/1993 | Stef et al. |
| 5,212,476 A | 5/1993 | Maloney |
| 5,213,331 A | 5/1993 | Avanzini |
| 5,215,523 A | 6/1993 | Williams et al. |
| 5,218,343 A | 6/1993 | Stobbe et al. |
| 5,218,957 A | 6/1993 | Strickland |
| 5,226,429 A | 7/1993 | Kuzmak |
| 5,226,604 A | 7/1993 | Seiffert et al. |
| 5,230,694 A | 7/1993 | Rosenblum |
| 5,233,985 A | 8/1993 | Hudrlik |
| 5,235,326 A | 8/1993 | Beigel et al. |
| 5,241,965 A | 9/1993 | Mick |
| 5,244,269 A | 9/1993 | Harriehausen et al. |
| 5,244,461 A | 9/1993 | Derlien et al. |
| 5,246,008 A | 9/1993 | Mueller et al. |
| 5,249,858 A | 10/1993 | Nusser |
| 5,250,020 A | 10/1993 | Bley |
| 5,254,096 A | 10/1993 | Rondelet et al. |
| 5,256,157 A | 10/1993 | Samiotes et al. |
| 5,263,244 A | 11/1993 | Centa et al. |
| 5,263,981 A | 11/1993 | Polyak et al. |
| 5,267,940 A | 12/1993 | Moulder |
| 5,267,942 A | 12/1993 | Saperston |
| 5,269,891 A | 12/1993 | Colin et al. |
| 5,271,395 A | 12/1993 | Wahlstrand et al. |
| 5,274,859 A | 1/1994 | Redman et al. |
| 5,280,789 A | 1/1994 | Potts |
| 5,282,839 A | 2/1994 | Roline et al. |
| 5,282,840 A | 2/1994 | Hudrlik |
| 5,291,894 A | 3/1994 | Nagy |
| 5,292,219 A | 3/1994 | Merin et al. |
| 5,295,967 A | 3/1994 | Rondelet et al. |
| 5,298,022 A | 3/1994 | Bernardi et al. |
| 5,298,884 A | 3/1994 | Gilmore et al. |
| 5,300,093 A | 4/1994 | Koestner et al. |
| 5,300,120 A | 4/1994 | Knapp et al. |
| 5,304,112 A | 4/1994 | Mrklas et al. |
| 5,305,923 A | 4/1994 | Kirschner et al. |
| 5,312,443 A | 5/1994 | Adams et al. |
| 5,312,452 A | 5/1994 | Salo |
| 5,312,453 A | 5/1994 | Shelton et al. |
| 5,313,953 A | 5/1994 | Yomtov et al. |
| 5,314,451 A | 5/1994 | Mulier |
| 5,314,457 A | 5/1994 | Jeutter et al. |
| 5,324,315 A | 6/1994 | Grevious |
| 5,325,834 A | 7/1994 | Ballheimer et al. |
| 5,326,249 A | 7/1994 | Weissfloch et al. |
| 5,328,460 A | 7/1994 | Lord et al. |
| 5,330,511 A | 7/1994 | Boute et al. |
| 5,337,750 A | 8/1994 | Walloch |
| 5,341,430 A | 8/1994 | Aulia et al. |
| 5,342,401 A | 8/1994 | Spano et al. |
| 5,342,406 A | 8/1994 | Thompson |
| 5,344,388 A | 9/1994 | Maxwell et al. |
| 5,347,476 A | 9/1994 | McBean, Sr. |
| 5,348,210 A | 9/1994 | Linzell et al. |
| 5,348,536 A | 9/1994 | Young et al. |
| 5,350,413 A | 9/1994 | Miller et al. |
| 5,352,180 A | 10/1994 | Candelon et al. |
| 5,353,622 A | 10/1994 | Theener |
| 5,353,800 A | 10/1994 | Pohndorf et al. |
| 5,354,200 A | 10/1994 | Klein et al. |
| 5,354,316 A | 10/1994 | Keimel |
| 5,354,319 A | 10/1994 | Wyborny et al. |
| 5,360,407 A | 11/1994 | Leonard et al. |
| 5,365,462 A | 11/1994 | McBean, Sr. |
| 5,365,619 A | 11/1994 | Solomon |
| 5,365,985 A | 11/1994 | Todd et al. |
| 5,368,040 A | 11/1994 | Carney |
| 5,370,665 A | 12/1994 | Hudrlik |
| 5,373,852 A | 12/1994 | Harrison et al. |
| 5,375,073 A | 12/1994 | McBean |
| 5,377,128 A | 12/1994 | McBean |
| 5,378,231 A | 1/1995 | Johnson et al. |
| 5,382,232 A | 1/1995 | Hague et al. |
| 5,383,893 A | 1/1995 | Daneshvar |
| 5,383,915 A | 1/1995 | Adams |
| 5,388,578 A | 2/1995 | Yomtov et al. |
| 5,388,586 A | 2/1995 | Lee et al. |
| 5,388,831 A | 2/1995 | Quadri et al. |
| 5,394,909 A | 3/1995 | Mitchell et al. |
| 5,396,899 A | 3/1995 | Strittmatter |
| 5,402,944 A | 4/1995 | Pape et al. |
| 5,406,957 A | 4/1995 | Tansey |
| 5,409,009 A | 4/1995 | Olson |
| 5,411,031 A | 5/1995 | Yomtov |
| 5,411,551 A | 5/1995 | Winston et al. |
| 5,411,552 A | 5/1995 | Andersen et al. |
| 5,416,372 A | 5/1995 | Ljungstroem et al. |
| 5,417,226 A | 5/1995 | Juma |
| 5,417,717 A | 5/1995 | Salo et al. |
| 5,425,362 A | 6/1995 | Siker et al. |
| 5,425,713 A | 6/1995 | Taylor et al. |
| 5,431,171 A | 7/1995 | Harrison et al. |
| 5,431,629 A | 7/1995 | Lampropoulos et al. |
| 5,431,694 A | 7/1995 | Snaper et al. |
| 5,433,694 A | 7/1995 | Lim et al. |
| 5,437,605 A | 8/1995 | Helmy et al. |
| 5,443,215 A | 8/1995 | Fackler |
| 5,447,519 A | 9/1995 | Peterson |
| 5,449,345 A | 9/1995 | Taylor et al. |
| 5,449,368 A | 9/1995 | Kuzmak |
| 5,456,690 A | 10/1995 | Duong-Van |
| 5,461,293 A | 10/1995 | Rozman et al. |
| 5,461,390 A | 10/1995 | Hoshen |
| 5,464,435 A | 11/1995 | Neumann |
| 5,467,627 A | 11/1995 | Smith et al. |
| 5,474,226 A | 12/1995 | Joseph |
| 5,479,818 A | 1/1996 | Walter et al. |
| 5,482,049 A | 1/1996 | Addiss et al. |
| 5,487,760 A | 1/1996 | Villafana |
| 5,490,514 A | 2/1996 | Rosenberg |
| 5,493,738 A | 2/1996 | Sanderson et al. |
| 5,494,036 A | 2/1996 | Uber, III et al. |
| 5,494,193 A | 2/1996 | Kirschner et al. |
| 5,504,474 A | 4/1996 | Libman et al. |
| 5,505,916 A | 4/1996 | Berry, Jr. |

| | | | | | | |
|---|---|---|---|---|---|---|
| 5,507,412 A | 4/1996 | Ebert et al. | | 5,765,568 A | 6/1998 | Sweezer, Jr. et al. |
| 5,507,737 A | 4/1996 | Palmskog et al. | | 5,769,812 A | 6/1998 | Stevens et al. |
| 5,507,785 A | 4/1996 | Deno | | 5,771,903 A | 6/1998 | Jakobsson |
| 5,509,888 A | 4/1996 | Miller | | 5,782,774 A | 7/1998 | Shmulewitz |
| 5,509,891 A | 4/1996 | DeRidder | | 5,787,520 A | 8/1998 | Dunbar |
| 5,513,945 A | 5/1996 | Hartmann et al. | | 5,791,344 A | 8/1998 | Schulman et al. |
| 5,514,103 A | 5/1996 | Srisathapat et al. | | 5,792,094 A | 8/1998 | Stevens et al. |
| 5,518,504 A | 5/1996 | Polyak | | 5,792,179 A | 8/1998 | Sideris |
| 5,520,606 A | 5/1996 | Schoolman et al. | | 5,795,325 A | 8/1998 | Valley et al. |
| 5,523,740 A | 6/1996 | Burgmann et al. | | 5,796,827 A | 8/1998 | Coppersmith et al. |
| 5,534,018 A | 7/1996 | Wahlstrand et al. | | 5,797,403 A | 8/1998 | DiLorenzo |
| 5,535,752 A | 7/1996 | Halperin et al. | | 5,800,375 A | 9/1998 | Sweezer et al. |
| 5,538,005 A | 7/1996 | Harrison et al. | | 5,803,917 A | 9/1998 | Butterfield et al. |
| 5,540,731 A | 7/1996 | Testerman | | 5,807,265 A | 9/1998 | Itoigawa et al. |
| 5,541,857 A | 7/1996 | Walter et al. | | 5,807,336 A | 9/1998 | Russo et al. |
| 5,545,140 A | 8/1996 | Conero et al. | | 5,810,015 A | 9/1998 | Flaherty |
| 5,545,151 A | 8/1996 | O'Connor et al. | | 5,810,757 A | 9/1998 | Sweezer, Jr. et al. |
| 5,545,186 A | 8/1996 | Olson et al. | | 5,810,841 A | 9/1998 | McNeirney et al. |
| 5,545,214 A | 8/1996 | Stevens | | 5,814,016 A | 9/1998 | Valley et al. |
| 5,547,470 A | 8/1996 | Johnson et al. | | 5,817,093 A | 10/1998 | Williamson, IV et al. |
| 5,549,654 A | 8/1996 | Powell | | 5,833,603 A | 11/1998 | Kovacs et al. |
| 5,551,427 A | 9/1996 | Altman | | 5,836,300 A | 11/1998 | Mault |
| 5,551,439 A | 9/1996 | Hickey | | 5,836,886 A | 11/1998 | Itoigawa et al. |
| 5,554,185 A | 9/1996 | Block et al. | | 5,840,081 A | 11/1998 | Andersen et al. |
| 5,558,644 A | 9/1996 | Boyd et al. | | 5,849,225 A | 12/1998 | Ebina et al. |
| 5,564,434 A | 10/1996 | Halperin et al. | | 5,855,597 A | 1/1999 | Jayaraman et al. |
| 5,575,770 A | 11/1996 | Melsky et al. | | 5,855,601 A | 1/1999 | Bessler et al. |
| 5,584,803 A | 12/1996 | Stevens et al. | | 5,860,938 A | 1/1999 | Lafontaine et al. |
| 5,586,629 A | 12/1996 | Shoberg et al. | | 5,861,018 A | 1/1999 | Feierbach |
| 5,591,171 A | 1/1997 | Brown | | 5,863,366 A | 1/1999 | Snow |
| 5,592,939 A | 1/1997 | Martinelli | | 5,868,702 A | 2/1999 | Stevens et al. |
| 5,593,430 A | 1/1997 | Renger | | 5,873,837 A | 2/1999 | Lieber et al. |
| 5,594,665 A | 1/1997 | Walter et al. | | 5,875,953 A | 3/1999 | Shioya et al. |
| 5,596,986 A | 1/1997 | Goldfarb | | 5,879,499 A | 3/1999 | Corvi |
| 5,597,284 A | 1/1997 | Weltlich et al. | | 5,881,919 A | 3/1999 | Womac et al. |
| 5,610,083 A | 3/1997 | Chan et al. | | 5,885,238 A | 3/1999 | Stevens et al. |
| 5,611,768 A | 3/1997 | Tutrone, Jr. | | 5,886,093 A | 3/1999 | Davies et al. |
| 5,612,497 A | 3/1997 | Walter et al. | | 5,887,475 A | 3/1999 | Muldner |
| 5,615,671 A | 4/1997 | Schoonen et al. | | 5,899,927 A | 5/1999 | Ecker et al. |
| 5,619,991 A | 4/1997 | Sloane | | 5,916,179 A | 6/1999 | Sharrock |
| 5,622,869 A | 4/1997 | Lewis et al. | | 5,916,237 A | 6/1999 | Schu |
| 5,625,946 A | 5/1997 | Wildeson et al. | | 5,928,182 A | 7/1999 | Kraus et al. |
| 5,626,623 A | 5/1997 | Kieval et al. | | 5,935,078 A | 8/1999 | Feierbach |
| 5,626,630 A | 5/1997 | Markowitz et al. | | 5,935,083 A | 8/1999 | Williams |
| 5,630,836 A | 5/1997 | Prem et al. | | 5,938,669 A | 8/1999 | Klaiber et al. |
| 5,634,255 A | 6/1997 | Bishop et al. | | 5,951,487 A | 9/1999 | Brehmeier-Flick et al. |
| 5,637,083 A | 6/1997 | Bertrand et al. | | 5,957,861 A * | 9/1999 | Combs et al. ................. 600/547 |
| 5,643,207 A | 7/1997 | Rise | | 5,967,986 A | 10/1999 | Cimochowski et al. |
| 5,645,065 A | 7/1997 | Shapiro et al. | | 5,970,801 A | 10/1999 | Ciobanu et al. |
| 5,645,116 A | 7/1997 | McDonald | | 5,971,934 A | 10/1999 | Scherer et al. |
| 5,650,766 A | 7/1997 | Burgmann et al. | | 5,974,873 A | 11/1999 | Nelson et al. |
| 5,673,585 A | 10/1997 | Bishop et al. | | 5,978,985 A | 11/1999 | Thurman |
| 5,676,690 A | 10/1997 | Noren et al. | | 5,991,664 A | 11/1999 | Seligman |
| 5,681,285 A | 10/1997 | Ford et al. | | 5,993,395 A | 11/1999 | Shulze |
| 5,686,831 A | 11/1997 | Vandervalk et al. | | 5,993,398 A | 11/1999 | Alperin |
| 5,687,734 A | 11/1997 | Dempsey et al. | | 5,995,874 A | 11/1999 | Borza et al. |
| 5,693,076 A | 12/1997 | Kaemmerer | | 6,009,878 A | 1/2000 | Weijand et al. |
| 5,702,368 A | 12/1997 | Stevens et al. | | 6,010,482 A | 1/2000 | Kriesel et al. |
| 5,702,427 A | 12/1997 | Ecker et al. | | 6,015,386 A | 1/2000 | Kensey et al. |
| 5,702,431 A | 12/1997 | Wang et al. | | 6,015,387 A | 1/2000 | Schwartz et al. |
| 5,704,352 A | 1/1998 | Tremblay et al. | | 6,016,477 A | 1/2000 | Ehnebuske et al. |
| 5,711,302 A | 1/1998 | Lampropoulos et al. | | 6,019,729 A | 2/2000 | Itoigawa et al. |
| 5,715,786 A | 2/1998 | Seiberth et al. | | 6,024,704 A | 2/2000 | Meador et al. |
| 5,715,837 A | 2/1998 | Chen | | 6,030,413 A | 2/2000 | Lazarus |
| 5,716,342 A | 2/1998 | Dumbraveanu et al. | | 6,033,366 A | 3/2000 | Brockway et al. |
| 5,720,436 A | 2/1998 | Buschor et al. | | 6,035,461 A | 3/2000 | Nguyen |
| 5,721,382 A | 2/1998 | Kriesel et al. | | 6,053,873 A | 4/2000 | Govari et al. |
| 5,724,985 A | 3/1998 | Snell et al. | | 6,056,723 A | 5/2000 | Donlon |
| 5,730,101 A | 3/1998 | Aupperle et al. | | 6,058,330 A | 5/2000 | Borza et al. |
| 5,732,710 A | 3/1998 | Rabinovich et al. | | 6,059,757 A | 5/2000 | Macoviak et al. |
| 5,733,313 A | 3/1998 | Barreras, Sr. et al. | | 6,067,467 A * | 5/2000 | John ............................ 600/544 |
| 5,738,104 A * | 4/1998 | Lo et al. ........................ 600/521 | | 6,067,474 A | 5/2000 | Schulman et al. |
| 5,738,652 A | 4/1998 | Boyd et al. | | 6,067,991 A | 5/2000 | Forsell et al. |
| 5,742,233 A | 4/1998 | Hoffman et al. | | 6,071,267 A | 6/2000 | Zamierowski |
| 5,743,267 A | 4/1998 | Nikolic et al. | | 6,076,016 A | 6/2000 | Feierbach |
| 5,749,369 A | 5/1998 | Rabinovich et al. | | 6,083,174 A | 7/2000 | Brehmeier-Flick et al. |
| 5,749,909 A | 5/1998 | Schroeppel et al. | | 6,087,831 A | 7/2000 | Bornert et al. |
| 5,755,687 A | 5/1998 | Donlon | | 6,089,831 A | 7/2000 | Bruehmann et al. |
| 5,755,748 A | 5/1998 | Borza et al. | | 6,090,096 A | 7/2000 | St. Goar et al. |

| | | | | | | | |
|---|---|---|---|---|---|---|---|
| 6,102,678 | A | 8/2000 | Peclat et al. | 6,503,189 | B1 | 1/2003 | Forsell et al. |
| 6,102,856 | A | 8/2000 | Groff et al. | 6,503,208 | B1 | 1/2003 | Skovlund et al. |
| 6,102,922 | A | 8/2000 | Jakobsson et al. | 6,504,286 | B1 | 1/2003 | Porat et al. |
| 6,106,477 | A | 8/2000 | Miesel et al. | 6,505,062 | B1 | 1/2003 | Ritter et al. |
| 6,106,551 | A | 8/2000 | Crossett et al. | 6,511,490 | B2 * | 1/2003 | Robert .......................... 606/151 |
| 6,110,145 | A | 8/2000 | Macoviak | 6,516,212 | B1 | 2/2003 | Bladen et al. |
| 6,113,553 | A | 9/2000 | Chubbuck | 6,531,739 | B2 | 3/2003 | Cable et al. |
| 6,131,664 | A | 10/2000 | Sonnier | 6,533,719 | B2 | 3/2003 | Kuyava et al. |
| 6,135,945 | A | 10/2000 | Sultan | 6,533,733 | B1 | 3/2003 | Ericson et al. |
| 6,152,885 | A | 11/2000 | Taepke | 6,542,350 | B1 | 4/2003 | Rogers |
| 6,158,965 | A | 12/2000 | Butterfield et al. | 6,543,907 | B2 | 4/2003 | Nishiyama et al. |
| 6,159,156 | A | 12/2000 | Van Bockel et al. | 6,547,801 | B1 | 4/2003 | Dargent et al. |
| 6,162,180 | A | 12/2000 | Miesel et al. | 6,554,698 | B2 | 4/2003 | Kranzdorf et al. |
| 6,162,245 | A | 12/2000 | Jayaraman et al. | 6,558,321 | B1 | 5/2003 | Burd et al. |
| 6,168,614 | B1 | 1/2001 | Andersen et al. | 6,558,994 | B2 | 5/2003 | Cha et al. |
| 6,171,252 | B1 | 1/2001 | Roberts | 6,573,563 | B2 | 6/2003 | Lee et al. |
| 6,210,347 | B1 | 4/2001 | Forsell | 6,582,462 | B1 | 6/2003 | Andersen et al. |
| 6,216,028 | B1 | 4/2001 | Haynor et al. | 6,587,709 | B2 | 7/2003 | Solf et al. |
| 6,234,745 | B1 | 5/2001 | Pugh et al. | 6,589,189 | B2 | 7/2003 | Meyerson et al. |
| 6,240,316 | B1 | 5/2001 | Richmond et al. | 6,599,250 | B2 | 7/2003 | Webb et al. |
| 6,240,318 | B1 | 5/2001 | Phillips | 6,605,112 | B1 | 8/2003 | Moll et al. |
| 6,245,102 | B1 | 6/2001 | Jayaraman | 6,629,534 | B1 | 10/2003 | St. Goar et al. |
| 6,248,080 | B1 | 6/2001 | Miesel et al. | 6,640,137 | B2 | 10/2003 | MacDonald |
| 6,251,093 | B1 | 6/2001 | Valley et al. | 6,641,610 | B2 | 11/2003 | Wolf et al. |
| 6,262,728 | B1 | 7/2001 | Alexander | 6,645,143 | B2 | 11/2003 | VanTassel et al. |
| 6,269,819 | B1 | 8/2001 | Oz et al. | 6,654,629 | B2 | 11/2003 | Montegrande |
| 6,270,482 | B1 | 8/2001 | Rosoff et al. | 6,673,109 | B2 | 1/2004 | Cox |
| 6,277,078 | B1 | 8/2001 | Porat et al. | 6,678,561 | B2 | 1/2004 | Forsell et al. |
| 6,285,897 | B1 | 9/2001 | Kilcoyne et al. | 6,682,480 | B1 | 1/2004 | Habib et al. |
| 6,292,697 | B1 | 9/2001 | Roberts | 6,682,503 | B1 | 1/2004 | Fariss et al. |
| 6,305,381 | B1 | 10/2001 | Weijand et al. | 6,682,559 | B2 | 1/2004 | Myers et al. |
| 6,309,350 | B1 | 10/2001 | VanTassel et al. | 6,689,046 | B2 | 2/2004 | Sayet et al. |
| 6,315,769 | B1 | 11/2001 | Peer et al. | 6,690,963 | B2 | 2/2004 | Ben-Haim et al. |
| 6,319,208 | B1 | 11/2001 | Abita et al. | 6,695,866 | B1 | 2/2004 | Kuehn et al. |
| 6,328,699 | B1 | 12/2001 | Eigler et al. | 6,709,385 | B2 | 3/2004 | Forsell et al. |
| 6,338,735 | B1 | 1/2002 | Stevens | 6,718,200 | B2 | 4/2004 | Marmaropoulos et al. |
| 6,357,438 | B1 | 3/2002 | Hansen | 6,719,787 | B2 | 4/2004 | Cox |
| 6,360,122 | B1 | 3/2002 | Fischell et al. | 6,719,788 | B2 | 4/2004 | Cox |
| 6,360,822 | B1 | 3/2002 | Robertson et al. | 6,719,789 | B2 | 4/2004 | Cox |
| 6,366,799 | B1 | 4/2002 | Acker et al. | 6,731,976 | B2 | 5/2004 | Penn et al. |
| 6,366,817 | B1 | 4/2002 | Kung | 6,733,525 | B2 | 5/2004 | Yang et al. |
| 6,379,308 | B1 | 4/2002 | Brockway et al. | 6,736,846 | B2 | 5/2004 | Cox |
| 6,379,380 | B1 | 4/2002 | Satz | 6,752,813 | B2 | 6/2004 | Goldfarb et al. |
| 6,398,752 | B1 | 6/2002 | Sweezer, Jr. et al. | 6,757,557 | B1 | 6/2004 | Bladen et al. |
| 6,409,674 | B1 | 6/2002 | Brockway et al. | 6,779,851 | B2 | 8/2004 | Bouchiere |
| 6,416,291 | B1 | 7/2002 | Butterfield et al. | 6,796,942 | B1 | 9/2004 | Kreiner et al. |
| 6,423,031 | B1 | 7/2002 | Donlon | 6,822,343 | B2 | 11/2004 | Estevez |
| 6,430,444 | B1 | 8/2002 | Borza et al. | 6,851,628 | B1 | 2/2005 | Garrison et al. |
| 6,431,175 | B1 | 8/2002 | Penner et al. | 6,855,115 | B2 | 2/2005 | Fonseca et al. |
| 6,432,040 | B1 | 8/2002 | Meah | 6,889,772 | B2 | 5/2005 | Buytaert et al. |
| 6,443,887 | B1 | 9/2002 | Derus et al. | 6,890,300 | B2 | 5/2005 | Lloyd et al. |
| 6,443,893 | B1 | 9/2002 | Schnakenberg et al. | 6,896,651 | B2 | 5/2005 | Gross et al. |
| 6,450,173 | B1 | 9/2002 | Forsell et al. | 6,896,690 | B1 | 5/2005 | Lambrecht et al. |
| 6,450,543 | B1 | 9/2002 | Fukano et al. | 6,913,600 | B2 | 7/2005 | Valley et al. |
| 6,450,946 | B1 | 9/2002 | Forsell et al. | 6,915,165 | B2 | 7/2005 | Forsell et al. |
| 6,453,907 | B1 | 9/2002 | Forsell et al. | 6,926,246 | B2 | 8/2005 | Ginggen et al. |
| 6,454,698 | B1 | 9/2002 | Forsell et al. | 6,929,653 | B2 | 8/2005 | Strecter |
| 6,454,699 | B1 | 9/2002 | Forsell et al. | 6,932,792 | B1 | 8/2005 | St. Goar et al. |
| 6,454,700 | B1 | 9/2002 | Forsell et al. | 6,951,229 | B2 | 10/2005 | Garrison et al. |
| 6,454,701 | B1 | 9/2002 | Forsell et al. | 6,951,571 | B1 | 10/2005 | Srivastava |
| 6,460,543 | B1 | 10/2002 | Forsell | 6,953,429 | B2 | 10/2005 | Forsell et al. |
| 6,461,292 | B1 | 10/2002 | Forsell et al. | 6,961,619 | B2 | 11/2005 | Casey |
| 6,461,293 | B1 | 10/2002 | Forsell et al. | 6,970,742 | B2 | 11/2005 | Mann et al. |
| 6,463,329 | B1 | 10/2002 | Goedeke | 6,979,350 | B2 | 12/2005 | Moll et al. |
| 6,463,935 | B1 | 10/2002 | Forsell et al. | 6,985,078 | B2 | 1/2006 | Suzuki et al. |
| 6,464,628 | B1 | 10/2002 | Forsell et al. | 6,989,027 | B2 | 1/2006 | Allen et al. |
| 6,470,212 | B1 | 10/2002 | Weijand et al. | 7,011,095 | B2 | 3/2006 | Wolf et al. |
| 6,470,213 | B1 | 10/2002 | Alley | 7,011,624 | B2 | 3/2006 | Forsell et al. |
| 6,470,892 | B1 | 10/2002 | Forsell et al. | 7,017,583 | B2 | 3/2006 | Forsell et al. |
| 6,471,635 | B1 | 10/2002 | Forsell et al. | 7,018,406 | B2 | 3/2006 | Seguin et al. |
| 6,475,136 | B1 | 11/2002 | Forsell et al. | 7,021,402 | B2 | 4/2006 | Beato et al. |
| 6,475,170 | B1 | 11/2002 | Doron et al. | 7,025,727 | B2 | 4/2006 | Brockway et al. |
| 6,478,745 | B2 | 11/2002 | Nakagawa et al. | 7,044,920 | B2 | 5/2006 | Letort et al. |
| 6,481,292 | B1 | 11/2002 | Reich | 7,060,080 | B2 | 6/2006 | Bachmann et al. |
| 6,482,145 | B1 | 11/2002 | Forsell et al. | 7,081,683 | B2 | 7/2006 | Ariav et al. |
| 6,482,171 | B1 | 11/2002 | Corvi et al. | 7,109,933 | B2 | 9/2006 | Ito et al. |
| 6,482,177 | B1 | 11/2002 | Leinders et al. | 7,131,447 | B2 | 11/2006 | Sterman et al. |
| 6,485,462 | B1 | 11/2002 | Kriesel | 7,131,945 | B2 | 11/2006 | Fink et al. |
| 6,486,588 | B2 | 11/2002 | Doron et al. | 7,134,580 | B2 | 11/2006 | Garrison et al. |

| Patent/Pub No. | Date | Name |
|---|---|---|
| 7,143,462 B2 | 12/2006 | Hohlbein |
| 7,144,400 B2 | 12/2006 | Byrum et al. |
| 7,147,640 B2 | 12/2006 | Huebner et al. |
| 7,153,262 B2 | 12/2006 | Stivoric et al. |
| 7,187,978 B2 | 3/2007 | Malek et al. |
| 7,225,032 B2 | 5/2007 | Schmeling et al. |
| 7,257,438 B2 | 8/2007 | Kinast |
| 7,285,090 B2 | 10/2007 | Stivoric et al. |
| 7,351,240 B2 | 4/2008 | Hassler, Jr. et al. |
| 7,374,565 B2 | 5/2008 | Hassler, Jr. et al. |
| 7,390,294 B2 | 6/2008 | Hassler, Jr. |
| 7,442,165 B2 | 10/2008 | Forsell |
| 7,481,763 B2 | 1/2009 | Hassler, Jr. et al. |
| 7,585,280 B2 | 9/2009 | Wilson et al. |
| 7,601,162 B2 | 10/2009 | Hassler, Jr. et al. |
| 7,616,991 B2 | 11/2009 | Mann et al. |
| 7,658,196 B2 | 2/2010 | Ferreri et al. |
| 7,699,770 B2 | 4/2010 | Hassler, Jr. et al. |
| 7,775,215 B2 | 8/2010 | Hassler, Jr. et al. |
| 7,775,966 B2 | 8/2010 | Dlugos et al. |
| 2001/0011543 A1 | 8/2001 | Forsell |
| 2001/0041823 A1 | 11/2001 | Snyder et al. |
| 2002/0049394 A1 | 4/2002 | Roy et al. |
| 2002/0120200 A1 | 8/2002 | Brockway et al. |
| 2002/0123671 A1* | 9/2002 | Haaland ................ 600/300 |
| 2002/0138009 A1 | 9/2002 | Brockway et al. |
| 2002/0138512 A1 | 9/2002 | Buresh et al. |
| 2002/0177782 A1 | 11/2002 | Penner |
| 2003/0009201 A1 | 1/2003 | Forsell |
| 2003/0023134 A1 | 1/2003 | Tracey |
| 2003/0030893 A1 | 2/2003 | Cornelius et al. |
| 2003/0032857 A1 | 2/2003 | Forsell |
| 2003/0037591 A1 | 2/2003 | Ashton et al. |
| 2003/0045775 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0093117 A1 | 5/2003 | Saadat |
| 2003/0100929 A1 | 5/2003 | Forsell |
| 2003/0105385 A1 | 6/2003 | Forsell |
| 2003/0109771 A1 | 6/2003 | Forsell |
| 2003/0114729 A1 | 6/2003 | Forsell |
| 2003/0120150 A1 | 6/2003 | Govari |
| 2003/0125605 A1 | 7/2003 | Forsell |
| 2003/0125768 A1 | 7/2003 | Peter |
| 2003/0135089 A1 | 7/2003 | Forsell |
| 2003/0135090 A1 | 7/2003 | Forsell |
| 2003/0136417 A1 | 7/2003 | Fonseca et al. |
| 2003/0144648 A1 | 7/2003 | Forsell |
| 2003/0144711 A1 | 7/2003 | Pless et al. |
| 2003/0163079 A1 | 8/2003 | Burnett |
| 2003/0216666 A1 | 11/2003 | Ericson et al. |
| 2003/0225371 A1 | 12/2003 | Hadzic et al. |
| 2004/0014456 A1 | 1/2004 | Vnnen |
| 2004/0016874 A1 | 1/2004 | Rao et al. |
| 2004/0034289 A1* | 2/2004 | Teller et al. ................ 600/300 |
| 2004/0039256 A1 | 2/2004 | Kawatahara et al. |
| 2004/0054295 A1 | 3/2004 | Ramseth |
| 2004/0054351 A1 | 3/2004 | Deniega et al. |
| 2004/0054352 A1 | 3/2004 | Adams et al. |
| 2004/0055610 A1 | 3/2004 | Forsell |
| 2004/0064030 A1 | 4/2004 | Forsell |
| 2004/0082867 A1 | 4/2004 | Esch et al. |
| 2004/0082904 A1 | 4/2004 | Houde et al. |
| 2004/0098113 A1 | 5/2004 | Forsell et al. |
| 2004/0106874 A1 | 6/2004 | Eigler et al. |
| 2004/0113790 A1 | 6/2004 | Hamel et al. |
| 2004/0133092 A1 | 7/2004 | Kain |
| 2004/0143212 A1 | 7/2004 | Trombley et al. |
| 2004/0147969 A1 | 7/2004 | Mann et al. |
| 2004/0148969 A1 | 8/2004 | Nikander |
| 2004/0172087 A1 | 9/2004 | Forsell |
| 2004/0186396 A1 | 9/2004 | Roy et al. |
| 2004/0193045 A1 | 9/2004 | Scarborough et al. |
| 2004/0215159 A1 | 10/2004 | Forsell |
| 2004/0215492 A1 | 10/2004 | Choi |
| 2004/0225203 A1 | 11/2004 | Jemison et al. |
| 2004/0243148 A1 | 12/2004 | Wasielewski |
| 2004/0249421 A1 | 12/2004 | Harel et al. |
| 2004/0254537 A1 | 12/2004 | Conlon et al. |
| 2004/0260319 A1 | 12/2004 | Egle |
| 2004/0267377 A1 | 12/2004 | Egle |
| 2005/0004516 A1 | 1/2005 | Vanney |
| 2005/0015014 A1 | 1/2005 | Fonseca et al. |
| 2005/0025979 A1 | 2/2005 | Sandt et al. |
| 2005/0027175 A1 | 2/2005 | Yang |
| 2005/0027998 A1 | 2/2005 | Teglia et al. |
| 2005/0038328 A1 | 2/2005 | Stoehrer et al. |
| 2005/0061079 A1 | 3/2005 | Schulman |
| 2005/0065450 A1 | 3/2005 | Stuebe et al. |
| 2005/0070778 A1 | 3/2005 | Lackey et al. |
| 2005/0102026 A1 | 5/2005 | Turner et al. |
| 2005/0107836 A1 | 5/2005 | Noren |
| 2005/0143668 A1* | 6/2005 | Lu et al. ................ 600/509 |
| 2005/0143765 A1 | 6/2005 | Bachmann et al. |
| 2005/0143766 A1 | 6/2005 | Bachmann et al. |
| 2005/0159789 A1 | 7/2005 | Brockway et al. |
| 2005/0165317 A1 | 7/2005 | Turner et al. |
| 2005/0182330 A1 | 8/2005 | Brockway et al. |
| 2005/0187482 A1 | 8/2005 | O'Brien et al. |
| 2005/0187488 A1 | 8/2005 | Wolf |
| 2005/0192629 A1 | 9/2005 | Saadat et al. |
| 2005/0192642 A1 | 9/2005 | Forsell |
| 2005/0203360 A1 | 9/2005 | Brauker et al. |
| 2005/0240144 A1 | 10/2005 | Wassemann et al. |
| 2005/0240155 A1 | 10/2005 | Conlon |
| 2005/0240156 A1 | 10/2005 | Conlon |
| 2005/0250979 A1 | 11/2005 | Coe |
| 2005/0267406 A1 | 12/2005 | Hassler |
| 2005/0267500 A1 | 12/2005 | Hassler et al. |
| 2005/0272968 A1 | 12/2005 | Byrum et al. |
| 2005/0277960 A1 | 12/2005 | Hassler et al. |
| 2005/0277974 A1 | 12/2005 | Hassler et al. |
| 2005/0288604 A1 | 12/2005 | Eigler et al. |
| 2005/0288720 A1 | 12/2005 | Ross et al. |
| 2005/0288721 A1 | 12/2005 | Girouard et al. |
| 2005/0288739 A1 | 12/2005 | Hassler et al. |
| 2005/0288740 A1 | 12/2005 | Hassler et al. |
| 2005/0288741 A1 | 12/2005 | Hassler et al. |
| 2005/0288742 A1 | 12/2005 | Giordano et al. |
| 2006/0002035 A1 | 1/2006 | Gao et al. |
| 2006/0010090 A1 | 1/2006 | Brockway et al. |
| 2006/0020224 A1 | 1/2006 | Geiger |
| 2006/0020305 A1 | 1/2006 | Desai et al. |
| 2006/0035446 A1 | 2/2006 | Chang et al. |
| 2006/0047205 A1 | 3/2006 | Ludomirsky et al. |
| 2006/0049714 A1 | 3/2006 | Liu et al. |
| 2006/0058627 A1 | 3/2006 | Flaherty et al. |
| 2006/0064134 A1 | 3/2006 | Mazar et al. |
| 2006/0085051 A1 | 4/2006 | Fritsch |
| 2006/0089571 A1 | 4/2006 | Gertner |
| 2006/0089619 A1 | 4/2006 | Ginggen |
| 2006/0094966 A1 | 5/2006 | Brockway et al. |
| 2006/0100531 A1 | 5/2006 | Moser |
| 2006/0113187 A1 | 6/2006 | Deng et al. |
| 2006/0118793 A1 | 6/2006 | Yang et al. |
| 2006/0122285 A1 | 6/2006 | Falloon et al. |
| 2006/0122863 A1 | 6/2006 | Gottesman et al. |
| 2006/0142635 A1 | 6/2006 | Forsell |
| 2006/0149124 A1 | 7/2006 | Forsell |
| 2006/0149161 A1 | 7/2006 | Wilson et al. |
| 2006/0149324 A1 | 7/2006 | Mann et al. |
| 2006/0149327 A1 | 7/2006 | Hedberg et al. |
| 2006/0157701 A1 | 7/2006 | Bauer et al. |
| 2006/0161186 A1 | 7/2006 | Hassler et al. |
| 2006/0178617 A1 | 8/2006 | Adams et al. |
| 2006/0178695 A1 | 8/2006 | Decant et al. |
| 2006/0183967 A1 | 8/2006 | Lechner |
| 2006/0184206 A1 | 8/2006 | Baker et al. |
| 2006/0189887 A1 | 8/2006 | Hassler et al. |
| 2006/0189888 A1 | 8/2006 | Hassler et al. |
| 2006/0189889 A1 | 8/2006 | Gertner |
| 2006/0199997 A1 | 9/2006 | Hassler et al. |
| 2006/0211912 A1 | 9/2006 | Dlugos et al. |
| 2006/0211913 A1 | 9/2006 | Dlugos et al. |
| 2006/0211914 A1 | 9/2006 | Hassler et al. |
| 2006/0217668 A1 | 9/2006 | Schulze et al. |
| 2006/0217673 A1 | 9/2006 | Schulze et al. |

| | | | | | | |
|---|---|---|---|---|---|---|
| 2006/0235310 | A1 | 10/2006 | O'Brien et al. | EP | 0888079 A1 | 1/1999 |
| 2006/0235439 | A1 | 10/2006 | Molitor et al. | EP | 914059 | 5/1999 |
| 2006/0235448 | A1 | 10/2006 | Roslin et al. | EP | 0914059 A1 | 5/1999 |
| 2006/0244914 | A1 | 11/2006 | Cech et al. | EP | 0941712 A1 | 9/1999 |
| 2006/0247682 | A1 | 11/2006 | Gerber et al. | EP | 981293 | 3/2000 |
| 2006/0247719 | A1 | 11/2006 | Maschino et al. | EP | 0981293 A1 | 3/2000 |
| 2006/0247721 | A1 | 11/2006 | Maschino et al. | EP | 997680 | 5/2000 |
| 2006/0247722 | A1 | 11/2006 | Maschino et al. | EP | 0997680 A2 | 5/2000 |
| 2006/0247723 | A1 | 11/2006 | Gerber et al. | EP | 1003021 | 5/2000 |
| 2006/0247724 | A1 | 11/2006 | Gerber et al. | EP | 1022983 | 8/2000 |
| 2006/0247725 | A1 | 11/2006 | Gerber et al. | EP | 1050265 | 11/2000 |
| 2006/0252982 | A1 | 11/2006 | Hassler et al. | EP | 1115329 | 7/2001 |
| 2006/0293625 | A1 | 12/2006 | Hunt et al. | EP | 1119314 | 8/2001 |
| 2006/0293626 | A1 | 12/2006 | Byrum et al. | EP | 1128871 | 9/2001 |
| 2006/0293627 | A1 | 12/2006 | Byrum et al. | EP | 1202674 | 5/2002 |
| 2007/0010790 | A1 | 1/2007 | Byrum et al. | EP | 1213991 | 6/2002 |
| 2007/0027356 | A1 | 2/2007 | Ortiz | EP | 1253877 | 11/2002 |
| 2007/0027493 | A1 | 2/2007 | Ben-Haim et al. | EP | 1253879 | 11/2002 |
| 2007/0067206 | A1 | 3/2007 | Haggerty et al. | EP | 1253880 | 11/2002 |
| 2007/0070906 | A1 | 3/2007 | Thakur | EP | 1253881 | 11/2002 |
| 2007/0072452 | A1 | 3/2007 | Inagaki et al. | EP | 1253883 | 11/2002 |
| 2007/0081304 | A1 | 4/2007 | Takeguchi | EP | 1253888 | 11/2002 |
| 2007/0156013 | A1 | 7/2007 | Birk | EP | 1255511 | 11/2002 |
| 2007/0161958 | A1 | 7/2007 | Glenn | EP | 1255513 | 11/2002 |
| 2007/0167672 | A1 | 7/2007 | Dlugos et al. | EP | 1255514 | 11/2002 |
| 2007/0173881 | A1 | 7/2007 | Birk et al. | EP | 1263355 | 12/2002 |
| 2007/0179583 | A1 | 8/2007 | Goetzinger et al. | EP | 1263357 | 12/2002 |
| 2007/0208313 | A1 | 9/2007 | Conlon et al. | EP | 1284691 | 2/2003 |
| 2007/0225781 | A1 | 9/2007 | Saadat et al. | EP | 1374758 | 1/2004 |
| 2007/0235083 | A1 | 10/2007 | Dlugos | EP | 1442715 A2 | 8/2004 |
| 2008/0009680 | A1 | 1/2008 | Hassler | EP | 1488735 | 12/2004 |
| 2008/0015406 | A1 | 1/2008 | Dlugos et al. | EP | 1500411 | 1/2005 |
| 2008/0172072 | A1 | 7/2008 | Pool et al. | EP | 1510306 | 3/2005 |
| 2008/0221598 | A1 | 9/2008 | Dlugos et al. | EP | 1518514 | 3/2005 |
| 2008/0249806 | A1 | 10/2008 | Dlugos et al. | EP | 1545303 | 6/2005 |
| 2008/0250340 | A1 | 10/2008 | Dlugos et al. | EP | 1547549 | 6/2005 |
| 2008/0250341 | A1 | 10/2008 | Dlugos et al. | EP | 1563814 | 8/2005 |
| 2009/0005703 | A1 | 1/2009 | Fasciano | EP | 1568338 | 8/2005 |
| 2010/0179488 | A1 | 7/2010 | Spiegel et al. | EP | 1582175 | 10/2005 |
| | | | | EP | 1582176 | 10/2005 |
| FOREIGN PATENT DOCUMENTS | | | | EP | 1584303 | 10/2005 |
| CA | 1059035 | 7/1979 | | EP | 1586283 | 10/2005 |
| CA | 1119469 | 3/1982 | | EP | 1591086 | 11/2005 |
| CA | 1275135 | 10/1990 | | EP | 1593359 | 11/2005 |
| CA | 1277885 | 12/1990 | | EP | 1598030 | 11/2005 |
| CA | 1317482 | 5/1993 | | EP | 1600120 A1 | 11/2005 |
| CA | 2082015 | 5/1993 | | EP | 1609440 | 12/2005 |
| CA | 1327191 | 2/1994 | | EP | 1649884 A1 | 4/2006 |
| CA | 2119101 | 9/1994 | | EP | 1674033 | 6/2006 |
| CA | 2305998 | 4/1999 | | EP | 1676527 A1 | 7/2006 |
| CN | 1059035 | 2/1992 | | EP | 1704833 A2 | 9/2006 |
| CN | 1119469 | 3/1996 | | EP | 1736123 | 12/2006 |
| CN | 1241003 | 1/2000 | | EP | 1799119 | 6/2007 |
| DE | 9416395 U1 | 12/1994 | | EP | 1815881 A1 | 8/2007 |
| DE | 10156494 A1 | 6/2003 | | EP | 1832252 A2 | 9/2007 |
| EA | 4581 | 6/2004 | | EP | 1832253 A1 | 9/2007 |
| EP | 056730 A1 | 7/1982 | | EP | 1967168 A2 | 9/2008 |
| EP | 125387 B1 | 11/1984 | | FR | 2730158 | 8/1996 |
| EP | 417171 | 3/1991 | | GB | 1486822 A | 9/1977 |
| EP | 508141 | 10/1992 | | GB | 1486833 A | 9/1977 |
| EP | 0508141 A1 | 10/1992 | | GB | 2355937 | 5/2001 |
| EP | 568730 | 11/1993 | | JP | 2006175191 A | 7/2006 |
| EP | 0568730 A1 | 11/1993 | | WO | WO-8911244 | 11/1989 |
| EP | 605302 | 7/1994 | | WO | WO-8911701 | 11/1989 |
| EP | 0605302 A2 | 7/1994 | | WO | WO-9004368 | 5/1990 |
| EP | 0654232 A1 | 5/1995 | | WO | WO-9511057 | 4/1995 |
| EP | 660482 | 6/1995 | | WO | WO-9715351 | 5/1997 |
| EP | 0660482 A1 | 6/1995 | | WO | WO-9733513 | 9/1997 |
| EP | 714017 | 5/1996 | | WO | WO-9833554 | 8/1998 |
| EP | 0714017 A1 | 5/1996 | | WO | WO-9835610 | 8/1998 |
| EP | 769340 | 4/1997 | | WO | WO-9901063 | 1/1999 |
| EP | 0769340 A1 | 4/1997 | | WO | WO-9918850 | 4/1999 |
| EP | 846475 | 6/1998 | | WO | WO-0004945 | 2/2000 |
| EP | 0846475 A2 | 6/1998 | | WO | WO-0009047 A1 | 2/2000 |
| EP | 848780 | 6/1998 | | WO | WO-0033738 | 6/2000 |
| EP | 0848780 A1 | 6/1998 | | WO | WO-0072899 | 12/2000 |
| EP | 876808 | 11/1998 | | WO | WO-0104487 | 1/2001 |
| EP | 0876808 A1 | 11/1998 | | WO | WO-0108597 A1 | 2/2001 |
| EP | 888079 | 1/1999 | | WO | WO-0112075 | 2/2001 |

| | | |
|---|---|---|
| WO | WO-0112076 | 2/2001 |
| WO | WO-0112077 | 2/2001 |
| WO | WO-0112078 | 2/2001 |
| WO | WO-0121066 | 3/2001 |
| WO | WO-0136014 | 5/2001 |
| WO | WO-0145485 | 6/2001 |
| WO | WO-0145486 | 6/2001 |
| WO | WO-0147431 | 7/2001 |
| WO | WO-0147432 | 7/2001 |
| WO | WO-0147433 | 7/2001 |
| WO | WO-0147434 | 7/2001 |
| WO | WO-0147435 | 7/2001 |
| WO | WO-0147440 | 7/2001 |
| WO | WO-0147575 | 7/2001 |
| WO | WO-0148451 | 7/2001 |
| WO | WO-0149245 | 7/2001 |
| WO | WO-0150832 | 7/2001 |
| WO | WO-0150833 | 7/2001 |
| WO | WO-0151108 A1 | 7/2001 |
| WO | WO-0154626 | 8/2001 |
| WO | WO-0158388 | 8/2001 |
| WO | WO-0158390 | 8/2001 |
| WO | WO-0158391 | 8/2001 |
| WO | WO-0158393 | 8/2001 |
| WO | WO-0160453 | 8/2001 |
| WO | WO-0181890 | 11/2001 |
| WO | WO-0200118 | 1/2002 |
| WO | WO-0215769 | 2/2002 |
| WO | WO-0226161 | 4/2002 |
| WO | WO-02053228 | 7/2002 |
| WO | WO-02053228 A1 | 7/2002 |
| WO | WO-02055126 | 7/2002 |
| WO | WO-02055126 A2 | 7/2002 |
| WO | WO-02058551 | 8/2002 |
| WO | WO-02058551 A2 | 8/2002 |
| WO | WO-02065894 | 8/2002 |
| WO | WO-02065894 A2 | 8/2002 |
| WO | WO-02076289 | 10/2002 |
| WO | WO-02076289 A2 | 10/2002 |
| WO | WO-02082984 | 10/2002 |
| WO | WO-02089655 | 11/2002 |
| WO | WO-02089655 A2 | 11/2002 |
| WO | WO-02090894 | 11/2002 |
| WO | WO-02090894 A1 | 11/2002 |
| WO | WO-02100481 | 12/2002 |
| WO | WO-03002192 | 1/2003 |
| WO | WO-03002193 | 1/2003 |
| WO | WO-03020182 | 3/2003 |
| WO | WO-03020182 A1 | 3/2003 |
| WO | WO-03043534 A2 | 5/2003 |
| WO | WO-03061467 | 7/2003 |
| WO | WO-03061504 | 7/2003 |
| WO | WO-03096889 | 11/2003 |
| WO | WO-03096889 A1 | 11/2003 |
| WO | WO-03105732 A1 | 12/2003 |
| WO | WO-2004014245 A1 | 2/2004 |
| WO | WO-2004014456 | 2/2004 |
| WO | WO-2004019773 | 3/2004 |
| WO | WO-2004030541 A1 | 4/2004 |
| WO | WO-2004058101 | 7/2004 |
| WO | WO-2004066879 | 8/2004 |
| WO | WO-2004110263 | 12/2004 |
| WO | WO-2005000206 | 1/2005 |
| WO | WO-2005007075 | 1/2005 |
| WO | WO 2005007232 A2 * | 1/2005 |
| WO | WO-2005027998 A2 | 3/2005 |
| WO | WO-2005084544 A1 | 9/2005 |
| WO | WO-2005107583 | 11/2005 |
| WO | WO-2006001851 | 1/2006 |
| WO | WO-2006018927 A1 | 2/2006 |
| WO | WO-2006035446 | 4/2006 |
| WO | WO-2006108203 A2 | 10/2006 |
| WO | WO-2006113187 | 10/2006 |
| WO | WO-2006118790 A2 | 11/2006 |
| WO | WO-2006118793 A2 | 11/2006 |
| WO | WO-2006122285 | 11/2006 |
| WO | WO-2007067206 | 6/2007 |
| WO | WO-2007070906 | 6/2007 |
| WO | WO-2007072452 | 6/2007 |
| WO | WO-2007081304 | 7/2007 |
| WO | WO-2007104356 | 9/2007 |
| WO | WO-2007140430 A2 | 12/2007 |
| WO | WO-2008088949 A1 | 7/2008 |

OTHER PUBLICATIONS

"Rad Hard Aerospace Components Products", Honeywell product and service information from website http://www.honeywell.com/sites/portal?smap=aerospace&page=Radiation-Hardened-Electronics3&theme=T6&catID=C815147E4-8786-29FE-49EB-C21C8790AA99&id=H0166BA51-5344-E57E-5C37-C6333EA43F61&sel=1; 1 page.

"Radiation Hardened Electronics and Radiation Technology", Honeywell product and service information from website http://www.honeywell.com/sites/portal?smap=aerospace&page=Radiation-Hardened-Electronics&theme=T4; 2 pages.

Kirchner, G., "Honeywell and Synopsys: Concept-to-Parts Solutions for Next Generation Rad-Hard ASICs", in online magazine Compiler, http://www.synopsys.com/news/pubs/compiler/artlead_redasic-apr05.html, Apr. 2005, 5 pages.

P.A. Neukomm and H. Kundig, "Passive Wireless Actuator Control and Sensor Signal Transmission," Sensors and Actuators, A21-A23 (1990) 258-262.

U.S. Appl. No. 12/039,002, filed Feb. 28, 2008, Dlugos, Jr. et al.

U.S. Appl. No. 12/039,024, filed Feb. 28, 2008, Dlugos, Jr. et al.

U.S. Appl. No. 12/039,031, filed Feb. 28, 2008, Dlugos, Jr. et al.

European Search Report dated Sep. 25, 2009 for European Application No. EP09250590, 9 pages.

Author Unknown—Gastric Band "On Demand"—Translation by Corporate Translations, Inc.

Author Unknown—"Report—Wireless in Healthcare"—The FocalPoint Group—2004.

Codman Brochure "ICP Express" © *CODMAN & Shurtleff, inc.*, 2001.

EPO Search Report dated Jul. 12, 2007, for EP Application No. 07250931.8.

EPO Search Report dated Jul. 23, 2007, for EP Application No. 07250932.6.

User's Manual HD2114.0-HD2134.0, HD2164.0-HD2114B.0, HD2114, 2-HD2134.2, HD2164.2-HD2114B; Rev. 1.0, Oct. 1, 2004, Delta OHM, Via G. Marconi, 5-35020 Caselle Di Selvazzano(PD)—Italy, XP002376759, pp. 2-6.

European Search Report dated Dec. 9, 2008 for Application No. 06250968.

European Search Report dated Sep. 25, 2009 for Application No. 09250600.

European Search Report re: 06250968 dated May 2, 2008.

European Examination Report dated Dec. 9, 2008 for Application No. EP 06250968.

European Examination Report dated Jul. 23, 2007 for Application No. 06253286.

European Search Report dated Aug. 13, 2009 for Application No. 08251093.

European Search Report dated Mar. 5, 2006 for Application No. 06250156.4.

European Search Report dated Feb. 10, 2009 for Application No. 07250915.

European Search Report, Application No. 08253986.7, Issued Mar. 30, 2009, 5 pages.

European Search Report dated Jul. 10, 2009 for Application No. 09250590.

European Search Report, Application No. 09250497.6, Issued May 13, 2009, 11 pages.

Examination Report dated Feb. 20, 2007 for Application No. 06250156.

Extended EPO Search Report dated Apr. 22, 2009 for Application No. 08250782.

European Search Report dated Jun. 19, 2009 for Application No. 09250581.

Partial EPO Search Report dated Jan. 13, 2009 for Application No. 08250782.

European Search Report dated May 2, 2008 for Application No. EP 06250968.

European Search Report date Oct. 30, 2006 for Application No. 06253276.

J. Ekstedt: "CSFS hydrodynamic studies in ma, 1. Method of constant pressure CSF infusion", Journal of Neurology, Neurosurgery and Psychiatry; vol. 40, 1977, pp. 105-119.

Shapiro, K. et al.: "Characterization of Clinical CSF Dynamics and Neural Axis Compliance Using the Pressure-Volume Index: I. the Normal Pressure-Volume Index", Annals of Neurology, vol. 7, No. 6, Jun. 1980; pp. 0364-5134.

Lechner, Wolfgang—Controllable Gastirc Band—At Patent Specification—R43301.

Lechner, Wolfgang—Controllable Gastric Band—At Patent Specification—R43431.

Lechner, Wolfgang—Controllable Gastric Band—PCT Request and Application—Austrian Patent Office.

Lechner, Wolfgang, et al.—"In Vivo Band Manometry: a New Access to Band Adjustment"—*Obesity Surgery*, 15, 1432-1436—2005.

International Search Report and Written Opinion dated Sep. 22, 2008 for Application No. PCT/US2008/053394.

Greenway et al., "Comparison of the Effects of the Heptatic Nerve Stimulation on Arterial Flow, Distriubtion of Arterial Portal Flows and Blood Content in the Livers of Anaesthetized Cats and Dogs," J. Physiol. 1972, 227, 487-501.

Suga et al., "Instantaneous Pressure-Volume Relationships and Their Ratio in the Excised, Supported Canine Left Ventricle," Circ. Res. 1974, 35, 117-126.

* cited by examiner

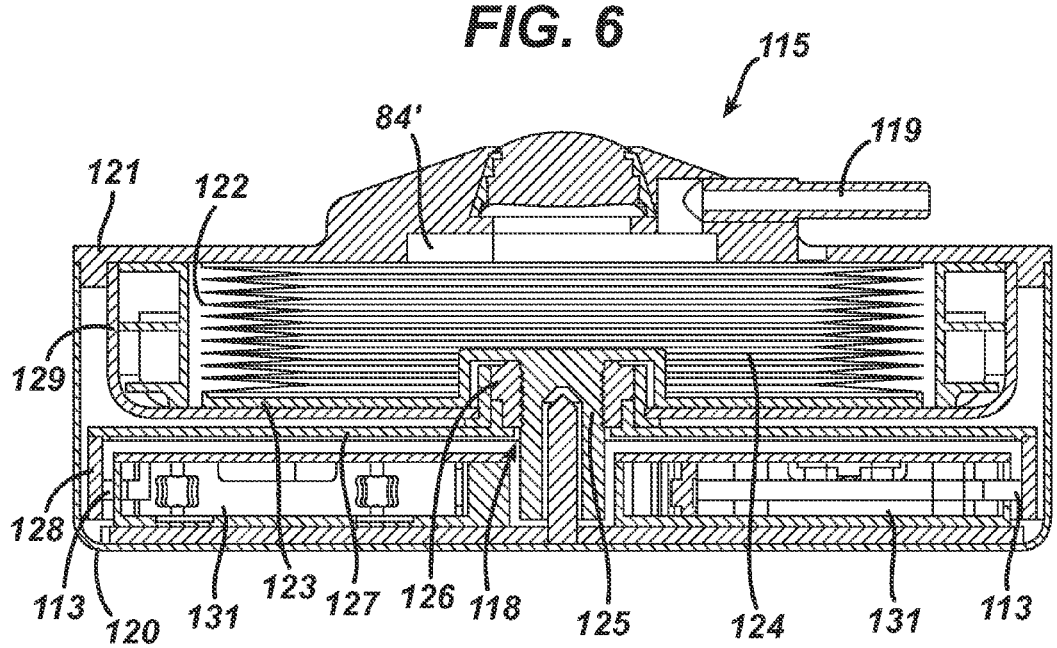
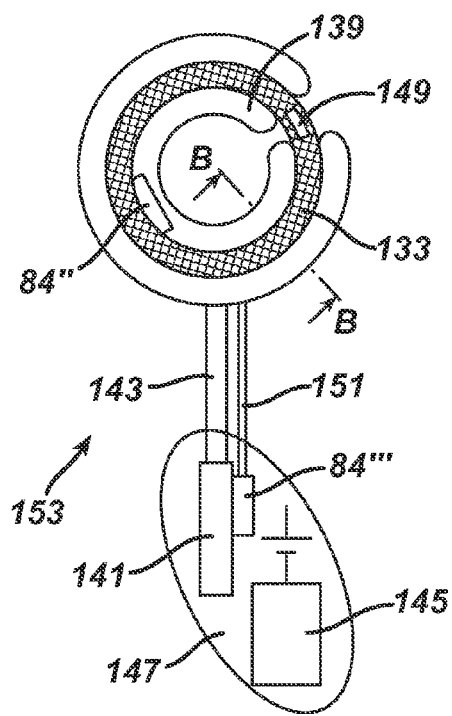
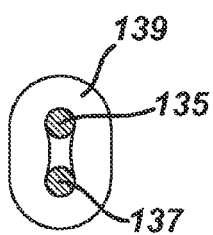

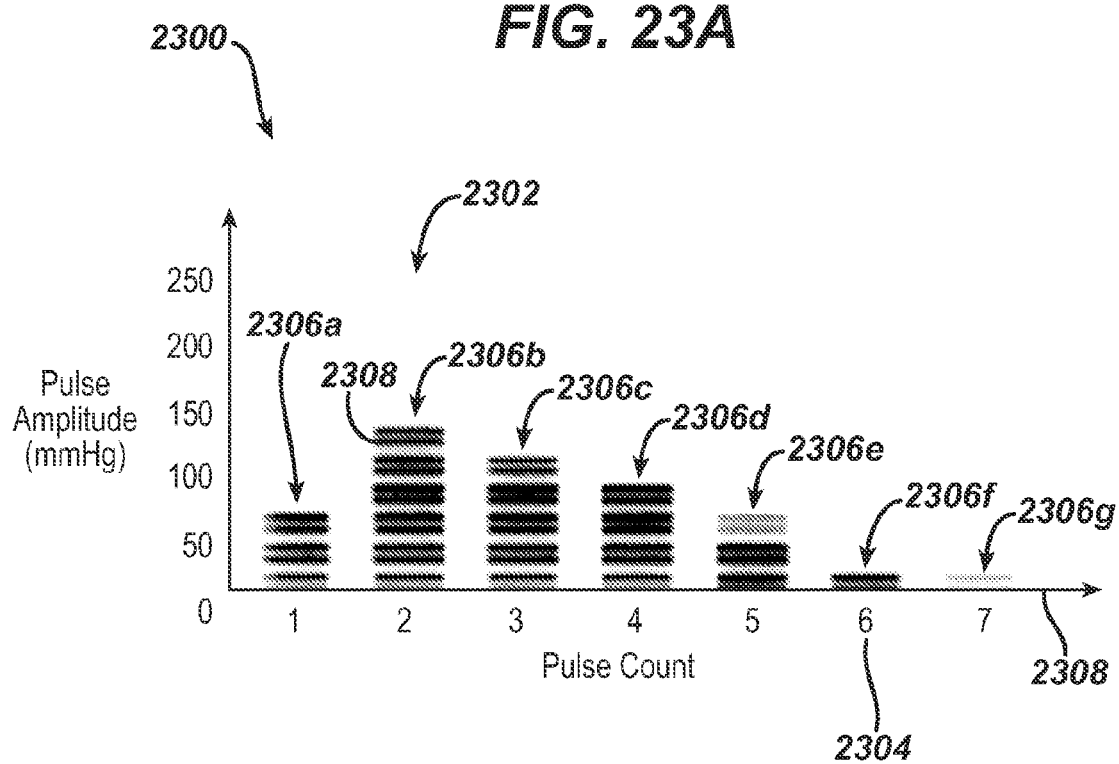

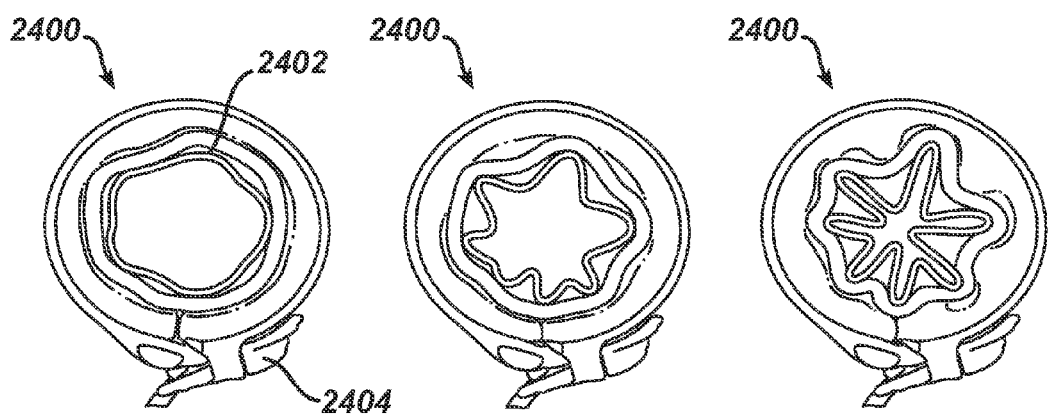
FIG. 24A  FIG. 24B  FIG. 24C
FIG. 25
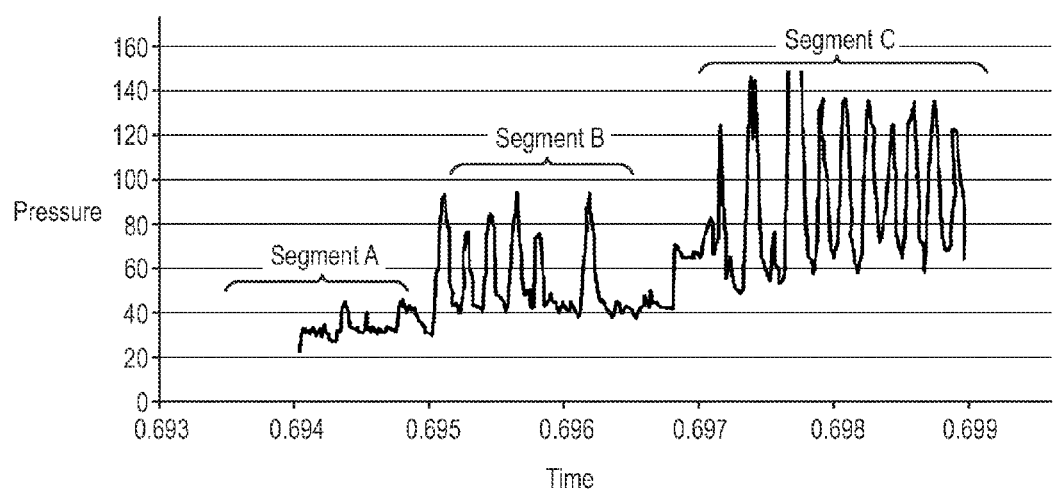

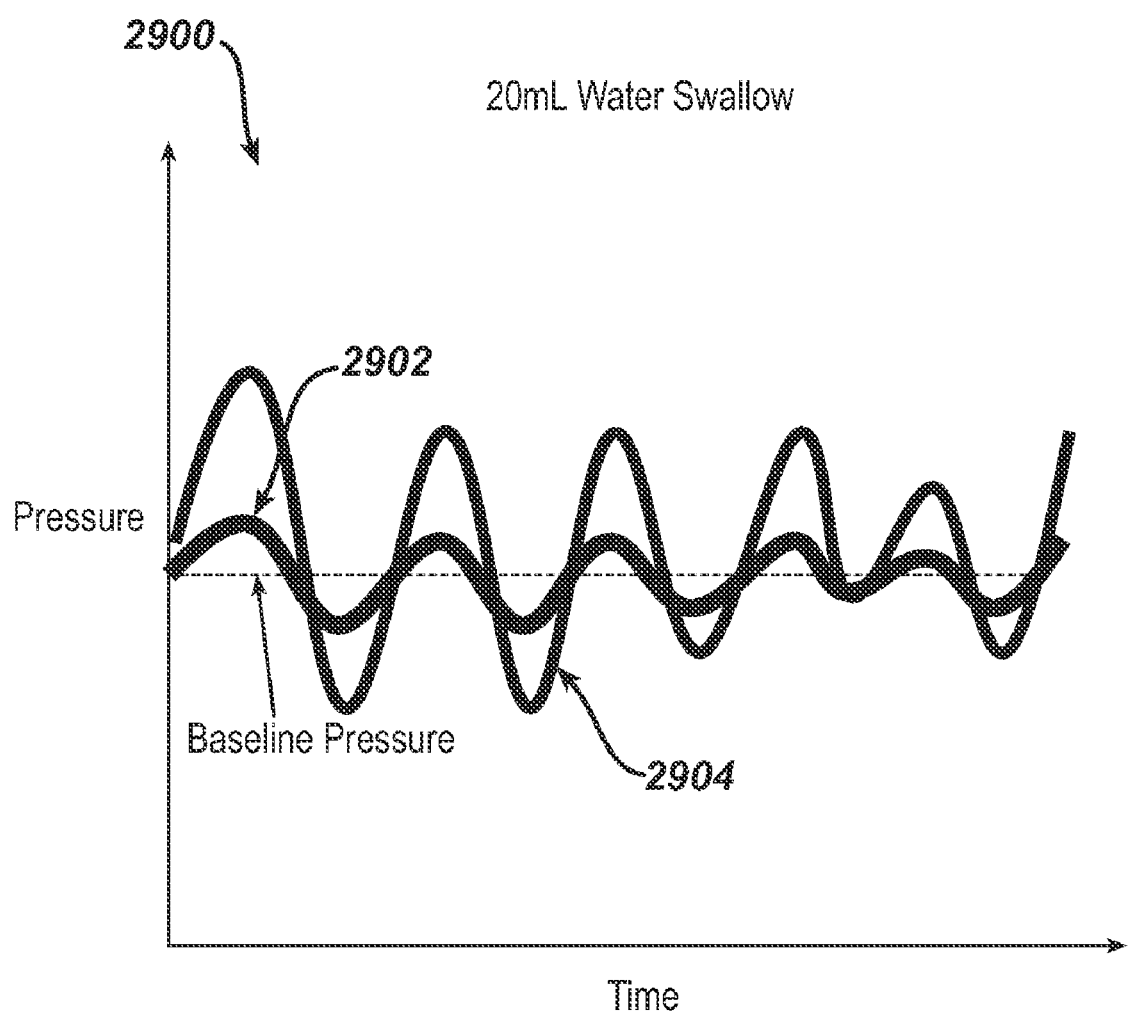

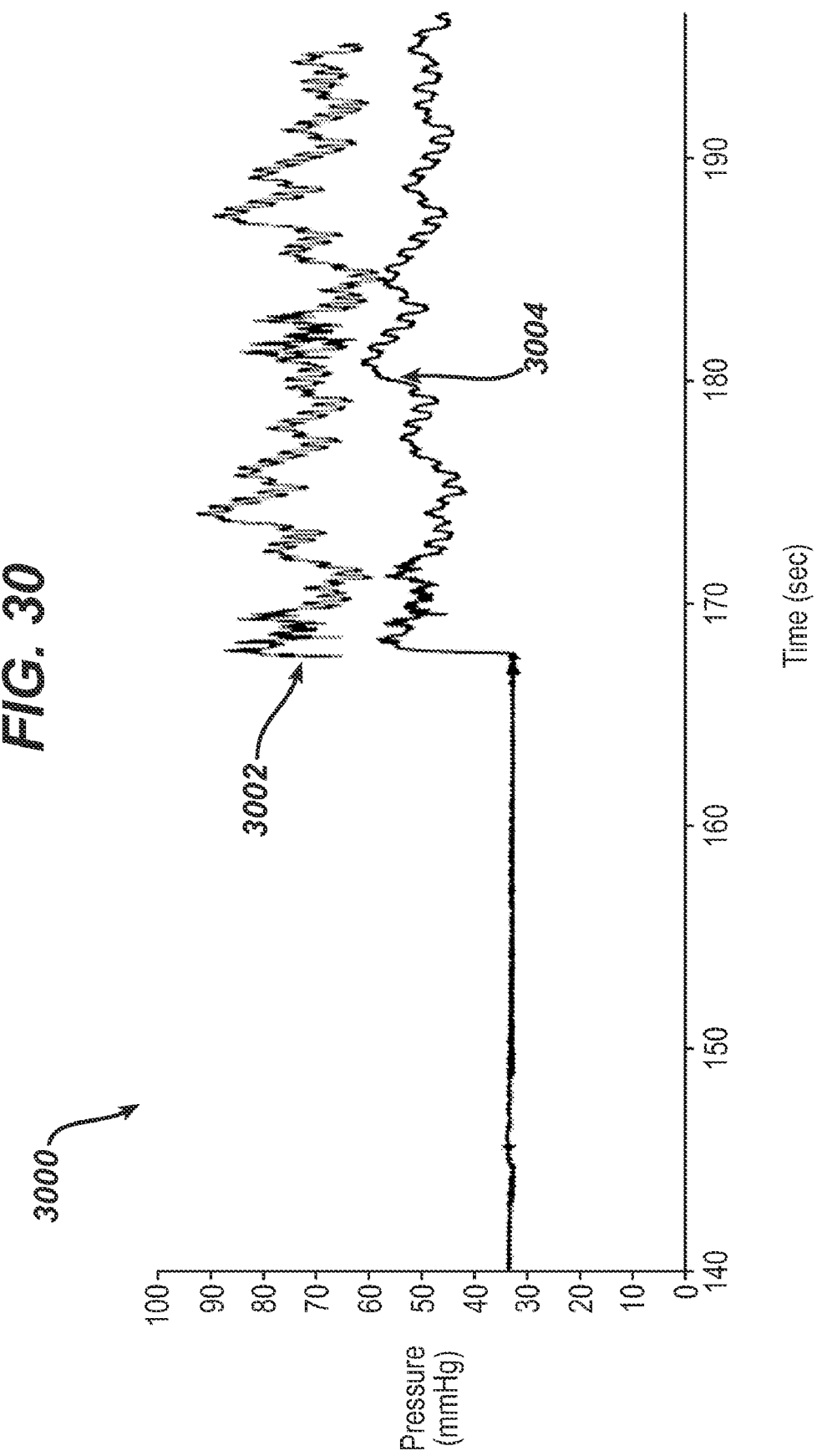

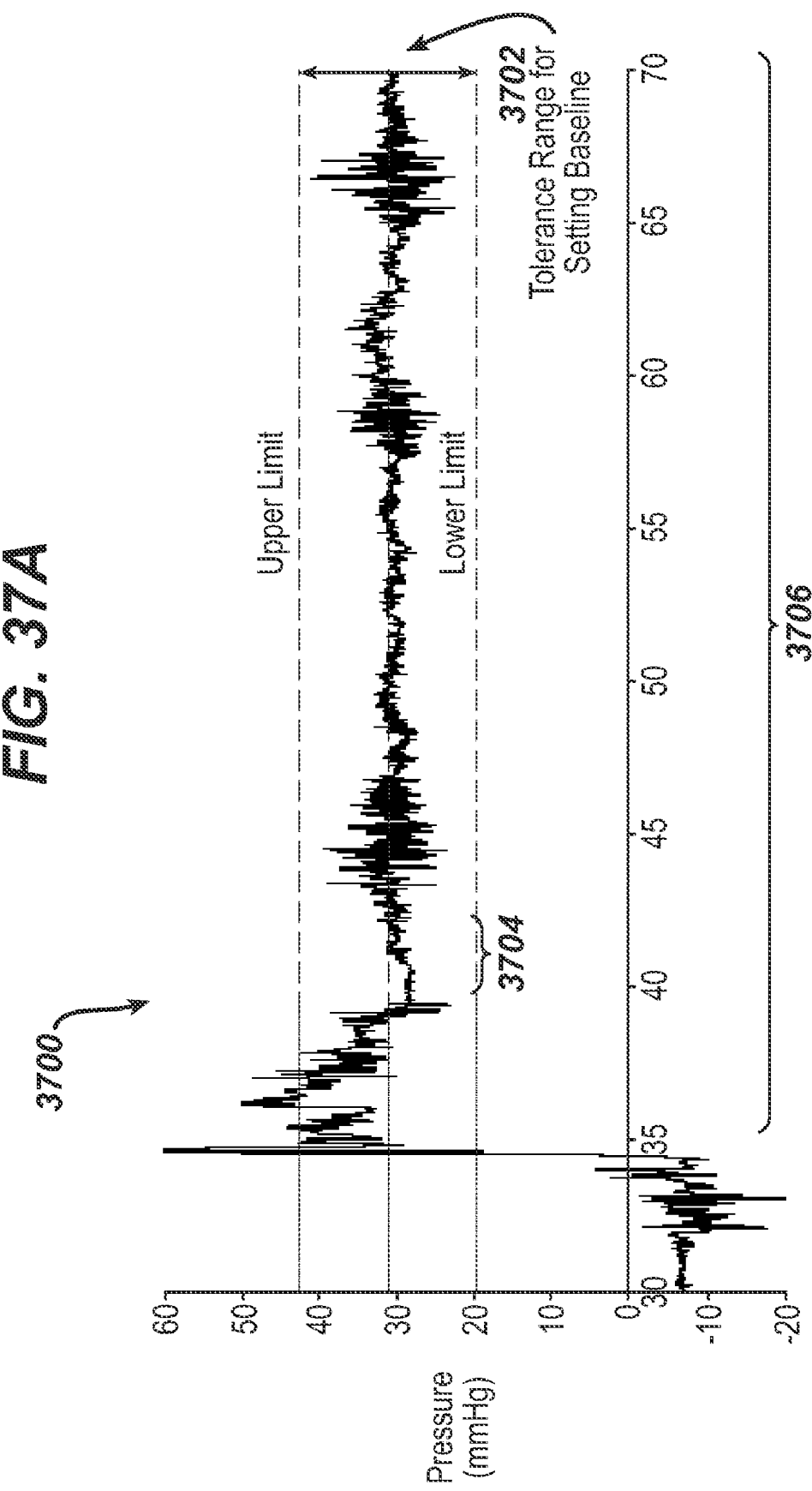

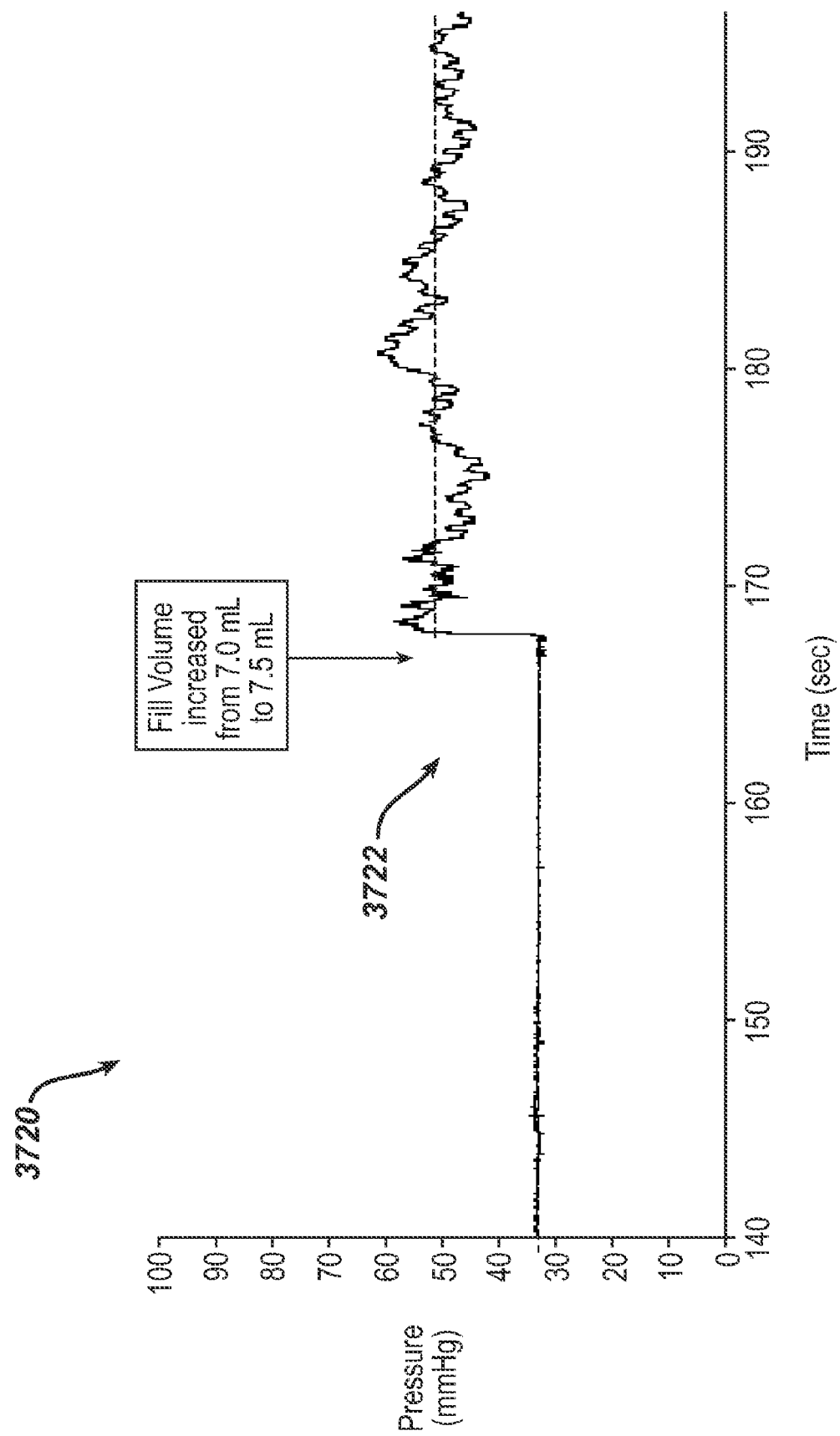

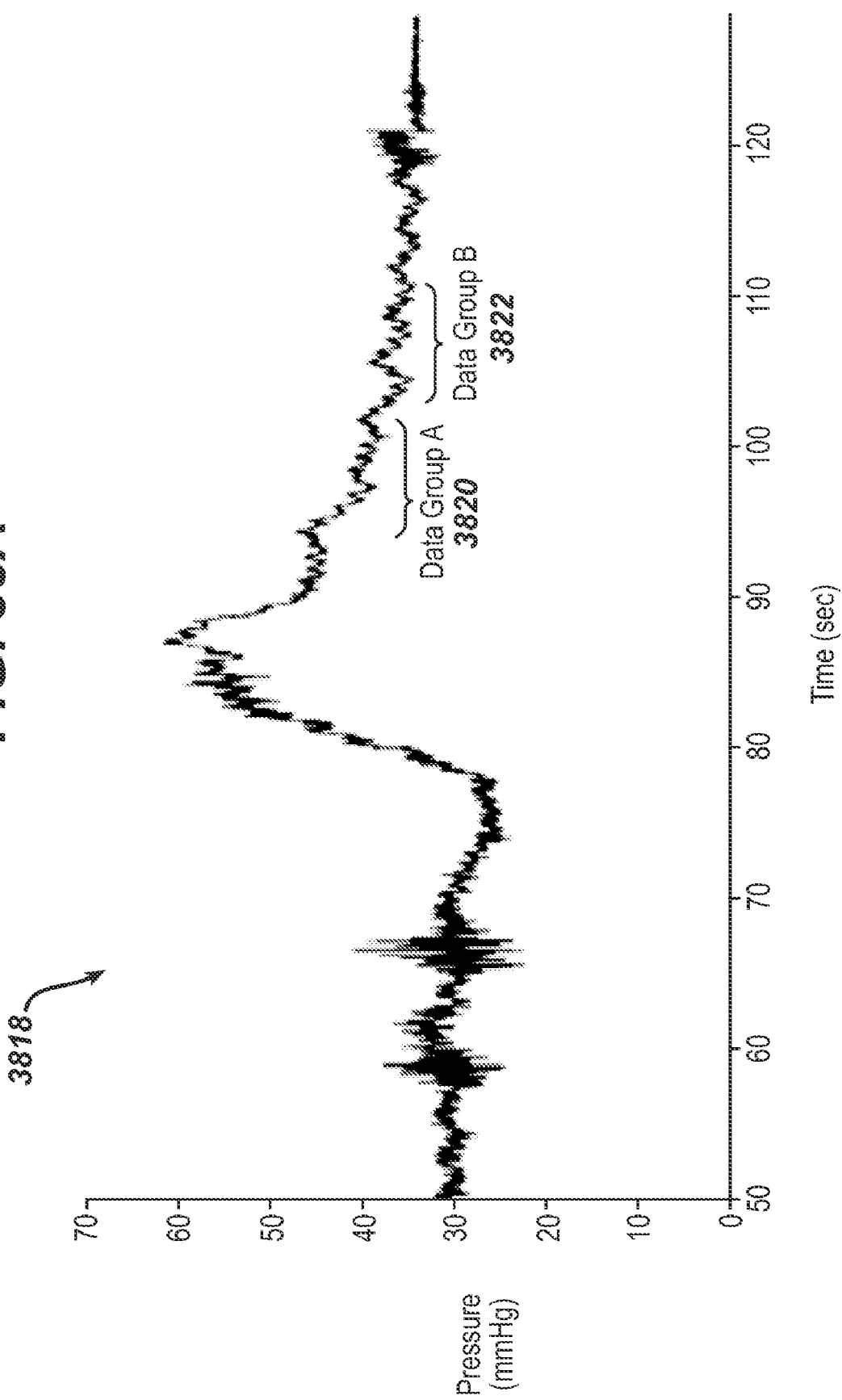

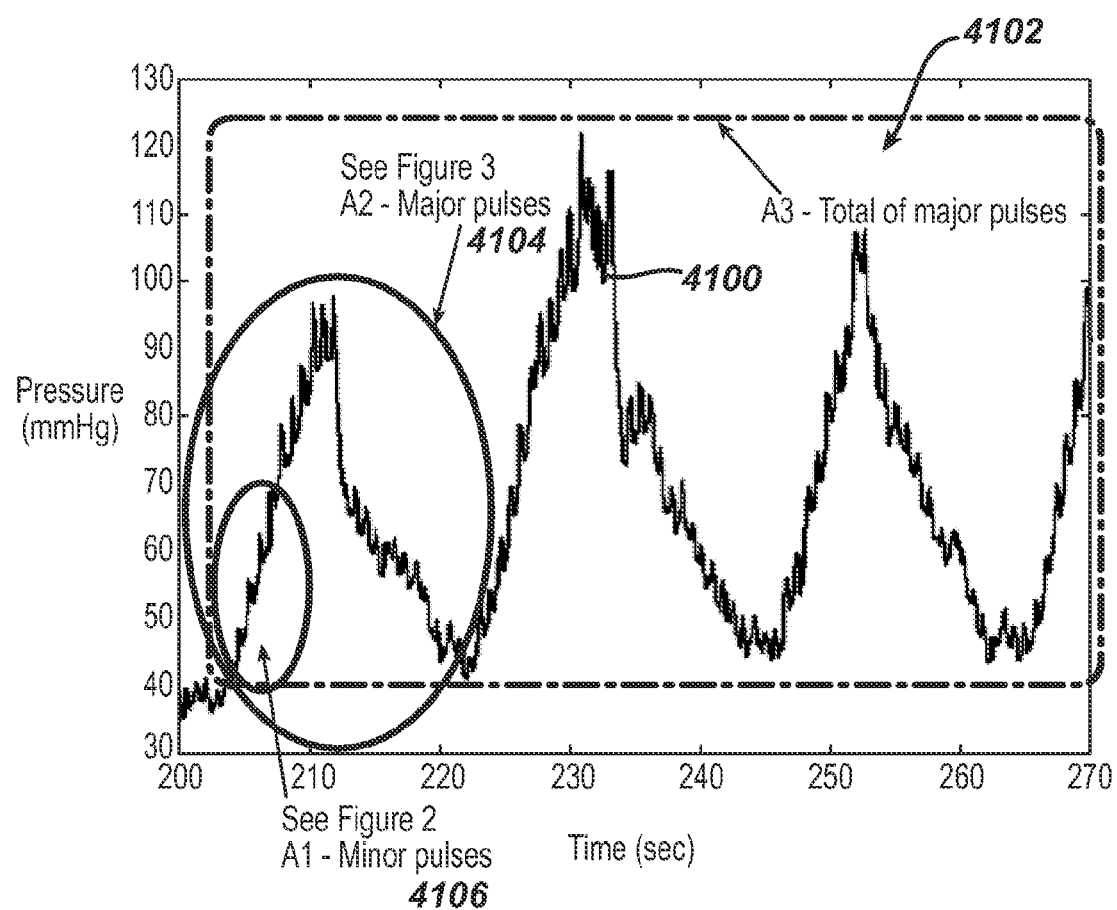

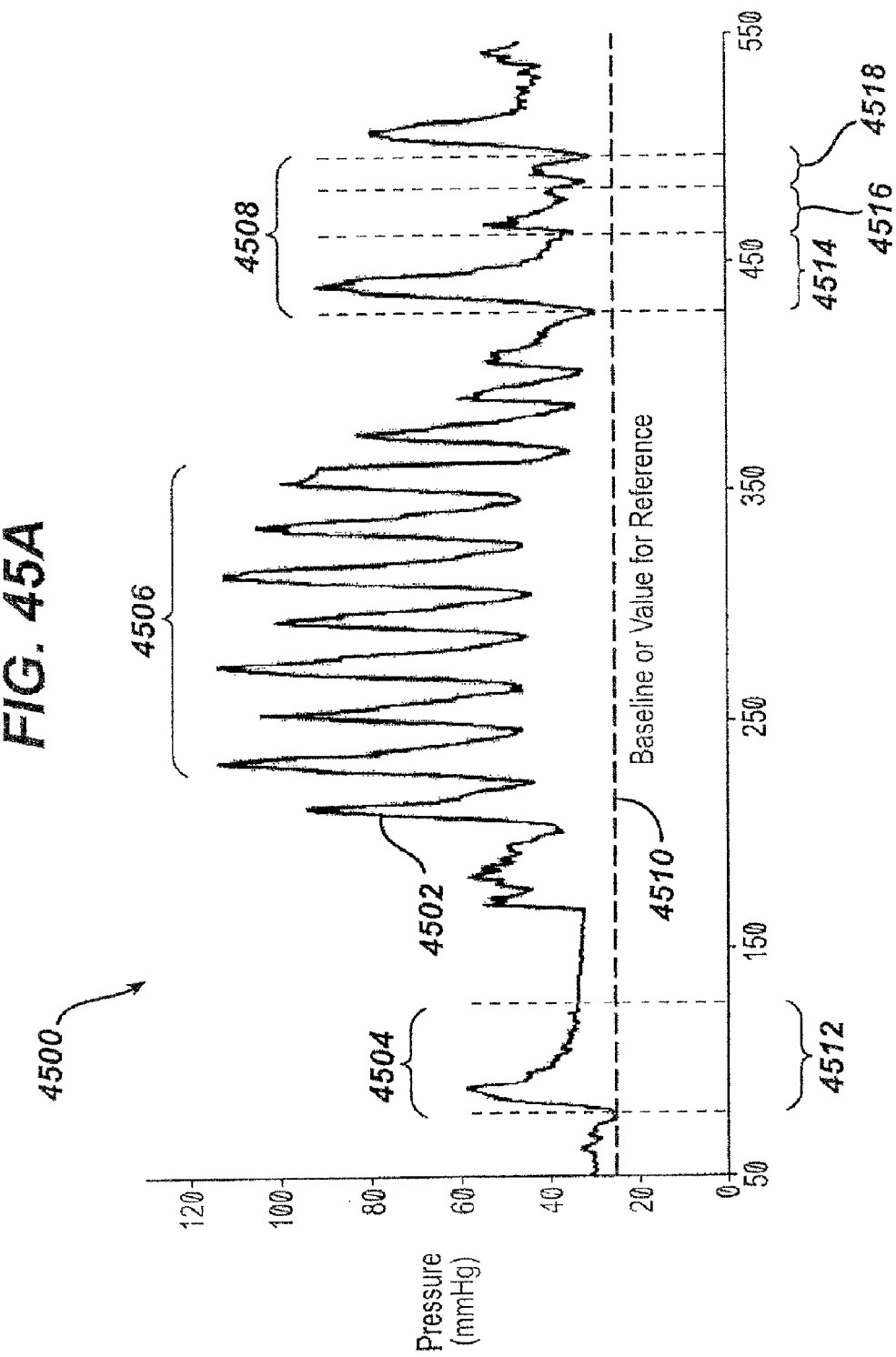

PHYSIOLOGICAL PARAMETER ANALYSIS FOR AN IMPLANTABLE RESTRICTION DEVICE AND A DATA LOGGER

CROSS-REFERENCE TO RELATED APPLICATION

This application is a continuation-in-part of U.S. patent application Ser. No. 11/398,940, filed Apr. 6, 2006, entitled "Monitoring of a Food Intake Restriction Device" (now published as US 2006/0199997), the teachings of which are hereby incorporated by reference in their entirety.

FIELD OF THE INVENTION

Embodiments of the present invention relate generally to an implanted restrictive opening device and, more particularly, to a communication system for monitoring physiological parameters related to an implanted food intake restriction device.

BACKGROUND OF THE INVENTION

Obesity is a growing concern, particularly in the United States, as the number of obese people continues to increase, and more is learned about the negative health effects of obesity. Morbid obesity, in which a person is 100 pounds or more over ideal body weight, in particular poses significant risks for severe health problems. Accordingly, a great deal of attention is being focused on treating obese patients. One method of treating morbid obesity has been to place a restriction device, such as an elongated band, about the upper portion of the stomach. Gastric bands have typically comprised a fluid-filled elastomeric balloon with fixed endpoints that encircles the stomach just inferior to the esophageal-gastric junction to form a small gastric pouch above the band and a reduced stoma opening in the stomach. When fluid is infused into the balloon, the band expands against the stomach creating a food intake restriction or stoma in the stomach. To decrease this restriction, fluid is removed from the band. The effect of the band is to reduce the available stomach volume and thus the amount of food that can be consumed before becoming "full."

Food restriction devices have also comprised mechanically adjusted bands that similarly encircle the upper portion of the stomach. These bands include any number of resilient materials or gearing devices, as well as drive members, for adjusting the bands. Additionally, gastric bands have been developed that include both hydraulic and mechanical drive elements. An example of such an adjustable gastric band is disclosed in U.S. Pat. No. 6,067,991, entitled "Mechanical Food Intake Restriction Device" which issued on May 30, 2000, and is incorporated herein by reference. It is also known to restrict the available food volume in the stomach cavity by implanting an inflatable elastomeric balloon within the stomach cavity itself. The balloon is filled with a fluid to expand against the stomach walls and, thereby, decrease the available food volume within the stomach.

With each of the above-described food restriction devices, safe, effective treatment requires that the device be regularly monitored and adjusted to vary the degree of restriction applied to the stomach. With banding devices, the gastric pouch above the band will substantially increase in size following the initial implantation. Accordingly, the stoma opening in the stomach must initially be made large enough to enable the patient to receive adequate nutrition while the stomach adapts to the banding device. As the gastric pouch increases in size, the band may be adjusted to vary the stoma size. In addition, it is desirable to vary the stoma size in order to accommodate changes in the patient's body or treatment regime, or in a more urgent case, to relieve an obstruction or severe esophageal dilatation. Traditionally, adjusting a hydraulic gastric band required a scheduled clinician visit during which a Huber needle and syringe were used to penetrate the patient's skin and add or remove fluid from the balloon via the injection port. More recently, implantable pumps have been developed which enable non-invasive adjustments of the band. An external programmer communicates with the implanted pump using telemetry to control the pump. During a scheduled visit, a physician places a hand-held portion of the programmer near the gastric implant and transmits power and command signals to the implant. The implant in turn adjusts the fluid levels in the band and transmits a response command to the programmer.

During these gastric band adjustments, it has been difficult to determine how the adjustment is proceeding, and whether the adjustment will have the intended effect. In an attempt to determine the efficacy of an adjustment, some physicians have utilized fluoroscopy with a Barium swallow as the adjustment is being performed, although fluoroscopy can be both expensive and raise concerns about radiation dosage. Other physicians have instructed the patient to drink a glass of water during or after the adjustment to determine whether the water can pass through the adjusted stoma. This method, however, only assures that the patient is not obstructed, and does not provide any information about the efficacy of the adjustment. Oftentimes, a physician may simply adopt a "try as you go" method based upon their prior experience, and the results of an adjustment may not be discovered until hours or days later, when the patient experiences a complete obstruction of the stomach cavity, or the band induces erosion of the stomach tissue due to excessive pressure on the tissue walls.

In addition, tracking or monitoring the long-term performance of the gastric band and/or the patient has been difficult in the past, but promises a wide range of benefits. For example, obtaining and displaying data from or related to the gastric band over a period of time (or real-time data) may be useful for adjustment, diagnostic, monitoring, or other purposes. It may be further advantageous to store such data, process it to obtain other kinds of meaningful data and/or communicate it to a remote location. Allowing a physician or patient to manipulate or track such information would add a new dimension to obesity treatment or other forms of treatment. The foregoing examples are merely illustrative and not exhaustive. While a variety of techniques and devices have been used treat obesity, it is believed that no one prior to the inventors has previously made or used an invention as described in the appended claims.

Accordingly, methods and devices are provided for use with an implantable restriction device, and in particular for logging, displaying, analyzing, and/or processing data from or related to an implantable restriction device.

SUMMARY OF THE INVENTION

In one aspect, a display for a physiological monitoring device displaying information from or related to an implantable restriction device is provided. For example, an exemplary display can include a simulated graphic of a disposition of a region enclosed by an implantable restriction device, such as an adjustable gastric band, the simulated graphic indicating a size of the disposition through the region. The indicated size can be based at least in part on a parameter sensed by the implantable restriction device and communicated to the physiological monitoring device. Sensed parameters, in this and other embodiments described herein, can include a wide variety of parameters such as pressure, pulse count, pulse width, pulse duration, pulse amplitude, pulse frequency, sensed electrical characteristics, and so on. In some embodiments, the simulated graphic can include one or more isobars displayed on the graphic representation of the enclosed region, the isobars representing sensed parameter values so that a perimeter of the disposition in the region is indicative of the sensed parameter. The isobars can change color to signal a condition related to the sensed parameter values. In other embodiments, the simulated graphic can include an image of a cross-section of a stoma, an image of the restriction device disposed around an anatomical lumen, an image of a bolus, icons, markings, and/or three dimensional images. The simulated graphic also can include a video image for showing a change in the size of the opening in accordance with pressure (or other parameter) sensed by the implantable restriction device over a time period. The simulated graphic also can be based on an image obtained from the body of a patient in which the implantable restriction device is implanted. The display can further include a textual indicator of a sensed parameter, sensed parameter data shown on a graph or dial indicator, and/or an indication of a restriction state of the implantable restriction device.

In another aspect, an exemplary display can include a graph of a sensed parameter over time, the graph including a graphic representation of data representing parameter values sensed by an implantable restriction device, for example an adjustable gastric band, and communicated to the physiological monitoring device. The display can also include one or more annotation markers disposed on the graphic representation to indicate a presence of an annotation at a selected time, the one or more annotation markers each associated with a description, such as text or an image. The associated description can include, for example, a description of a medical event, description of a physiological state, description of a symptom, a patient comment, and/or a physician comment. The graphic representation can include a curve plotting sensed pressure values. The display can further include a list of predefined annotation events from which a user can select the description.

In another aspect, an exemplary display can include a plurality of graphic representations of parameter/volume datasets (for example, parameter datasets, such as pressure, pulse count, pulse width, pulse amplitude, pulse frequency, and so on), each parameter/volume dataset corresponding to an implantable restriction device, such as an adjustable gastric band, in a patient and comprising one or more associations of (a) a fill volume for the implantable restriction device, with (b) a parameter sensed by the implantable restriction device at the fill volume and communicated to the physiological monitoring device. One of the plurality of the graphic representations can represent a pressure/volume dataset for a current patient and another of the graphic representations can represent a parameter/volume dataset for another patient.

In some embodiments, one of the plurality of the graphic representations of a parameter/volume dataset represents a current patient and the remainder of the plurality of the graphic representations represent parameter/volume datasets for a patient population. The graphic representations can be, for example, curves plotted on a graph of parameter vs. fill volume. The graphic representations also can include curves plotted on a graph of parameter vs. fill volume, and wherein one of the plurality of the graphic representations represents a parameter/volume dataset for a current patient and another graphic representation represents an average parameter/volume dataset for a patient population, the average parameter/volume dataset comprising one or more associations of (a) a fill volume, and (b) an average of a parameter (such as pressure) sensed by implantable restriction devices at the fill volume across a patient population. The display can further include an upper bound trendline and a lower bound trendline and defining surrounding the line plotting the average parameter/volume dataset.

A method for monitoring an implantable restriction device can also be provided, which in one embodiment can include providing a plurality of parameter/volume datasets, each corresponding to an implantable restriction device in a patient and comprising one or more associations of (a) a fill volume for the implantable restriction device, and (b) a parameter sensed by the implantable restriction device at the fill volume and communicated to an external device. The method can also include displaying a graphic representation of a selected parameter/volume dataset corresponding to a selected implantable restriction device along with one or more other graphic representations of one or more other parameter/volume datasets corresponding to one or more other implantable restriction devices. The method also can include calculating an average pressure for each volume across the one or more other parameter/volume datasets to create an average parameter/volume dataset, and displaying a graphic representation of the average parameter/volume dataset.

In yet another aspect, an exemplary display can include a graph which includes a parameter axis and a pulse count axis for relating a parameter sensed by an implantable restriction device, such as an adjustable gastric band, with a pulse count. The pulse count can represent a sequence number of a pulse of the sensed parameter within a sequence of pulses in a swallowing event. The display can also include a plurality of discrete indicators disposed on the graph at an intersection of parameter and pulse count, wherein each discrete indicator represents a predetermined parameter amplitude and the plurality of discrete indicators thereby represents a total parameter amplitude measured for each pulse in a sequence of pulses. In some embodiments, a time stamp can be displayed for at least one pulse in the sequence of pulses. The time stamp can indicate the time at which the pulse occurred, the duration of the pulse, the intra-pulse time, or other metrics.

In yet another aspect, an exemplary display can include a parameter vs. time graph, the parameter (such as pressure, or any other parameter, as previously mentioned) being sensed by an implantable restriction device, a graphic representation indicating a value related to the parameter sensed by an implantable restriction device, such as an adjustable gastric band, during a first time period, and a graphic representation indicating a value related to the parameter sensed by an implantable restriction device during a second and later time period. In some embodiments, the graphic representation for the first time period overlays at least in part the graphic representation for the second time period. The first time period can be before a medical action and the second and later time period can be after a medical action, and the medical action can be the adjustment of the implantable restriction device. In some embodiments, the graphic representations for the first time period and for the second and later time period comprise curves plotted on the graph having one or more parameter pulses therewithin. The graphic representations for the first time period and second time period can be overlaid such that at least one parameter pulse in the graphic representations for the first time period overlaps with at least one parameter pulse in the graphic representations for the second time period.

In yet another aspect, an exemplary display can include a pressure screen displaying a sensed pressure, the sensed pressure being sensed by an implantable restriction device (such as an adjustable gastric band) and communicated to the physiological monitoring device and a pulse count display indicating a number of pulses in sensed pressure that occur during a swallowing event, and/or pressure display having an indicator for sensed pressure, the indicator falling within one of a plurality of pressure ranges corresponding to a condition of the implantable restriction device. The pressure display can include, for example, a graph displaying pressure over time, wherein the sensed pressure is represented by a plotted curve, a linear meter comprising a plurality of discrete indicators, wherein in each discrete indicator corresponds to a predetermined sensed pressure, an indicator adapted to change color to indicate a condition, a circular pressure meter, and/or a textual indicator. The pressure ranges can correspond to conditions for a fluid-filled implantable restriction device that include "overfilled," "optimal" and "under-filled." In some embodiments, the graph, the linear meter, the circular pressure meter, and/or the textual indicator can be configured to signal a visual warning or alarm condition. In other embodiments, an audible alarm can be configured to activate when any of the graph, the linear meter, the circular pressure meter, and the textual indicator indicates a value above a threshold.

In yet another aspect, an exemplary method can include obtaining a physiological monitoring device having any of the foregoing displays or attributes, and repurposing the physiological monitoring device and/or the display. Repurposing can include, for example, reconstructing the device or display, modifying, reprogramming, erasing, or customizing the device or display. Repurposing also can include repairing, reconditioning, or sterilizing the device or display.

Data obtained from the implanted device can be used, processed, and/or analyzed in a wide variety of ways. For example, one exemplary method of obtaining information about a physiological parameter can include collecting data from an implantable restriction device over a time period, the collected data containing information about values of a parameter (such as pressure) sensed within a body during the time period, and, analyzing the data in data processing device to determine information about a physiological parameter (e.g., heart rate, breathing rate, rate of pulses caused by a peristaltic event, baseline parameter, etc.) for at least a portion of the time period. The determined information can include, for example, frequency, value, amplitude, change in value over at least a portion of a time period, and average value over a time period. In one embodiment, the method can include determining the frequency content of variations in the values of the sensed parameter during the time period and identifying one or more frequencies in the frequency content as a frequency of the physiological parameter. The method can further include comparing one or more frequencies (or an average of them) to one or more predetermined frequencies that are designated as frequencies associated with the physiological parameter. In some embodiments, the method can include determining the frequency content of variations in the values of pressure over at least a portion of the time period, selecting one or more frequencies existing in the frequency content that fall within a predetermined range of frequencies designated as possible rates of the physiological event (e.g., heart rate, breath rate, and so on), and identifying a rate for the physiological event based on the one or more selected frequencies. Determining the frequency content can further be accomplished by applying Fourier analyses. In other embodiments, the method can include calculating a frequency exhibited in the variations in the value of pressure over at least a portion of the time period, and comparing the frequency to a predetermined range of frequencies designated as possible rates of the physiological event to determine if the frequency falls within the range. Calculating the frequency can be achieved by, for example, recording at least two times at which values of pressure are at a local maximum or minimum; and calculating the frequency based on the difference between the at least two times. The method can further include determining an amplitude of the variations in the values of pressure at the calculated frequency, and comparing the amplitude to a predetermined range of amplitudes designated as possible physiological event amplitudes to determine if the amplitude falls within the range. In yet other embodiments, the method can include calculating the difference between (i) a value of pressure at a time within the time period, and (ii) an average value of pressure at the time, wherein the difference represents a value corresponding to the physiological parameter. The average value can be calculated, for example, based on values falling within a window of time. Further, the determination of physiological events or rates can lead to alarms, or can cause the data processing device to generate reports.

In another aspect, an exemplary method for analyzing data from an implantable restriction device to determine a baseline value for a physiological parameter can include collecting data from an implantable restriction device over a time period, the collected data containing information about values of a parameter sensed within a body over the time period. The method can also include defining a range of values to represent a tolerance range, and comparing one or more values of the sensed parameter during the time period to the tolerance range to determine if all of the one or more values fell within the tolerance range, and if so, identifying a baseline as having been established. The range of values can be defined in a variety of ways, including with respect to the running average, or by setting an upper limit that exceeds the running average and a lower limit that is less than the running average. The method can further include calculating a running average based on the values of the sensed parameter during an averaging window within the time period; and, identifying the running average as the baseline value. In some embodiments, the method can further include calculating a running average based on the values of the sensed parameter during an averaging window within the time period; and identifying the running average as the baseline value. In other embodiments, the method can include generating an alarm or report upon the occurrence of an event, such as (i) identification of the baseline value; (ii) failure to identify the baseline value within a threshold time; and (iii) identification of the baseline value and the baseline value passes a threshold value. In some embodiments, fluid can be added or removed from the implantable restriction device, and/or the determined baseline value can be correlated to a condition of the implantable restriction device, the condition being one of optimally-filled, over-filled, or under-filled (or optimally tighted, over-tightened, and under-tightened).

In another aspect, an exemplary method for analyzing data from an implantable restriction device to determine information about a baseline of a physiological parameter can be provided. The method can include collecting data from an implantable restriction device over a time period, the collected data containing information about values of a parameter sensed within a body during the time period. The method can further include calculating, based at least in part on one or more values of the sensed parameter during the time period, a predicted amount of time until the values of the physiological parameter will have a rate of change that is about zero. In some embodiments, calculating the predicted amount of time can involve calculating a rate of change of the values of the sensed parameter for a window within the time period, calculating a rate of change of the rate of change of the values of the sensed parameter for the window, and calculating the predicted amount of time until the values of the sensed parameter will have a rate of change that is about zero, based at least in part on the rate of change and the rate of change of the rate of change. In some embodiments, a predicted baseline value can be calculated, for example, by extrapolating from one or more values within the window to the predicted baseline value of the sensed parameter, and by multiplying the rate of change of the values of the sensed parameter for the window within the time period and the predicted amount of time. In some embodiments, an alarm or report can be generated if the rate of change passes a threshold value. Further, the rate of change can be correlated to a condition of the implantable restriction device, the condition being one of: optimally-filled, over-filled, or under-filled (or optimally tighted, over-tightened, and under-tightened).

In another aspect, an exemplary method for analyzing data from an implantable restriction device to identify the presence of a pulse can be provided. The method can include can include collecting data from an implantable restriction device over a time period, the collected data containing information about values of a parameter sensed within a body over the time period, identifying the presence of a pulse in the values of the sensed parameter. Identifying can comprise finding one or more values of the sensed parameter that exceeds a first threshold value and finding one or more subsequent values of the sensed parameter that fall below the first threshold or a second threshold (such thresholds can be defined relative to a baseline value for the parameter, and/or can be different or the same values). In some embodiments, identifying can further comprise finding one or more subsequent values of the sensed parameter that fall below a second threshold within a time window, the time window being within the time period and beginning at a time associated with the one or more values that exceeded the first threshold. Another exemplary method for analyzing data from an implantable restriction device to determine the presence of a pulse can include collecting data from an implantable restriction device over a time period, the collected data containing information about values of a parameter sensed within a body over the time period, and identifying the presence of a pulse in the values of the sensed parameter. Identifying can comprise finding one or more values of the sensed parameter that exceed a first threshold value, finding one or more subsequent values of the sensed parameter that are followed by decreasing values, the one or more subsequent values representing a peak value; and finding one or more other subsequent values of the sensed parameter that fall below a second threshold within a time window. The time window can be within the time period, beginning at virtually any time, such as when a peak value occurs, or otherwise. In some embodiments, an alarm or report can be generated upon identification of a pulse or if the number of pulses passes a threshold value during a predetermined time period. Further, such information can be correlated to a condition of the implantable restriction device, the condition being one of: optimally-filled, over-filled, or under-filled (or optimally tighted, over-tightened, and under-tightened).

In another aspect, an exemplary method for analyzing data from an implantable restriction device to detect the presence of a physiological condition or a condition related to an implantable restriction device can be provided. The method can include collecting data from an implantable restriction device over a time period, the collected data containing information about values of a parameter sensed within a body during the time period, finding one or more areas corresponding to an area under a pressure vs. time curve, and, comparing the areas, the result of the comparison being correlated to a condition. In some embodiments, finding one or more areas can include for each of the one or more areas, evaluating an integral (including numerical integration in some embodiments) based on values of the sensed parameter over each of a window within the time period, the evaluation of the integration producing a result representing the area under the pressure vs. time curve (which can be the area under one or more pulses). The method can further include correlating a decreasing sequence of areas that occurs at a first predetermined rate to an optimally filled implantable restriction device, correlating a sequence of areas that are substantially equal to an overfilled implantable restriction device, and/or can include correlating a decreasing sequence of areas that occurs at a second predetermined rate to an underfilled implantable restriction device.

In another aspect, an exemplary method of analyzing data from an implantable restriction device to remove noise in the data can be provided. Such a method can include collecting data from an implantable restriction device over a time period, the collected data containing information about values of a parameter sensed within a body over the time period, and conditioning the sensed parameter values for display or further analysis. Conditioning can include filtering and/or converting the sensed parameters from a first sampling rate to a second and lower sampling rate, and/or can include calculating a root mean square of the sensed parameters or performing a regression analysis on the sensed parameters. In some embodiments, conditioning can include calculating an average value of the sensed parameters at each time in the time period based on a group of surrounding sensed parameter values. In other embodiments, conditioning can include dividing at least a portion of the time period into a plurality of averaging windows of a predetermined size; and, calculating the average value of the sensed parameter in each averaging window. Conditioned values can be stored as compressed information.

In another aspect, an exemplary method for analyzing data from an implantable restriction device can include collecting data from an implantable restriction device over a time period, the collected data containing information about values of a parameter sensed within a body over the time period. The method can further include calculating an average value of the physiological parameter for a time X within the time period, the average value being calculated based on one or more values of the sensed parameter within an averaging window in the time period. In some embodiments, the averaging window (i) can precede the time X or (ii) can surround the time X. The method can further include displaying the average value on a graph of the sensed parameter vs. time.

In yet another aspect, an exemplary method can include obtaining a data processing device for processing data as described in any of the foregoing embodiments, and repurposing the device. Repurposing can include, for example, reconstructing the device, modifying, reprogramming, erasing, or customizing the device hardware/software. Repurposing also can include repairing, reconditioning, or sterilizing the device.

Still other examples, features, aspects, embodiments, and advantages of the invention will become apparent to those skilled in the art from the following description, which includes by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 6 is a cross-sectional view of an alternative bi-directional infuser for the food intake restriction device of FIG. 2;

FIG. 7A is a schematic diagram of a mechanically adjustable restriction device incorporating a pressure transducer;

FIG. 7B is a cross-sectional view of the mechanically adjustable device of FIG. 7A taken along line B-B;

FIG. 23A shows another exemplary pulse counter display for a graphical user interface;

FIG. 24A shows an exemplary display of a stoma enclosed by a restriction device;

FIG. 24B shows the display of FIG. 24A after a change in pressure sensed by the restriction device;

FIG. 24C shows the display of FIG. 24A after another change in pressure sensed by the restriction device;

FIG. 25 shows an exemplary graph of pressure over time which can be correlated to the displays shown in FIG. 24A-C;

FIG. 27A shows the display shown in FIG. 27A after a change in pressure;

FIG. 29 shows an exemplary display with one set of data overlaying another set of data;

FIG. 30 shows another exemplary display with one set of data overlaying another set of data;

FIG. 37A is an exemplary plot of pressure values over time collected from a restriction device with annotations related to calculating a baseline value;

FIG. 37C is an exemplary plot of pressure values over time exhibiting a change in baseline value;

FIG. 38A is an exemplary plot of pressure values over time collected from a restriction device with annotations related to predicting characteristics of a baseline value;

FIG. 41A is an exemplary plot of pressure values over time collected from a restriction device exhibiting superimposed pulses of differing frequencies;

DETAILED DESCRIPTION OF THE INVENTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive. The features illustrated or described in connection with one exemplary embodiment may be combined with the features of other embodiments. Such modifications and variations are intended to be included within the scope of the present invention.

Figure 1:
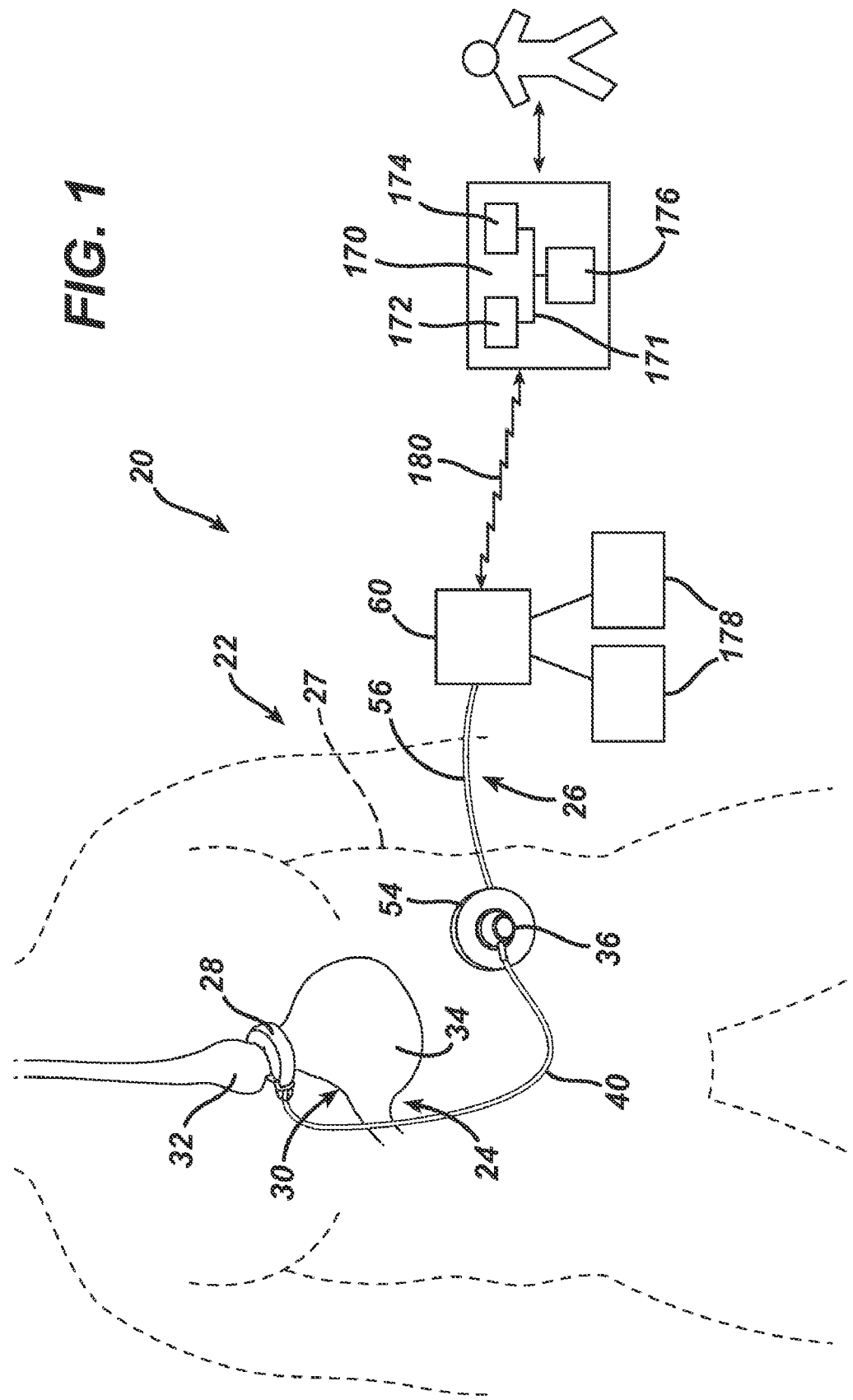
FIG. 1 is a simplified, schematic diagram of an implanted restrictive opening device and a bi-directional communication system between the implanted device and a remote monitoring unit.

Referring now to the drawings in detail, wherein like numerals indicate the same elements throughout the views, FIG. 1 provides a simplified, schematic diagram of a bi-directional communication system 20 for transmitting data between an implanted restrictive opening device and a remotely located monitoring unit. Through communication system 20, data and command signals may be transmitted between the implanted device and a remotely located physician for monitoring and affecting patient treatment. The communication system of the invention enables a physician to control the restrictive opening device and monitor treatment without meeting face-to-face with the patient. For purposes of the disclosure herein, the terms "remote" and "remotely located" are defined as being at a distance of greater than six feet. In FIG. 1 and the following disclosure, the restrictive opening device is shown and described as being a food intake restriction device 22 for use in bariatric treatment. The use of a food intake restriction device is only representative however, and the present invention may be utilized with other types of implanted restrictive opening devices without departing from the scope of the invention. In addition, it should be understood that the restriction device 22 can be (or include) any category of restrictive device, such as a fluid-fillable restriction device, mechanically based restriction device, and so on.

As shown in FIG. 1, a first portion 24 of intake restriction device 22 is implanted beneath a patient's skin 27, while a second portion 26 is located external to the patient's skin. Implanted portion 24 comprises an adjustable restriction band 28 that is implanted about the gastrointestinal tract for the treatment of morbid obesity. In this application, adjustable band 28 is looped about the outer wall of a stomach 30 to create a stoma between an upper pouch 32 and a lower pouch 34 of the stomach. Adjustable band 28 may include a cavity made of silicone rubber, or another type of biocompatible material, that inflates inwardly against stomach 30 when filled with a fluid. Alternatively, band 28 may comprise a mechanically adjustable device having a fluid cavity that experiences pressure changes with band adjustments, or a combination hydraulic/mechanical adjustable band.

An injection port 36, which will be described in greater detail below, is implanted in a body region accessible for needle injections and telemetry communication signals. In the embodiment shown, injection port 36 fluidly communicates with adjustable band 28 via a catheter 40. A surgeon may position and permanently implant injection port 36 inside the body of the patient in order to perform adjustments of the food intake restriction or stoma. Injection port 36 is typically implanted in the lateral, subcostal region of the patient's abdomen under the skin and layers of fatty tissue. Alternatively, the surgeon may implant injection port 36 on the sternum of the patient.

Figure 2:
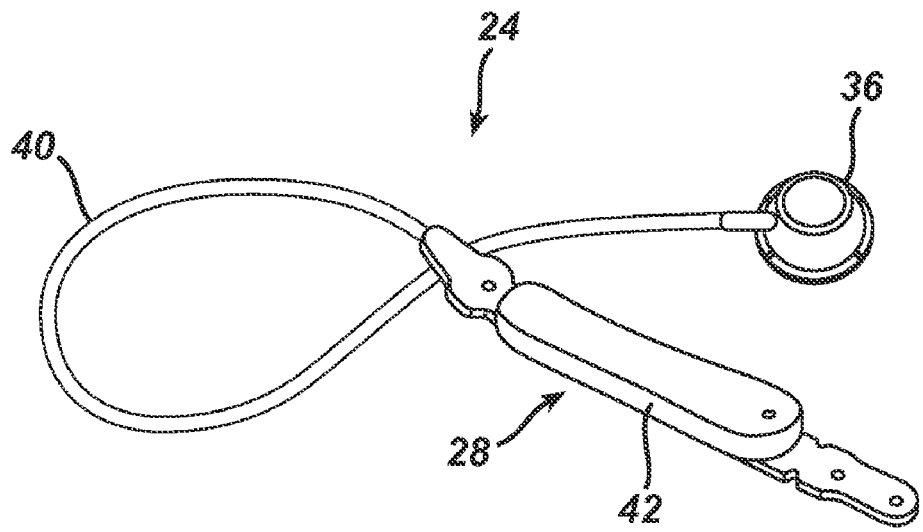
FIG. 2 is a more detailed, perspective view of an implantable portion of the food intake restriction device shown in FIG. 1.

FIG. 2 illustrates adjustable band 28 in greater detail. In this embodiment, band 28 includes a variable volume cavity 42 that expands or contracts against the outer wall of the stomach to form an adjustable stoma for controllably restricting food intake into the stomach. A physician may decrease the size of the stoma opening by adding fluid to variable volume cavity 42 or, alternatively, may increase the stoma size by withdrawing fluid from the cavity. Fluid may be added or withdrawn by inserting a needle into injection port 36. The fluid may be, but is not restricted to, a 0.9 percent saline solution.

Returning now to FIG. 1, external portion 26 of intake restriction device 22 comprises a hand-held antenna 54 electrically connected (in this embodiment via an electrical cable assembly 56) to a local unit 60. Electrical cable assembly 56 may be detachably connected to local unit 60 or antenna 54 to facilitate cleaning, maintenance, usage, and storage of external portion 26. Local unit 60 is a microprocessor-controlled device that communicates with implanted device 22 and a remote unit 170, as will be described further below. Through antenna 54, local unit 60 non-invasively communicates with implanted injection port 36. Antenna 54 may be held against the patient's skin near the location of injection port 36 to transmit telemetry and power signals to injection port 36.

Figure 3:
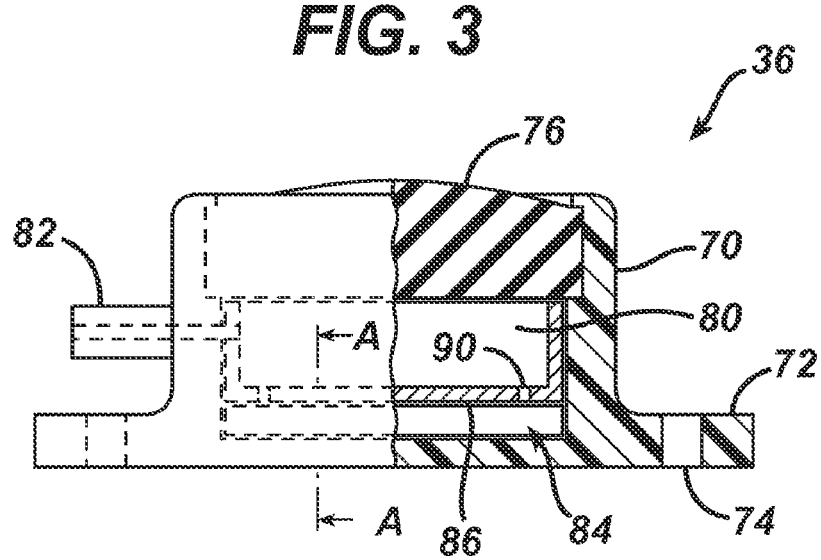
FIG. 3 is a side, partially sectioned view of the injection port shown in FIG. 2.

Turning now to FIG. 3, which depicts a side, partially sectioned view of an exemplary injection port 36. As shown in FIG. 3, injection port 36 comprises a rigid housing 70 having an annular flange 72 containing a plurality of attachment holes 74 for fastening the injection port to tissue in a patient. A surgeon may attach injection port 36 to the tissue, such as the fascia covering an abdominal muscle, using any one of numerous surgical fasteners including suture filaments, staples, and clips. Injection port 36 further comprises a septum 76 typically made of a silicone rubber and compressively retained in housing 70. Septum 76 is penetrable by a Huber needle, or a similar type of injection instrument, for adding or withdrawing fluid from the port. Septum 76 self-seals upon withdrawal of the syringe needle to maintain the volume of fluid inside of injection port 36. Injection port 36 further comprises a reservoir 80 for retaining the fluid and a catheter connector 82. Connector 82 attaches to catheter 40, shown in FIG. 2, to form a closed hydraulic circuit between reservoir 80 and cavity 42. Housing 70 and connector 82 may be integrally molded from a biocompatible polymer or constructed from a metal such as titanium or stainless steel.

Injection port 36 also comprises a pressure sensor 84 for measuring fluid pressure within the device. The pressure measured by sensor 84 corresponds to the amount of restriction applied by band 28 to the patient's stomach or other body cavity. The pressure measurement is transmitted from sensor 84 to local unit 60 via telemetry signals using antenna 54. Local unit 60 may display, print and/or transmit the pressure measurement signal to a remote monitoring unit for evaluation, as will be described in more detail below. In the embodiment shown in FIG. 3, pressure sensor 84 is positioned at the bottom of fluid reservoir 80 within housing 70. A retaining cover 86 extends above pressure sensor 84 to substantially separate the sensor surface from reservoir 80, and protect the sensor from needle penetration. Retaining cover 86 may be made of a ceramic material such as, for example, alumina, which resists needle penetration yet does not interfere with electronic communications between pressure sensor 84 and antenna 54. Retaining cover 86 includes a vent 90 that allows fluid inside of reservoir 80 to flow to and impact upon the surface of pressure sensor 84.

Figure 4:
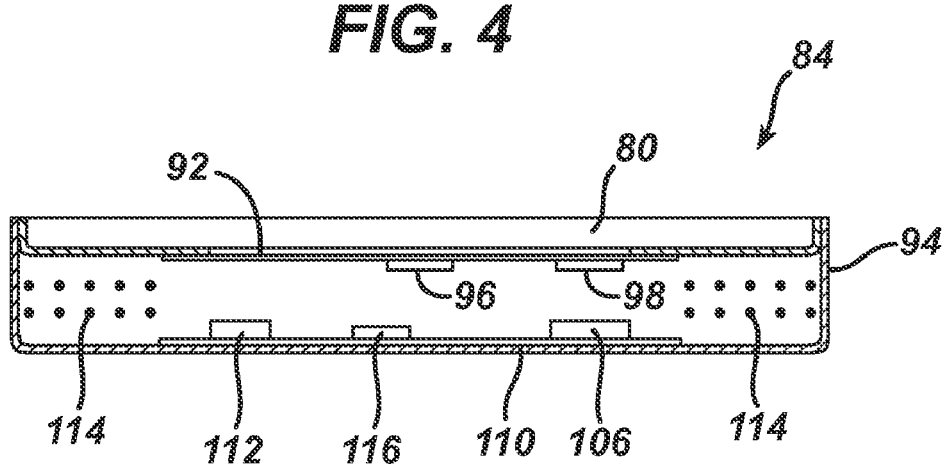
FIG. 4 is a side, sectional view, taken along line A-A of FIG. 3, illustrating an exemplary pressure sensor for measuring fluid pressure in the intake restriction device of FIG. 2.

FIG. 4 is a side, sectional view of pressure sensor 84, taken along line A-A of FIG. 3, illustrating an exemplary embodiment for measuring fluid pressure. Pressure sensor 84 is hermetically sealed within a housing 94 to prevent fluid infiltrating and effecting the operation of the sensor. The exterior of pressure sensor 84 includes a diaphragm 92 having a deformable surface. Diaphragm 92 is formed by thinning out a section of the bottom of titanium reservoir 80 to a thickness between 0.001" and 0.002". As fluid flows through vent 90 in reservoir 80, the fluid impacts upon the surface of diaphragm 92, causing the surface to mechanically displace. The mechanical displacement of diaphragm 92 is converted to an electrical signal by a pair of variable resistance, silicon strain gauges 96, 98. Strain gauges 96, 98 are attached to diaphragm 92 on the side opposite the working fluid in reservoir 80. Strain gauge 96 is attached to a center portion of diaphragm 92 to measure the displacement of the diaphragm. The second, matched strain gauge 98 is attached near the outer edge of diaphragm 92. Strain gauges 96, 98 may be attached to diaphragm 92 by adhesives, or may be diffused into the diaphragm structure. As fluid pressure within band 28 fluctuates, the surface of diaphragm 92 deforms up or down at the bottom of reservoir 80. The deformation of diaphragm 92 produces a resistance change in the center strain gauge 96.

Figure 5:
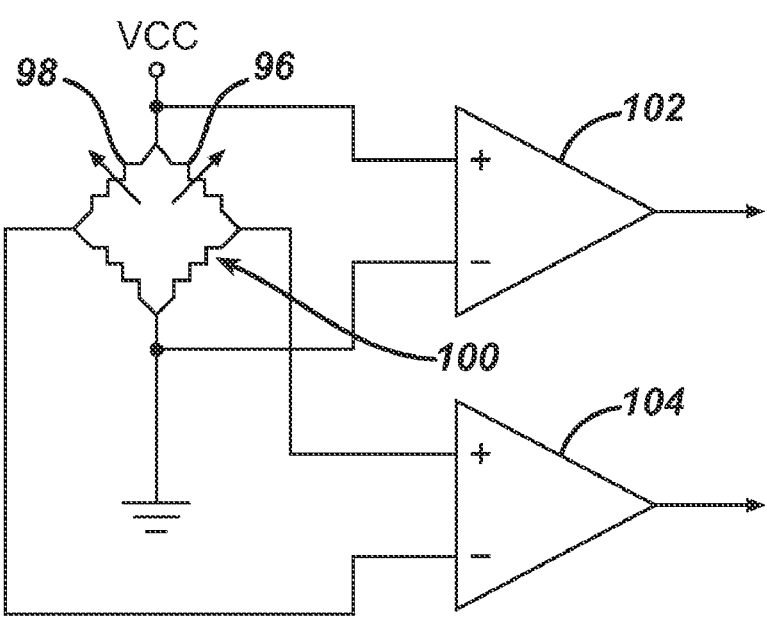
FIG. 5 is a simplified schematic of a variable resistance circuit for the pressure sensor shown in FIG. 4.

As shown in FIG. 5, strain gauges 96, 98 form the top two resistance elements of a half-compensated, Wheatstone bridge circuit 100. As strain gauge 96 reacts to the mechanical displacements of diaphragm 92, the changing resistance of the gauge changes the potential across the top portion of the bridge circuit. Strain gauge 98 is matched to strain gauge 96 and athermalizes the Wheatstone bridge circuit. Differential amplifiers 102, 104 are connected to bridge circuit 100 to measure the change in potential within the bridge circuit due to the variable resistance strain gauges. In particular, differential amplifier 102 measures the voltage across the entire bridge circuit, while differential amplifier 104 measures the differential voltage across the strain gauge half of bridge circuit 100. The greater the differential between the strain gauge voltages, for a fixed voltage across the bridge, the greater the pressure difference. If desired, a fully compensated Wheatstone bridge circuit could also be used to increase the sensitivity and accuracy of the pressure sensor 84. In a fully compensated bridge circuit, four strain gauges are attached to the surface of diaphragm 92, rather than only two strain gauges as shown in FIG. 4.

Returning to FIG. 4, the output signals from differential amplifiers 102, 104 are applied to a microcontroller 106. Microcontroller 106 is integrated into a circuit board 110 within housing 94. A temperature sensor 112 measures the temperature within injection port 36 and inputs a temperature signal to microcontroller 106. Microcontroller 106 uses the temperature signal from sensor 112 to compensate for variations in body temperature and residual temperature errors not accounted for by strain gauge 98. Compensating the pressure measurement signal for variations in body temperature increases the accuracy of the pressure sensor 84. Additionally, a TET/telemetry coil 114 is located within housing 94. Coil 114 is connected to a capacitor 116 to form a tuned tank circuit for receiving power from and transmitting physiological data, including the measured fluid pressure, to local unit 60. FIGS. 3-5 illustrate one exemplary embodiment for measuring fluid pressure within an intake restriction device. Additional embodiments for measuring fluid pressure are described in U.S. patent application Ser. No. 11/065,410 entitled "Non-invasive Measurement of Fluid Pressure in a Bariatric Device," (now published as U.S. Patent Publication No. 2006/0189888) the disclosure of which is incorporated herein by reference.

As an alternative to injection port 36, implanted portion 24 may include a bi-directional infuser for varying the fluid level within the adjustable restriction band 28. With an infuser, fluid can be added or withdrawn from band 28 via telemetry command signals, without the need to insert a syringe through the patient's skin and into the port septum. FIG. 6 is a cross-sectional view of an exemplary infuser 115. As shown in FIG. 6, infuser 115 includes a pump, designated generally as 118, for non-invasively transferring fluid into or out of the band in response to telemetry command signals. Pump 118 is encased within a cylindrical outer housing 120 having an annular cover 121 extending across a top portion. A collapsible bellows 122 is securely attached at a top peripheral edge to cover 121. Bellows 122 is comprised of a suitable material, such as titanium, which is capable of repeated flexure at the folds of the bellows, but which is sufficiently rigid so as to be non-compliant to variations in pressure. A lower peripheral edge of bellows 122 is secured to an annular bellows cap 123, which translates vertically within pump 118. The combination of cover 121, bellows 122 and bellows cap 123 defines the volume of a fluid reservoir 124. A catheter connector 119 attaches to catheter 40 (shown in FIG. 2) to form a closed hydraulic circuit between the band and fluid reservoir 124. The volume in reservoir 124 may be expanded by moving bellows cap 123 in a downward direction, away from cover 121. As bellows cap 123 descends, the folds of bellows 122 are stretched, creating a vacuum to pull fluid from the band, through catheter 40 and connector 119, and into reservoir 124. Similarly, the volume in reservoir 124 may be decreased by moving bellows cap 123 in an upward direction towards cover 121, thereby compressing the folds of bellows 122 and forcing fluid from the reservoir through catheter 40 and connector 119 and into band 28.

Bellows cap 123 includes an integrally formed lead screw portion 125 that operatively engages a matching thread on a cylindrical nut 126. The outer circumference of nut 126 is securely attached to an axial bore of a rotary drive plate 127. A cylindrical drive ring 128 is in turn mounted about the outer annular edge of rotary drive plate 127. Nut 126, drive plate 127 and drive ring 128 are all securely attached together by any suitable means to form an assembly that rotates as a unit about an axis formed by screw portion 125. A bushing frame 129 encloses TET and telemetry coils (not shown) for transmitting power and data signals between antenna 54 and pump 118.

Drive ring 128 is rotatably driven by one or more piezoelectric harmonic motors. In the embodiment shown in FIG. 6, two harmonic motors 131 are positioned so that a tip 113 of each motor is in frictional contact with the inner circumference of drive ring 128. When motors 131 are energized, tips 113 vibrate against drive ring 128, producing a "walking" motion along the inner circumference of the ring that rotates the ring. A microcontroller (not shown) in pump 118 is electrically connected to the TET and telemetry coils for receiving power to drive motors 131, as well as receiving and transmitting data signals for the pump. To alter the fluid level in band cavity 42, an adjustment prescription is transmitted by telemetry from antenna 54. The telemetry coil in infuser 115 detects and transmits the prescription signal to the microcontroller. The microcontroller in turn drives motors 131 an appropriate amount to collapse or expand bellows 122 and drive the desired amount of fluid to/from band 28.

In order to measure pressure variations within infuser 115, and, thus, the size of the stoma opening, a pressure sensor, indicated by block 84', is included within bellows 122. Pressure sensor 84' is similar to pressure sensor 84 described above. As the pressure against band 28 varies due to, for example, peristaltic pressure from swallowing, the fluid in band 28 experiences pressure changes. These pressure changes are conveyed back through the fluid in catheter 40 to bellows 122. The diaphragm in pressure sensor 84' deflects in response to the fluid pressure changes within bellows 122. The diaphragm deflections are converted into an electrical signal indicative of the applied pressure in the manner described above with respect to FIGS. 4 and 5. The pressure signal is input to the infuser microcontroller, which transmits the pressure to a monitoring unit external to the patient via the telemetry coil. Additional details regarding the operation of bi-directional infuser 115 may be found in commonly-assigned, co-pending U.S. patent application Ser. No. 11/065,410 entitled "Non-invasive Measurement of Fluid Pressure in a Bariatric Device" which has been incorporated herein by reference.

FIGS. 7A and 7B depict a mechanically adjustable band 153 for creating a food intake restriction in the abdomen of a patient. Mechanical band 153 may be used as an alternative to hydraulically adjustable band 28 for creating a stoma. Mechanically adjustable band 153 comprises a substantially circular resilient core 133 having overlapping end portions 135, 137. Core 133 is substantially enclosed in a fluid-filled compliant housing 139. A releasable and lockable joint 149 of core 133 protrudes from the ends of housing 139 to enable the core and housing to be placed around the esophagus or stomach of a patient to form a stoma. An implanted motor 141 is spaced from core 133 to mechanically adjust the overlap of the core end portions 135, 137 and, accordingly, the stoma size formed by the core. Motor 141 adjusts the size of core 133 through a drive shaft 143 that is connected to a drive wheel (not shown) within housing 139. Motor 141 is molded together with a remote-controlled power supply unit 145 in a body 147 comprised of silicon rubber, or another similar material.

As motor 141 changes the size of core 133, the pressure of the fluid within housing 139 varies. To measure the pressure variations, a pressure sensor, similar to that described above, is placed in communication with the fluid of housing 139. The pressure sensor may be placed within housing 139, as shown by block 84", so that the pressure variations within the stoma opening are transferred through the fluid in housing 139 to the diaphragm of the sensor. Sensor 84" translates the deflections of the diaphragm into a pressure measurement signal, which is transmitted to an external unit via telemetry in the manner described above. In an alternative scenario, the pressure sensor may be placed within the implanted motor body 147, as indicated by block 84'", and fluidly connected to housing 139 via a tube 151 extending alongside drive shaft 143. As fluid pressure varies in housing 139 due to pressure changes within the stoma opening, the pressure differentials are transferred through the fluid in tube 151 to sensor 84'". Sensor 84'" generates an electrical signal indicative of the fluid pressure. This signal is transmitted from the patient to an external unit in the manner described above.

Figure 8:
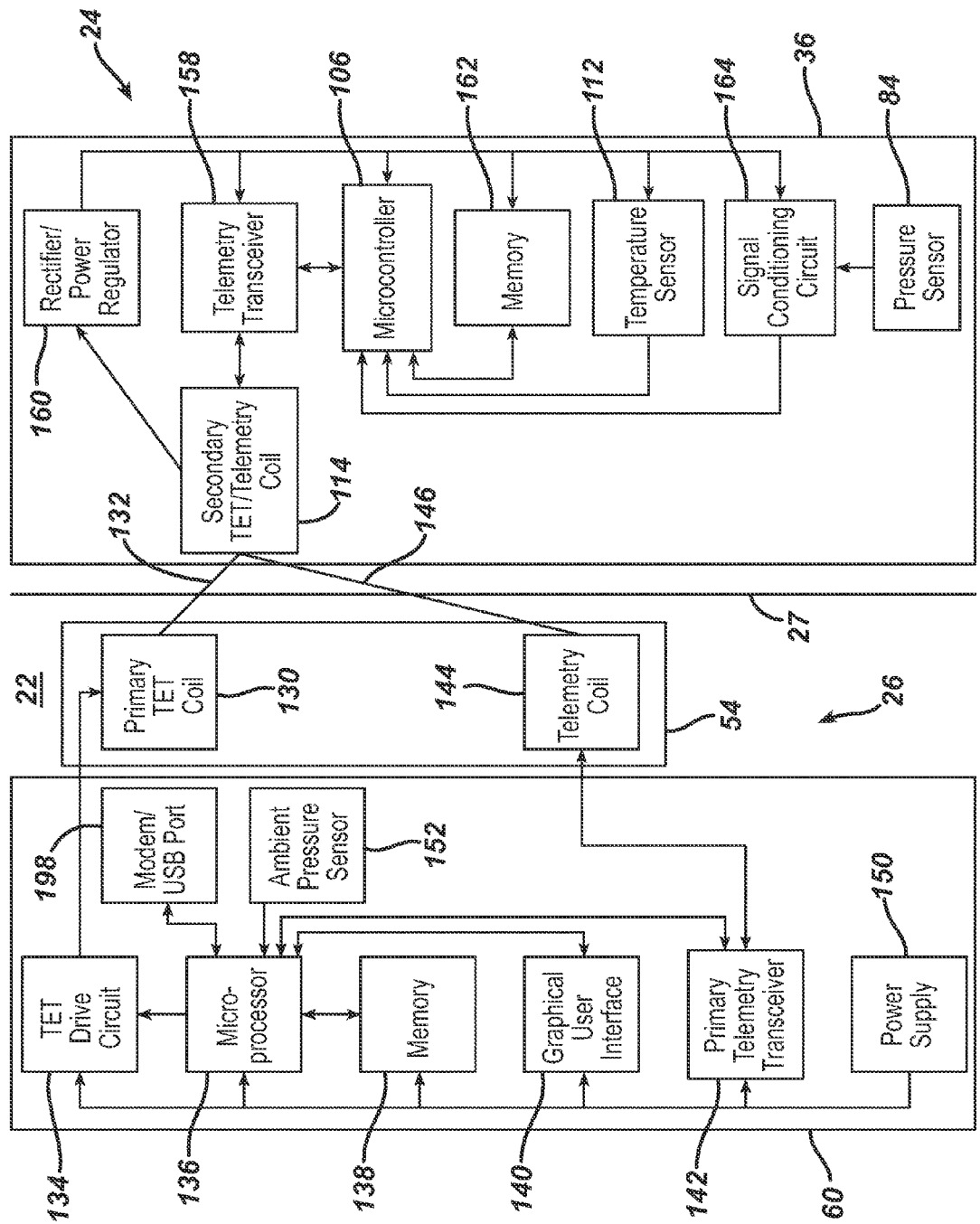
FIG. 8 is a block diagram of the major internal and external components of the intake restriction device shown in FIG. 1.

FIG. 8 is a block diagram illustrating the major components of implanted and external portions 24, 26 of intake restriction device 22. As shown in FIG. 8, external portion 26 includes a primary TET coil 130 for transmitting a power signal 132 to implanted portion 24. A telemetry coil 144 is also included for transmitting data signals to implanted portion 24. Primary TET coil 130 and telemetry coil 144 combine to form antenna 54 as shown. Local unit 60 of external portion 26 includes a TET drive circuit 134 for controlling the application of power to primary TET coil 130. TET drive circuit 134 is controlled by a microprocessor 136. A graphical user interface 140 is connected to microprocessor 136 for inputting patient information and displaying and/or printing data and physician instructions. Through user interface 140, the patient or clinician can transmit an adjustment request to the physician and also enter reasons for the request. Additionally, user interface 140 enables the patient to read and respond to instructions from the physician.

Local unit 60 also includes a primary telemetry transceiver 142 for transmitting interrogation commands to and receiving response data, including sensed fluid pressure, from implanted microcontroller 106. Primary transceiver 142 is electrically connected to microprocessor 136 for inputting and receiving command and data signals. Primary transceiver 142 drives telemetry coil 144 to resonate at a selected RF communication frequency. The resonating circuit generates a downlink alternating magnetic field 146 that transmits command data to implanted microcontroller 106. Alternatively, transceiver 142 may receive telemetry signals transmitted from secondary coil 114. The received data may be stored in a memory 138 associated with microprocessor 136. A power supply 150 supplies energy to local unit 60 in order to power intake restriction device 22. An ambient pressure sensor 152 is connected to microprocessor 136. Microprocessor 136 uses the signal from ambient pressure sensor 152 to adjust the received fluid pressure measurement for variations in atmospheric pressure due to, for example, variations in barometric conditions or altitude.

FIG. 8 also illustrates the major components of implanted portion 24 of device 22. As shown in FIG. 8, secondary TET/telemetry coil 114 receives power and communication signals from external antenna 54. Coil 114 forms a tuned tank circuit that is inductively coupled with either primary TET coil 130 to power the implant, or primary telemetry coil 144 to receive and transmit data. A telemetry transceiver 158 controls data exchange with coil 114. Additionally, implanted portion 24 includes a rectifier/power regulator 160, microcontroller 106 described above, a memory 162 associated with the microcontroller, temperature sensor 112, pressure sensor 84 and a signal conditioning circuit 164 for amplifying the signal from the pressure sensor. The implanted components transmit the temperature adjusted pressure measurement from sensor 84 to local unit 60 via antenna 54. The pressure measurement may be stored in memory 138 within local unit 60, shown on a display within local unit 60, or transmitted in real time to a remote monitoring station.

As mentioned hereinabove, it is desirable to provide a communication system for the remote monitoring and control of an intake restriction device. Through the communication system, a physician may retrieve a history of fluid pressure measurements from the restriction device to evaluate the efficacy of the bariatric treatment. Additionally, a physician may downlink instructions for a device adjustment. A remotely located clinician may access the adjustment instructions through local unit 60. Using the instructions, the clinician may inject a syringe into injection port 36 and add or remove saline from fluid reservoir 80 to accomplish the device adjustment. Alternatively, the patient may access the instructions through local unit 60, and non-invasively execute the instructions in infuser 115 or mechanically adjustable band 153 using antenna 54. Real-time pressure measurements may be uplinked to the physician during the adjustment for immediate feedback on the effects of the adjustment. Alternatively, the patient or clinician may uplink pressure measurements to the physician after an adjustment for confirmation and evaluation of the adjustment.

As shown in FIG. 1, communication system 20 includes local unit 60 and a remote monitoring unit 170, also referred to herein as a base unit. Remote unit 170 may be located at a physician's office, a hospital or clinic, or elsewhere. Remote unit 170 of the present example is a personal computer type device comprising a microprocessor 172, which may be, for example, an Intel Pentium® microprocessor or the like. Alternatively, remote unit 170 may comprise a dedicated or non-dedicated server that is accessible over a network such as the Internet. In the present example, a system bus 171 interconnects microprocessor 172 with a memory 174 for storing data such as, for example, physiological parameters and patient instructions. A graphical user interface 176 is also interconnected to microprocessor 172 for displaying data and inputting instructions and correspondence to the patient. User interface 176 may comprise a video monitor, a touchscreen, or other display device, as well as a keyboard or stylus for entering information into remote unit 170. Other devices and configurations suitable for providing a remote unit 170 will be apparent to those of ordinary skill in the art.

A number of peripheral devices 178 may interface directly with local unit 60 for inputting physiological data related to the patient's condition. This physiological data may be stored in local unit 60 and uploaded to remote unit 170 during an interrogation or other data exchange. Examples of peripheral devices that can be utilized with the present invention include a weight scale, blood pressure monitor, thermometer, blood glucose monitor, or any other type of device that could be used outside of a physician's office to provide input regarding the current physiological condition of the patient. A weight scale, for example, can electrically communicate with local unit 60 either directly, or wirelessly through antenna 54, to generate a weight loss record for the patient. The weight loss record can be stored in memory 138 of local unit 60. During a subsequent interrogation by remote unit 170, or automatically at prescheduled intervals, the weight loss record can be uploaded by microprocessor 136 to remote unit 170. The weight loss record may be stored in memory 174 of remote unit 170 until accessed by the physician.

Figure 9:
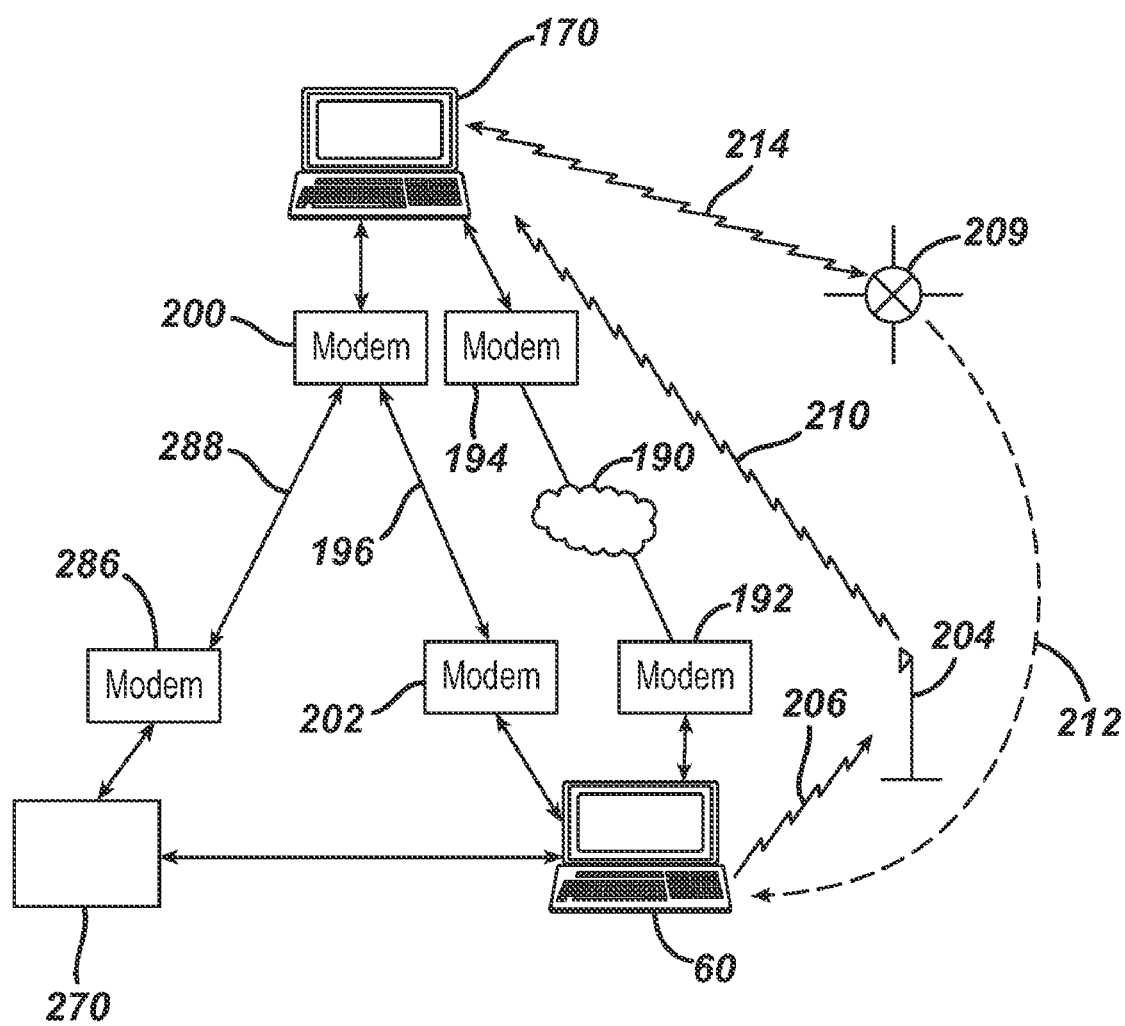
FIG. 9 is a schematic diagram illustrating a number of different communication links between the local and remote units of FIG. 1.

Also as shown in FIG. 1, a communication link 180 is created between local unit 60 and remote unit 170 for transmitting data, including voice, video, instructional information and command signals, between the units. Communication link 180 may comprise any of a broad range of data transmission media including web-based systems utilizing high-speed cable or dial-up connections, public telephone lines, wireless RF networks, satellite, T1 lines or any other type of communication medium suitable for transmitting data between remote locations. FIG. 9 illustrates various media for communication link 180 in greater detail. As shown in FIG. 9, local and remote units 60, 170 may communicate through a number of different direct and wireless connections. In particular, the units may communicate through the Internet 190 using cable or telephone modems 192, 194 or any other suitable device(s). In this instance, data may be transmitted through any suitable Internet communication medium such as, for example, e-mail, instant messaging, web pages, or document transmission. Alternatively, local and remote units 60, 170 may be connected through a public telephone network 196 using modems 200, 202. Units 60, 170 may also communicate through a microwave or RF antenna 204 via tunable frequency waves 206, 210. A communication link may also be established via a satellite 209 and tunable frequency waves 212, 214. In addition to the links described above, it is envisioned that other types of transmission media, that are either known in the art or which may be later developed, could also be utilized to provide the desired data communication between local and remote units 60, 170 without departing from the scope of the invention.

Figure 10:
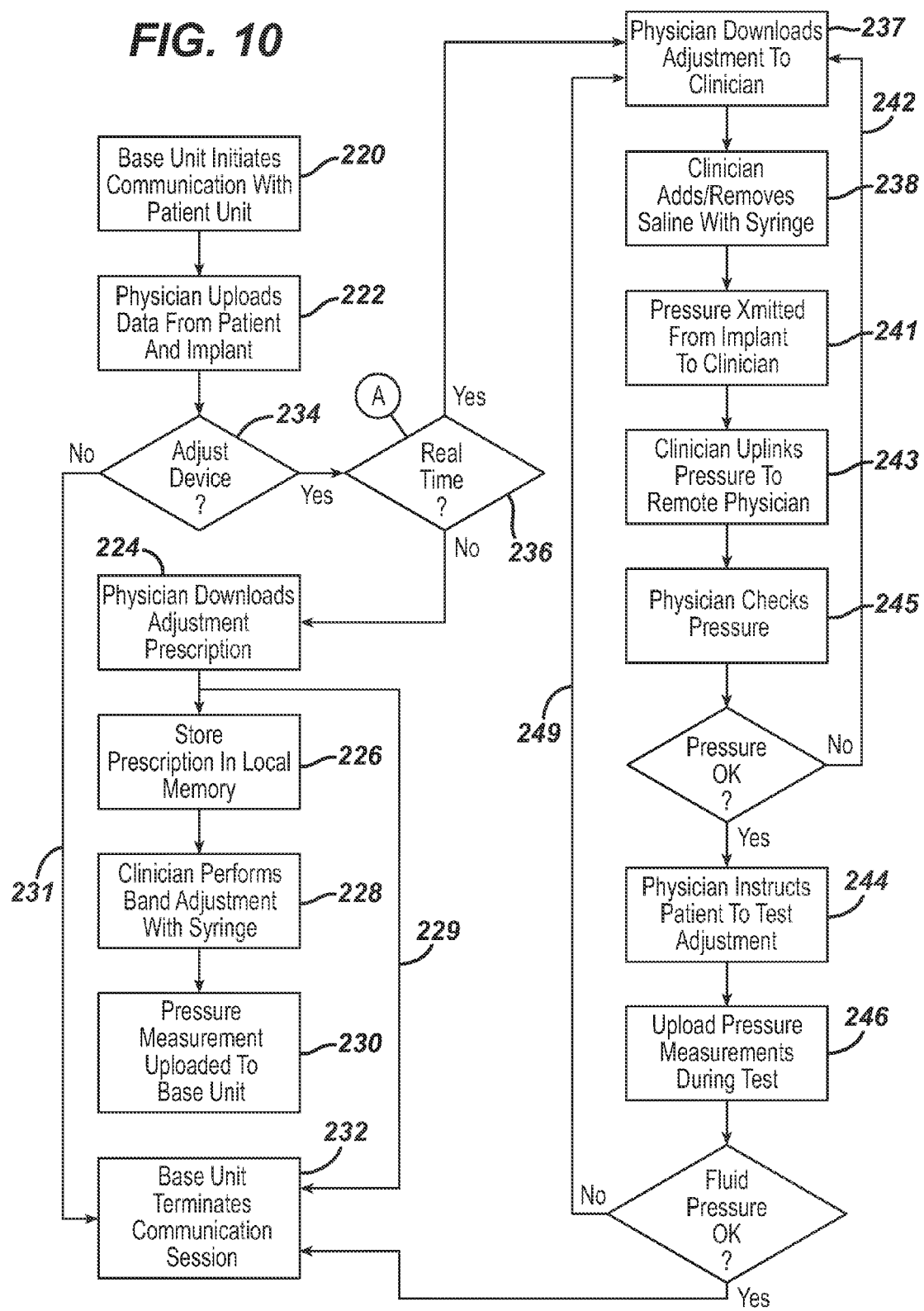
FIG. 10 is a flow diagram of an exemplary communication protocol between the local and remote units for a manually adjustable restriction device.

FIG. 10 is a data flow diagram of an exemplary interaction using bi-directional communication system 20. In this interaction, a physician may download an adjustment prescription that is subsequently manually executed by a clinician present with the patient. A physician initiates the communication session between remote unit 170 and local unit 60 as shown at step 220. The session may be initiated by transmitting an e-mail or instant message via the Internet link 190, or through any of the other communication links described with respect to FIG. 9. During the communication session, the physician may download instructions to memory 138, or may upload previously stored data obtained from device 22 or peripheral devices 178, as shown at step 222. This data may include fluid pressure, a weight history, or a patient compliance report. After the data is uploaded, the physician may evaluate the data and determine the need for a device adjustment, as shown at step 234. If an adjustment is indicated, the physician may download an adjustment prescription command to local unit 60 as shown at step 224. Local unit 60 stores the prescription in memory 138 for subsequent action by a clinician, as shown by step 226. With the patient present, the clinician accesses the prescription from memory 138. The clinician then inserts a syringe into septum 76 of injection port 36 and adds or withdraws the fluid volume specified in the prescription. Following the adjustment, the clinician places antenna 54 over the implant and instructs microcontroller 106 to transmit pressure measurements from sensor 84 to local unit 60. The pressure measurements are uploaded by microprocessor 136 in local unit 60 to remote unit 170, as shown at step 230, to provide a confirmation to the physician that the adjustment instructions were executed, and an indication of the resulting effect on the patient. In an off-line adjustment, the base unit terminates communication with local unit 60 following the downloading of the adjustment prescription, as shown by line 229, or following receipt of the patient data if an adjustment is not indicated, as shown by line 231.

In addition to the off-line adjustment session of steps 220-234, a physician may initiate a real-time interactive adjustment, as indicated at step 236, in order to monitor the patient's condition before, during and after the adjustment. In this instance, the physician downloads an adjustment prescription, as shown at step 237, while the patient is present with a clinician. The clinician inserts a syringe into septum 76 of injection port 36 and adds or withdraws the specified fluid from reservoir 80, as shown at step 238, to execute the prescription. After the injection, the physician instructs the clinician to place antenna 54 over the implant, as shown at step 241, to transmit fluid pressure measurements from the implant to local unit 60. The pressure measurements are then uplinked to the physician through link 180, as shown at step 243. The physician evaluates the pressure measurements at step 245. Based upon the evaluation, the physician may provide further instructions through link 180 to readjust the band as indicated by line 242. Additionally, the physician may provide instructions for the patient to take a particular action, such as eating or drinking, to test the adjustment, as shown at step 244. As the patient performs the test, the physician may upload pressure measurements from the implant, as shown at step 246, to evaluate the peristaltic pressure against the band as the food or liquid attempts to pass through the stoma. If the pressure measurements are too high, indicating a possible obstruction, the physician may immediately transmit additional command signals to the clinician to readjust the band and relieve the obstruction, as indicated by line 249. After the physician is satisfied with the results of the adjustment, the communication session is terminated at step 232. As shown in the flow diagram, communication link 180 enables a physician and patient to interact in a virtual treatment session during which the physician can prescribe adjustments and receive real-time fluid pressure feedback to evaluate the efficacy of the treatment.

Figure 11:
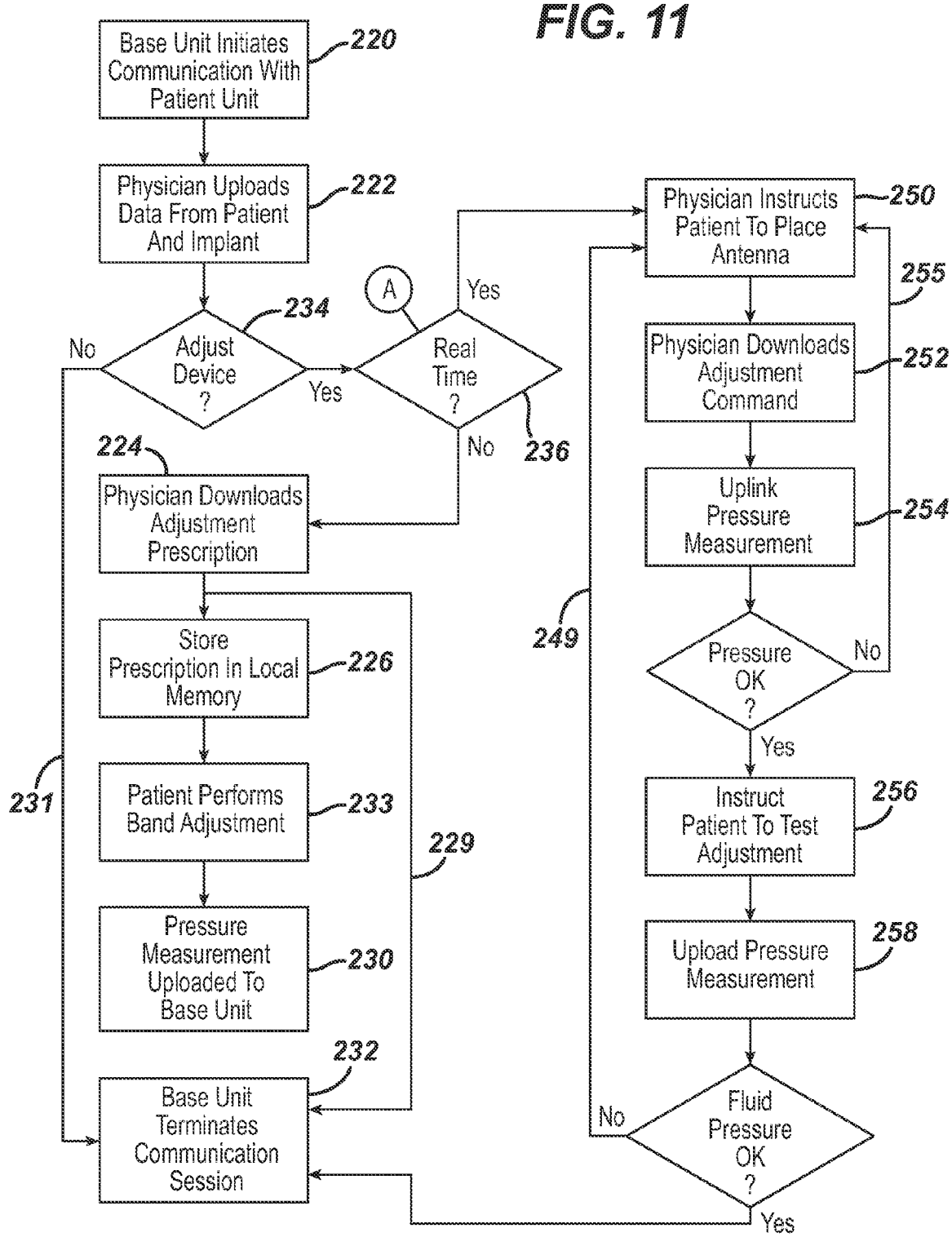
FIG. 11 is a flow diagram of an exemplary communication protocol between the local and remote units for a remotely adjustable restriction device.

In a second exemplary interaction, shown in FIG. 11, the physician downloads an adjustment prescription for a remotely adjustable device, such as infuser 115 shown in FIG. 6. The physician initiates this communication session through link 180 as shown at step 220. After initiating communications, the physician uploads previously stored data, such as fluid pressure histories, from memory 138 of local unit 60. The physician evaluates the data and determines whether an adjustment is indicated. If the physician chooses an off-line adjustment, an adjustment command is downloaded to local unit 60 and stored in memory 138, as indicated in step 224. With the prescription stored in memory 138, the patient, at his convenience, places antenna 54 over the implant area and initiates the adjustment through local unit 60, as indicated in step 233. Local unit 60 then transmits power and command signals to the implanted microcontroller 106 to execute the adjustment. After the adjustment, the patient establishes a communication link with remote monitoring unit 170 and uploads a series of pressure measurements from the implant to the remote unit. These pressure measurements may be stored in memory 174 of remote unit 170 until accessed by the physician.

In an alternative scenario, the patient may perform a real-time adjustment during a virtual treatment session with the physician. In this situation, the physician establishes communication with the patient through link 180. Once connected through link 180, the physician instructs the patient to place antenna 54 over the implant area, as shown at step 250. After antenna 54 is in position, the physician downloads an adjustment command to infuser 115 through link 180, as shown at step 252. During and/or after the adjustment is executed in infuser 115, a series of pressure measurements are uplinked from infuser 115 to the physician through link 180, as shown at step 254. The physician performs an immediate review of the fluid pressure changes resulting from the adjustment. If the resulting fluid pressure levels are too high or too low, the physician may immediately readjust the restriction band, as indicated by line 255. The physician may also instruct the patient to perform a particular action to test the adjustment, such as drinking or eating, as shown at step 256. As the patient performs the test, the physician may upload pressure measurements from the pressure sensor, as shown at step 258, to evaluate the peristaltic pressure against the band as the patient attempts to pass food or liquid through the stoma. If the pressure measurements are too high, indicating a possible obstruction, the physician may immediately transmit additional command signals to readjust the band and relieve the obstruction, as indicated by line 259. After the physician is satisfied with the results of the adjustment, the communication session is terminated at step 232. In the present invention, local unit 60 is at all times a slave to remote unit 170 so that only a physician can prescribe adjustments, and the patient is prevented from independently executing adjustments through local unit 60.

Figure 12:
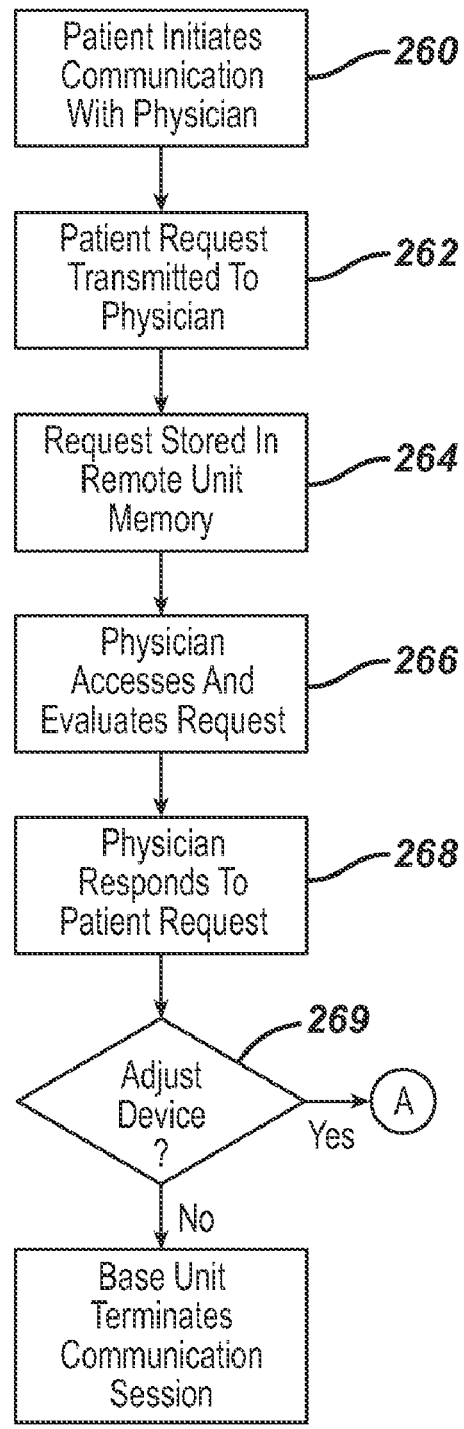
FIG. 12 is a flow diagram of an exemplary communication protocol in which communication is initiated by the patient.

In a third exemplary communication session, shown in FIG. 12, a patient may initiate an interaction with remote unit 170 by entering a request through user interface 140, as shown at step 260. This request may be in the form of an e-mail or other electronic message. At step 262, the patient's request is transmitted through communication link 180 to remote unit 170. At remote unit 170, the patient's request is stored in memory 174 until retrieved at the physician's convenience (step 264). After the physician has reviewed the patient's request (step 266), instructions may be entered through user interface 176 and downloaded to local unit 60. The physician may communicate with the patient regarding treatment or the decision to execute or deny a particular adjustment request, as shown at step 268. If the physician determines at step 269 that an adjustment is required, the physician may initiate a communication session similar to those shown in the flow diagrams of FIGS. 10 and 11. If an adjustment is not indicated, the base unit terminates the session following the responsive communication of step 268.

In addition to the above scenarios, a physician may access local unit 60 at any time to check on patient compliance with previous adjustment instructions, or to remind the patient to perform an adjustment. In these interactions, the physician may contact local unit 60 to request a data upload from memory 138, or transmit a reminder to be stored in memory 138 and displayed the next time the patient turns on local unit 60. Additionally, local unit 60 can include an alarm feature to remind the patient to perform regularly scheduled adjustments, such as diurnal relaxations.

Figure 13:
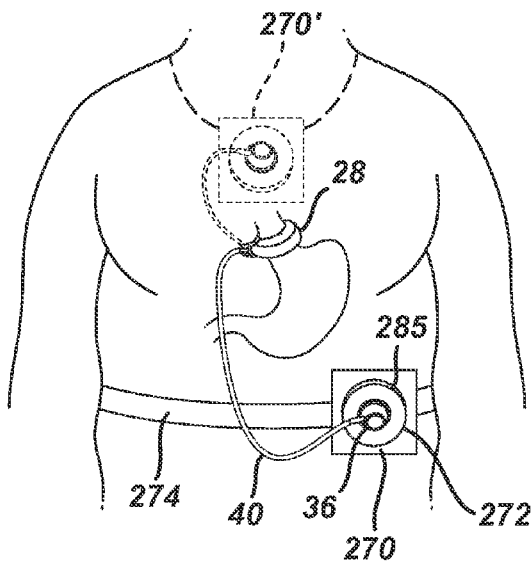
FIG. 13 is a simplified schematic diagram of a data logger for recording pressure measurements from the implanted restriction device.

As mentioned above, communication system 20 can be used to uplink a fluid pressure history to remote unit 170 to allow the physician to evaluate the performance of device 22 over a designated time period. FIG. 13 illustrates a data logger 270 that may be used in conjunction with communication system 22 of the present invention to record fluid pressure measurements over a period of time. In this example, data logger 270 is external to the patient, and is positioned over the region under which injection port 36 is implanted within the patient. In another embodiment, data logger 270 is also implanted within the patient. As shown in FIG. 13, data logger 270 comprises TET and telemetry coils 285, 272 which may be worn by the patient so as to lie adjacent to implanted portion 24. TET coil 285 provides power to the implant, while telemetry coil 272 interrogates the implant and receives data signals, including fluid pressure measurements, through secondary telemetry coil 114. In another embodiment, TET coil 285 and telemetry coil 272 are consolidated into a single coil, and alternate between TET and telemetry functions at any suitable rate for any suitable durations.

The fluid pressure within the restriction band 28 is repeatedly sensed and transmitted to data logger 270 at an update rate sufficient to measure peristaltic pulses against the band. Typically, this update rate is in the range of 10-20 pressure measurements per second. As shown in FIG. 13, data logger 270 may be worn on a belt 274 about the patient's waist to position coils 272 adjacent injection port 36 when the port is implanted in the patient's abdominal area. Alternatively, data logger 270 can be worn about the patient's neck, as shown by device 270', when injection port 36 is implanted on the patient's sternum. Data logger 270 is worn during waking periods to record fluid pressure variations during the patient's meals and daily routines. At the end of the day, or another set time period, data logger 270 may be removed and the recorded fluid pressure data downloaded to memory 138 of local unit 60. The fluid pressure history may be uploaded from memory 138 to remote unit 170 during a subsequent communication session. Alternatively, fluid pressure data may be directly uploaded from data logger 270 to remote unit 170 using communication link 180.

Figure 14:
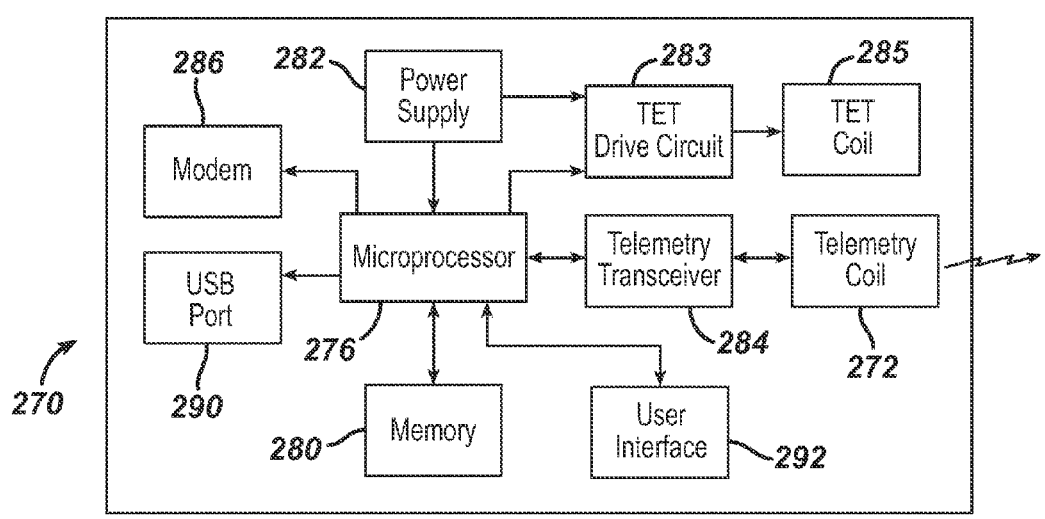
FIG. 14 is a block diagram illustrating the major components of the data logger shown in FIG. 13.

FIG. 14 shows data logger 270 in greater detail. As shown in FIG. 14, data logger 270 includes a microprocessor 276 for controlling telemetry communications with implanted device 24. Microprocessor 276 is connected to a memory 280 for, among other functions, storing pressure measurements from device 24. In the present example, memory 280 comprises 40 Mb of SRAM and is configured to store 100 hours of time stamped pressure data. Of course, any other type of memory 280 may be used, and memory 280 may store any amount of and any other type of data. By way of example only, any other type of volatile memory or any type of non-volatile memory may be used, including but not limited to flash memory, hard drive memory, etc. While data logger 270 of the present example is operational, fluid pressure is read and stored in memory 280 at a designated data rate controlled by microprocessor 276. Microprocessor 276 is energized by a power supply 282. In one embodiment, power supply 282 comprises a rechargeable cell (not shown), such as a rechargeable battery. In one version of this embodiment, the rechargeable cell is removable and may be recharged using a recharging unit and replaced with another rechargeable cell while the spent cell is recharging. In another version of this embodiment, the rechargeable cell is recharged by plugging a recharging adapter into a data logger 270 and a wall unit. In yet another version of this embodiment, the rechargeable cell is recharged wirelessly by a wireless recharging unit. In another embodiment, power supply 282 comprises an ultra capacitor, which may also be recharged. Of course, any other type of power supply 282 may be used.

To record fluid pressure, microprocessor 276 initially transmits a power signal to implanted portion 24 via TET drive circuit 283 and TET coil 285. After the power signal, microprocessor 276 transmits an interrogation signal to implanted portion 24 via telemetry transceiver 284 and telemetry coil 272. The interrogation signal is intercepted by telemetry coil 114 and transmitted to microcontroller 106. Microcontroller 106 sends a responsive, temperature-adjusted pressure reading from sensor 84 via transceiver 158 and secondary telemetry coil 114. The pressure reading is received through coil 272 and directed by transceiver 284 to microprocessor 276. Microprocessor 276 subsequently stores the pressure measurement and initiates the next interrogation request.

When the patient is finished measuring and recording fluid pressure, logger 270 is removed and the recorded pressure data downloaded to local unit 60, or directly to remote unit 170. As shown in FIGS. 9 and 14, data logger 270 may comprise a modem 286 for transmitting the sensed fluid pressure directly to remote unit 170 using a telephone line 288. The patient may connect logger modem 286 to a telephone line, dial the physician's modem, and select a "send" button on user interface 292. Once connected, microprocessor 276 transmits the stored pressure history through the phone line to microprocessor 172 in remote unit 170. Alternatively, data logger 270 may include a USB port 290 for connecting the logger to local unit 60. Logger USB port 290 may be connected to a USB port 198 on local unit 60 (shown in FIG. 8), and the "send" switch activated to download pressure data to memory 138 in the local unit. After the pressure data is downloaded, logger 270 may be turned off through user interface 292, or reset and placed back on the patient's body for continued pressure measurement.

Figure 15:
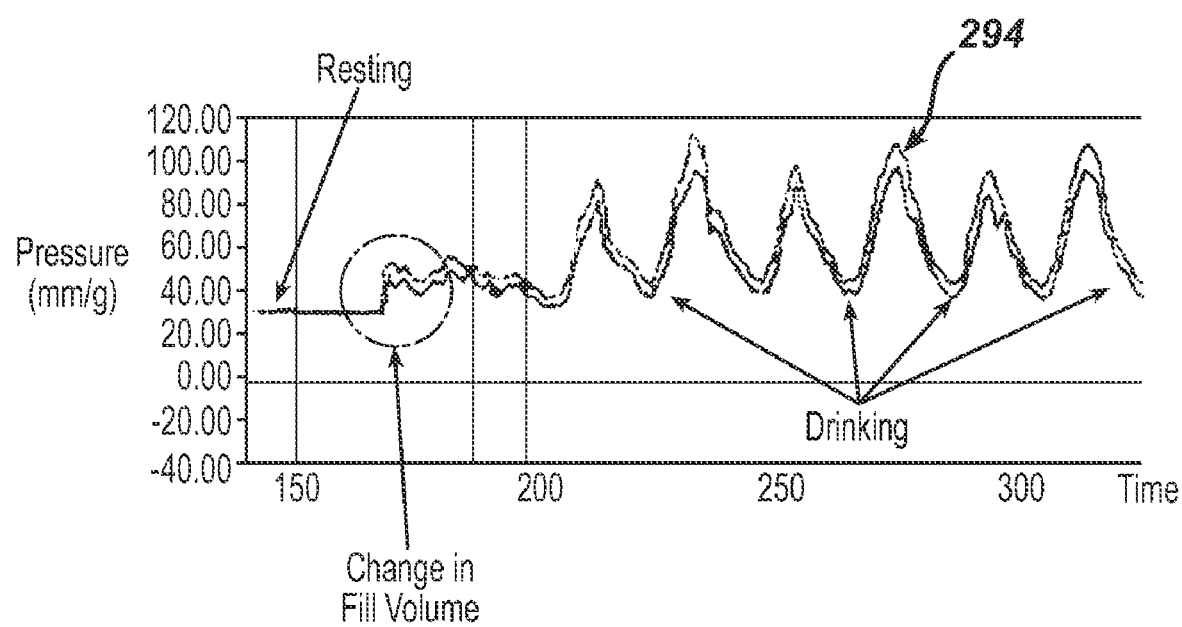
FIG. 15 is a graphical representation of a fluid pressure measurement from the sensor shown in FIG. 4, as communicated through the system of the present invention.

FIG. 15 is a graphical representation of an exemplary pressure signal 294 as measured by sensor 84 during repeated interrogation by local unit 60 or data logger 270 over a sampling time period. Pressure signal 294 may be displayed using graphical user interface 140 of local unit 60 or graphical user interface 176 of remote unit 170. In the example shown in FIG. 15, the fluid pressure in band 28 is initially measured while the patient is stable, resulting in a steady pressure reading as shown. Next, an adjustment is applied to band 28 to decrease the stoma size. During the band adjustment, pressure sensor 84 continues to measure the fluid pressure and transmit the pressure readings through the patient's skin to local unit 60. As seen in the graph of FIG. 15, fluid pressure rises following the band adjustment.

In the example shown, the patient is asked to drink a liquid after the adjustment to check the accuracy of the adjustment. As the patient drinks, pressure sensor 84 continues to measure the pressure spikes due to the peristaltic pressure of swallowing the liquid. The physician may evaluate these pressure spikes from a remote location in order to evaluate and direct the patient's treatment. If the graph indicates pressure spikes exceeding desired levels, the physician may immediately take corrective action through communication system 20, and view the results of the corrective action, until the desired results are achieved. Accordingly, through communication system 20 a physician can perform an adjustment and visually see the results of the adjustment, even when located at a considerable distance from the patient.

In addition to adjustments, communication system 20 can be used to track the performance of an intake restriction device over a period of time. In particular, a sampling of pressure measurements from data logger 270 may be uploaded to the physician's office for evaluation. The physician may visually check a graph of the pressure readings to evaluate the performance of the restriction device. It will be appreciated that long term pressure data may be helpful in seeing when the patient eats or drinks during the day and how much. Such data may thus be useful in compliance management.

Pressure measurement logs can also be regularly transmitted to remote monitoring unit 170 to provide a physician with a diagnostic tool to ensure that a food intake restriction device is operating effectively. For instance, pressure data may be helpful in seeing how much band 28 pressure or tightness varies, and if band 28 tends to obstruct at times. If any abnormalities appear, the physician may use communication system 20 to contact the patient and request additional physiological data, prescribe an adjustment, or, where components permit, administer an adjustment. In particular, communication system 20 may be utilized to detect a no pressure condition within band 28, indicating a fluid leakage. Alternatively, system 20 may be used to detect excessive pressure spikes within band 28 or pressure being stuck at a fixed level, which may indicate a kink in catheter 40 or a blockage within the stoma.

Local unit 60, another type of docking station 360, remote unit 170, or some other device may further comprise a logic that is configured to process pressure data and actively provide an alert to a physician, the patient, or someone else when a dramatic change in pressure is detected or under other predefined conditions. Such an alert may comprise any of the following: an e-mail, a phone call, an audible signal, or any other type of alert. The conditions for and/or type of an alert may also vary relative to the recipient of the alert. For instance, with respect to alerts for physicians, such alerts may be limited to those provided upon an indication that some component of implanted portion 24 has structurally failed (e.g., a kink in catheter 40, a burst band 28, etc.). With respect to alerts for patients, such alerts may be limited to those provided upon an indication that the patient is eating too much, eating to quickly, or if the bite sizes are too big. A variety of other conditions under which alerts may be directed to a physician or patient will be apparent to those of ordinary skill in the art. In addition, it will be appreciated that physicians and patients may receive alerts under similar conditions, or that either party may simply not receive alerts at all.

To the extent that local unit 60 has a graphical user interface permitting the patient to see pressure data, local unit 60 may be used by the patient to evaluate pressure readings at home and notify their physician when the band 28 pressure drops below a specified baseline, indicating the need for an adjustment of the device. Communication system 20 thus has benefits as a diagnostic and monitoring tool during patient treatment with a bariatric device. The convenience of evaluating an intake restriction device 22 through communication system 20 facilitates more frequent monitoring and, components permitting, adjustments of the device.

Figure 19A:
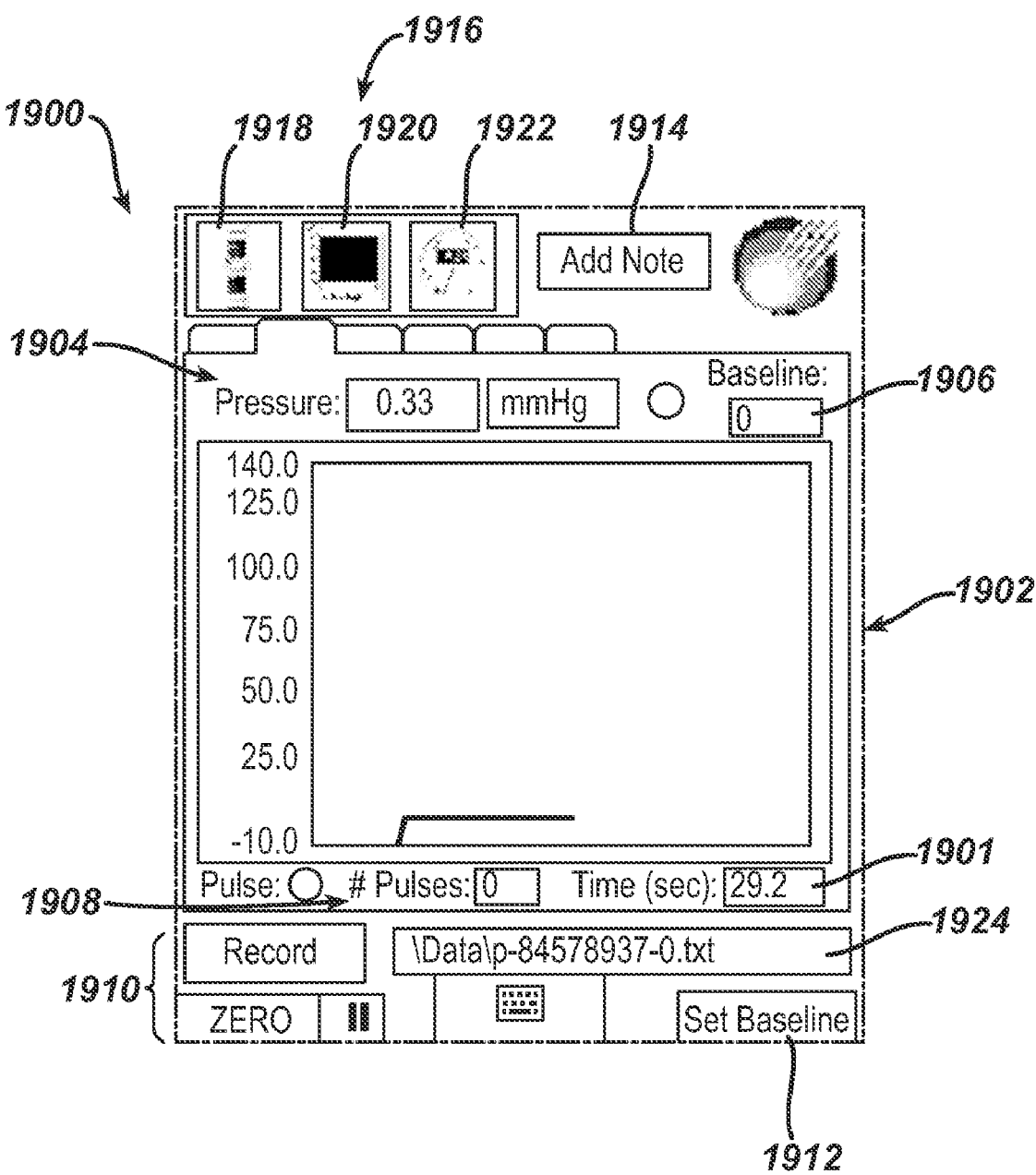
FIG. 19A shows an exemplary pressure graph display for a graphical user interface.

The graphical user interface of local unit 60, remote monitoring unit 170, or another external or physiological monitoring device in the communication system 20, can provide a wide variety of displays based on or related to data or information from the restriction device 22. Further, in some embodiments, the data logger 270 can have such a graphical user interface. The displays can include information about measurements taken by the restriction device 22, such as the measurements of the fluid pressure sensed within a fluid-fillable restriction device, pressure in a mechanically-adjustable restriction device, or other parameters (e.g., pulse widths, pulse durations, pulse amplitude, pulse count or pulse frequency, sensed electrical characteristics, etc.), or about physiological events, conditions (e.g., of the restriction device 22, such as its restricted or fill state), or trends. FIG. 19A, for example, shows one exemplary embodiment of a display 1900 that can be used as part of a graphical user interface. As shown, the display includes a plot or graph 1902 of pressure over time, which is shown as a line graph but could also be a bar graph, scatter graph, or virtually any other graphic representation. The time scale along the horizontal axis 1901 can be automatically sized to the amount of pressure data available or can be user-adjustable, e.g., to examine a time period of interest. The display 1900 can also include a textual indicator 1904, which as shown numerically provides a current or instantaneous pressure reading. A wide variety of other kinds of information also can be presented on display 1900, including a baseline indicator 1906 showing a steady-state or baseline value of the pressure and pulse indicators 1908 showing the number of pulses (for example, the pulses may be pressure pulses which can represent or be caused by the peristaltic contractions of a patient swallowing). In some embodiments, this information can be obtained through user input (via the "Set Baseline" button 1912 or by entering visually detected pulses, for example), but in many embodiments this information can be obtained by analyzing, filtering or otherwise processing pressure or other data from the restriction device 22 and/or data logger 270 via one or more algorithms, which will be discussed in more detail below. The local unit 60, remote monitoring unit 170 or other device can implement these algorithms and continuously update the display 1900 with the results. The display 1900 can also include a cluster 1910 of recording controls to allow a user to control when pressure is recorded or logged to a file, and the location of such a log file can be shown in window 1924. In addition, an annotation function can be provided via control 1914. In other embodiments, the display 1900 can include pressure readings taken from prior visits (for example, prior visits of the same patient, or from previous adjustments of the restriction device), and/or pressure readings of previous peristaltic events representing swallowing, breathing rate, or virtually any other physiological parameter. The display 1900 also can include a patient's name or other identifying information, along with notes, lists of activities or guidelines for the patient, and so on.

Figure 19B:
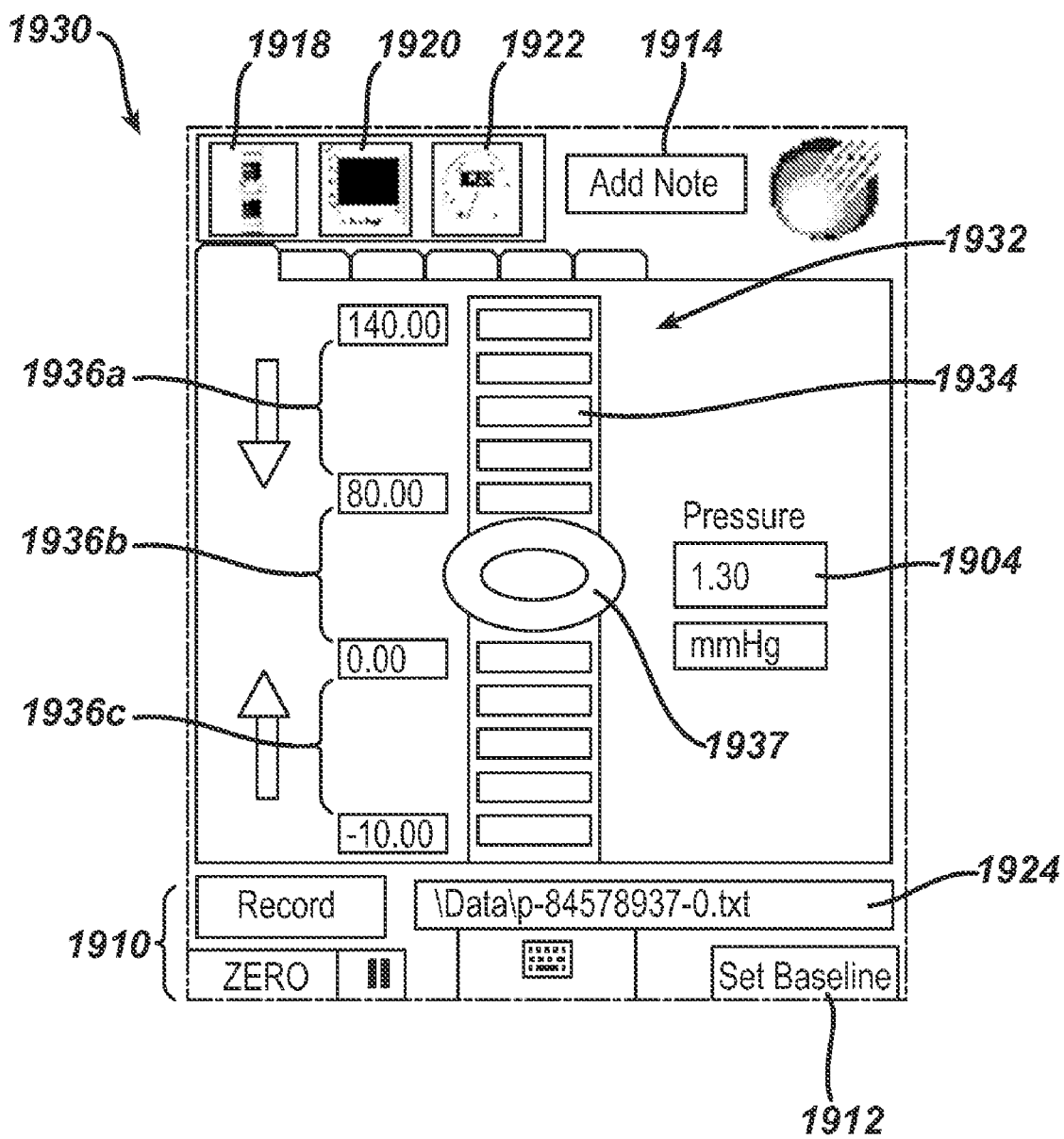
FIG. 19B shows an exemplary pressure meter display for a graphical user interface.

In FIG. 19A, the display 1900 has a menu 1916 that includes three graphics or icons 1918, 1920, 1922. Selection of each one of these icons can cause a different display screen to be presented. As shown in FIG. 19A, the second icon 1920 is selected and the graph 1902 of sensed pressure over time is shown. Selection of the first icon 1918 can lead to a display 1930 as shown in FIG. 19B, which indicates pressure via a meter 1932. In this embodiment the meter 1932 is vertical and linear, however, a wide variety of other orientations and shapes can be used, such as a horizontal meter, circular, and so on. The meter 1932 can include discrete indicators or bars 1934 which can be divided into one or more zones or ranges 1936a-c. As shown, three discrete pressure ranges 1936a-c are provided with limits (in this example, 80 to 140 mmHg, 0 to 80 mmHg, and −10 to 0 mmHg), however any number of pressure ranges can be provided, and their size and endpoints can be adjustable. As one skilled in the art will understand, the ranges 1936a-c can be set by a physician or other user and can vary from patient to patient. In some embodiments, the pressure ranges 1936a-c can correspond to conditions related to an implantable restriction device, for example, the highest range can indicate that the restriction device is over-filled or over-tightened, the middle range can indicate an optimally filled or optimally tightened restriction device, and the lower range can indicate an under-filled or loose restriction device. In use, the pressure can be indicated by a marker 1937, which can represent current pressure, average pressure, or other metrics related to pressure. In some embodiments, the marker 1937 can move continuously along the meter 1932, while in other embodiments, the marker 1936 can move in a discrete fashion from bar 1934 to bar 1934. Display 1930 also can contain many of the same or similar interface elements as in display 1900 shown in FIG. 19A, such as an cluster 1910 of recording controls, a window 1924 showing the location of a log file, and/or an annotation control 1914.

Figure 19C:
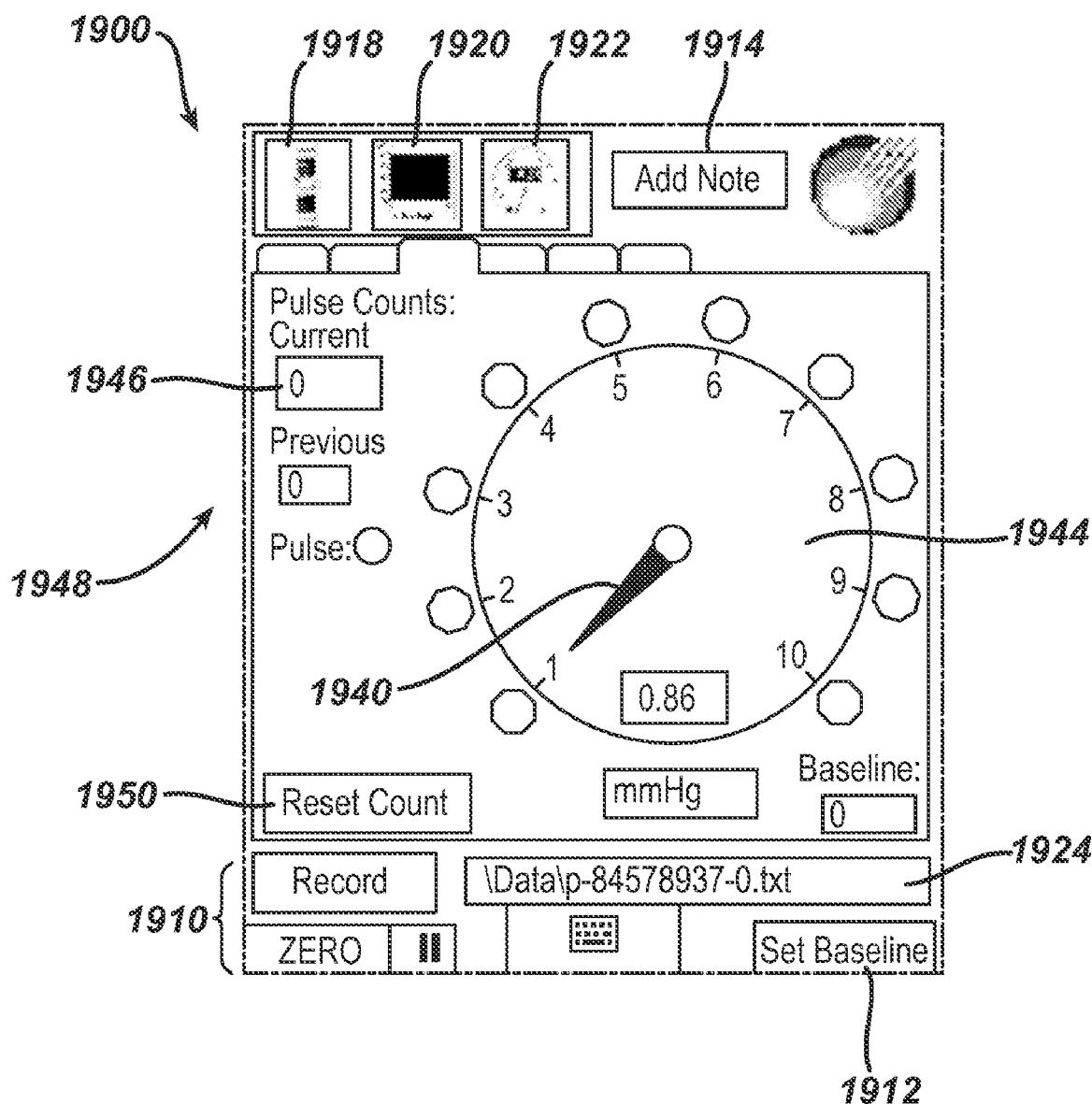
FIG. 19C shows an exemplary pulse counter display for a graphical user interface.

Returning to FIG. 19A, selection of the third icon 1922 can lead to a pulse count display 1940, as shown in FIG. 19C, for counting the number of pulses in a sequence of pulses. The sequence of pulses can represent a peristaltic event such as swallowing. The display 1940 can include a circular meter 1944 with numbering or indicators around its periphery. In use, an indicator needle 1932 can rotate within meter 1944 to provide an indication of the number of pulses detected in a sequence. Textual indicators 1946, 1948 can also be provided to indicate the number of pulses in the current or a past sequence of pulses. Control 1950 can reset the count.

Figure 20:
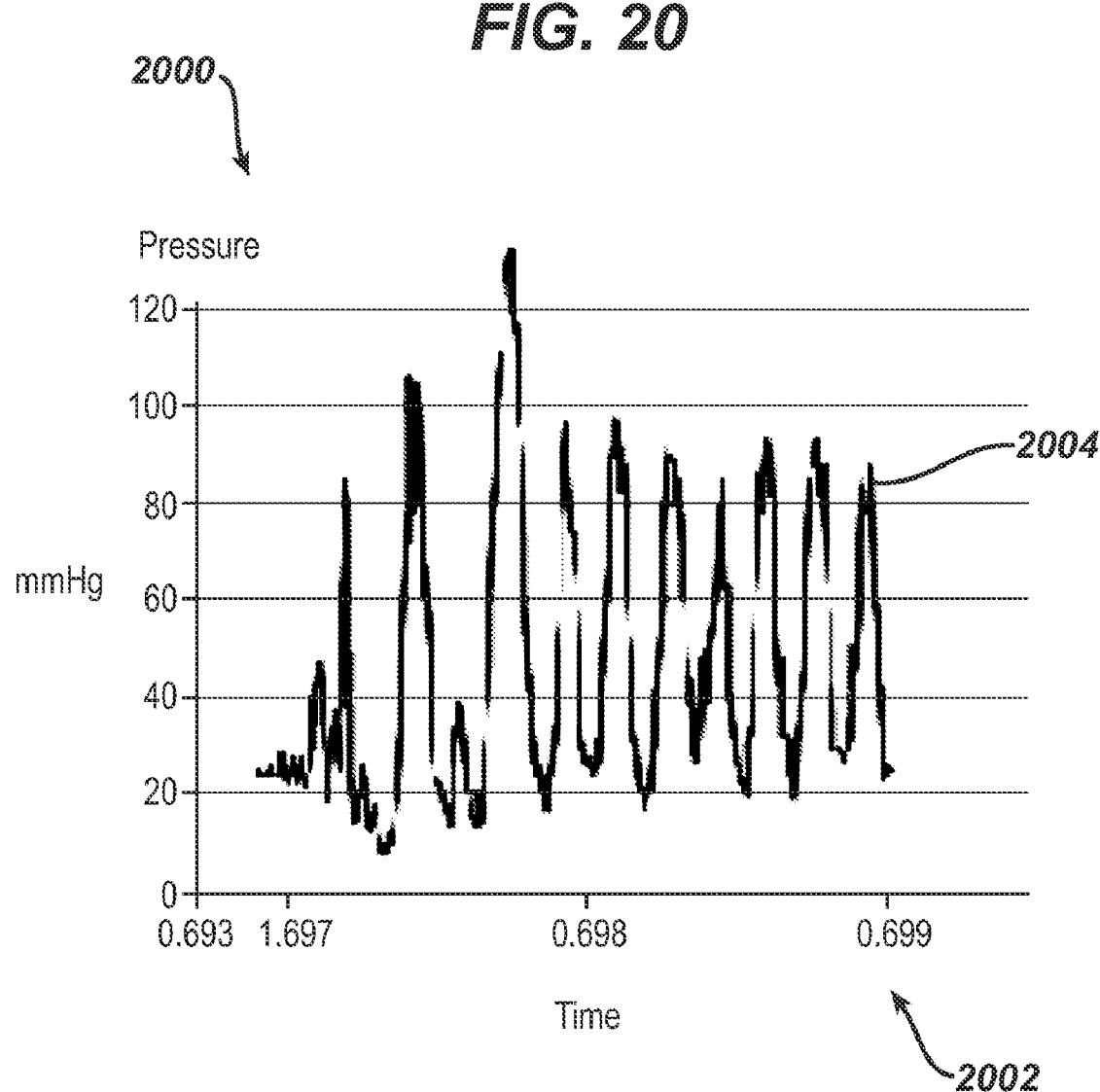
FIG. 20 shows another exemplary pressure graph display for a graphical user interface.

A wide variety of other displays for pressure, pulses, and for other physiological parameters and events can be provided. For example, FIG. 20 shows an alternate waveform display 2000 of pressure vs. time, which provides a time scale delineated by textual markers 2002 along the x-axis. The pressure sensed by the restriction device 22 can be plotted as waveform 2004 in this display 2000. In addition, any of the displays, or the indicator, meters, graphs, or other display elements within them, can be configured to signal an alarm. For example, the pressure graph 1902, the textual indicator 1904, or the meters 1931, 1944 (or other display elements) can flash when the pressure, or other parameter, passes a threshold value. The alarm can also be indicated by an illumination change (e.g., the color, intensity, hue, etc. can change) of the display or a warning message, or other visual indicator. An audible alarm can also be included in addition to or instead of a visual alarm. Any of the displays described herein can use a green-yellow-red bar, circle, or other representative geometric figure, graphic representation or indicator in which color shift occurs as the parameter being sensed changes. For example, the color of an indicator can turn red as the stoma opening nears occlusion (e.g., as indicated by pressure, or otherwise), since this may be health endangering, but can turn yellow as the restriction device loosens (e.g., as indicated by pressure or otherwise), as this may not be considered a life threatening issue. In some embodiments, such colors can be achieved using color light emitting diodes (LEDs) or liquid crystal display (LCD) screens.

Figure 21:
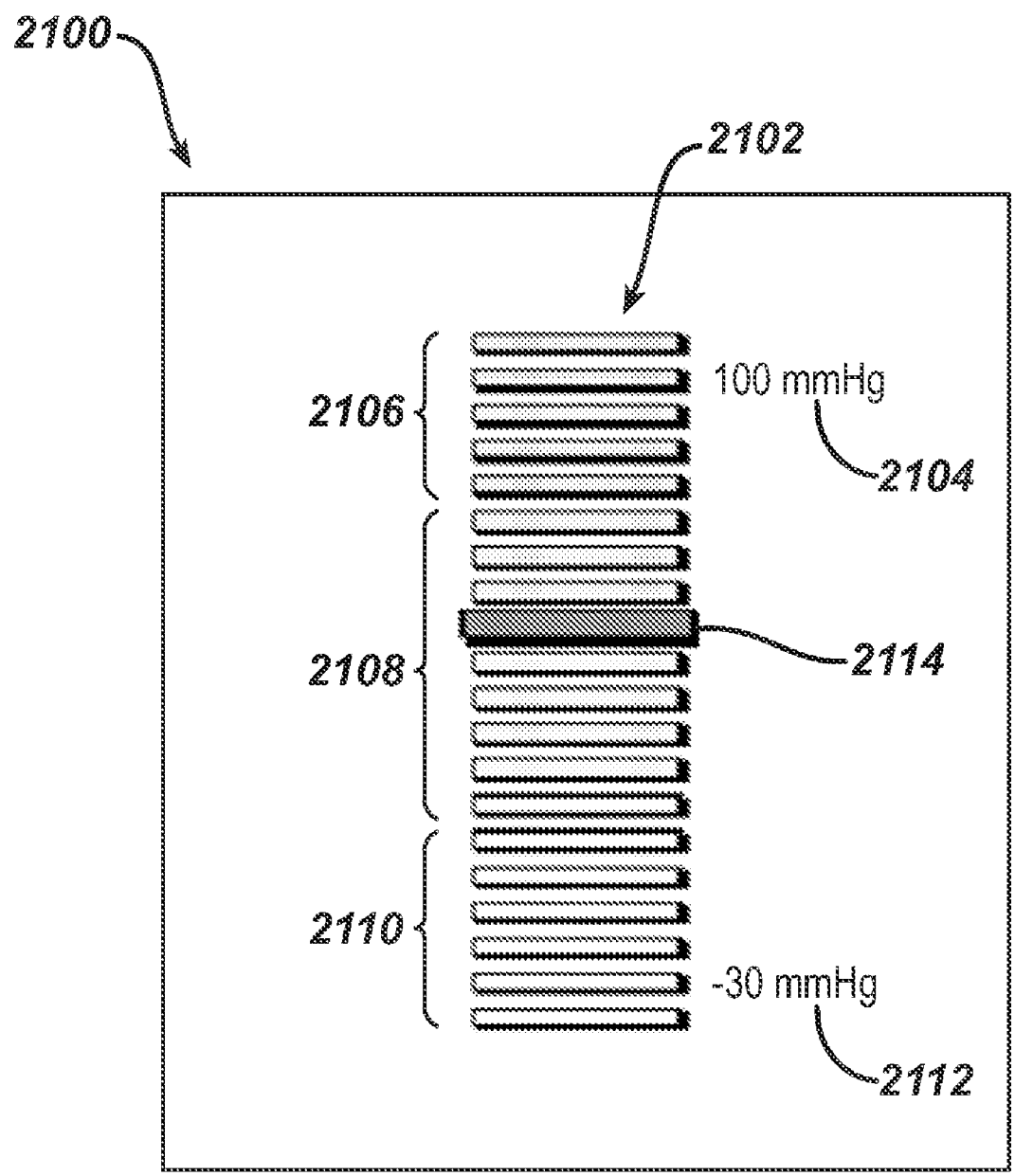
FIG. 21 shows another exemplary pressure meter display for a graphical user interface.

FIG. 21 shows an alternate embodiment of a display 2100 which indicates pressure (for example, current pressure, or pressure at a selected point on display 2000, etc.). Display 2100 can include a vertical meter 2103 that is divided into discrete segments 2102. Each segment can represent a group of pressures, illuminating when the sensed pressure is within the group. As shown in FIG. 21, segment 2114 is illuminated. Labels 2104, 2112 can identify the group. The segments 2102 can be grouped into zones or ranges which can be differentiated by a color. As shown in FIG. 21, the meter 2103 includes three ranges 2106, 2108, 2110 (e.g., red, yellow, green) which can correspond to high, medium, and low pressure, respectively. The ranges 2106, 2108, 2110 can be user-configurable and can correspond to a variety of conditions, for example the high range can correspond to a restriction device 22 being too tight, and so on. A medium range, which can be designated by green, can correspond to an optimally restricted adjustment zone. In use, the meter 2100 can display static and/or dynamic pressure measurements. In static measurements, for example, the meter 2100 can present a baseline pressure or pressure sensed by the restriction device 22, which can be advantageous after implantation or adjustment of the device 22. In dynamic or instantaneous measurements, for example, the meter 2100 can present the pressure detected in the restriction device 22 during a swallowing event. As a result, the illuminated segment 2102 can rise and fall along with changes in pressure.

Figure 22:
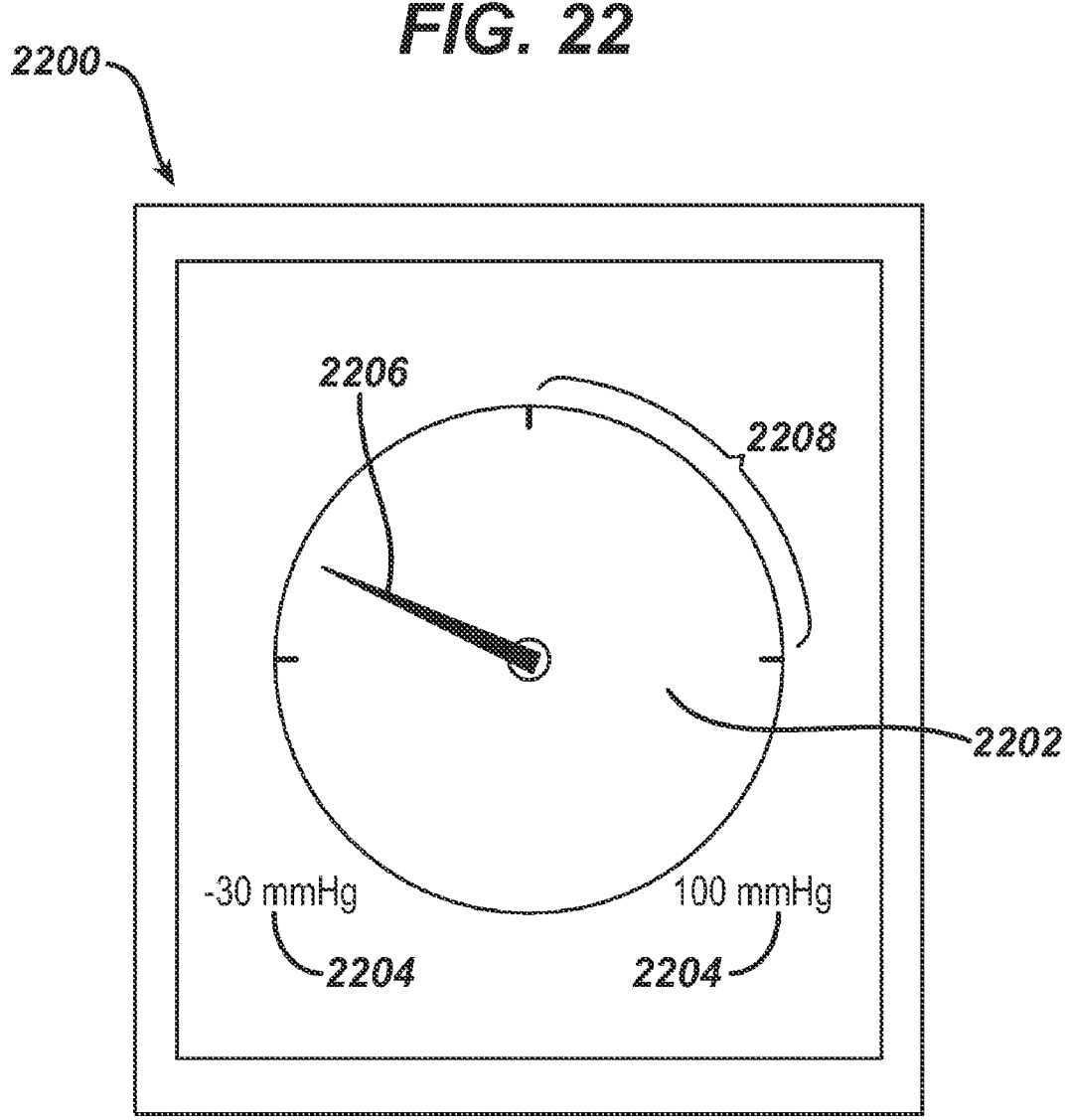
FIG. 22 shows yet another exemplary pressure meter display for a graphical user interface.

FIG. 22 shows another alternate embodiment of a display 2200 which indicates pressure. In this illustrated embodiment, the display 2200 is in the form of a circular meter 2202 with a rotating needle 2206 and labels 2204 located around the periphery of the meter 2202. The meter 2002 can be divided in a plurality of zones or ranges 2208, which can function as previously described. In use, the needle 2206 can rotate to point to the pressure reading, such as baseline pressure, average pressure, static or dynamic pressure, and so on.

Figure 23B:
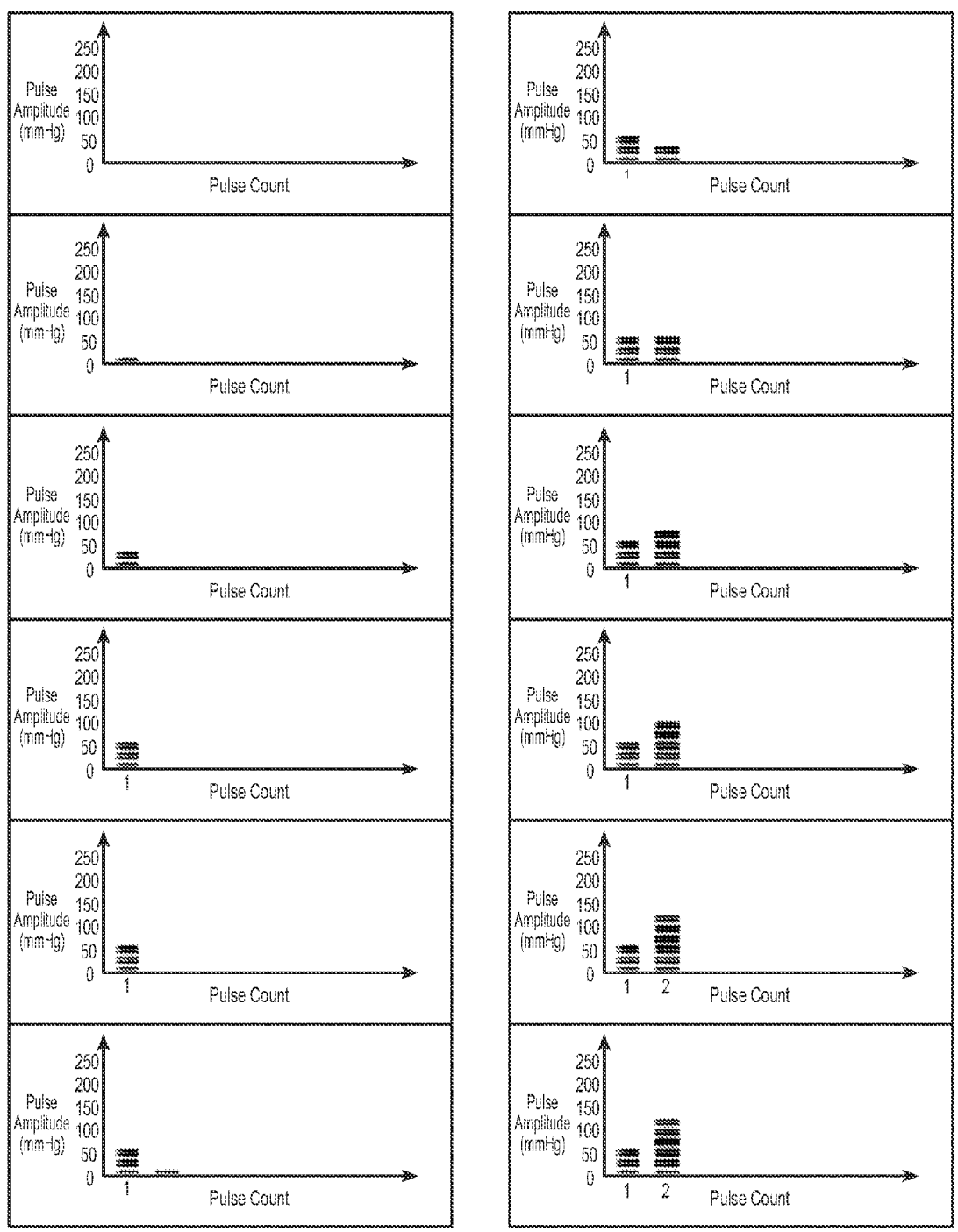
FIG. 23B shows the pulse counter display shown in FIG. 23A over the course of a two-pulse sequence.

FIG. 23A shows an alternate embodiment of a display 2300 which presents information about a sequence of pulses in a parameter, such as can occur with pressure pulses during a swallowing event. As shown, display 2300 includes a graph 2302 of pulse amplitude vs. pulse count. In other embodiments, the magnitude of another parameter can be displayed instead of pressure. The pulse count can correspond to the number of the pulse in a sequence. For example, as shown pulse label 2304 identifies the sixth pulse in a seven pulse sequence. (It should be noted that although the example illustrated in FIG. 23A shows 7 pulses, any number of pulses may be determined and displayed.) In use, vertical bars 2306 can indicate the pulse amplitude of each pulse in the pulse sequence. Each vertical bar 2306a-g can be composed of segments or discrete indicators 2308, each of which can represent a pressure or group of pressures. The height of the vertical bar can represent the magnitude or amplitude of the pressure, which can be an absolute pressure reading or a change in pressure from a baseline pressure or other pressure reference. In use, the vertical bars 2306*a-g* can be displayed as pulses are detected. For example, as the pressure detected by the restriction device 22 rises, the display 2300 can present a rising vertical pressure bar 2306*a* at the left hand side of the graph 2302. If that rise in pressure is considered a pulse, which for example can be determined via algorithms which will be discussed below, then the vertical bar 2306*a* can rise and stop at the peak of the pulse, and a pulse count of "1" can appear on the bottom axis 2308. If another pulse occurs, another bar 2306*b* can appear in similar fashion, accompanied by a pulse count under it reading "2." This can continue until the pressure no longer exhibits pulse events, until the user indicates that the event is over, until the pulses become infrequent (as measured by, for example, inter-pulse periods), or until through the expiration of a predetermined timer, and so on. By way of illustration, FIG. 23B shows a series of displays 2312, as they might appear during the course of a two-pulse sequence.

The display can also include a time stamp for a pulse. For example, as shown on FIG. 23A, a time stamp 2314 can be placed near the pulse count number to indicate the time at which the pulse was detected (e.g., at a time of 4 seconds within a time sample period) or, alternatively, the stamp can indicate the measured duration of the pulse (e.g., the pulse was 4 seconds long), the time since the last pulse (e.g, 4 seconds since the onset, peak or, end, other point of a previous pulse), or any of a wide variety of time metrics related to the pulses. As one skilled in the art will understand, although FIG. 23A shows one time stamp 2314 as an example, time stamps can be associated with other pulses as well.

FIGS. 24-28 show yet other exemplary displays for the graphical user interface of the local unit 60, remote monitoring unit 170, data logger 270, or other device. Generally, these displays can present a static or dynamic image of the stoma, restriction device, and/or surrounding physiology which can change or otherwise be representative of a parameter (such as pressure) sensed by the restriction device. The displays can be still images shown in sequence or at appropriate times, video, or other kind of image. For example, FIG. 24A shows one exemplary display 2400, which has a simulated graphic of the disposition of a region enclosed by a restriction device 2404, which in this example includes a cross-section of the esophagus and stoma 2402 enclosed by a restriction device 2404. The graphic can show the size, shape, configuration, effect of the restriction device 2404 on the region, or other aspect of the region's disposition. The illustration of the esophagus and stoma 2402 region herein is by way of example only, as virtually any region within the body and particularly any anatomical lumen, can be illustrated.

In use, the display 2400 can change in accordance with pressure sensed by the restriction device. For example, FIGS. 24B-C show display 2400 as it might appear after a rise in pressure, with the stoma 2402 decreasing in size and surrounding tissue becoming more constricted. In some embodiments, the display 2400 can be continuously updating (as in a live display), but in other embodiments it can be composed of static or still images which are shown as necessary, each image corresponding to a range of pressures. For example, FIG. 25 shows an exemplary plot of pressure over a time period, and includes three segments labeled A, B, C, each exhibiting a different sensed pressure. FIG. 24A can correspond to segment A, FIG. 24B can correspond to segment B, and FIG. 24C can correspond to segment C. In some embodiments, the segments A,B,C, might correspond to the condition of the restriction device 2404, such as the restriction state or fill state of the restriction device 2404, for example, segment A might be correlated to the restriction device being too loose or under-filled, segment B might represent optimal adjustment, and segment C might represent an overly tight or over-filled or restriction device. In other embodiments, the display 2400 can change in accordance with different sensed pulse amplitudes, pulse counts, or pulse frequencies, and so on (such pulse information obtained, for example, in response to a standardized tests such as a water swallow, or by monitoring pulses characteristics over a prescribed amount of time).

Display 2400 can have a wide variety of other configurations. In some embodiments, one or more reference lines, isobars, or other indicators can be shown on the display 2400. For example, a circle (or one or more concentric circles) can be shown on display 2400, allowing a physician or other user to more easily visualize changes in the size of the stoma 2402 or other changes in the disposition of the region. In some embodiments, the size of the circles can be chosen and labeled to indicate a measured pressure, for example, a label on a circle can represent a sensed pressure, and when the size of the stoma or opening 2402 substantially matches the size of the circle, the sensed pressure can be substantially equal to that labeled pressure. Information such as the sensed pressure and/or the state of the restriction device can also be presented textually on display 2400, or by using color, for example, the image of the stoma turning red as the stoma opening neared occlusion, and so on.

Figures 26A, 26B, 26C:
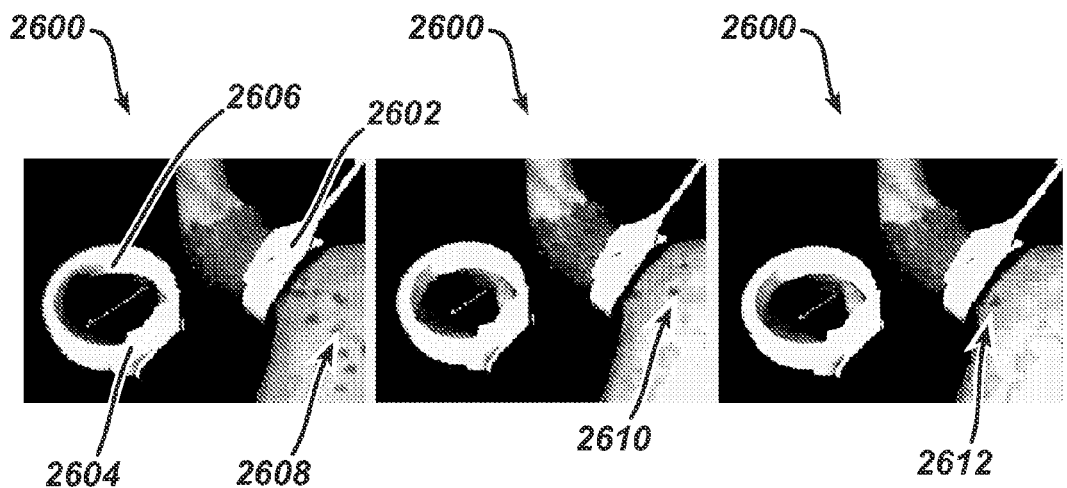
FIG. 26A shows an exemplary display of an implanted restriction device.
FIG. 26B shows the display of FIG. 26A after a change in pressure sensed by the restriction device.
FIG. 26C shows the display of FIG. 26A after another change in pressure sensed by the restriction device.

Furthermore, while in FIGS. 24A-C the display 2400 presents a cross-sectional image, in other embodiments other two-dimensional images (such as a side view, a view of the restriction device alone, and so on), or three-dimensional graphics can be provided. FIGS. 26A-C show an exemplary display 2600 with simulated three-dimensional graphics. As shown, the display 2600 includes a three-dimensional graphic of the disposition of the outside of the esophagus and a portion of the stomach. A restriction device 2602 can be seen enclosing an upper portion of the stomach. The display 2600 can further include a graphic 2604 of the restriction device 2602 that is removed from the upper portion of the stomach which provides a view of the opening 2606 through the restriction device. Labels or other arrows can be used to provide information about the size and shape of the opening 2606. The three-dimensional display 2600 can be updated based on the changing pressures, as was described above in connection with FIGS. 24A-C and 25. For example, FIG. 26A can be shown and correspond to segment A (as shown in FIG. 25), FIG. 26B can be shown and correspond to segment B, and FIG. 26C can be shown and correspond to segment C. Arrows 2608, 2610, and 2612 point to exemplary representations of food particles entering the stomach (e.g., following a swallow) which can be included in each of FIGS. 26A, 26B, and 26C. As illustrated in this embodiment, FIG. 26A shows the largest number of food particles, corresponding to a lower pressure and/or looser fit of the restriction device (relative to FIGS. 26B and 26C). FIG. 26C shows the smallest number of food particles corresponding to a higher pressure and/or tighter fit of the restriction device (relative to FIGS. 26A and 26B). FIG. 26B shows amount of food particles in between FIGS. 26A and 26C, corresponding to a pressure and/or fit that is in between the pressure and/or fit for FIGS. 26A and 26C.

Figures 27A, 27B:
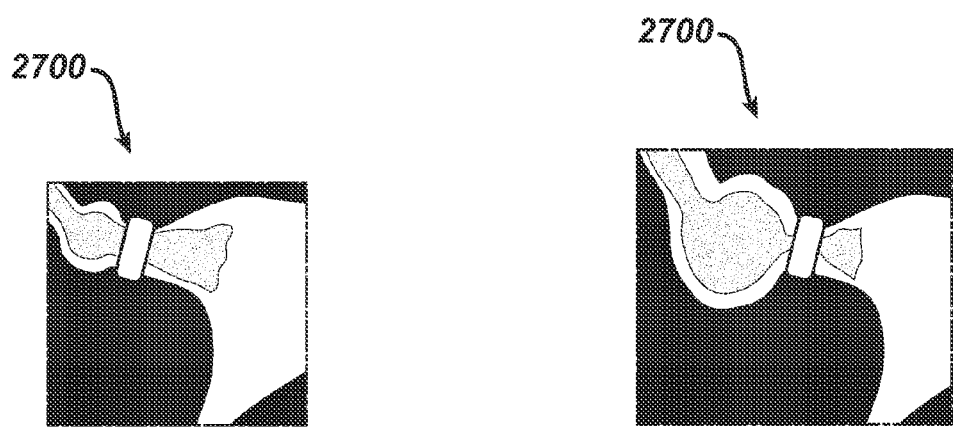
FIG. 27A shows another exemplary display of an implanted restriction device.
Figure 28:
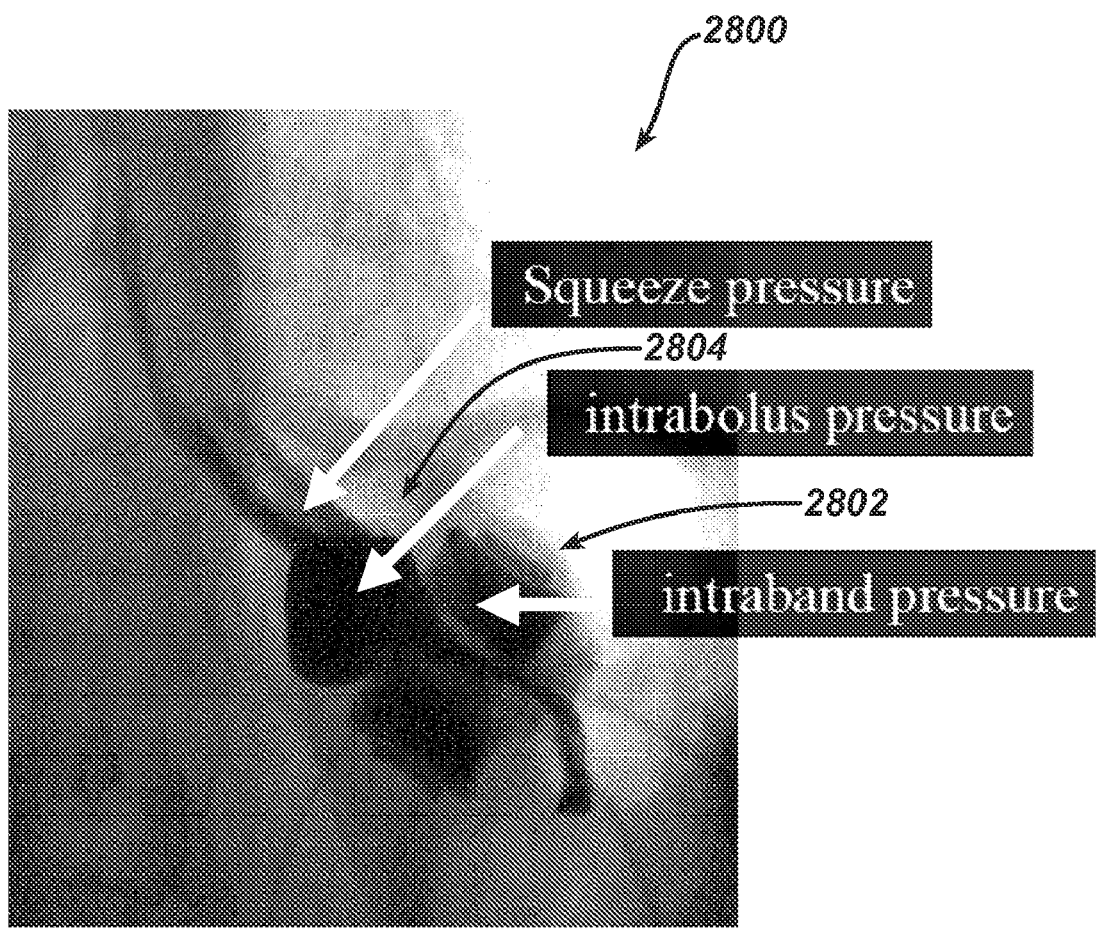
FIG. 28 shows yet another exemplary display of an implanted restriction device.

The display 2600 can be based on or can itself be actual images taken from a body, such as fluoroscopic images, and can include still images or continuously updating images (such as video). In some embodiments, the display 2600 can show barium sulfate passing through the opening defined by the restriction device 2606. Such an arrangement can be advantageous by allowing a user to view how the tissue changes during swallowing and/or to display the fluoroscopy image of the fluoroscopic media (e.g., barium sulfate) passing through the restriction device 2606 with the restriction device at a known setting (e.g., a known fill volume). The fluoroscopic images can be based on a patient's own fluoroscopy or on generic images, any of which can be taken by the user and loaded into the external device. The patient's images or generic images selected to match the patient's body type (or generic images) can then be displayed in response to the sensed pressure. FIGS. 27A-B show an exemplary display 2700 presenting fluoroscopic images in accordance with the detected pressure. FIG. 27A, for example, can correspond to segment A in FIG. 25, while FIG. 27B can correspond to segment B. A fluoroscopic display can also be advantageous for diagnosing physiological conditions related to the restriction device. For example, FIG. 28 shows another exemplary display 2800 based on fluoroscopic imagery. A patient who swallows fluoroscopic media but exhibits insignificant changes or pulses in pressure (e.g., pressure sensed by the restriction device) might be suffering from esophageal peristalsis exhaustion, in which gravity is the only or primary force causing the substance to pass through the esophagus. The display 2800 shown in FIG. 28, which presents a graphic of a restriction device 2802 and a bolus pouch 2804, can be used to diagnose this condition or when this condition is detected. Other forms of medical imaging, such as X-ray, MRI, and so on, can also be used.

As previously mentioned, the graphical user interface of the local unit 60, remote monitoring unit 170, or other external device can be suited to presenting historical trends or data analysis, for example based on parameter data captured by the data logger 270. Such functionality can be useful, for example, when a patient visits a physician to review progress, to address a complication, and/or to adjust an implanted restriction device 22. In one exemplary embodiment, shown in FIG. 29, a display 2900 can present a graph or plot of pressure over a time period, however other physiological parameters such as heart rate, blood pressure, breathing rate, etc., also can be displayed. The display 2900 can include multiple sets of data, for example, a trendline 2902 or other graphical representation of data from a first time period (e.g., a first visit to the physician) and another trendline 2904 or graphical representation of data captured at a later time period (e.g., a second visit to the physician) overlaid on the trendline 2902 from the first time period. The overlay of data from two different time periods can allow a user to compare the trendlines. In some embodiments, the later time period can follow some significant medical event, such as the adjustment of the restriction device 22, and the overlay of data allows for the assessment of the adjustment to the restriction device 22. Although FIG. 29 shows an example with pressure over a time period resulting from a water swallow, pressure from any source or time period can be used. Additionally, a wide variety of data can be plotted in this manner, including weight, weight loss, body mass index, body dimensions, intraband pressure, heart rate (resting and under exercise), breathing rate (resting and under exercise). By way of illustration, FIG. 30 shows an exemplary display 3000 which overlays a trendline 3002 representing patient's breathing rate after one adjustment of a restriction device with a second trendline 3004 representing the breathing rate after a later adjustment. Different types of data can be presented in an overlaid fashion (e.g., pressure trendlines with overlaid heart rate trendlines).

Figure 31A:
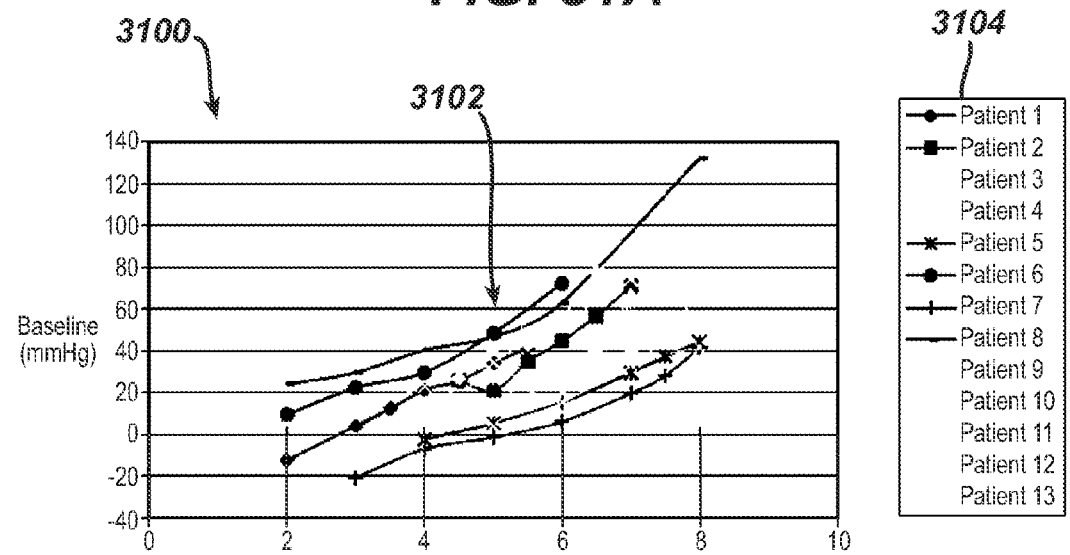
FIG. 31A shows an exemplary graph of population data related to restriction devices.

FIG. 31A shows one exemplary display 3100 which presents data for a population or group of patients. The population data can come from a wide variety of datasets, including data collected by a physician, regional data, nationwide data, and/or data selected from a larger dataset to match the body type (or other physiological/medically significant characteristics) of a particular patient. A variety of parameters can be plotted and compared, but as shown, display 3100 presents a plot of pressure vs. fill volume for a fluid-fillable restriction device. Other parameters such as pulse count, pulse amplitude, pulse width, pulse amplitude, and pulse frequency, can also be plotted against fill volume, and as previously mentioned, such pulse information can be obtained, for example, in response to a tests such as a water or bolus swallow, which can be of a standardized volume and/or viscosity, or by monitoring pulse characteristics over a prescribed amount of time. Display 3100 can also includes several trendlines 3102 (although a bar graph, scatter graph, or other graphical representations of the data can be used), each trendline plotting data from patient, as shown in the legend 3104. More specifically, the trendlines 3102 can represent pressure (baseline pressure, average pressure, or any other pressure measurement) sensed for each patient for a given fill volumes of their restriction device. In some embodiment, this data can come from the data logger 270, but in this example the trendlines 3102 represent static volume measurements taken by adding a known volume of liquid (e.g., 1 ml) at a time to the restriction device 22 and measuring the resulting pressure. As can be seen, the trendlines 3102 exhibit a range of pressures at each volume, which can be due to variability in anatomy or restriction device placement and fit from patient-to-patient. The display 3100 can be useful to allow a physician or other user to visualize how one patient compares to another patient or to a population.

Figure 31B:
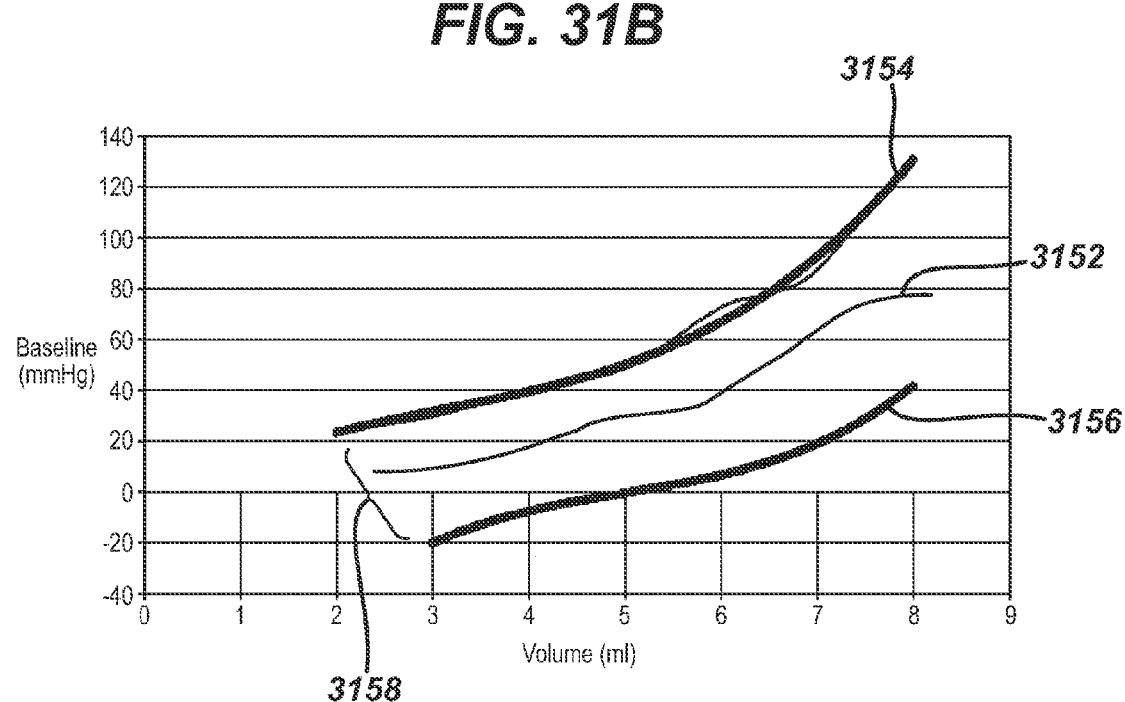
FIG. 31B shows another exemplary graph of population data related to restriction devices.

FIG. 31B shows another exemplary display 3150 which presents data for a population of patients. As shown in FIG. 31B, display 3150 includes a plot of pressure vs. fill volume. The display 3150 includes a trendline 3152 representing a nominal value of the pressure for a group or population of patients. In this embodiment, the nominal value is a mean value, but in other cases it can be a midpoint, weighted average, minimum, maximum, range, standard deviation, or the result of any other mathematical calculation. The display 3150 also can include an upper bound trendline 3154 and a lower bound trendline 3156, which collectively can define a range 3158 around the nominal value. In some embodiments, a trendline for a particular patient can be overlaid onto the display 3152, revealing where the patient falls relative to the population. In other embodiments, the display 3152 can be presented without overlaid data for a particular patient.

Figure 33:
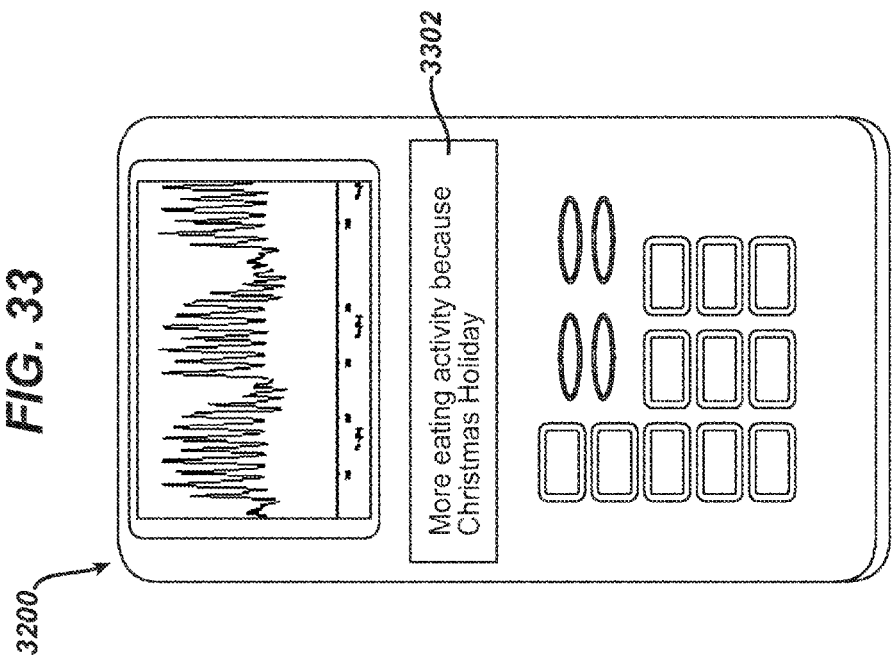
FIG. 33 shows a display device with a screen showing data values which can be annotated via text entered in a text box via an input device.
Figure 32:
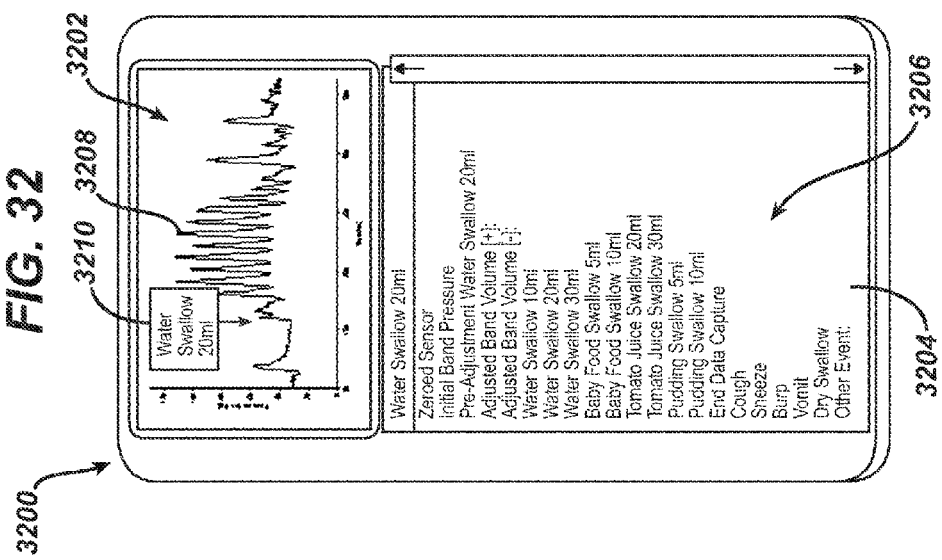
FIG. 32 shows a display device with a screen showing annotated data values, and a menu of annotation events.

Displays also can provide the ability to annotate historical data, particularly data that is collected over an extended time period (e.g., by the data logger). FIG. 32 shows an external device 3200, such as the local unit 60 with a display 3202. It should be understood that the external device 3200 can represent any external device for display and/or physiological monitoring, including the remote monitoring unit 170. As shown, the display 3200 presents a plot of pressure values over a time period and provides the ability to annotate the plotted values using a pull-down menu 3204. The menu 3204 can include a variety of descriptions of predefined events 3206, such as a tests conducted, symptoms, observations by a user or physician, and so on. By way of illustration, in FIG. 32 an annotation 3210 is disposed on the waveform 3208 and includes an annotation marker 2310 which indicates that at a particular point in time a "Water Swallow—20 ml" occurred. A user can annotate historical data in a variety of ways. For example, the external device 3200 can be adapted for home use, and the patient can annotate events on a day-to-day basis. Such an embodiment can be useful if the data logger 270 is capturing data over several days, for example. Alternatively, the external device 3200 can be updated by a physician during patient visits or when the restriction device 22 is adjusted. The physician can annotate the day-to-day data, or can conduct additional tests (such as a Water Swallow) to create data logs separate from any day-to-day monitoring. It should be understood that while display 3200 presents predefined events for annotation, in many embodiments the user can create their own user-defined events for annotation, and/or can enter free-form descriptions about the data values. FIG. 33 shows one exemplary embodiment display 3300 on the external device 3200 in which descriptions can be entered into a text box 3302. In some embodiments, an image or icon can also be used for the description, for example, an icon of a cup can indicate a "Water Swallow" event.

Figure 34:
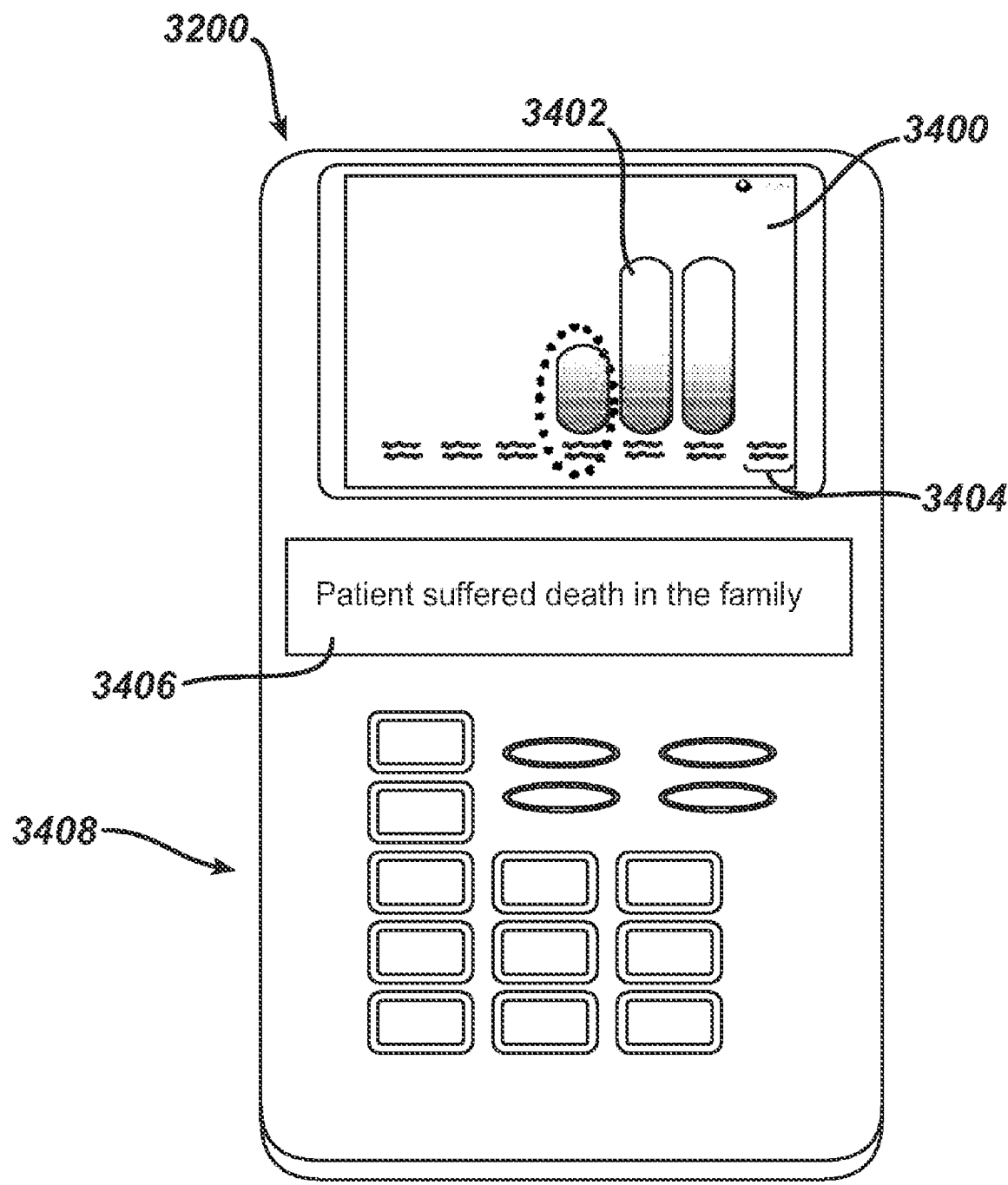
FIG. 34 shows the display device of FIG. 33 with another exemplary screen of data values.

The ability to present data with annotations is not limited to pressure data. For example, FIG. 34 shows a display 3400 that includes a graphical representation, in this case a bar graph, of weight loss over time, with the amplitude of the bars 3402 corresponding to the amount of the weight loss. As shown, a bar 3402 is provided for a series of dates 3404. A user can enter comments or annotations associated with each bar 3402 and/or date 3404 in text box 3406, which can be helpful for tracking and/or revealing events in the patient's life that affect weight loss. The external device 3200 can include a keypad 3408 or other user input device for this purpose.

Any or all of the preceding displays can be provided in virtually any combination to create a graphical user interface for the local unit 60, remote monitoring unit 170, data logger 270, or other physiological monitoring device. In some embodiments, a remote server can be provided to allow users to download displays and/or display elements they desire to a local unit 60 or remote monitoring unit 170. For example, a library of display screens, display modes, visual skins, desktop images, screensavers, and other display configurations can be available for download, allowing a user to customize the graphical user interfaces of the devices. In addition, the remote server can provide the ability to store and categorize displays and/or display elements that were customized or designed and uploaded by users. Such functionality can allow users to exchange and to share display elements with one another.

In addition, any or all of the graphical user interface and/or displays described herein can be repurposed by being modified, altered, erased, reprogrammed, upgraded, revised, added to, and so on. For example, a device having a graphical user interface can be obtained, and desired modifications can be made by programming the appropriate software through a data input port or docking station (e.g., USB port 198 shown in FIG. 8) of the local unit 60, remote monitoring unit 170, or other physiological monitoring unit. In other embodiments, such modifications can be performed telemetrically. For example, additional icons, graphs, indicators and so on can be added, displays customized for a particular user, and so on. Use of such techniques, and the resulting device, are all within the scope of the present application.

Figure 16:
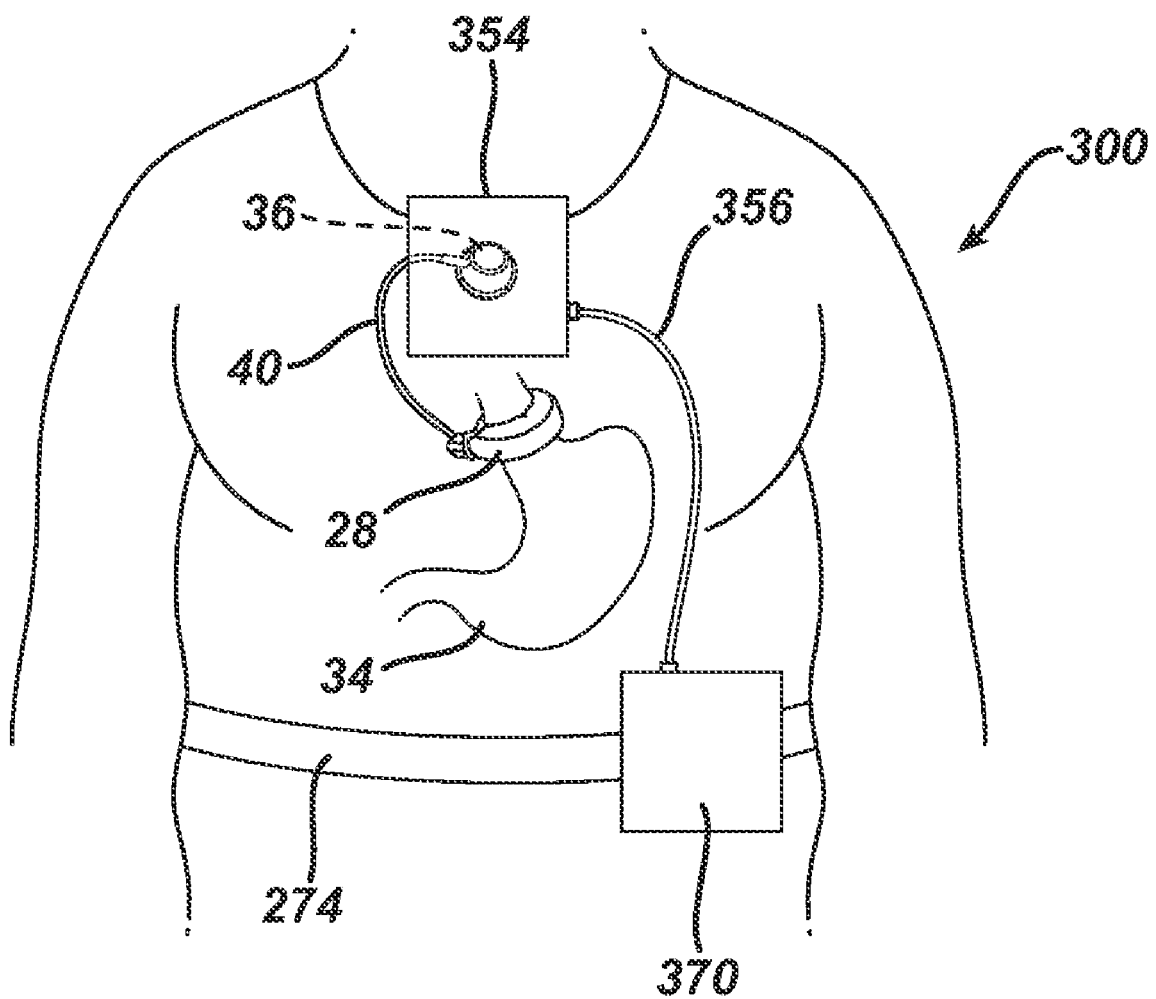
FIG. 16 is a simplified schematic diagram of a data logging system for recording pressure measurements from the food intake restriction device shown in FIG. 1.

An alternate embodiment of a data logging system 300 is shown in FIG. 16. In this example, data logging system 300 comprises a coil head 354 and a data logger 370. Coil head 354 and data logger 370 are in communication via a cable 356. Cable 356 is detachable from coil head 354 and data logger 370. Of course, it will be appreciated that cable 356 is merely exemplary, and that any suitable alternative may be used, including but not limited to a wireless transmitter/receiver system. In the present example, coil head 354 is worn around the neck of the patient, and is positioned generally over injection port 36. Data logger 370 is worn on a belt 274 about the patient's waist. Of course, these respective locations are merely exemplary, and it will be appreciated that coil head 354 and data logger 370 may be positioned elsewhere. By way of example only, where injection port 36 is implanted in the patient's abdomen, coil head 354 may be worn on a belt 274. It will also be appreciated that coil head 354 and data logger 370 are represented as simple blocks in FIG. 16 for illustrative purposes only, and that either of coil head 354 or data logger 370 may be provided in a variety of shapes, sizes, and configurations.

Figure 17:
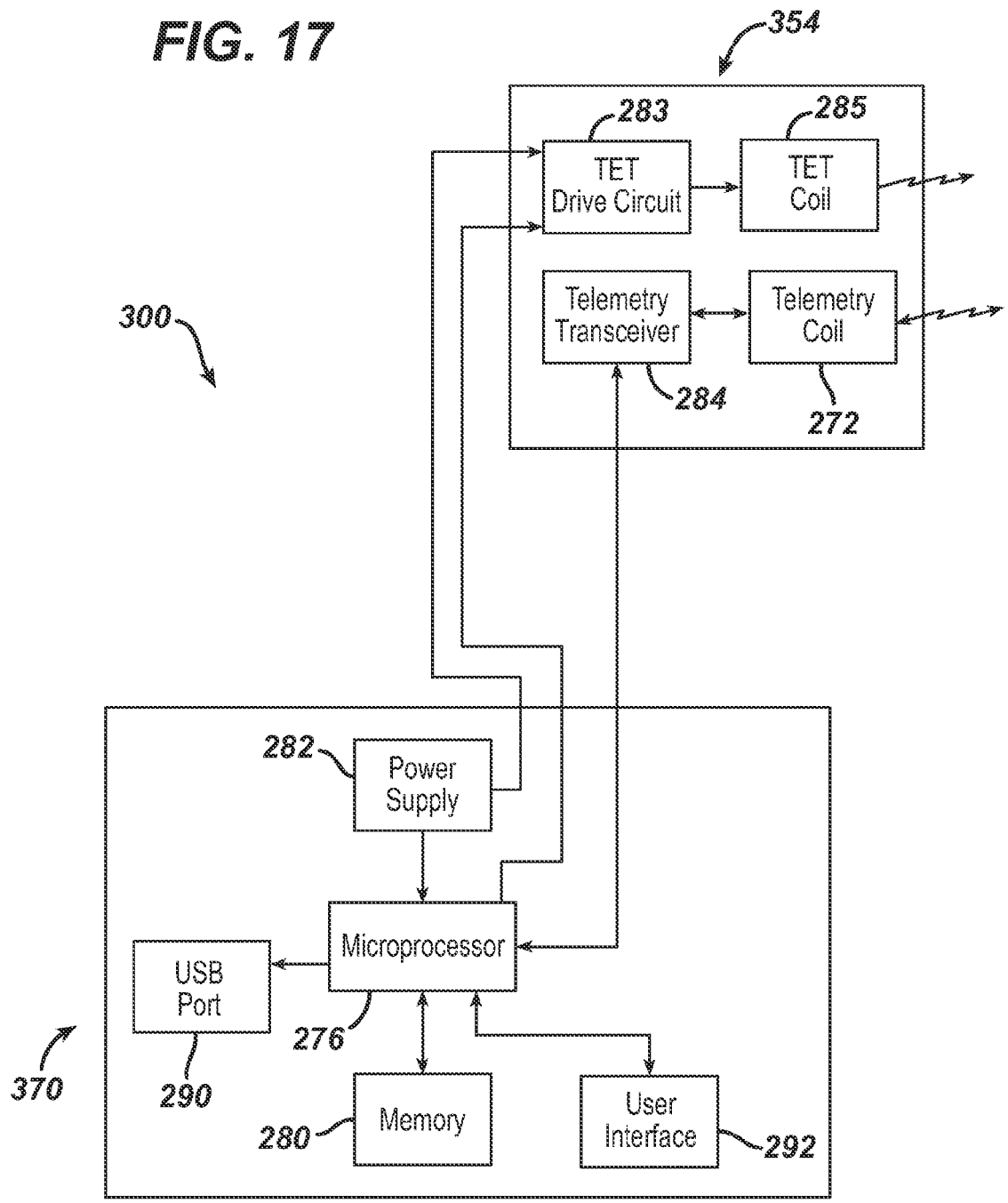
FIG. 17 is a block diagram illustrating several components of the data logging system shown in FIG. 16.

Exemplary components of data logging system 300 are shown in FIG. 17. As shown, data logger 370 comprises a microprocessor 276, a memory 280, a power supply 282, a USB port 290, and a user interface 292. Coil head 354 comprises a TET drive circuit 283, a telemetry transceiver 284, a TET coil 285, and a telemetry coil 272. TET drive circuit 283 is configured to receive power from power supply 282 via cable 356. TET drive circuit is further configured to receive signals from microprocessor 276 via cable 356. Telemetry transceiver 284 is configured to receive signals from microprocessor 276, and transmit signals to microprocessor 276, via cable 356. In another embodiment, telemetry transceiver 284 is configured to only transmit signals to microprocessor 276. It will be appreciated that many of the components depicted in FIG. 17 are similar to those depicted in FIG. 14 and described in the accompanying text. Accordingly, the above discussion of such components with reference to FIG. 14 may also be applied to the components shown in FIG. 17. In the present example, coil head 354 and data logger 370 may be viewed as a separation of components comprising data logger 270 (described above) into two physically separate units. It will further be appreciated that any of the components shown in FIG. 17, as well as their relationships, functions, etc., may be varied in any suitable way.

In the present example, coil head 354 is configured similar to and functions in a manner similar to antenna 54 described above. TET coil 285 of coil head 354 is configured to provide power to injection port 36. Of course, to the extent that any other devices (e.g., a pump, etc.) are implanted in the patient that are configured to receive power from a TET coil 285, TET coil 285 may also provide power to such devices. Power provided by TET coil 285 may be provided to TET coil 285 by and regulated by TET drive circuit 285, which may itself receive power from power supply 282 via cable 356. Such power provided to TET drive circuit 283 may be regulated by microprocessor 276 via cable 356. In addition, or in the alternative, microprocessor 276 may regulate the manner in which TET drive circuit 285 provides power to TET coil 285. Other suitable configurations and relationships between these components, as well as alternative ways in which they may operate, will be apparent to those of ordinary skill in the art. It will also be appreciated that, while the present example contemplates the use of RF signaling through TET coil 285, any other type of powering technique, as well as alternative power communicators, may be used.

Telemetry coil 272 of coil head 354 is configured to receive signals from coil 114 of injection port 36, including signals indicative of the pressure of fluid within the implanted device (e.g., pressure of fluid within the injection port 36, within catheter 40, and/or within adjustable band 28, pressure obtained using pressure sensor 84, etc.) and signals indicative of temperature. It will be appreciated that telemetry coil 272 may also receive any other type of signal representing any other type of information from any other source. Signals received by telemetry coil 272 are communicated to telemetry transceiver 284, which is configured to communicate such signals to microprocessor 276 via cable 356. Telemetry transceiver 284 may perform any appropriate translation or processing of signals received from telemetry coil 272 before communicating signals to microprocessor 276. Other suitable configurations and relationships between these components, as well as alternative ways in which they may operate, will be apparent to those of ordinary skill in the art. It will also be appreciated that components may be combined. By way of example only, TET coil 285 and telemetry coil 272 may be consolidated into a single coil, and alternate between TET and telemetry functions at any suitable rate for any suitable durations. In addition, while the present example contemplates the use of RF signaling through telemetry coil 272, it will be appreciated that any other type of communication technique (e.g., ultrasonic, magnetic, etc.), as well as alternative communicators other than a coil, may be used.

Data logger 370 may receive pressure measurements throughout a given day, and store the same in memory 280, thereby recording fluid pressure variations during the patient's meals and daily routines. In the present example, memory 280 comprises 40 Mb of SRAM and is configured to store 100 hours of time stamped pressure data. Of course, any other type of memory 280 may be used, and memory 280 may store any amount of and any other type of data. By way of example only, any other type of volatile memory or any type of non-volatile memory may be used, including but not limited to flash memory, hard drive memory, etc. While data logger 370 of the present example is operational, fluid pressure is read and stored in memory 280 at a designated data rate controlled by microprocessor 276. In one embodiment, fluid pressure is repeatedly sensed and transmitted to data logger 370, then stored in memory 280, at an update rate sufficient to measure peristaltic pulses against adjustable band 28. By way of example only, the update rate may range between approximately 10-20 pressure measurements per second. Other suitable update rates may be used.

In another embodiment, implanted portion 24 comprises a memory (not shown). By way of example only, such implanted memory may be located in injection port 36 or elsewhere. Such implanted memory may be used for a variety of purposes, to the extent that such memory is included. For instance, such implanted memory may store the same data as memory 280 of data logger 370, such that implanted memory provides a backup for memory 280 of data logger 370. In this version, such data may be further retained in implanted memory for archival purposes, may be replaced on a daily basis, may be replaced or updated after data logger 370 transmits the same data to remote unit 170, or may otherwise be used. It will also be appreciated that an implanted memory may be used to store pre-selected information or pre-selected types of information. For instance, an implanted memory may store maximum and minimum pressure measurements, fluoroscopic images or video of a patient swallowing, and/or any other information. Other information suitable for storing in an implanted memory will be apparent to those of ordinary skill in the art. It will also be appreciated that any type of memory may be implanted, including but not limited to volatile (e.g., SRAM, etc.), non-volatile (e.g., flash, hard drive, etc.), or other memory.

In the present example, microprocessor 276 is energized by a power supply 282. In one embodiment, power supply 282 comprises a rechargeable cell (not shown), such as a rechargeable battery. In one version of this embodiment, the rechargeable cell is removable and may be recharged using a recharging unit and replaced with another rechargeable cell while the spent cell is recharging. In another version of this embodiment, the rechargeable cell is recharged by plugging a recharging adapter into a data logger 370 and a wall unit. In yet another version of this embodiment, the rechargeable cell is recharged wirelessly by a wireless recharging unit. In another embodiment, power supply 282 comprises an ultra capacitor, which may also be recharged. Of course, any other type of power supply 282 may be used.

Data logger 370 of the present example may be configured to provide an alert to the patient under a variety of circumstances in a variety of ways. For instance, data logger 370 may provide an audible and/or visual alert when there is a drastic change in fluid pressure. Alternatively, data logger 370 may provide an audible and/or visual alert upon a determination, based at least in part on pressure data, that the patient is eating too much, too quickly, etc. Data logger 370 may also alert the patient upon a determination that coil head 354 is not communicating with injection port 36 properly. Still other conditions under which a patient may be alerted by data logger 370 will be apparent to those of ordinary skill in the art. It will also be appreciated that user interface 292 may comprise any number or types of features, including but not limited to a speaker, an LED, and LCD display, an on/off switch, etc. In the present example, user interface 292 is configured to provide only output to the patient, and does not permit the patient to provide input to data logger 370. User interface 292 of the present example thus consists of a green LED to show that the power supply 282 is sufficiently charged and a red LED to show that the power supply 282 needs to be recharged. Of course, user interface 292 may alternatively permit the patient to provide input to data logger 370, and may comprise any suitable components and features.

Figure 18:
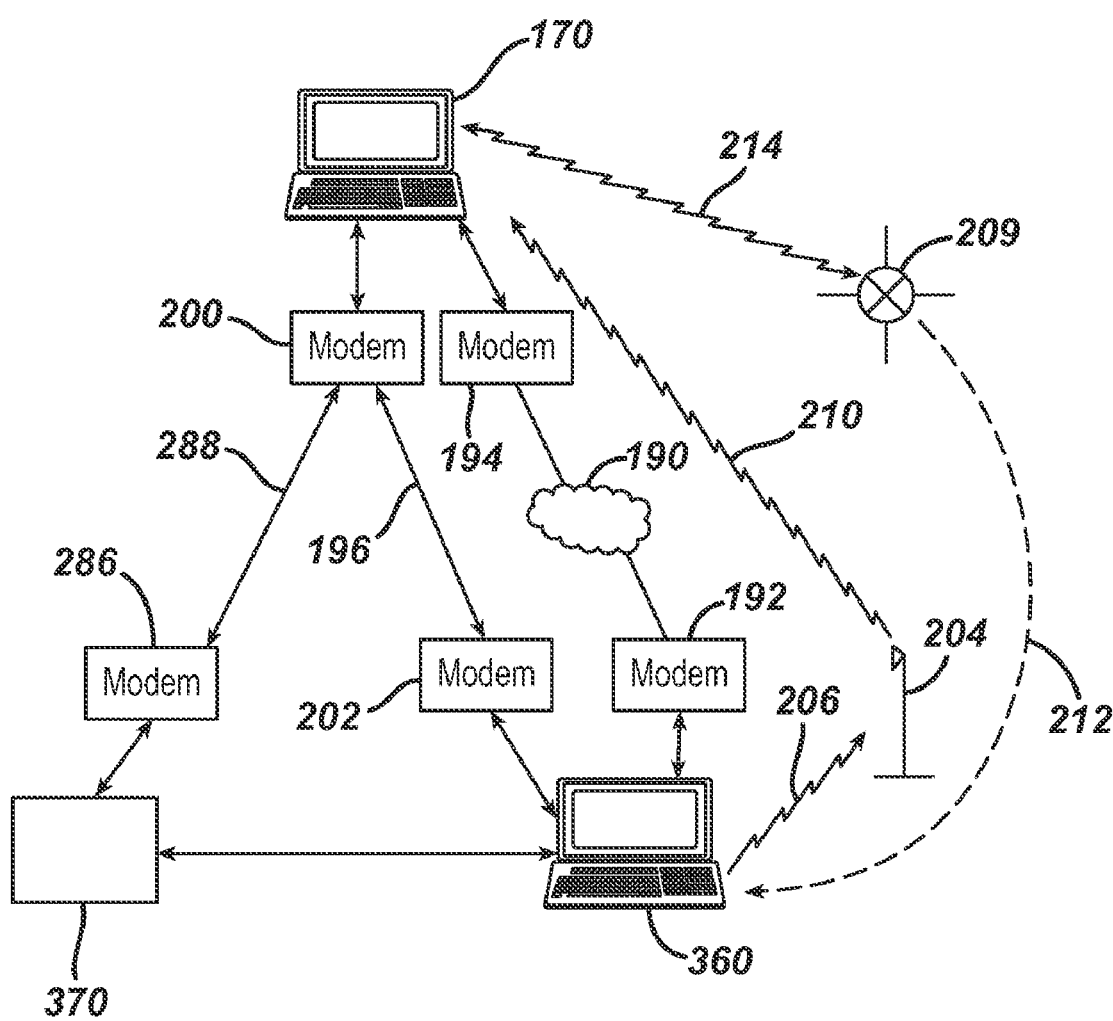
FIG. 18 is a simplified schematic diagram showing the data logging system shown in FIG. 16 in a docking state with a number of different communication links.

As shown in FIG. 18, data logging system 300 further comprises a docking station 360. Docking station 360 is configured to receive data communications from data logger 370, and is further configured to transmit data communications to remote unit 170. In the present example, data logger 370 comprises a USB port 290, such that docking station 360 may receive communications from data logger 370 via a USB cable (not shown) coupled with USB port 290. In one embodiment, docking station 360 comprises the patient's personal computer. Of course, docking station 360 may receive communications from data logger 370 in any other suitable way. For instance, such communications may be transmitted wirelessly (e.g., via RF signals, Bluetooth, ultrawideband, etc.).

In another embodiment, docking station 360 is dedicated to coupling with data logger 370, and comprises a cradle-like feature (not shown) configured to receive data logger 370. In this example, the cradle-like feature includes contacts configured to electrically engage corresponding contacts on data logger 370 to provide communication between docking station 360 and data logger 370. Docking station 360 may thus relate to data logger 370 in a manner similar to docking systems for personal digital assistants (PDAs), BLACKBERRY® devices, cordless telephones, etc. Other suitable ways in which data logger 370 and docking station 360 may communicate or otherwise engage will be apparent to those of ordinary skill in the art. It will also be appreciated that docking station 360 is depicted in FIG. 18 as a desktop computer for illustrative purposes only, and that docking station 360 may be provided in a variety of alternative shapes, sizes, and configurations.

In one embodiment, docking station 360 comprises local unit 60 described above. Accordingly, it will be appreciated that the above discussion referring to components depicted in FIG. 9 may also be applied to components depicted in FIG. 18. Similarly, methods such as those shown in FIGS. 10-12 and described in accompanying text may also be implemented with docking station 360. In another embodiment, data logger 370 comprises local unit 60. In yet another embodiment, data logger 370 is provided with an AC adapter or similar device operable to recharge power supply 282, and data logger 370 further comprises an Ethernet port (not shown) enabling data logger 370 to be connected directly to a network such as the Internet for transmitting information to remote unit 170. It will therefore be appreciated that any of the features and functions described herein with respect to local unit 60 and/or docking station 360 may alternatively be incorporated into data logger 370 or may be otherwise allocated.

In one exemplary use, the patient wears coil head 354 and data logger 370 throughout the day to record pressure measurements in memory 280. At night, the patient decouples data logger 370 from coil head 354 and couples data logger 370 with docking station 360. While data logger 370 and docking station 360 are coupled, docking station 360 transmits data received from data logger 370 to remote unit 170. To the extent that power supply 282 comprises a rechargeable cell, docking station 360 may be further configured to recharge the cell while data logger 370 is coupled with docking station 360. Of course, it will be immediately apparent to those of ordinary skill in the art that a patient need not necessarily decouple data logger 370 from coil head 354 in order to couple data logger 370 with docking station 360. It will also be appreciated that pressure measurements may be recorded in memory 280 during the night in addition to or as an alternative to recording such measurements during the day, and that pressure measurements may even be recorded twenty four hours a day. It is thus contemplated that the timing of pressure measurement taking and recordation need not be limited to the daytime only. It is also contemplated that every pressure measurement that is taken need not necessarily be recorded.

As described above, data logger 370 is configured to receive, store, and communicate data relating to the pressure of fluid. However, data logger 370 may receive, store, and/or communicate a variety of other types of data. By way of example only, data logger 370 may also receive, process, store, and/or communicate data relating to temperature, EKG measurements, eating frequency of the patient, the size of meals eaten by the patient, the amount of walking done by the patient, etc. It will therefore be appreciated that data logger 370 may be configured to process received data to create additional data for communicating to docking station 360. For instance, data logger 370 may process pressure data obtained via coil head 354 to create data indicative of the eating frequency of the patient. It will also be appreciated that data logger 370 may comprise additional components to obtain non-pressure data. For instance, data logger 370 may comprise a pedometer or accelerometer (not shown) to obtain data relating to the amount of walking done by the patient. Data obtained by such additional components may be stored in memory 280 and communicated to docking station 360 in a manner similar to pressure data. Data logger 370 may also comprise components for obtaining data to be factored in with internal fluid pressure measurements to account for effects of various conditions on the fluid pressure. For instance, data logger 370 may comprise a barometer for measuring atmospheric pressure. In another embodiment, data logger 370 comprises an inclinometer or similar device to determine the angle at which the patient is oriented (e.g., standing, lying down, etc.), which may be factored into pressure data to account for hydrostatic pressure effects caused by a patient's orientation. Alternatively, an inclinometer or other device for obtaining non-pressure data may be physically separate from data logger 370 (e.g., implanted). Still other types of data, ways in which such data may be obtained, and ways in which such data may be used will be apparent to those of ordinary skill in the art.

The data captured by the data logger 270 (or data logger 370, or any other data logger) can be processed and analyzed in a variety of ways. In many embodiments, the local unit 60, remote monitoring unit 170, data logger 270, 370 or other external device, can be configured to execute one or more data processing algorithms which can be used in tracking and analyzing physiological parameters and events, and also can produce results that can be presented in the graphical user interface displays previously described. It should be understood that the captured and/or logged data can provide information about a wide variety of sensed parameters, including without limitation pressure (e.g., of a fluid or otherwise). Sensed parameters can also include pulse counts, pulse widths, pulse amplitudes, pulse durations, pulse frequency, sensed electrical characteristics (e.g., voltages, capacitances, etc.), and so on.

Figure 35A:
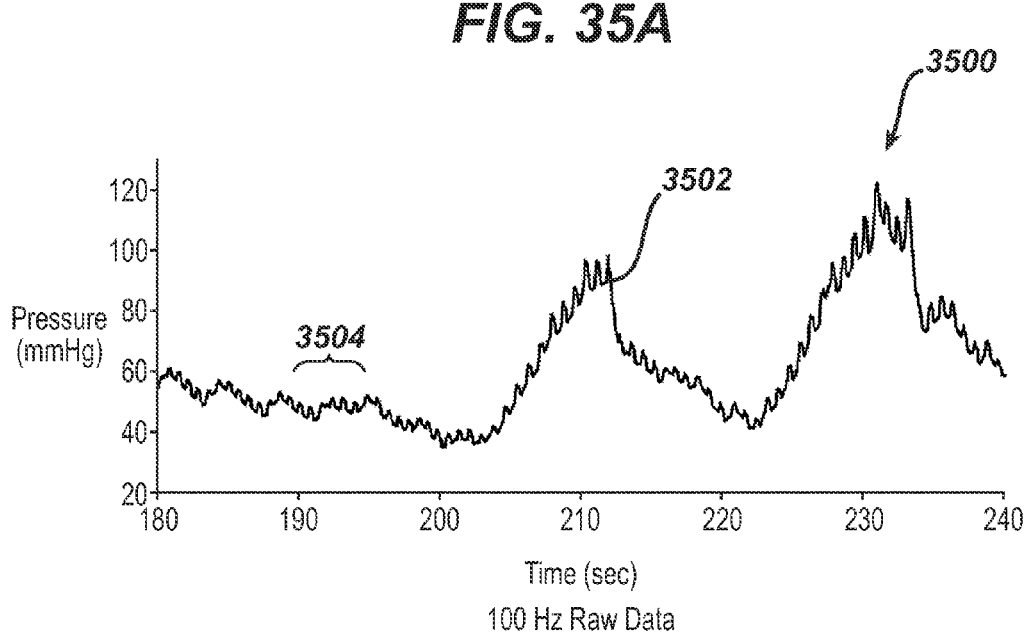
FIG. 35A shows an exemplary plot of pressure values over time collected from a restriction device at a 100 Hz data rate.
Figure 35B:
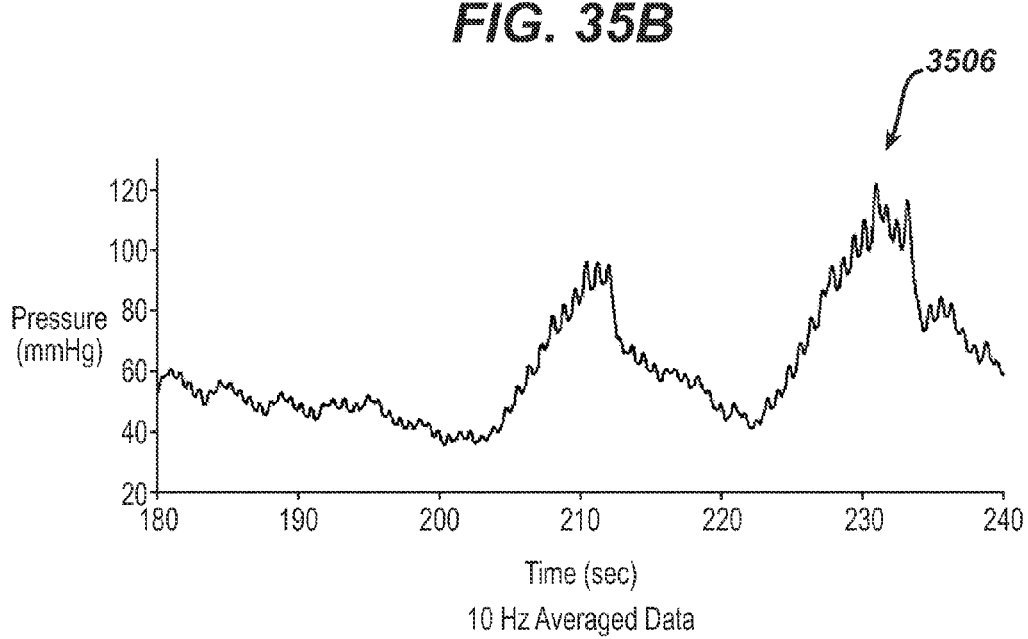
FIG. 35B shows an exemplary plot of pressure values over time from FIG. 35A which have been converted to a 10 Hz data rate.
Figure 35C:
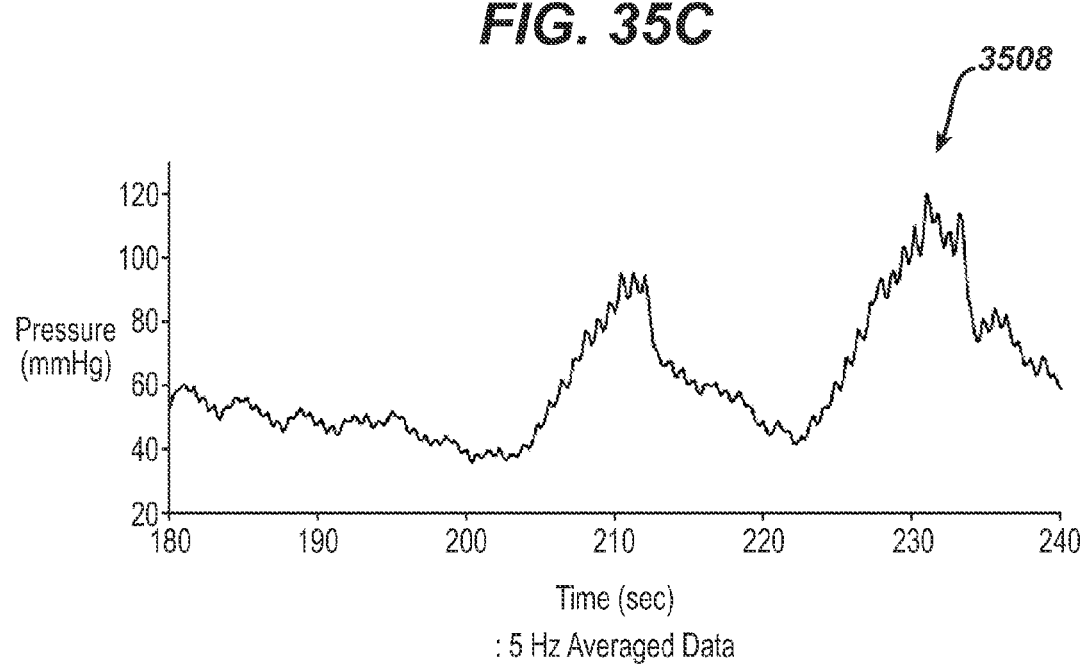
FIG. 35C shows an exemplary plot of pressure values over time from FIG. 35A which have been converted to a 5 Hz data rate.
Figure 35D:
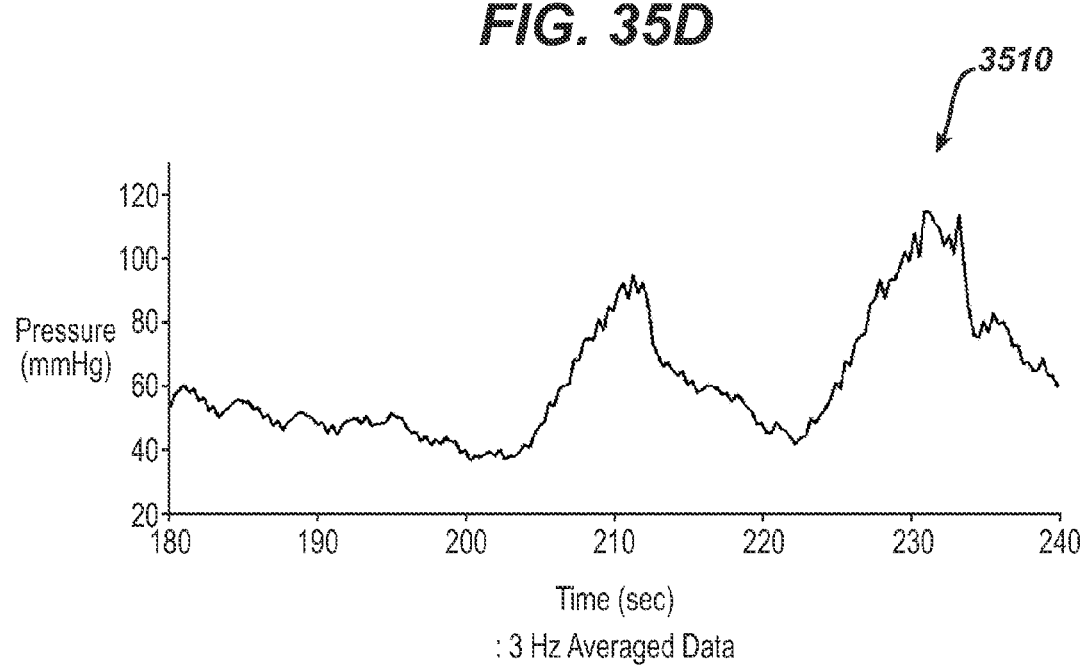
FIG. 35D shows an exemplary plot of pressure values over time from FIG. 35A which have been converted to a 3 Hz data rate.
Figure 35E:
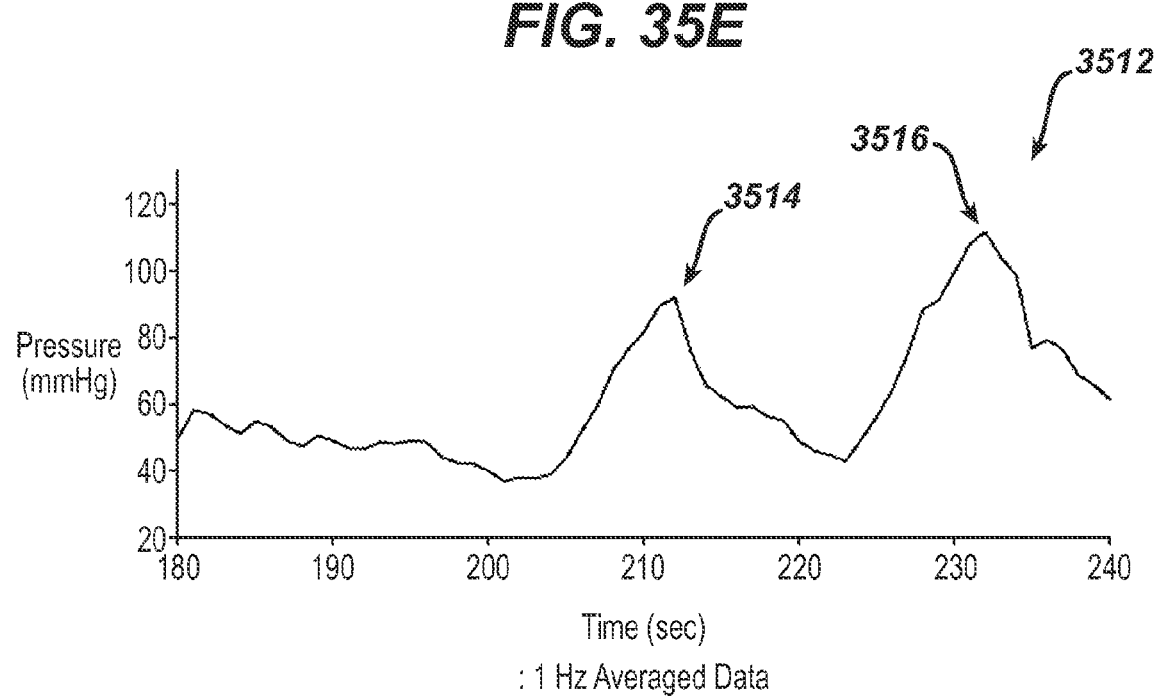
FIG. 35E shows an exemplary plot of pressure values over time from FIG. 35A which have been converted to a 1 Hz data rate.
Figure 35F:
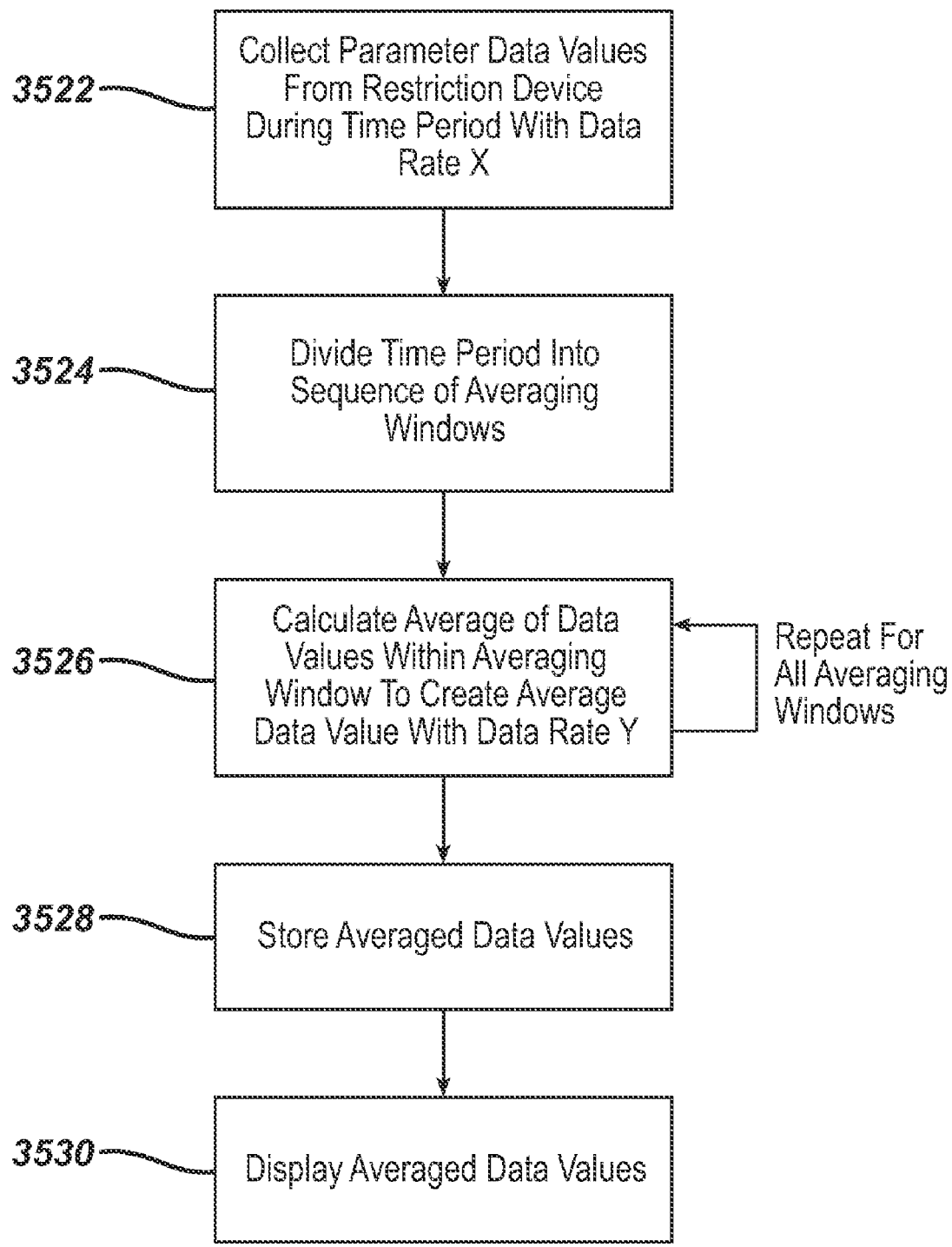
FIG. 35F is an exemplary flow diagram for converting collected data from a restriction device to other data rates.

Some data processing techniques or algorithms can be generally directed to smoothing or conditioning data, (e.g., converting, filtering or other conditioning) into a form suitable for later analysis (by computer or by a user) or for display. A wide variety of conditioning algorithms are possible. For example, FIG. 35A shows a plot 3500 of pressure values 3502 sensed by a restriction device 22 such as band 28 and pressure sensor 84. In this exemplary embodiment, the pressure values 3502 are sensed, or sampled, over a period of time, from a pressure signal developed by the pressure sensor 84 in the restriction device 22 (which, as previously mentioned, can be any kind of restriction device, including fluid-fillable or mechanically based devices). The sensed values can be captured by a data logger 270 via repeated interrogation of the restriction device 22. It should be understood that while pressure values are used as an example, any sensed parameter can be used in this algorithm, or any other algorithms described herein. FIG. 35A shows values that have been collected at a rate of 100 Hz, although virtually any sampling rate can be used. The values of the pressure can be converted to a lower rate, which can be helpful in presenting phenomena of interest (for example, a pulse from a swallowing event might occur on the order of 0.1 Hz), removing noise in the data, and/or compressing the size of the dataset, among other things. The conversion can be accomplished in a variety of ways, but in one exemplary embodiment, the pressure values 3502 can be averaged to effectively decrease the sampling rate, the results of which are shown in FIG. 35B, which shows a plot 3506 of the pressure values 3502 averaged down to a 10 Hz rate. The average can be calculated by defining an averaging window within the time period on the plot 3500 (for example, by dividing time period into a sequence of averaging windows 3504, each 1/10 of a second), and taking the average of the pressure values 3502 occurring within each window. The window can be defined by time (for example, every 10 seconds) or by the number of data points therein (for example, averaging every 10 values or data points). The size of the averaging window can be user-defined, and in some embodiments can be defined based on the phenomena or physiological parameter of interest. As one skilled in the art will understand, a wide variety of mathematical techniques can be used, for example, instead of averaging, the 100 Hz data can be directly converted to 10 Hz data by sampling the pressure values 3502 at 10 Hz, in other words, downsampling or filtering. FIGS. 35C-E show three plots 3508, 3510, and 3512 which present the results of converting the pressure values 3502 plotted in FIG. 35A to lower rates. As shown in FIG. 35E, some lower-frequency phenomena, such as a pulses 3514, 3516, are still discernible while smaller amplitude changes are removed. FIG. 35F shows an exemplary flow diagram illustrating an averaging algorithm.

Figure 36A:
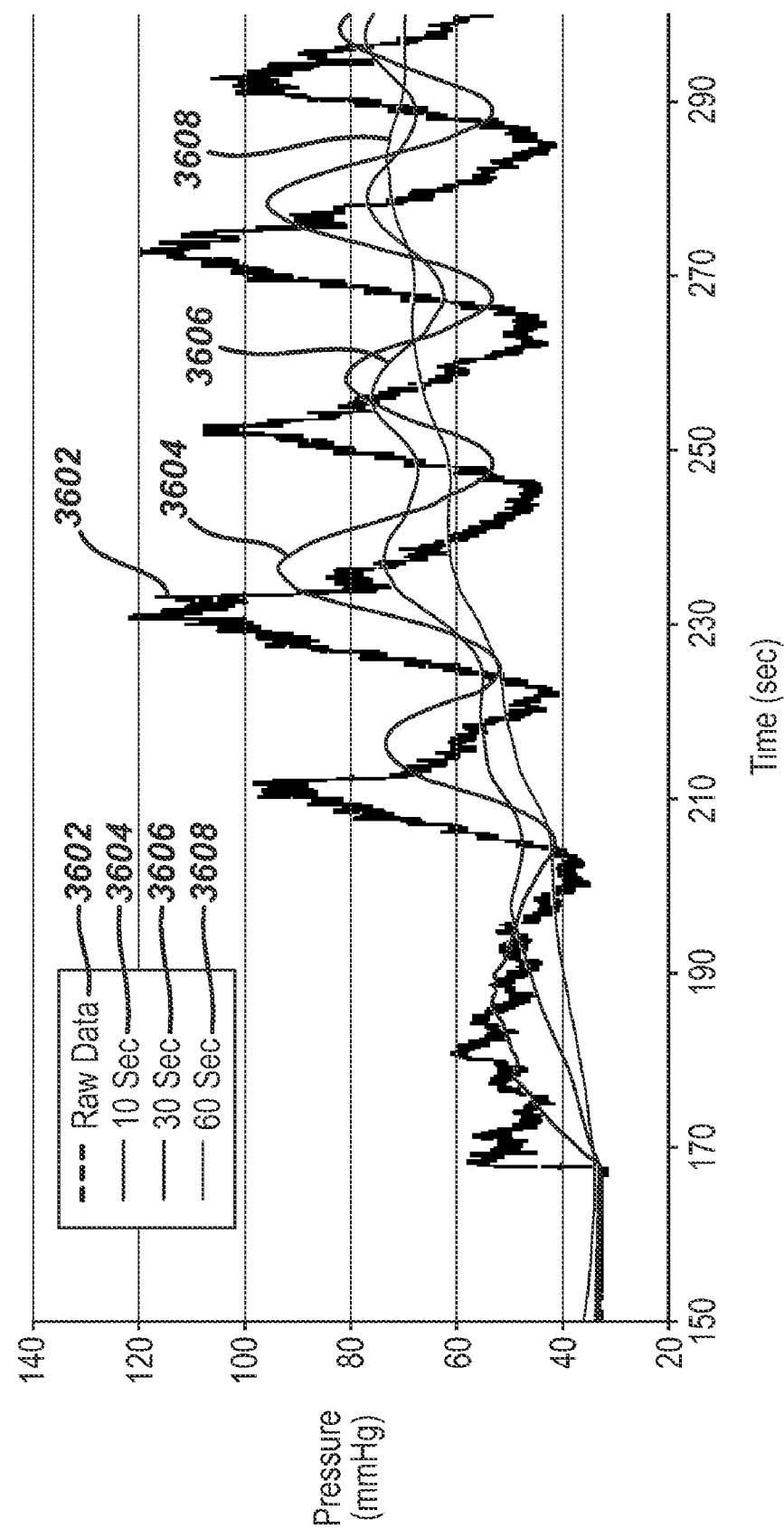
FIG. 36A is an exemplary plot of pressure values over time collected from a restriction device and overlaid with plots of running averages calculated from the pressure values according to a first technique.
Figure 36B:
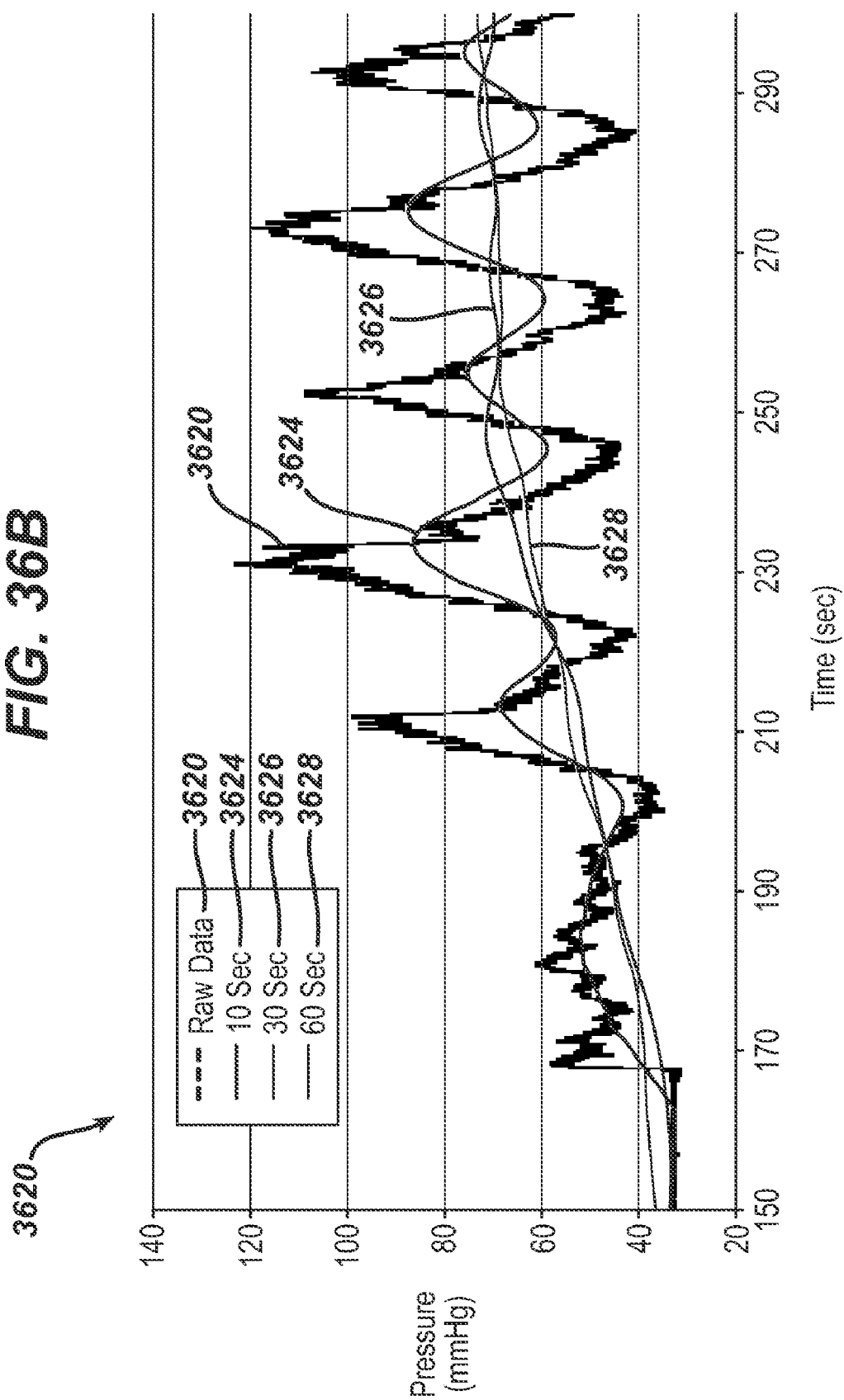
FIG. 36B is an exemplary plot of pressure values over time collected from a restriction device and overlaid with plots of running averages calculated from the pressure values according to a second technique.
Figure 36C:
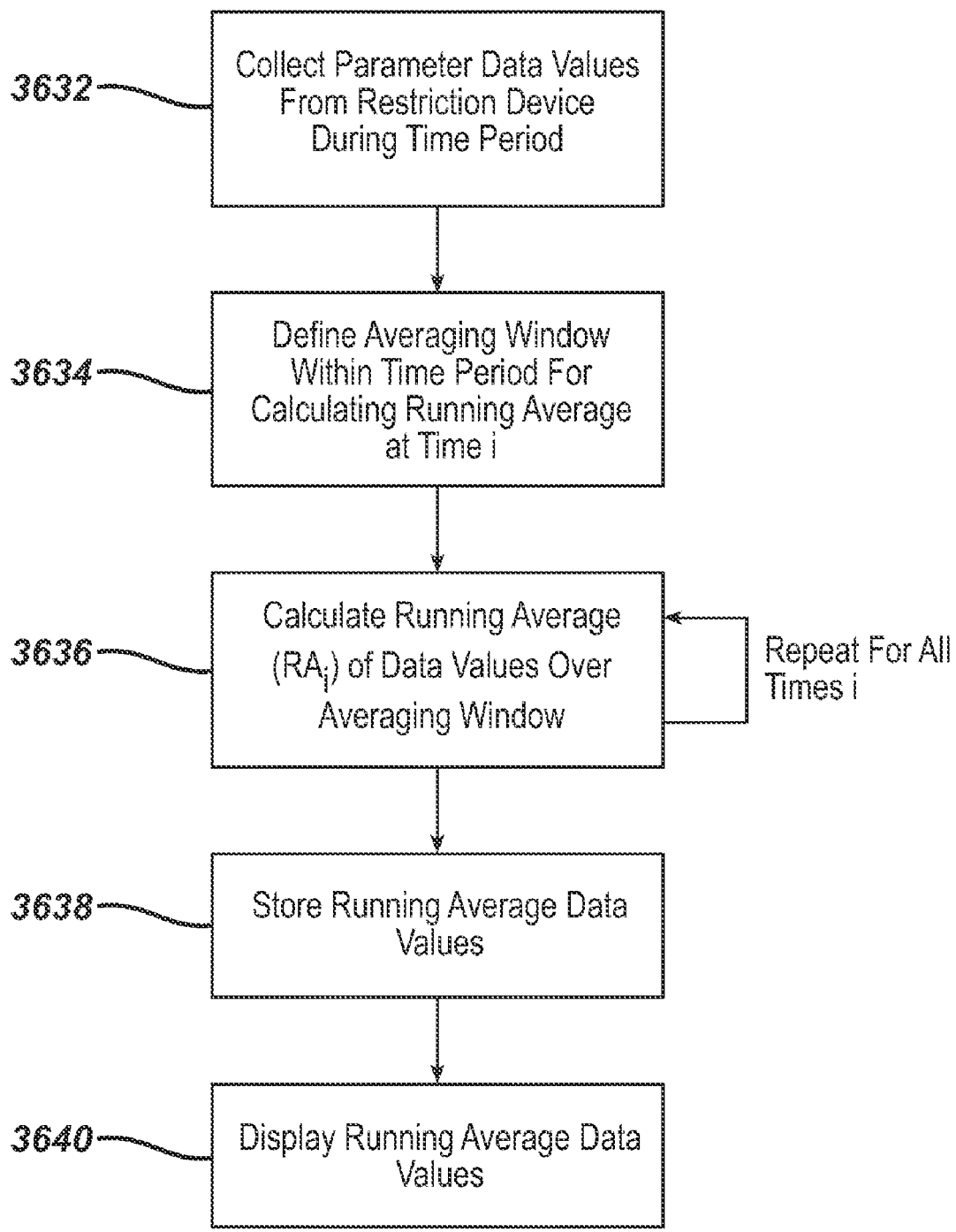
FIG. 36C is an exemplary flow diagram for calculating running averages of data collected from a restriction device.

FIGS. 36A-B illustrate the output of an exemplary running average algorithm that can be used with data captured by the data logger 270, and FIG. 36C shows such an exemplary running average algorithm. A running average algorithm can take a variety of forms, but in one embodiment it can include computing each value or data point for the running average based on an averaging window, which can be of user-defined size. The averaging window can be used to determine the number of data values (the data values representing pressure values, for example) that are averaged together to obtain each running average value. The averaging window can be shifted as each new data point is collected, so the running average value can be updated at the same rate as the sampling rate. In one embodiment, the running average value for a particular point in time can be computed by averaging the data values falling within a time window occurring before that point in time, in other words a backward-looking running average. The backward-looking running average can be defined by the following formula, where RA is the running average value, p is the data value, and n is the window sample number:

$$RA_i = \frac{1}{n} \sum_{i}^{i+n-1} p_i$$

In use, for each data value collected, the averaging window can be applied and the running average for that point in time can be calculated. The running average values can then be displayed, for example alone or with the original data values. FIG. 36A illustrates the result of running such an algorithm on pressure data. FIG. 36A presents a graph 3600 which includes a plot of raw data values 3602 that have not been averaged. Also shown on the graph 3600 are three plots 3604, 3606, 3608 which represent the data values following application of a backward-looking average running average algorithm. As shown, plot 3604 corresponds to a running average calculated with a 10 second averaging window, plot 3606 corresponds to a 30 second averaging window, and plot 3608 corresponds to a 60 second averaging window.

In another embodiment, the running average for a particular point in time can be computed by averaging the data values in an averaging window which includes data values both before and after the point in time, in other words a centralized running average method. If half of the averaging window precedes the point in time and half of the time window follows the averaging window, the centralized running average can be defined by the following formula, where RA is the running average value, p is the data value, and n is the window sample number:

$$RA_i = \frac{1}{n} \sum_{i-\frac{n}{2}}^{i+\frac{n}{2}-1} p_i$$

FIG. 36B illustrates the result of running such an algorithm on pressure data. Graph 3620 includes a plot 3622 of raw data values that have not been averaged. Also shown on the graph 3620 are three plots 3624, 3626, 3628 which represent the raw data following the application of the centralized running average algorithm. Plot 3624 corresponds to a running average calculated with a 10 second averaging window, plot 3626 corresponds to a 30 second averaging window, and plot 3628 corresponds to a 60 second averaging window. Other variations are possible in which the averaging window is not centered on the point of time for which the running average is being calculated but surrounds the data value in some other proportion. For example, the running average for a point in time can be calculated based on the data values in an averaging window in which one-quarter of the time window precedes and three-quarters of the averaging window follows the point in time. FIG. 36C shows an exemplary flow diagram illustrating the above-described exemplary running average algorithm.

In other embodiments, data conditioning can be performed through a variety of statistical and/or mathematical calculations, including root mean square calculations, mean absolute deviation calculations, regression analyses to produce fitted curves (both linear and non-linear), crest factor and form factor calculations, and so on. These approaches can be performed on the parameter data values as described above for the running average calculations. The use of other statistical and/or mathematical calculations can be chosen depending on the particular application. For example, root mean square calculations can be particularly advantageous in embodiments in which the data parameters produced by the restriction device 22 have both positive and negative values (such as an electrical voltage).

The determination of a running average value, or any other value resulting from a conditioning calculation, also can trigger a variety of alarms or can be recorded for reports maintained by the local unit 60, remote monitoring device 170, and/or the system 20. For example, an alarm or notification signal can be generated if the running average falls within a predetermined range, if it exceeds or falls below a threshold, if it changes too quickly (e.g., its rate of change exceeds a threshold), and so on. Alternatively, the occurrence of such events can be logged or stored for inclusion in a report or log produced by the local unit 60, remote monitoring device 170, and/or the system 20.

In some embodiments, analog filters can be employed in addition to or as an alternative to processing parameter data mathematically. A bank of analog filters (or selectable bank of such filters) can be included in one more devices for removing noise, or signals at undesired frequencies. For example, the conditioning and filtering achieved in the embodiment illustrated in FIGS. 35A-35E can be implanted via appropriate low-pass filtering. As one skilled in the art will understand, high-pass and band-pass filtering embodiments are also possible and depend on the desired results. The filters can be placed in a variety of locations, such as the injection port 36 (e.g., the injection port 36 that serves as a communication link for the restriction device 22), the local unit 60, the remote monitoring unit 170, or any other device in the signal path. In some embodiments, placing the filters in the implant (such as the injection port 36 or in the restriction device 22) can be advantageous because by pre-conditioning the information it can reduce the bandwidth and/or power requirements needed for telemetrically transmitting (or receiving) such data. In addition, by reducing the amount of data through analog filtering, the data processing requirements of the devices (for example, the remote monitoring device) in analyzing the data can be reduced.

Figure 37B:
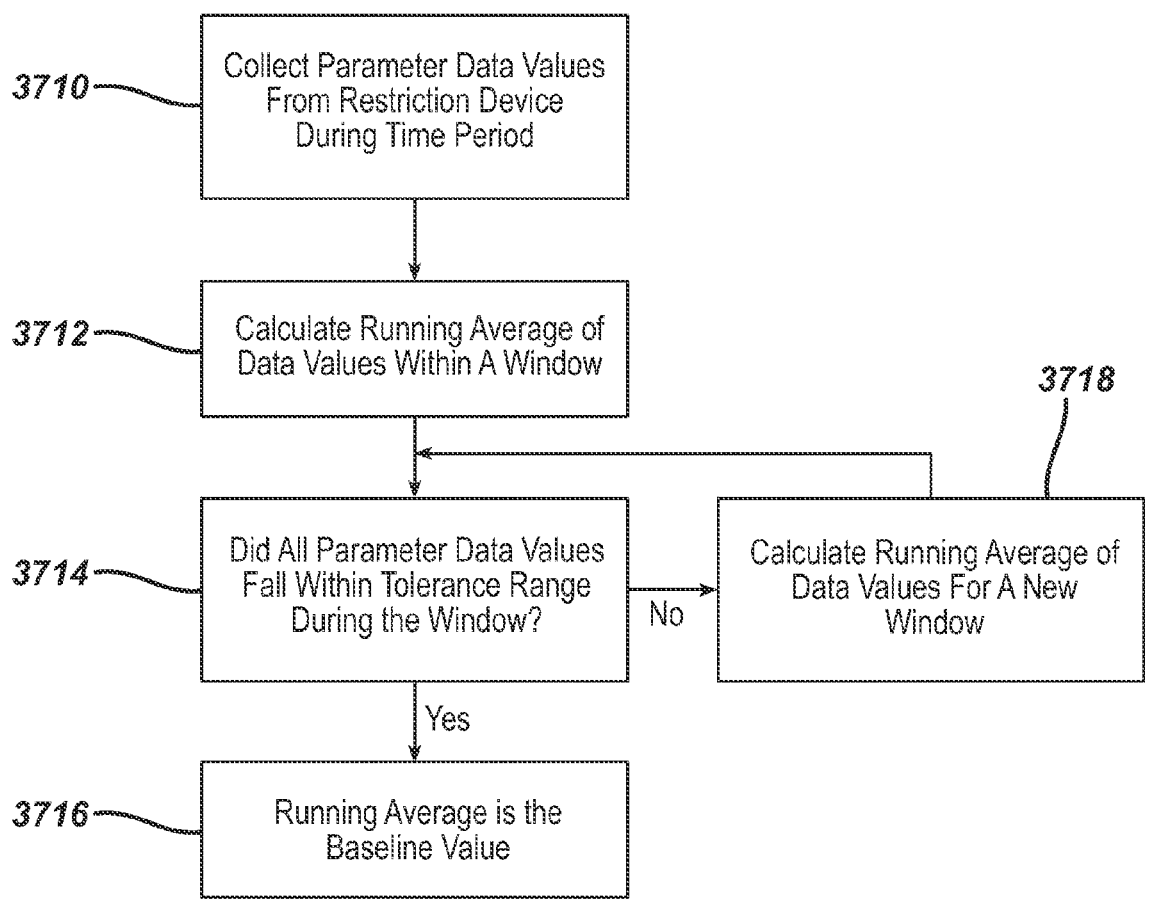
FIG. 37B is an exemplary flow diagram for determining the baseline value of a parameter from data collected from a restriction device.

Data processing algorithms also can be useful for determining baseline levels of a physiological parameter represented by the data collected from the restriction device 22. For example, the baseline pressure sensed by a fluid-filled restriction device 22 can be determined from collected pressure values. A wide variety of methods to determine a baseline value can be used. However, in one exemplary embodiment, which is illustrated via FIGS. 37A-B, an algorithm for finding a baseline can involve collecting data from a restriction device (box 3710 of flow diagram FIG. 37B) and calculating a running average value based on past data values (box 3712). The data used in the running average calculation can be defined by an averaging window (for example, an averaging window preceding the point in time for which a running average is being calculated, or covering a certain number of data values, e.g., the last ten values.) With the collection of each new data value, the running average can be updated. As shown in box 3714, the algorithm can determine whether a baseline value has been established by comparing the data values within the averaging window to a tolerance range, which can be defined around the running average, to determine if all of the values (or, alternatively, a portion of them) were within the tolerance range. If so, at box 3716 the algorithm can identify the running average as the baseline value of the parameter. If not, at box 3718 additional data values can be collected, which can involve the definition of a new averaging window, or the collection of a specified number of additional data values. A new running average can be computed, and the process repeated until a baseline value is found. As one skilled in the art will understand, any or all of the foregoing thresholds, limits, times, window sizes, or other variables can be user-defined. FIG. 37A shows a plot of data 3700 which illustrates the foregoing algorithm applied to collected data, and shows the tolerance range 3702 and the averaging window 3704, in the context of pressure values measured over a time period 3706.

In some embodiments, the occurrence of specified events can initiate an algorithm to determine or search for a baseline value. For example, it can be desirable to check or determine whether a new baseline value exists at the start of data collection, the expiration of a timer, or after an adjustment is made to a restriction device 22, which can involve adding or removing fluid. FIG. 37C shows a plot of pressure data 3720 over a time period which exhibits an upwards baseline shift 3722 due to the addition of approximately 7.5 ml to a fluid-filled restriction device. The adjustment can trigger the execution of a baseline-determining algorithm, such as those described above, to find the new baseline value.

Figure 38B:
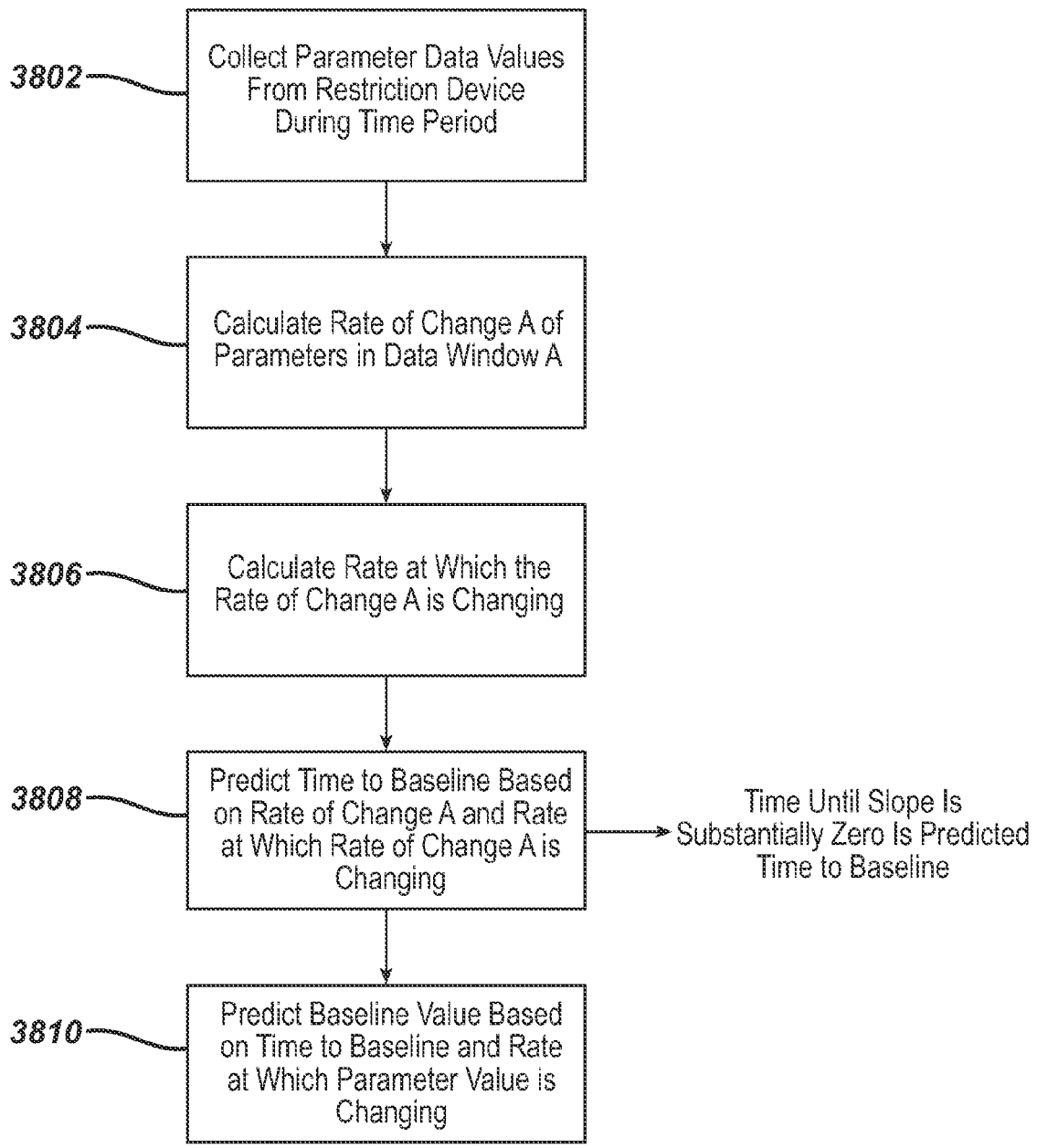
FIG. 38B is an exemplary flow diagram for predicting characteristics related to a baseline value of a parameter from data collected from a restriction device.

Another exemplary algorithm for determining or predicting baseline levels of a parameter is illustrated by FIGS. 38A-B. FIG. 38A shows an exemplary plot of data over time to illustrate application of the algorithm to a set of data and FIG. 38B shows an exemplary flow diagram. In this embodiment, the algorithm generally can involve calculating when the rate of change of the parameter values will be zero or substantially near zero, and what the parameter value will be at that time. A rate of change that is zero or substantially near zero can be treated as indicating that the baseline value has been reached. More specifically, with reference to boxes 3802, 3804 and FIG. 38B, the algorithm can include collecting parameter data values over a time period, and calculating a rate of change at a point of time or for a group of data values (group A) in a time window 3820 within the time period. For example, the rate of change can be determined by a slope calculation defined by $$\frac{d_{Parameter\,A}}{d_{time\,A}}.$$

With reference to box 3806, the algorithm can further include calculating how fast the rate of change is itself changing—in other words, the rate at which the rate of change is changing. The rate at which the rate of change is changing can be determined for example, by executing two slope calculations (e.g., group A in window 3820 and group B in window 3822), and then calculating the change in slopes. The windows 3820, 3822, can be defined by time (a time window) or by a group of data values, or in any other way suitable for selecting a portion of data values. For example:

$$SlopeA = \frac{d_{Parameter\,A}}{d_{time\,A}}$$

$$SlopeB = \frac{d_{Parameter\,B}}{d_{time\,B}}$$

$$\Delta Slope = SlopeB - SlopeA$$

Furthermore, the rate of change and how fast the rate of change is itself changing can be used to determine when the rate of change will be about zero, and what the value of the parameter will be at that time. For example, as indicated in box 3808, the time needed to reach a rate of change of about zero (which in this example indicates that the baseline value has been reached) can be predicted according to the following formula:

$$\text{Time to Baseline} = \frac{SlopeB}{\Delta Slope} * Period_B$$

The predicted baseline value can be calculated by extrapolation using a parameter value and the amount the parameter will change until the Time to Baseline, as shown by the following formula:

Baseline Value=(Time to Baseline)*(Slope*B*)+(Parameter Value in Group *B*)

As one skilled in the art will understand, the foregoing approach can be varied widely, without departing from the scope of the technique described herein. For example, the Time to Baseline and Baseline Value formulas can be cast in terms of Slope A and Period A as well, more than two data windows can be used, and/or the spacing between data windows 3820, 3822 can be modified. Further, one skilled in the art will understand that the foregoing approach can be described in terms of a derivative (for example, to represent a rate of change) and a second derivative (for example, to represent a rate at which the rate of change it itself changing).

The determination of a baseline value can trigger a variety of alarms or can be recorded for reports maintained by the local unit 60, remote monitoring device 170, and/or the system 20. For example, an alarm or notification signal can be generated if the baseline pressure exceeds or falls below a threshold (for example, for a specified time period), when there is a fluctuation in baseline pressure, when a baseline cannot be found after a specified time, when rate of change of the pressure exceeds a threshold value, and/or when the baseline pressure is determined. Alternatively, the occurrence of such events can be logged or stored for inclusion in a report or log produced by the local unit 60, remote monitoring device 170, and/or the system 20. In addition, the baseline value can be correlated (either alone or in conjunction with other data, as described herein) to the condition of the restriction device. The baseline value can indicate an over-tightened, optimally-tightened, or under-tightened restriction device, which for a fluid-fillable restriction can represent an over-filled, optimally-filled, or under-filled condition. For example, a baseline value that exceeds a predetermined threshold (e.g., a level considered to be "too high") can be indicative of an over-filled or over-tightened restriction device, while a baseline value that falls or remains below a predetermined threshold (e.g., a level considered to be "too low") can be indicative of an under-filled or loose restriction device, and so on. Predetermined thresholds can be obtained using historical patient data, group data, or other clinical data. Also, in other embodiments, the rate of change of the pressure (as described above with respect to baseline determinations) can be correlated to the condition of the restriction device. For example, a rate of change that exceeds a predetermined rate of change can indicate an over-filled fluid-fillable restriction band. A rate of change that falls below another threshold can indicate an under-filled restriction band.

Figure 39A:
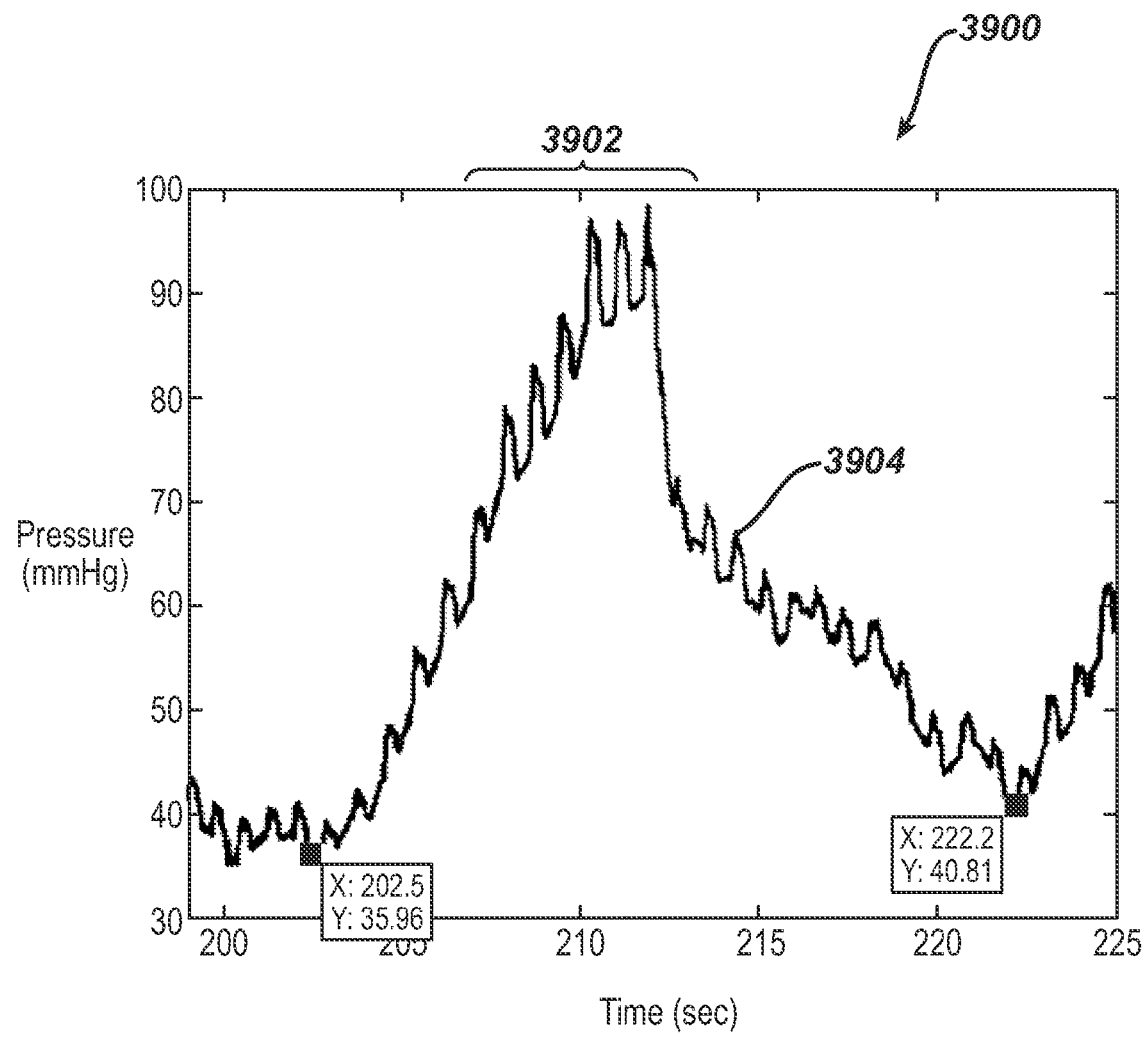
FIG. 39A is an exemplary plot of pressure values over time collected from a restriction device exhibiting superimposed pulses of differing frequencies.
Figure 39B:
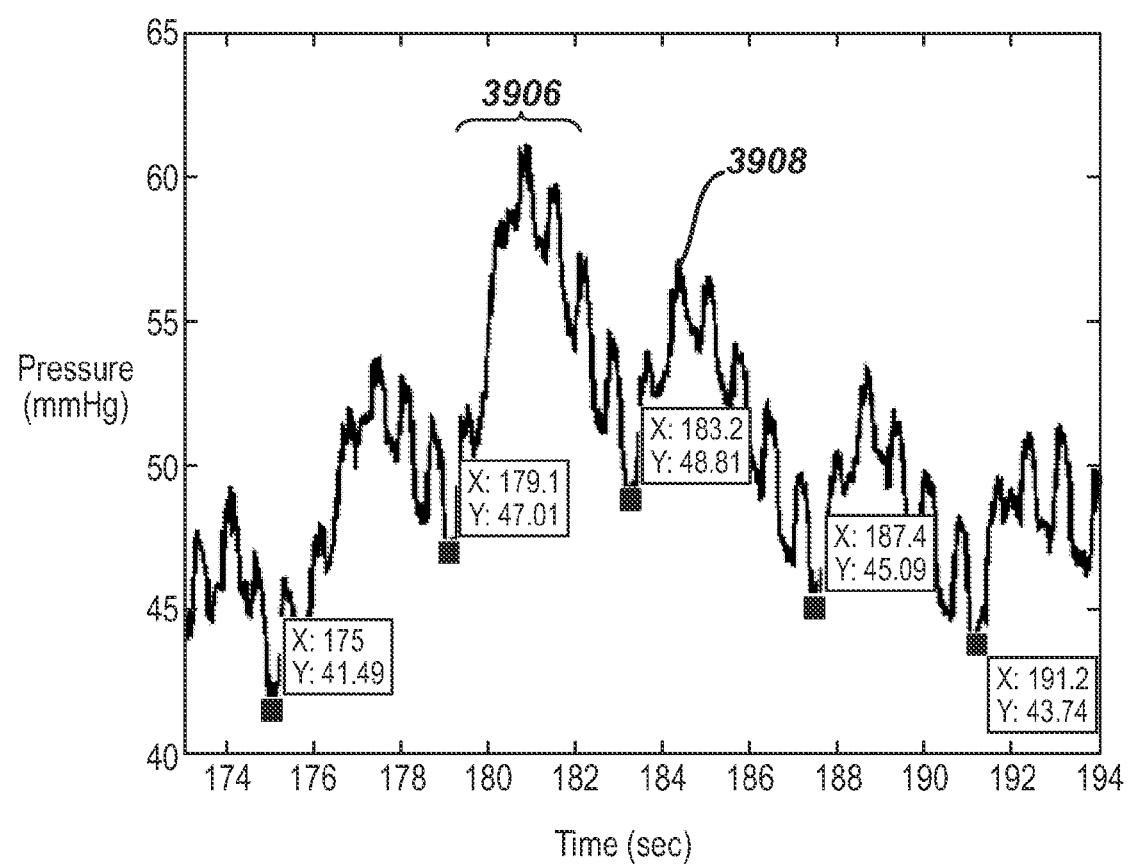
FIG. 39B is another exemplary plot of pressure values over time collected from a restriction device exhibiting superimposed pulses of differing frequency.

Data values collected by the data logger 270 can be used to obtain information about physiological parameters of a patient wearing a restriction device 22. For example, as previously mentioned, the data logger 270 can collect data representing pressure (or other parameter) sensed by an implanted restriction device 22. Information about physiological parameters such as heart rate, breathing rate, and others, can be determined from the collected pressure values (or values of another parameter). Information about peristaltic or swallowing events, which can manifest themselves as pulses or a series of pulses in pressure, can also be determined, and such information can include the number, rate, and duration of such pulses. As shown in FIGS. 39A-B, multiple frequencies can exist in a set of pressure data (or other data). As shown in FIG. 39A, relatively high frequency pulses 3904, which in FIG. 39A represent pressure changes caused by heartbeats (the heartbeat can exert a detectable force on the restriction device 22), can be superimposed on low-frequency pulses 3902, which in FIG. 39A represent swallowing events. FIG. 39B shows heartbeat pulses 3906 superimposed on pulses 3908 caused by breathing. As shown the breathing pulses are occurring about once every four seconds.

In one exemplary embodiment, the frequency content of pressure data can be analyzed. Frequency or frequencies in the data can be selected and identified as the frequency of a physiological parameter of interest, for example by comparing the frequency to a range of frequencies which are designated as the possible range for the particular physiological parameter. The amplitude, or other characteristics of the physiological parameter also can be determined by extracting or filtering the data at the selected frequencies. A variety of techniques can be used to analyze and extract information having a desired frequency content. The following examples refer to FIGS. 39A-C and sometimes use heart rate as an exemplary physiological parameter, but as one skilled in the art will understand, a variety of periodic physiological parameters can be analyzed, and data other than pressure data can be used.

Figure 39C:
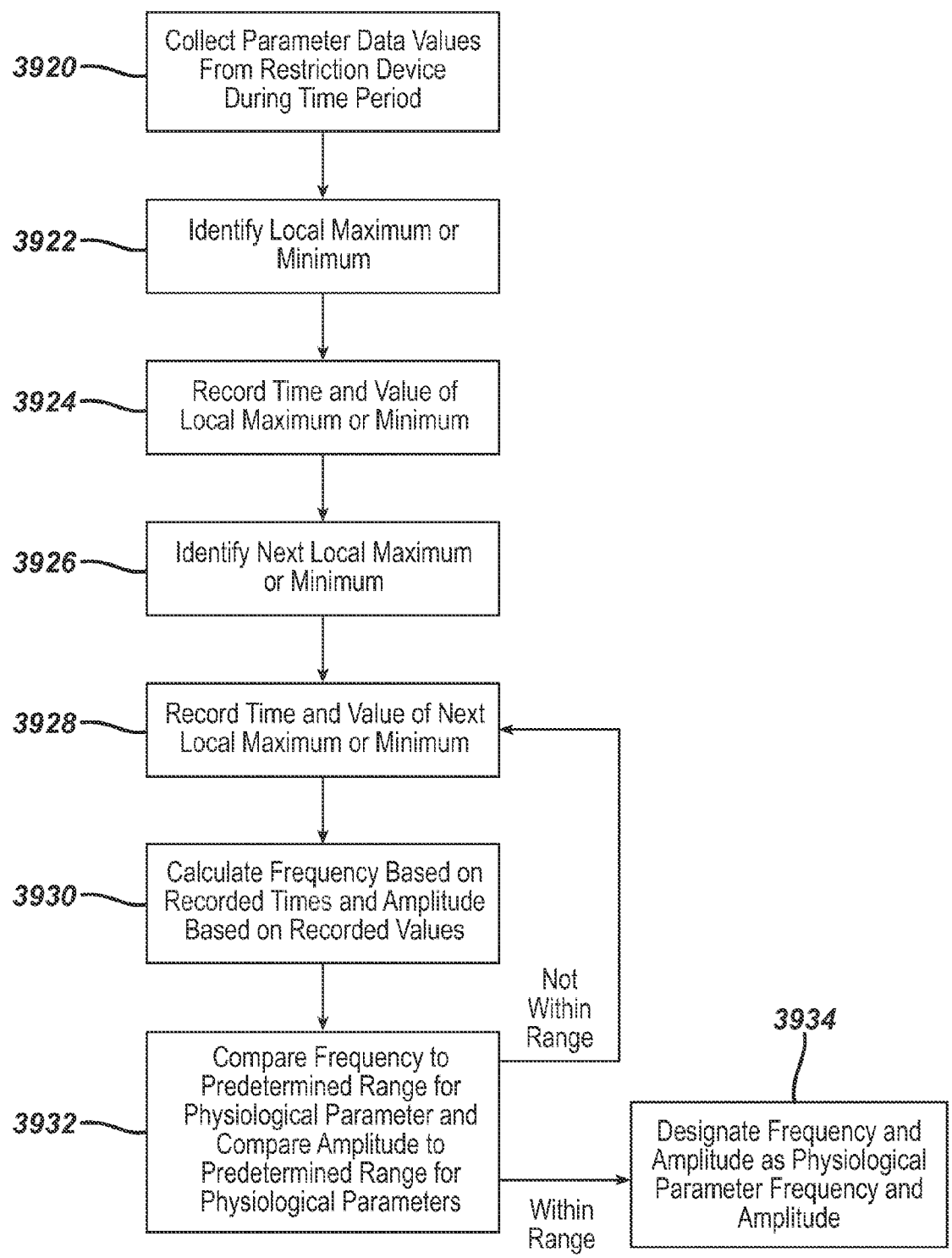
FIG. 39C is an exemplary flow diagram for determining information about a physiological parameter from data collected from a restriction device.

As illustrated in FIG. 39C, one exemplary algorithm can involve calculating the period of pulses or variations in the data values representing the sensed parameter. With reference to box 3920, a local maximum or minimum in the data can be identified, e.g., by determining when the slope changes passes through zero. The time can be recorded at that point (box 3922), and again at a subsequent maximum or minimum (box 3924). The period can be calculated based on the time between adjacent maxima and/or minima, and this period can be examined to see if it falls within a designated target range of possible frequencies associated with the physiological parameter of interest. For example, a heart rate might be associated with a frequency of 65 to 150 beats or cycles per minute, or about 1.1 to 2.5 Hz. The range can be defined by the device, or user-defined. If the calculated frequency falls within the range, at box 3926 the frequency can be identified or designated as the frequency of the physiological parameter. In some embodiments, the algorithm can include comparing the magnitude of the values at the maxima or minima to ensure that they are within a tolerance range of one another. As can be seen with reference to FIG. 39A, such an approach can enable the maximum, or peak, of a swallowing pulse to be distinguished from the maximum or peak of a heart rate pulse. Distinguishing between the two can determine the appropriate maxima to use in calculating the frequency for a particular physiological parameter. In some embodiments, the value of the parameter at the maximum or minimum also can be used to calculate the amplitude of the pulses, and the algorithm can also include comparing the amplitude to a predetermined target range associated with the physiological parameter to see if it whether it falls within the range. For example, heart rate pulses can have an amplitude of about 7-8 mmHg, as shown in FIG. 39B, and a range can be size to include at least 7-8 mmHg. As one skilled in the art will understand, the target frequencies and amplitudes described above will vary depending on the physiological parameter about which information is sought.

Figure 39D:
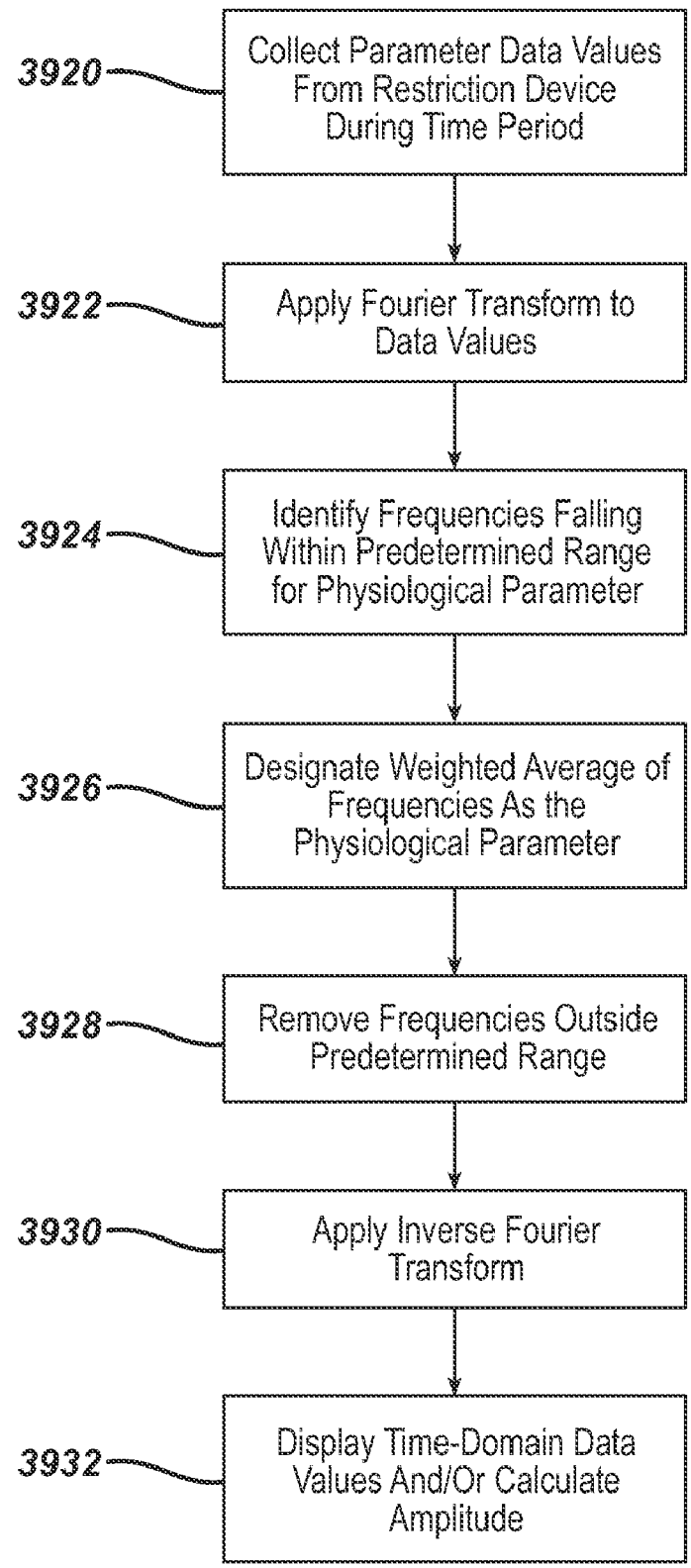
FIG. 39D is another exemplary flow diagram for determining information about a physiological parameter from data collected from a restriction device.

As illustrated in FIG. 39D, in another exemplary embodiment, a discrete Fourier transform (in many cases, computed by fast Fourier transform) can be applied to data values of a sensed parameter that were logged over a time period. The data values can thereby be transformed from time domain values to the frequency domain. The frequency content of the data values can be examined to identify a frequency or frequencies that exist in the data values that corresponds to a range of frequencies associated with a physiological parameter range. In some embodiments, the frequency content can be examined to identify one or more frequencies that exist and exceed a magnitude threshold, and that correspond to a range of frequencies associated with a physiological parameter. If multiple frequencies exist in the range, the frequency with the largest magnitude can be selected, or a weighted average of the frequencies can be computed, and designated as the frequency of the physiological parameter. The amplitude can be given by the Fourier coefficients of the identified frequencies. Alternatively, frequencies not falling within the target range can be removed from the data (for example, by setting the Fourier coefficients of unselected frequencies to zero), and the values of the sensed parameter in the time domain can be reconstructed by performing an inverse Fourier transform. The data values in the time domain can be displayed or analyzed further, e.g., analyzing the amplitude by comparing the values at the maxima and minima, etc.

Figure 40A:
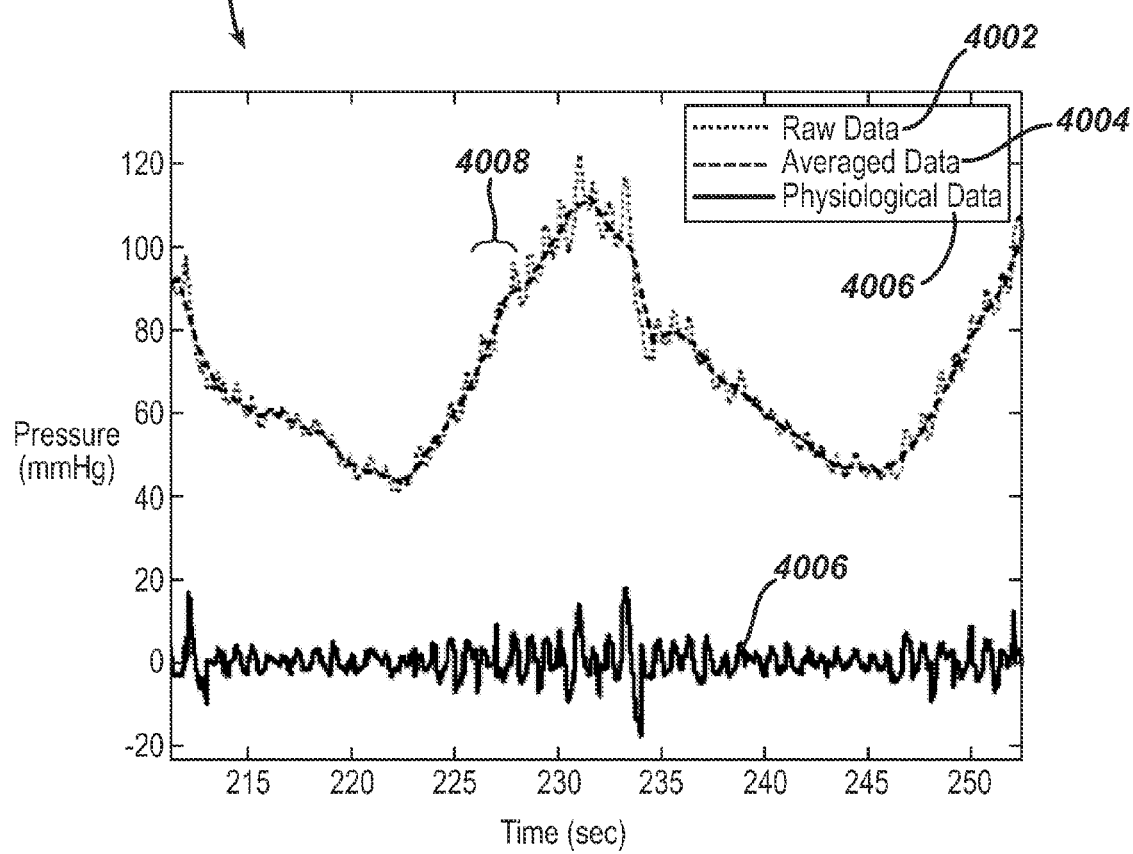
FIG. 40A is an exemplary plot of pressure values over time collected from a restriction device with information about a physiological parameter extracted therefrom.
Figure 40B:
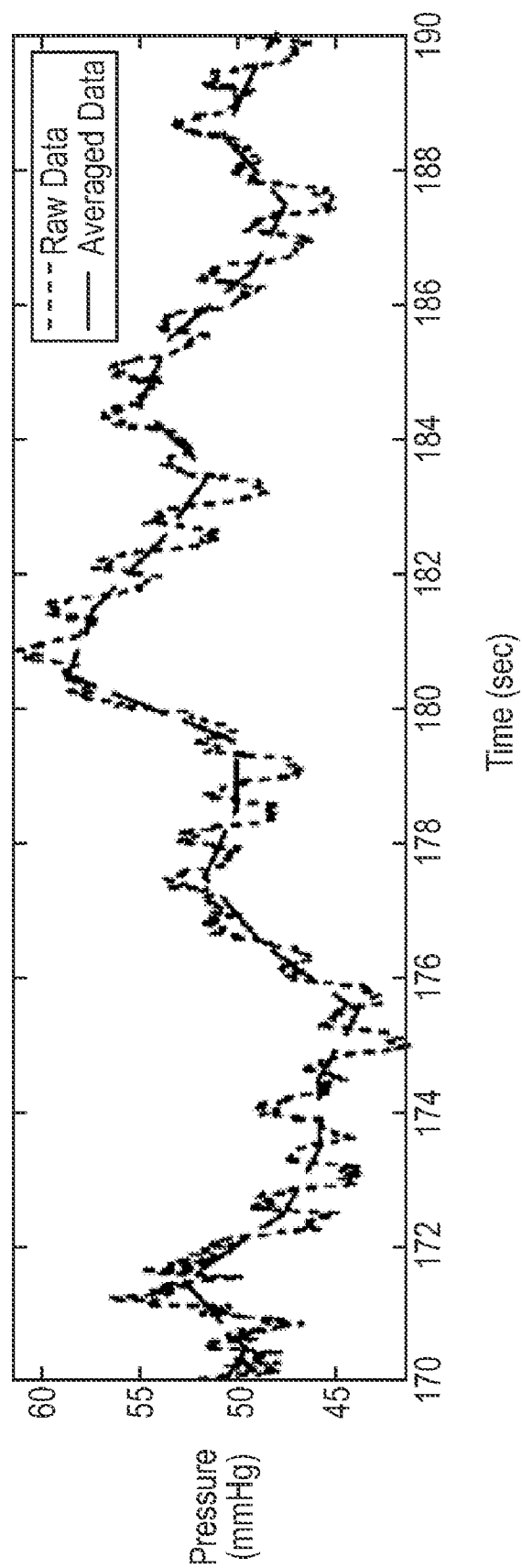
FIG. 40B is an exemplary plot of pressure values over time collected from a restriction device and averaged data overlaid therewith.
Figure 40C:
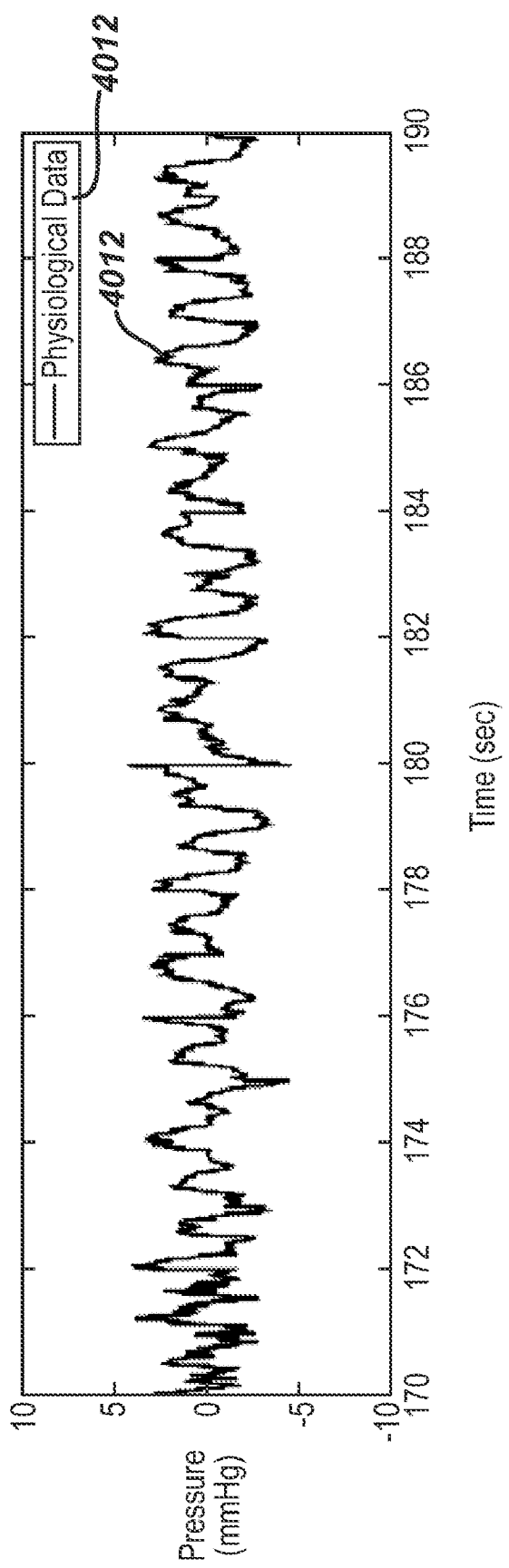
FIG. 40C is an exemplary plot of pressure values over time extracted from the data shown in FIG. 40B.
Figure 40D:
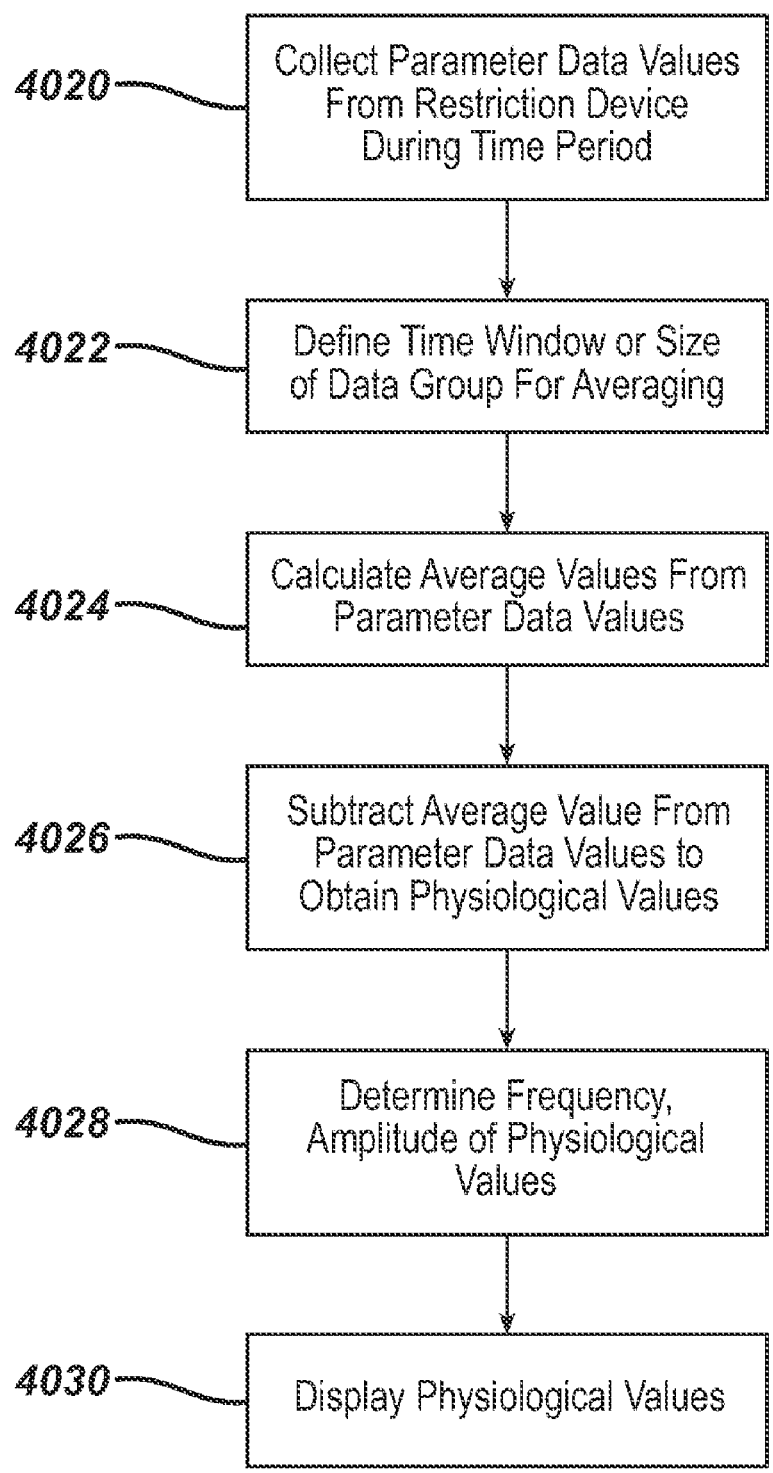
FIG. 40D is an exemplary flow diagram for determining a physiological parameter from data collected from a restriction device.

FIGS. 40A-C illustrate the output of another algorithm which can extract information about a physiological parameter from the value of a sensed parameter (such as pressure) from a restriction device 22 and collected by the data logger 270, and FIG. 40D shows an exemplary flow diagram of such an algorithm. In this exemplary embodiment, values of a sensed parameter, such as pressure values 4002, can be averaged to create average values 4004. In many embodiments, the average can be calculated by averaging the values falling within a averaging window within a time period, e.g., taking the average of every X seconds of data values, or computing the average of a defined number (a data group) of surrounding data values. The size of the averaging window can vary widely, and can be informed by the relationship between the phenomena of interest. For example, as shown in FIG. 40A, pressure values have been collected at a rate of about 100 Hz, while swallowing events can occur at about 0.1 Hz, and the average 4004 has been calculated and plotted by averaging every 100 data values, e.g., falling within window 4008. The average values 4004 can be subtracted from the original data, e.g., the pressure values 4002 in this example, to produce physiological parameter values 4006, such as values representing heart rate, breath rate, and so on. These physiological parameter values 4006 can be displayed. In addition, the frequency, amplitude, volatility, or other characteristics of the physiological values 4006 can be further analyzed, for example using one or more of the previously described algorithms. The foregoing average-and-subtract technique can be repeated on the physiological data 4006 (e.g., with a smaller averaging window) to extract another set of physiological values therefrom (for example, the pulse values can be separated from the breath rate values, then the breath rate values can be separated from the heart rate values).

FIG. 40B illustrates another set of exemplary pressure values 4010 and average values 4012 calculated therefrom. The averaged data 4012 also can be useful for analyzing physiological phenomena, such as relatively low-frequency phenomena and/or swallowing rates. FIG. 40C illustrates physiological values that can be obtained by taking the difference between the exemplary pressure values 4010 and the average values 4012.

Figure 41B:
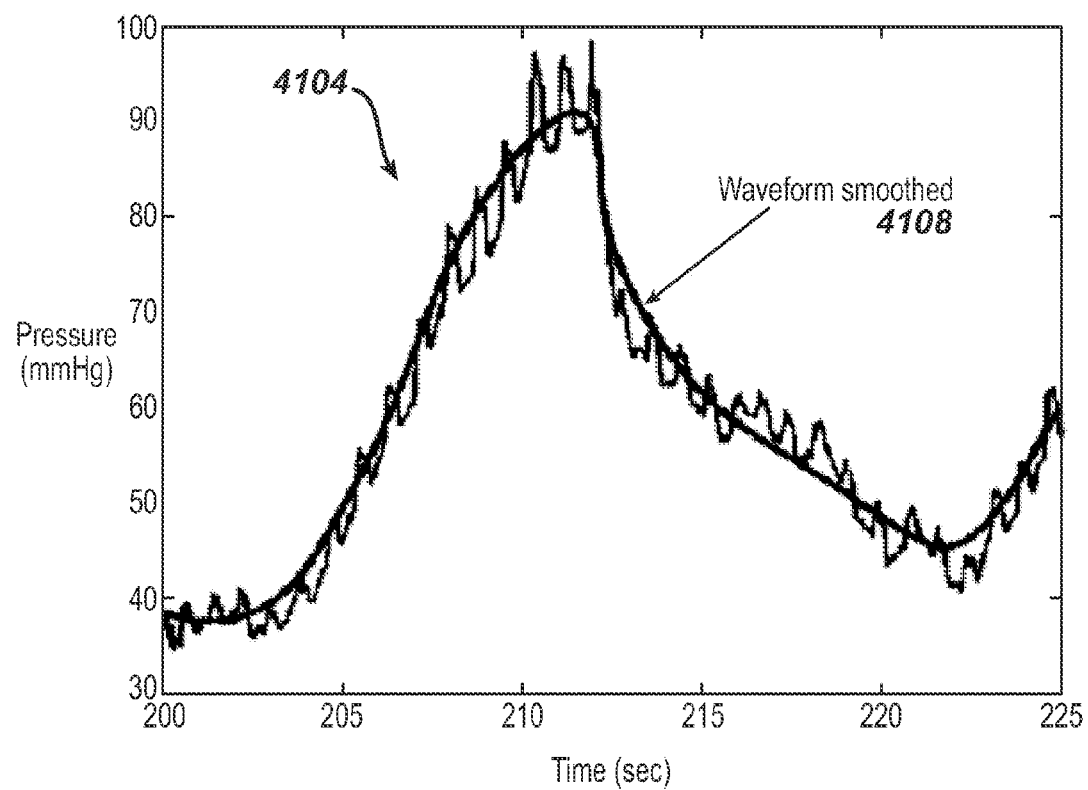
FIG. 41B is a detail view of the plot shown in FIG. 41A.
Figure 41C:
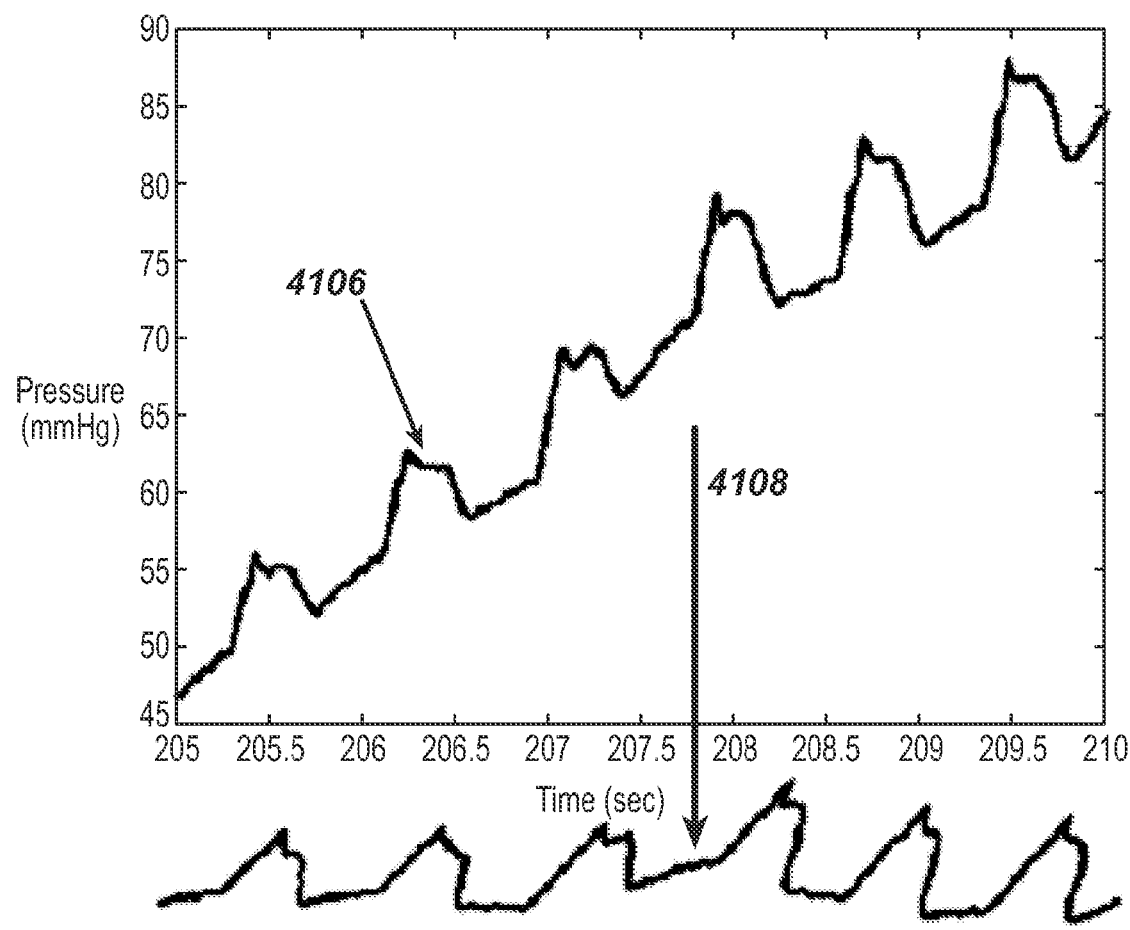
FIG. 41C is another detail view of the plot shown in FIG. 41A.

FIGS. 41A-C show another exemplary dataset which illustrates how pressure data can be differentiated to reveal information about various physiological responses. As shown in FIG. 41A, pressure values 4100 collected over a time period can be used to examine the total duration (e.g., examining amplitude and number of pulses) of a swallowing event or peristalsis represented by a series of pulses 4102, a single pulse 4104 from a peristaltic event, and/or superimposed or minor pulses 4106 representing other physiological parameters. FIG. 41B shows the single pulse 4104 in more detail. As shown, a smooth curve can be used (e.g., by calculating an average value) to analyze the amplitude, duration, or other characteristics of the pulse 4104. FIG. 41C shows the minor pulses 4106 in more detail, which can be converted to a linear (e.g., by one of the previously described approaches), as shown under arrow 4108, to measure frequency, amplitude or other characteristics.

The determination of a physiological rate, amplitude or other parameter can trigger a variety of alarms or can be recorded for reports maintained by the local unit 60, remote monitoring device 170, and/or the system 20. For example, an alarm or notification signal can be generated if the heart rate or breathing rate (or other rate) is too high, too low, cannot be detected, is changing drastically (e.g., has a rate of change that exceeds a threshold), and so on. Alternatively, the occurrence of such events or conditions can be logged or stored for inclusion in a report or log produced by the local unit 60, remote monitoring device 170, and/or the system 20.

Figure 42A:
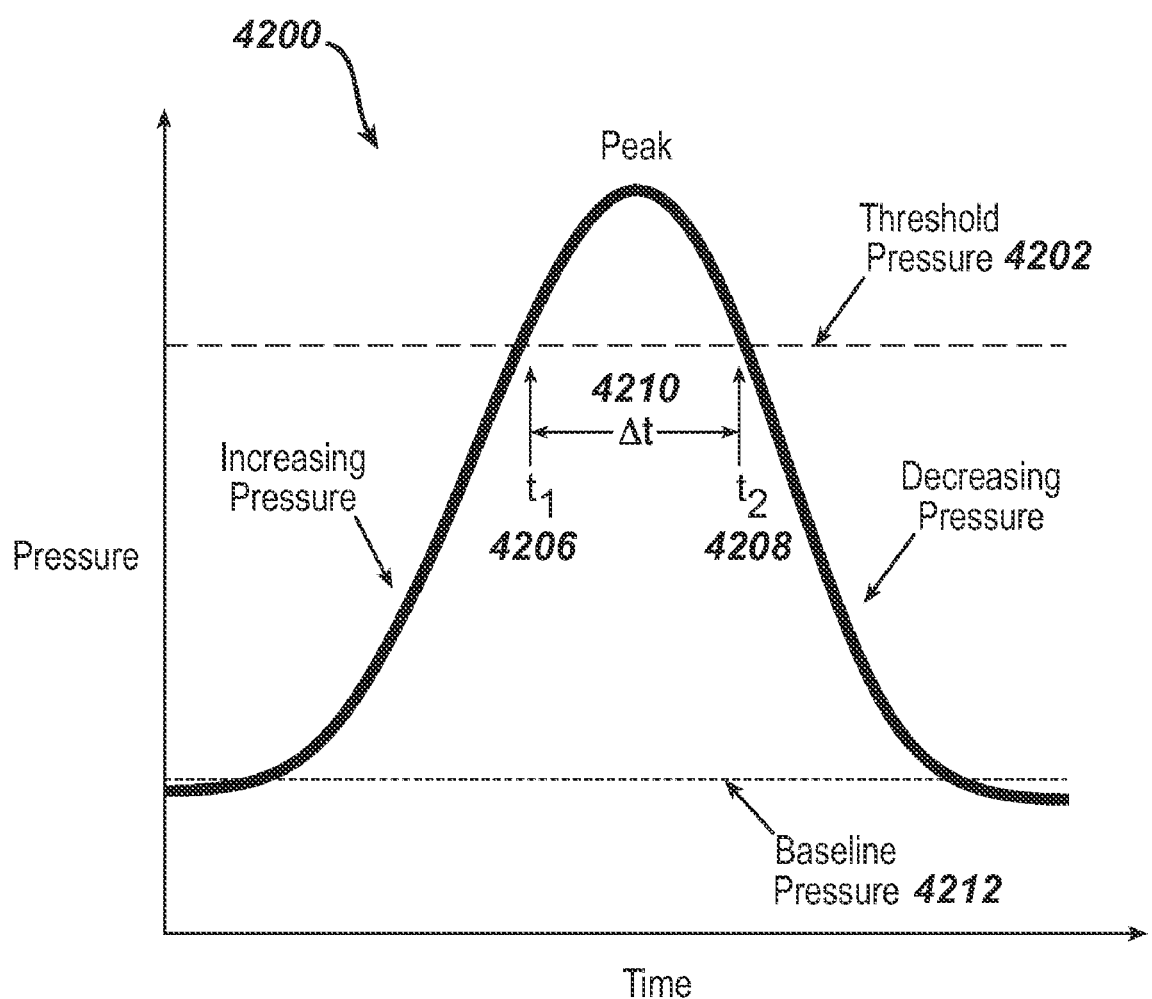
FIG. 42A is an exemplary plot of pressure values over time collected from a restriction device with annotations related to determining the presence of a pulse.
Figure 42B:
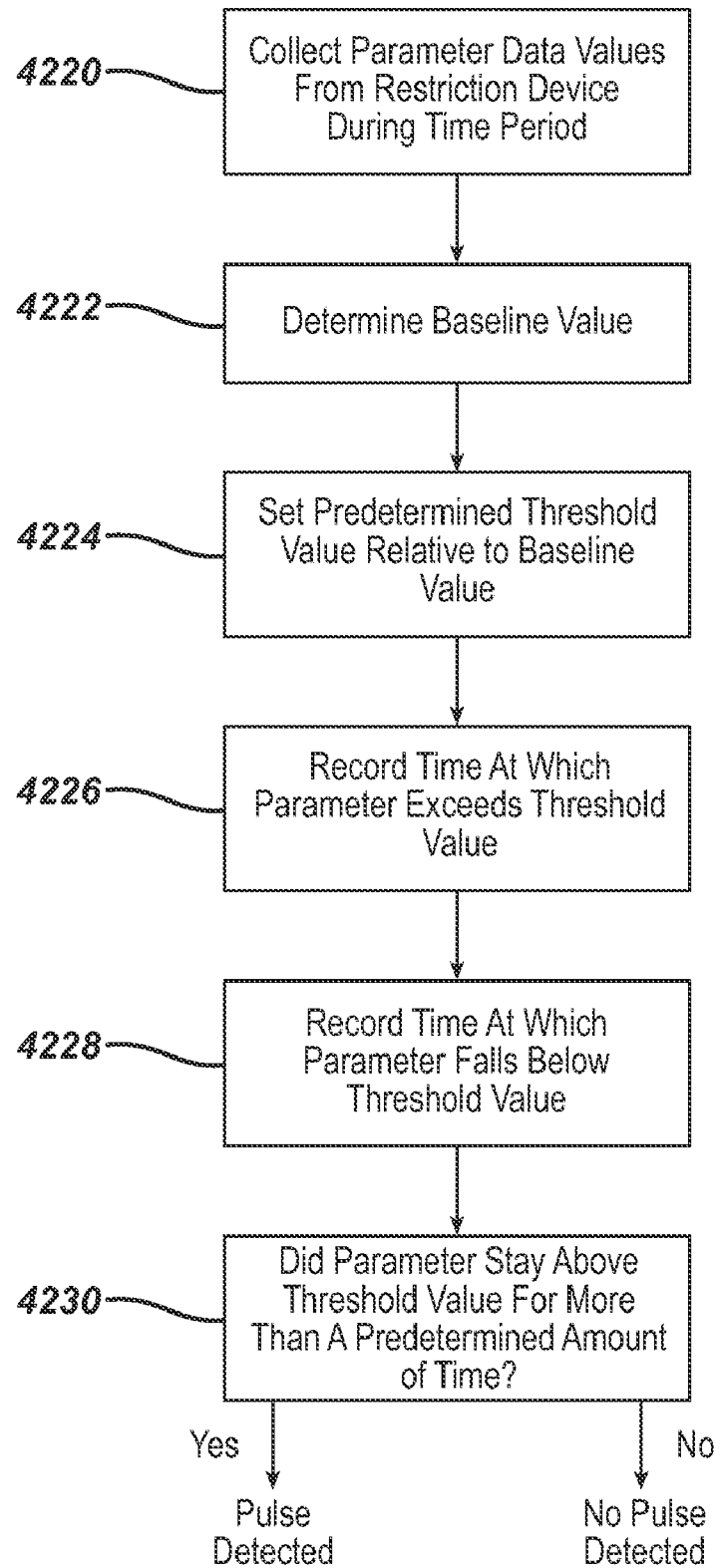
FIG. 42B is an exemplary flow diagram for determining the presence of a pulse in data collected from a restriction device.

A wide variety of algorithms can be used to detect the presence of pulses in pressure values or other data values collected by the data logger 270. One exemplary embodiment of such an algorithm is illustrated in FIGS. 42A-B. FIG. 42A shows a plot 4200 of exemplary pressure values over a time period, although any parameter values can be used. FIG. 42B shows a flow diagram illustrating exemplary steps of an algorithm. As shown, a predetermined threshold value 4202 can be defined relative to the baseline value 4212 (boxes 4222, 4224 of FIG. 42B). (For example, the threshold value can be set to be 10 mmHg above the baseline value 4212.) At box 4226, the algorithm can determine the time 4206 at which the parameter value exceeds the threshold value 4202. (As the threshold value 4202 can be relative to the baseline value 4212, in absolute terms, the time 4206 at which the parameter value exceeds the threshold value 4202 can occur when the parameter exceeds the baseline value 4212 plus the threshold value 4202.) If the parameter value decreases such that it no longer exceeds the threshold value 4202 within a predetermined time 4210, a pulse can be said to have occurred (boxes 4228-4230). The predetermined time 4210 also can be user-defined.

Figure 43A:
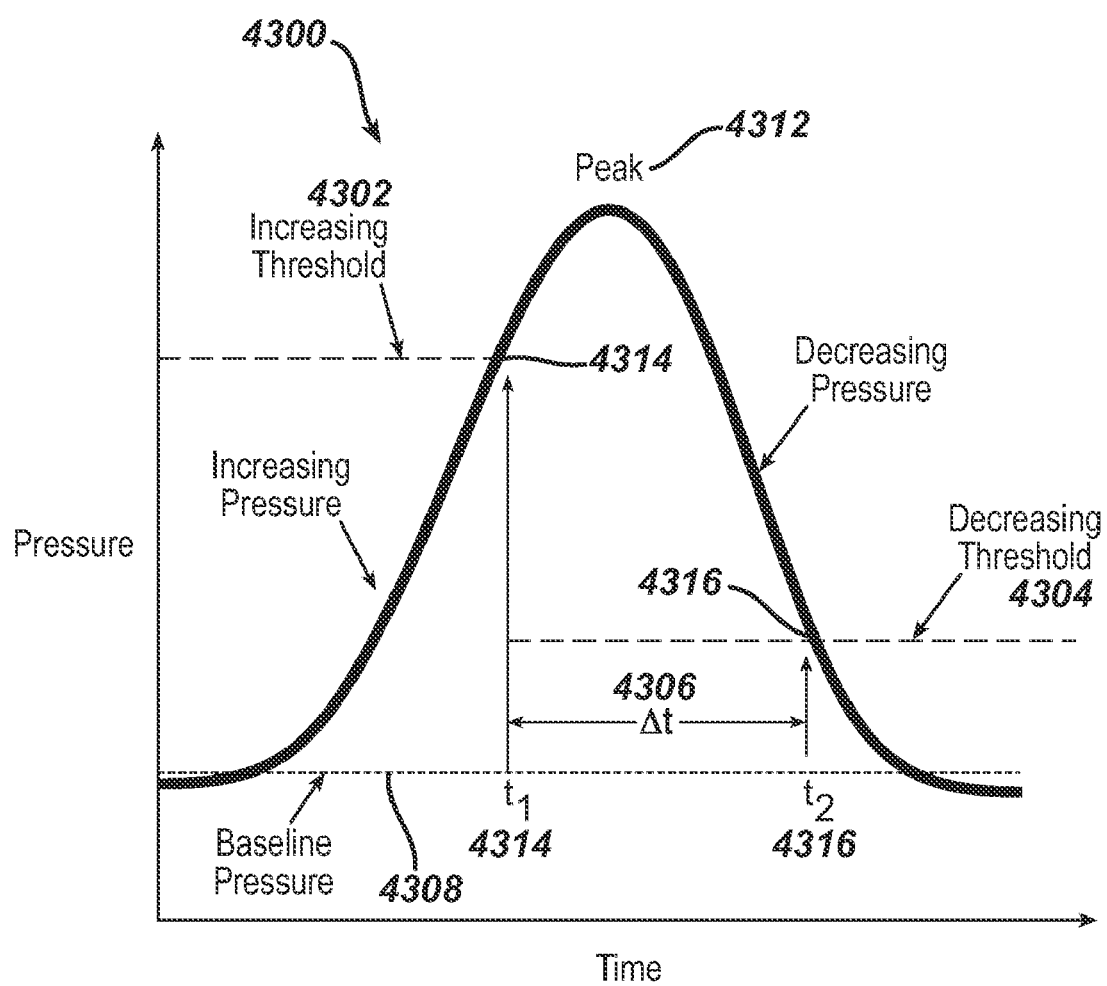
FIG. 43A is another exemplary plot of pressure values over time collected from a restriction device with annotations related to determining the presence of a pulse via another technique.
Figure 43B:
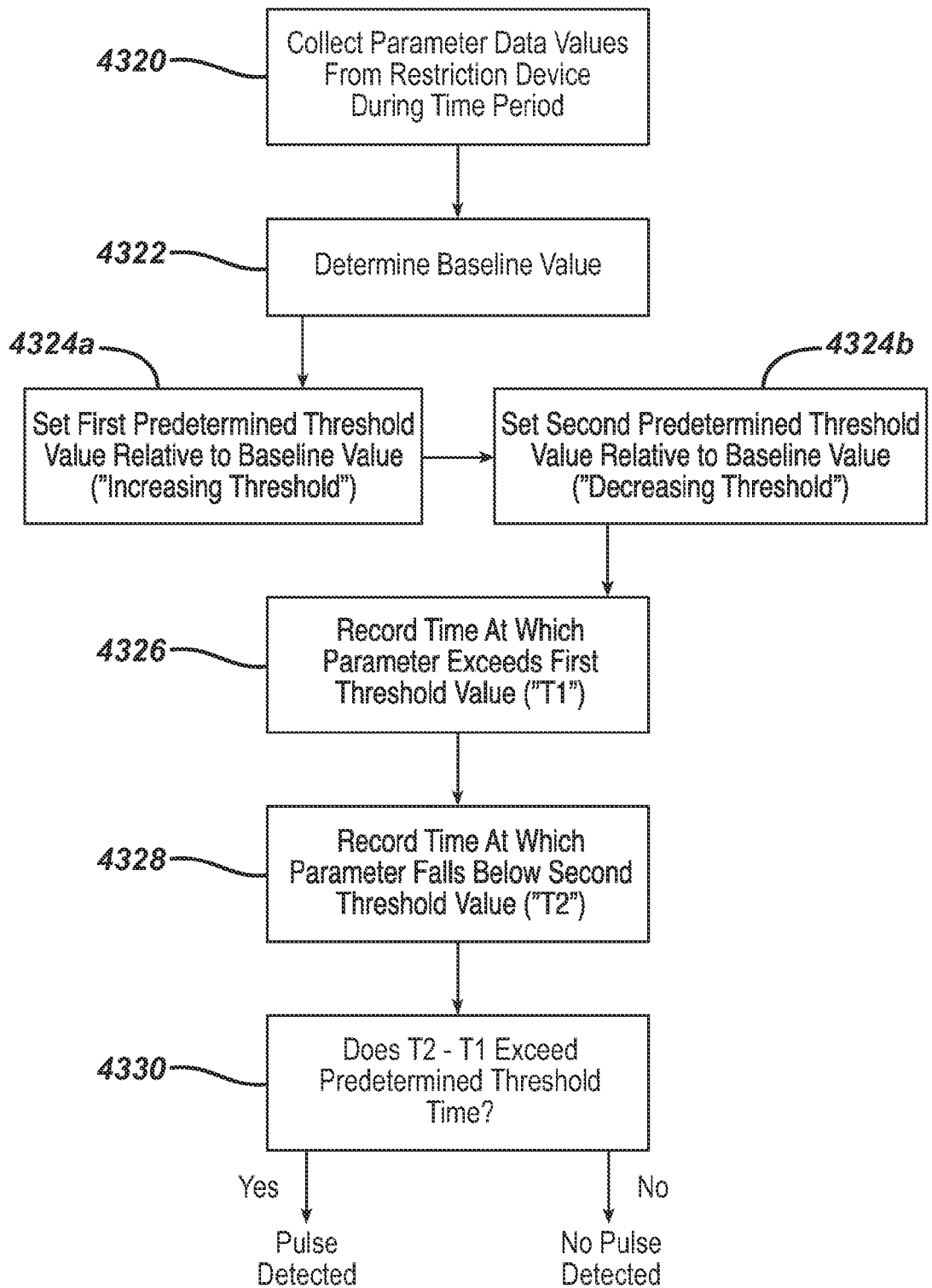
FIG. 43B is another exemplary flow diagram for determining, via the technique described in connection with FIG. 43A, the presence of a pulse in data collected from a restriction device.

FIG. 43A illustrates the application of an alternative embodiment of an algorithm that can be used to detect the presence of a pulse to a set of data, and FIG. 43B shows an exemplary flow diagram for such an algorithm. As shown, a first threshold value 4302 and a second threshold value 4304 can be defined (boxes 4324*a*, 4324*b*), both defined relative to the baseline value 4308, as discussed with respect to FIGS. 42A-B. The first threshold value 4302 can apply when the parameter is increasing (for example, before the peak of the pulse) and the second threshold 4304 can apply when the parameter is decreasing (for example, after the peak 4312). At box 4326, the algorithm can determine the time 4314 at which the parameter value exceeds the first threshold value 4302. If the parameter value then falls below the second threshold 4304 within a predetermined time 4306, a pulse can be said to have occurred (boxes 4328-4330).

Figure 44A:
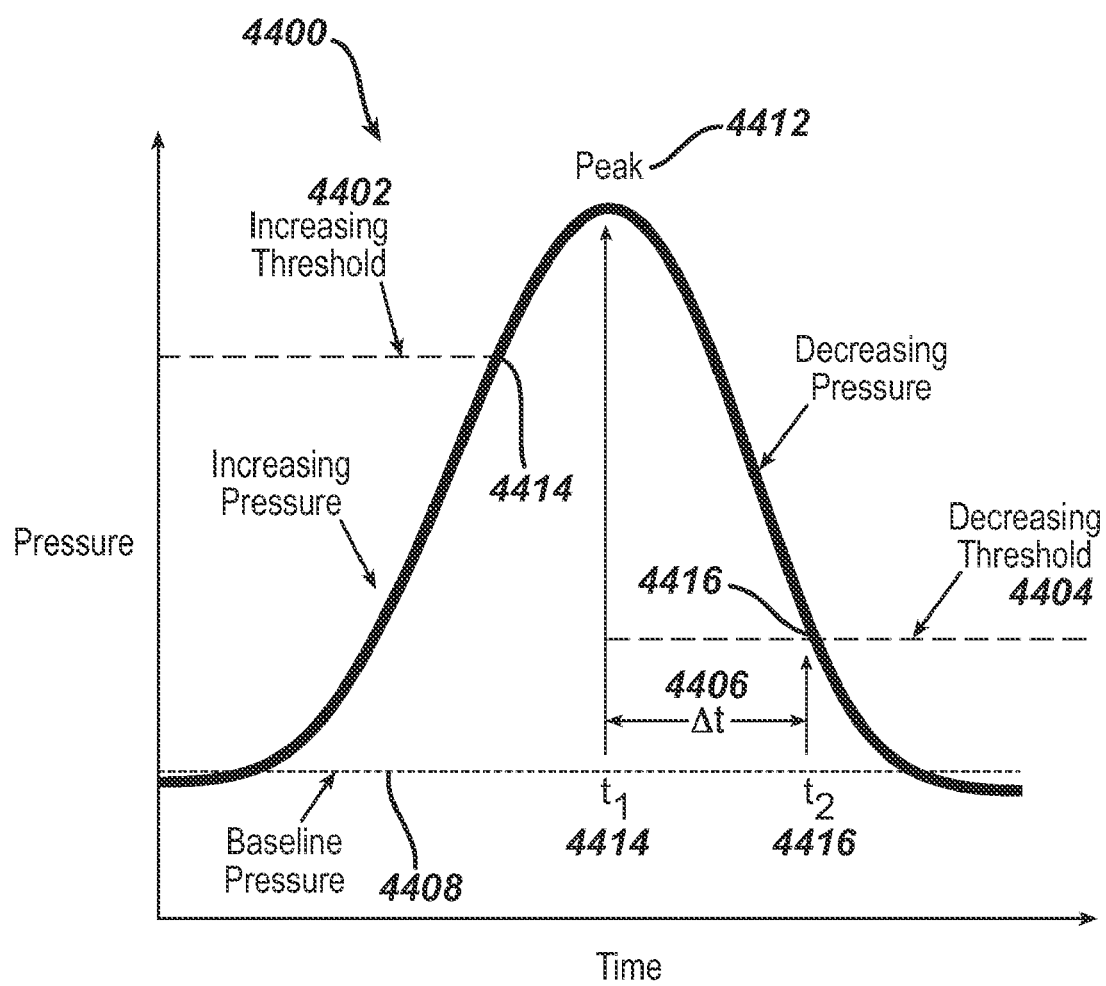
FIG. 44A is yet another exemplary plot of pressure values over time collected from a restriction device with annotations related to determining the presence of a pulse via yet another technique.
Figure 44B:
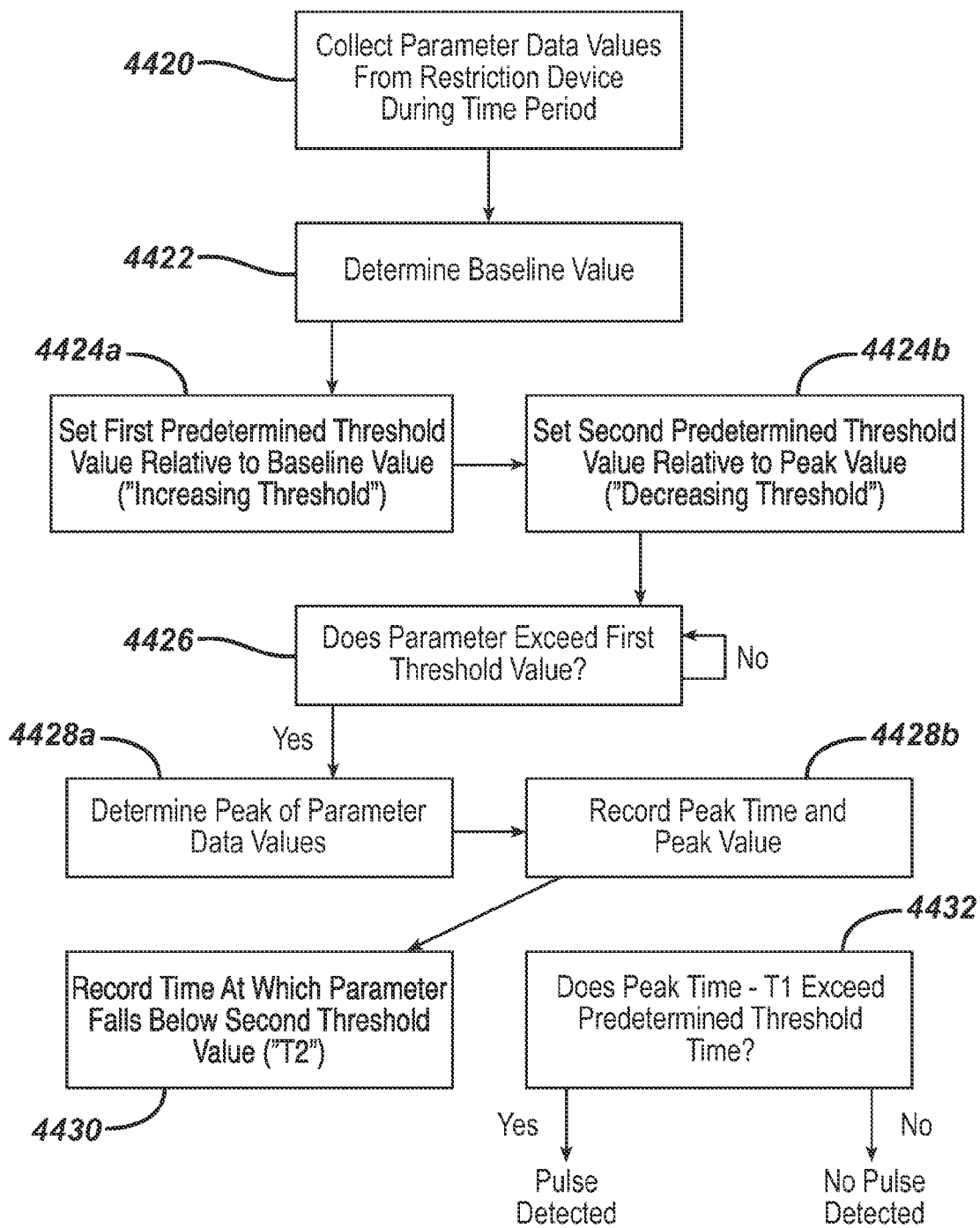
FIG. 44B is yet another exemplary flow diagram for determining, via the technique described in connection with FIG. 44A, the presence of a pulse in data collected from a restriction device.

FIG. 44A illustrates the application another alternative embodiment of an algorithm that can be used to detect the presence of a pulse in a set of data, and FIG. 44B shows an exemplary flow diagram for such an algorithm. In this embodiment, a first threshold 4402 can be defined relative to the baseline value 4408, and a second threshold 4404 can be defined relative to a peak value 4412 (boxes 4424*a-b* in FIG. 44B). The time 4414 at which the parameter exceeds the first threshold 4402 and the time 4412 at which the parameter reaches a peak (for example, when it has a zero slope) can be recorded (boxes 4426, 4428*a-b*). If the parameter value falls below the second threshold 4404 within a predetermined time 4406, then a pulse can be said to have occurred (boxes 4430, 4432). In many embodiments, the second threshold 4404 can be defined as a proportion of the peak value 4412 (e.g., 75% of the peak value), which the algorithm can then compute when it finds a peak value 4412. In other embodiments, the second threshold 4404 can be defined directly (e.g., 10 mmHg below the peak value 4412).

An algorithm for finding a pulse can also trigger a variety of alarms or can record pulse events for reports maintained by the local unit 60, remote monitoring device 170, and/or the system 20. For example, an alarm or notification signal can be generated when a pulse is detected, when no pulse can be detected, when a pulse appears during certain times (such as outside meal times), when a pulse count exceeds a threshold value, when pulses are detected for a specified period of time, when the rate of change pressure indicates either a start of a pulse or an end of a pulse, and so on. Alternatively, the occurrence of such events can be logged or stored for inclusion in a report or log produced by the local unit 60, remote monitoring device 170, and/or the system 20. In addition, the determination that one or more pulses has occurred can be correlated (either alone or in conjunction with other data, as described herein) to the condition of the restriction device. For example, if pulses continue to occur over a time period (e.g., during a predetermined time period, in some cases such as 5-6 minute window, although any time period is possible) can indicate that the restriction device is over-filled or too tight. The amplitude of the pulses and the time between pulses (either taken alone, or in conjunction with other metrics) can also be used or involved in this determination, e.g., pulses of a threshold amplitude can be considered. In other embodiments, the number of pulses in a sequence, or the number of pulses within a time period, can be used to make a correlation. Also, the absence of pulses over a predetermined time period can indicate that the restriction device is too loose or underfilled. Such pulse analysis can further involve giving water/food swallows or dry swallow instructions to a patient who is wearing a restriction band and monitoring the resulting pulse(s), either to determine an appropriate predetermined time period to watch for pulses, to assess the condition of the restriction device, or otherwise.

Figure 45B:
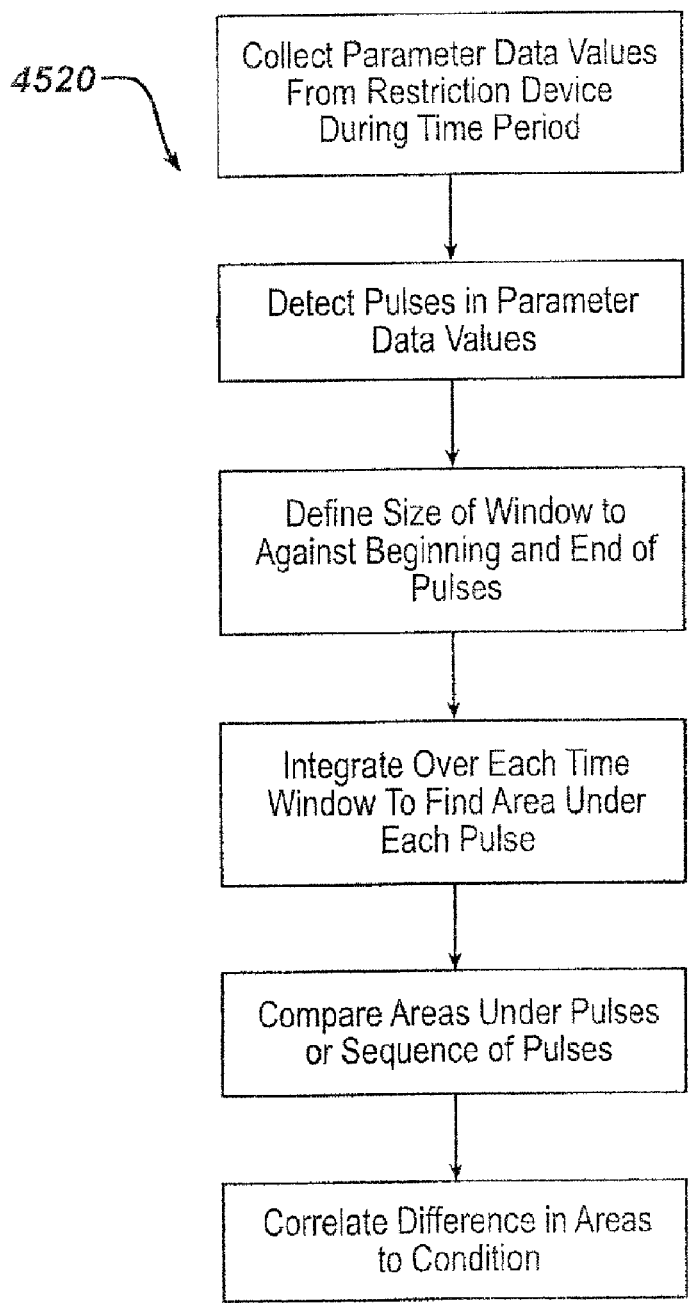
FIG. 45A is another exemplary plot of pressure values over time collected from a restriction device with annotations related to comparing pulse areas; and, FIG. 45B is an exemplary flow diagram for comparing pulses areas using data collected from a restriction device.

The area under a pulse, or sequence of pulses or other waveform, in parameter vs. time data can be used for analytical purposes. FIG. 45A shows an exemplary plot 4500 of pressure over a time period; FIG. 45B shows a flow diagram illustrating an exemplary algorithm 4520 for making such an analysis. As shown, the values of the pressure are represented by a graphical representation 4502, in this case a waveform, which exhibits a series of pulses. The areas under one or more pulses can be evaluated. The areas can be calculated by evaluating an integral for each pulse over a window, such as time windows 4512, 4514, 4516, 4518. The areas can be calculated with reference to a baseline value 4510 or to a zero value. In many embodiments, the window can be sized to cover the time of the pulse, for example, by beginning the window when the parameter value exceeds a threshold, and ending it when the parameter value falls below that threshold value, or by using any of the times discussed in connection with FIGS. 42-44, such as times T2-T1 illustrated in FIG. 43B or Peak Time-T1 in FIG. 44B. The results of the integrals can be compared, and the nature of sequence of areas (increasing, decreasing, etc.) as well as their magnitude can be correlated to conditions or events related to the restriction device 22, the patient, and so on. For example, the presence of pulses with substantially equivalent areas, generally indicated by bracket 4506 in FIG. 45A, can be indicative of a fluid-filled restriction device that is overfilled, or generally a restriction device that is too tight. The presence of pulses with decreasing areas, or areas decreasing at a predetermined rate, generally indicated by bracket 4508, can be indicative of an optimally filled or adjusted band. The decrease of such areas at a second predetermined rate (for example, a rate higher than that associated with an optimally filled band) can be correlated to an underfilled restriction device. The presence of a single pulse without any peaks following, as generally indicated by bracket 4504, can be indicative of a restriction device that is underfilled, or of coughing or talking.

It should be understood that any or all of the foregoing algorithms and techniques can be integrated with a graphical user interface to allow a user to provide input to the algorithm and to display results, both intermediate and final results. For example, plots of pressure over time can be displayed to a user, and the user can manually define or select windows for averaging, slope calculations, or for calculating the area of a pulse (e.g., by manually marking beginning and ending times). In other embodiments, the user can manually mark the baseline value by adjusting a horizontal line on the display after viewing pressure values for a timed period. Such variations are intended to be within the scope of this disclosure.

It will be appreciated that several embodiments described herein may enable health care providers or others to use pressure data as a feedback mechanism to identify, train, and/or prescribe dietary advice to a patient. Such a feedback mechanism may provide data or otherwise be used in multiple ways. For instance, pressure feedback may be obtained when a patient swallows a particular food portion, and based on such pressure feedback, the patient may be taught to eat smaller portions, larger portions, or portions equal to the portion tested. Of course, a food portion so prescribed may be tested by evaluating pressure feedback obtained when the patient swallows the prescribed food portion, such that a food portion prescription may be refined through reiteration. As another example, a patient may test desired foods for appropriateness based on pressure feedback together with portion size and/or based on any other parameters. It will also be appreciated that continuous pressure data monitoring may be used to enable portion size monitoring, food consistency monitoring (e.g., liquids vs. solids) and/or eating frequency. Still other ways in which pressure data may be used to provide dietary advice will be apparent to those of ordinary skill in the art. It will also be appreciated that such uses may be practiced locally, remotely (e.g., via remote unit 170), or combinations thereof.

While data logging system 300 is described herein as being implemented with injection port 36, it will be appreciated that data logging system 300 may alternatively be implemented with any other type of pressure sensing system or other implanted systems. By way of example only, data logging system 300 may be combined with any of the pressure sensing devices disclosed in U.S. Patent Publication No. 2006-0211914 (application Ser. No. 11/369,682), filed Mar. 7, 2006, and entitled "System and Method for Determining Implanted Device Positioning and Obtaining Pressure Data," and U.S. Patent Publication No. filed Mar. 6, 2007, and U.S. Non-Provisional patent application Ser. No. 11/682,459, entitled "Pressure Sensors for Gastric Band and Adjacent Tissue", the disclosures of both of which are incorporated by reference herein for illustrative purposes. For instance, data logging system 300 may receive pressure measurements obtained by any of the pressure sensors described in that patent application. In addition, the needle guidance sense head described in that patent application may be used with at least a portion of data logging system 300 to provide needle guidance for a local clinician to adjust fluid pressure in accordance with a remote physician's instructions that are based on pressure measurements obtained by the needle guidance sense head and communicated to the remote physician in substantially real-time. For instance, the needle guidance sense head may be coupled with data logger 370, which may connected directly to the Internet (or via docking station 360) to provide pressure measurements to the remote physician. Still other ways in which devices and components described herein may be combined with components described in U.S. Patent Application Publications US 2006-0211912, US 2006-0211913, and US 2006-0211914, hereby incorporated by reference, will be apparent to those of ordinary skill in the art.

It will become readily apparent to those skilled in the art that the above invention has equally applicability to other types of implantable bands. For example, bands are used for the treatment of fecal incontinence. One such band is described in U.S. Pat. No. 6,461,292 which is hereby incorporated herein by reference. Bands can also be used to treat urinary incontinence. One such band is described in U.S. Patent Application 2003/0105385 which is hereby incorporated herein by reference. Bands can also be used to treat heartburn and/or acid reflux. One such band is described in U.S. Pat. No. 6,470,892 which is hereby incorporated herein by reference. Bands can also be used to treat impotence. One such band is described in U.S. Patent Application 2003/0114729 which is hereby incorporated herein by reference.

Any of the devices disclosed herein can also be designed to be disposed of after a single use, or they can be designed to be used multiple times. Devices which can be external, such as the local unit, remote monitoring device, data loggers, and so on, are in many cases suitable for reuse. Devices can be reconditioned or reconstructed for reuse after at least one use. Reconditioning or reconstructing can include any combination of the steps of disassembly of the device, followed by replacement, upgrade, cleaning, or modification of particular pieces (including mechanical components, computer hardware and software, and so on) and subsequent reassembly. In particular, the device can be disassembled, and any number of the particular pieces or parts of the device can be selectively replaced or removed in any combination. The device can be reassembled for subsequent use either at a reconditioning facility, or by a physician before using the device with a patient. Those skilled in the art will appreciate that reconditioning or reconstructing of a device can utilize a variety of techniques for disassembly, cleaning and/or replacement, and reassembly. Additionally, repairs can be made to devices and/or to their individual parts or pieces. Use of such techniques, and the resulting reconditioned, reconstructed, or repaired device, are all within the scope of the present application.

The devices described herein, particularly including but not limited to those devices that can be implanted in or attached to a patient, preferably can be processed or sterilized before use. First, a new or used device (or part thereof) is obtained. The device can then be sterilized. In one sterilization technique, the device is placed in a closed and sealed container, such as a plastic or TYVEK bag. The container and device are then placed in a field of radiation that can penetrate the container, such as beta or gamma radiation, x-rays, or high-energy electrons. The radiation kills bacteria on the instrument and in the container. The sterilized instrument can then be stored in the sterile container. The sealed container keeps the instrument sterile until it is opened in a medical facility. In other embodiments, ethylene oxide, or steam can be used for sterilization.

While preferred embodiments of the present invention have been shown and described herein, it will be obvious to those skilled in the art that such embodiments are provided by way of example only. Numerous variations, changes, and substitutions will now occur to those skilled in the art without departing from the invention. For example, as would be apparent to those skilled in the art, the disclosures herein have equal application in robotic-assisted surgery. In addition, it should be understood that every structure described above has a function and such structure can be referred to as a means for performing that function. Accordingly, it is intended that the invention be limited only by the spirit and scope of the appended claims.

While the present invention has been illustrated by description of several embodiments, it is not the intention of the applicant to restrict or limit the spirit and scope of the appended claims to such detail. Numerous other variations, changes, and substitutions will occur to those skilled in the art without departing from the scope of the invention. For instance, the device and method of the present invention has been illustrated with respect to transmitting pressure data from the implant to the remote monitoring unit. However, other types of data may also be transmitted to enable a physician to monitor a plurality of different aspects of the restrictive opening implant. Additionally, the present invention is described with respect to a food intake restriction device for bariatric treatment. The present invention is not limited to this application, and may also be utilized with other restrictive opening implants or artificial sphincters without departing from the scope of the invention. The structure of each element associated with the present invention can be alternatively described as a means for providing the function performed by the element. It will be understood that the foregoing description is provided by way of example, and that other modifications may occur to those skilled in the art without departing from the scope and spirit of the appended Claims.

What is claimed is:

1. A method of obtaining information about a physiological parameter, comprising:
    collecting data from an implantable restriction device over a time period, the collected data containing information about values of a parameter sensed within a body during the time period; and
    in a data processing device, analyzing the collected data to determine information about a physiological parameter for at least a portion of the time period, wherein the analysis includes calculating a rate of change of the values of the sensed parameter for a window within the time period;
    calculating a rate at which the rate of change is changing; and
    dividing the rate of change by the rate at which the rate of change is changing and multiplying by a period of the window to obtain a predicted amount of time until the values of the sensed parameter will have a rate of change that is about zero, the value of the physiological parameter when the rate of change is about zero representing a baseline value.

2. The method of claim 1, wherein the sensed parameter from the body is pressure sensed by the implantable restriction device.

3. The method of claim 1, wherein the physiological parameter is at least one of: heart rate, breathing rate, peristaltic event occurrence, peristaltic event rate, baseline parameter value.

4. The method of claim 1, wherein the determined information about the physiological parameter is at least one of frequency, value, amplitude, change in value over at least a portion of the time period, and average value over the time period.

5. The method of claim 1, further comprising using the collected data to determine information about a second physiological parameter for at least a portion of the time period.

6. The method of claim 2, further comprising:
    determining a frequency content of variations in the values of the sensed parameter during the time period and identifying one or more frequencies in the frequency content as a frequency of the physiological parameter.

7. The method of claim 6, wherein identifying one or more frequencies comprises comparing one or more frequencies to one or more predetermined frequencies that are designated as frequencies associated with the physiological parameter.

8. The method of claim 2, wherein the physiological parameter is a rate of a physiological event, and analyzing the collected data comprises:
    determining a frequency content of variations in the values of pressure over at least a portion of the time period;
    selecting one or more frequencies existing in the frequency content that fall within a predetermined range of frequencies designated as possible rates of the physiological event; and
    identifying a rate for the physiological event based on the one or more selected frequencies.

9. The method of claim 8, wherein identifying comprises at least one of:
    (i) averaging the one or more selected frequencies; and
    (ii) designating one of the one or more frequencies as the rate.

10. The method of claim 8, wherein determining the frequency content comprises applying a Fourier transform to at least a portion of the collected data.

11. The method of claim 8, wherein the physiological event is heartbeat and the rate represents heart rate.

12. The method of claim 8, wherein the physiological event is breath and the rate represents breathing rate.

13. The method of claim 8, further comprising generating an alarm or report if the rate passes a threshold rate.

14. The method of claim 2, wherein the physiological parameter is a rate of a physiological event, and analyzing the collected data comprises:
calculating a frequency exhibited in the variations in the value of pressure over at least a portion of the time period; and
comparing the frequency to a predetermined range of frequencies designated as possible rates of the physiological event to determine if the frequency falls within the range.

15. The method of claim 14, wherein calculating the frequency comprises:
recording at least two times at which values of pressure are at a local maximum or minimum; and
calculating the frequency based on the difference between the at least two times.

16. The method of claim 14, further comprising:
determining an amplitude of the variations in the values of pressure at the calculated frequency; and
comparing the amplitude to a predetermined range of amplitudes designated as possible physiological event amplitudes to determine if the amplitude falls within the range.

17. The method of claim 14, wherein the physiological event is heartbeat and the rate represents heart rate.

18. The method of claim 14, wherein the physiological event is breath and the rate represents breathing rate.

19. The method of claim 14, further comprising generating an alarm or report if the rate passes a threshold rate.

20. The method of claim 2, wherein analyzing the collected data comprises:
calculating the difference between (i) a value of pressure at a time within the time period, and (ii) an average value of pressure at the time, wherein the difference represents a value corresponding to the physiological parameter.

21. The method of claim 20, wherein the physiological parameter is at least one of: heart rate and breathing rate.

22. The method of claim 20, wherein the average value is calculated based on a group of values in an averaging window that surrounds the value at the time.

23. A method of analyzing data from an implantable restriction device to determine information about a baseline of a physiological parameter, comprising:
collecting data from an implantable restriction device over a time period, the collected data containing information about values of a parameter sensed within a body during the time period; and
in a data processing device, calculating, based at least in part on one or more values of the sensed parameter during the time period, a predicted amount of time until the rate of change of values of the physiological parameter will be about zero, the value of the physiological parameter when the rate of change is about zero representing a baseline value, wherein calculating the predicted amount of time comprises:
calculating a rate of change of the values of the sensed parameter for a window within the time period;
calculating a rate at which the rate of change is changing; and
dividing the rate of change by the rate at which the rate of change is changing and multiplying by a period of the window to obtain the predicted amount of time until the values of the sensed parameter will have a rate of change that is about zero.

24. The method of claim 23, wherein the sensed parameter is pressure sensed by the implantable restriction device.

25. The method of claim 23, further comprising:
calculating, based at least in part on the values of the sensed parameter during the time period and the predicted amount of time, a predicted baseline value of the sensed parameter when the rate of change is about zero.

26. The method of claim 25, wherein calculating the predicted baseline value comprises:
extrapolating from one or more values within the window to the predicted baseline value of the sensed parameter, at least by multiplying the rate of change of the values of the sensed parameter for the window within the time period and the predicted amount of time until the values of the sensed parameter will have a rate of change that is about zero.

27. The method of claim 23, further comprising generating an alarm or report if the rate of change passes a threshold value.

28. The method of claim 23, wherein the implantable restriction device is fluid-finable, and further comprising correlating the rate of change to a condition of the implantable restriction device, the condition being one of: optimally-filled, over-filled, or under-filled.

* * * * *